US012195526B2

(12) United States Patent
Sabapathy et al.

(10) Patent No.: US 12,195,526 B2
(45) Date of Patent: Jan. 14, 2025

(54) ANTI-p53 ANTIBODIES

(71) Applicants: Agency for Science, Technology and Research, Singapore (SG); Singapore Health Services Pte. Ltd., Singapore (SG); National University of Singapore, Singapore (SG)

(72) Inventors: Tr Kanaga Sabapathy, Singapore (SG); David P. Lane, Singapore (SG); Le-Ann Hwang, Singapore (SG); Xin Yu Koh, Singapore (SG); Liew Oi Wah, Singapore (SG)

(73) Assignees: AGENCY FOR SCIENCE, TECHNOLOGY AND RESEARCH, Singapore (SG); Singapore Health Services Pte Ltd, Singapore (SG); NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 18/172,773

(22) Filed: Feb. 22, 2023

(65) Prior Publication Data

US 2023/0257457 A1  Aug. 17, 2023

Related U.S. Application Data

(63) Continuation of application No. 16/342,763, filed as application No. PCT/SG2017/050522 on Oct. 17, 2017, now Pat. No. 11,613,568.

(30) Foreign Application Priority Data

Oct. 17, 2016 (GB) ..................... 1617564

(51) Int. Cl.
C07K 16/18  (2006.01)
A61K 39/00  (2006.01)
A61K 49/00  (2006.01)
A61P 35/00  (2006.01)

(52) U.S. Cl.
CPC ............. *C07K 16/18* (2013.01); *A61K 39/00* (2013.01); *A61K 49/0058* (2013.01); *A61P 35/00* (2018.01); *A61K 2039/505* (2013.01); *A61K 2039/552* (2013.01); *A61K 2039/575* (2013.01); *A61K 2039/80* (2018.08); *C07K 2317/24* (2013.01); *C07K 2317/34* (2013.01)

(58) Field of Classification Search
CPC ......... C07K 16/18; A61P 35/00; A61K 39/00; A61K 49/0058
See application file for complete search history.

(56) References Cited

U.S. PATENT DOCUMENTS 6,083,709 A   7/2000  Reynolds, Jr. et al.
6,140,058 A  10/2000  Lane et al.
6,143,524 A  11/2000  McCoy et al.
8,728,479 B2  5/2014  Greene
2003/0086935 A1  5/2003  Levine
2010/0074908 A1  3/2010  Solomon
2012/0258920 A1* 10/2012  Sal .................. C07K 7/08
                                              435/7.8

FOREIGN PATENT DOCUMENTS

EP        1006364      6/2000
WO    WO 92/00311      1/1992
WO    WO 01/68801      9/2001
WO   WO 2006/100681    9/2006
WO   WO 2013/036208    3/2013

OTHER PUBLICATIONS

Lamminmaki et al. "Crystal structure of a recombinant anti-estradiol Fab fragment in complex with 17beta-estradiol", JBC 2001, 276:36687-36694 (Year: 2001).*
Rudikoff et al. "Single amino acid altering antigen-binding specificity", Proc Natl Acad Sci USA 1982 vol. 79 p. 1979 (Year: 1982).*
MacCallum et al. "Antibody-antigen Interactions: Contact Analysis and Binding Site Topography", J. Mol. Biol. (1996) 262, 732-745 (Year: 1996).*
Pascalis et al. "Grafting of "Abbreviated" Complementarity-Determining Regions Containing Specificity-Determining Residues Essential for Ligand Contact to Engineer a Less Immunogenic Humanized Monoclonal Antibody", The Journal of Immunology (2002) 169, 3076-3084 (Year: 2002).*
Casset et al. "A peptide mimetic of an anti-CD4 monoclonal antibody by rational design", BBRC 2003, 307:198-205 (Year: 2003).*
Vajdos et al. "Comprehensive functional maps of the antigen-binding site of an anti-ErbB2 antibody obtained with shotgun scanning mutagenesis", J. Mol. Biol. (2002) 320, 415-428 (Year: 2002).*
Chen et al. "Selection and analysis of an optimized anti-VEGF antibody: crystal structure of an affinity-matured Fab in complex with antigen", J. Mol. Bio. (1999) 293, 865-881 (Year: 1999).*
Wu et al. "Humanization of a murine monoclonal antibody by simultaneous optimization of framework and CDR residues", J. Mol. Biol. (1999) 294, 151-162 (Year: 1999).*
Padlan et al. "Structure of an antibody-antigen complex: crystal structure of the HyHEL-10 Fab-lysozyme complex", PNAS 1989, 86:5938-5942 (Year: 1989).*

(Continued)

*Primary Examiner* — Amy E Juedes
*Assistant Examiner* — Peter Johansen
(74) *Attorney, Agent, or Firm* — MARSHALL, GERSTEIN & BORUN LLP

(57) ABSTRACT

The invention relates to methods for producing an antibody which is specific for a mutant p53 polypeptide over wildtype p53 polypeptide, comprising using as an immunogen a peptide or polypeptide comprising: (i) an antigen sequence, comprising an amino acid sequence of the mutant p53 polypeptide including the mutation and at least one amino acid immediately adjacent to the mutation, and (ii) a scaffold sequence for providing the antigen sequence in a solvent-accessible configuration. Also provided are antibodies produced by such methods, and uses thereof.

11 Claims, 95 Drawing Sheets

Specification includes a Sequence Listing.

(56) References Cited

OTHER PUBLICATIONS

Seitz et al., A three component mix of thioredoxin-L2 antigens elicits broadly neutralizing responses against oncogenic human papillomaviruses, Vaccine 4014, 32(22): 2610-2617.
Roblek et al., "Monoclonal Antibodies Specific for Disease-Associate Point-Mutants: Lamic A/C R453W and R482W," PLos One 2010, 5(5):e10604.
Barrell et al., "Expressing an antibacterial protein in bacteria for raising antibodies," Protein Expr Purif, 2004, 33(1):153-159.
Lu et al., "the gain function of p53 cencer mutant in promoting mammary tumorigenesis," Oncogene 2013, 32(23):2900-2906.
Bolchi et al., Thioredoxin-Displayed Multipeptide Immunogens Peptide Antibodies: Methods Protocols, 1348: 135-152 (2015).
Baroni et al., "A global suppressor motif for p53 cancer mutants," PNAS, 101(14):4930-4935 (2004).
Bethuyne et al., "A nanobody modulates the p53 transcriptional program without perturbing its functional architecture," Nucleic Acids Research, 42(2): 12928-12938 (2014).
Canali et al., "A higher-performance thioredoxin-based scaffold for peptide immunogen construction: proof-of-concept testing with a human papillomavirus epitope," Scientific Reports, 4: 4729 1-11 (2014).
Govorko et al., "Single-chain antibody against the common epitope of mutant p53: isolation and intracytosolic expression in mammalian cells" Journal of Immunology, 258: 169-181 (2001).
Hwang et al., "Monoclonal Antibodies against Specific p53 Hotspot Mutants as Potential Tools for Precision Medicine," Cell Reports, 22: 299-312 (2018).
International Search Report for PCT/SG2017/050522, 6 pages (mailed Jan. 24, 2018).
Meiyalaghan, S. et al., Expression and purification of the antimicrobial peptide GSL1 in bacteria for raising antibodies, BMC Research Notes, 7: 777 (2014).
Moretto, N. et al., Conformation-sensitive Antibodies against Alzheimer Amyloid-I by Immunization with a Thioredoxin-constrained B-cell Epitope Peptide, The Journal of Biological Chemistry, 282(15): 11436-11445 (2007).
Orgad, S. et al., Single chain antibody against the common epitope of mutant p53 restores wild-type activity to mutant p53 protein, FEBS letters, 579: 5609-5615 (2005).
Vikhanskaya, F. et al., Cancer-serviced p53 mutants suppress p53-target gene expression-potential mechanism for gain of function of mutant p53, Nucleic Acids Research, 35(6): 20932104 (2007).
Written Opinion for PCT/SG2017/050522, 9 pages (mailed Jan. 24, 2018).

\* cited by examiner

R175H

```
          10               20              30
M S D K I I H L T D D S F D T D V L K A D G A I L V D F W A 40              50              60
E W C G P G S G S G Q H M T E V V R C P H H E R C S D G S 70              80              90
G T E V V R C P H H E R G S G V R C P H H E R G S G S G 100             110             120
P C K M I A P I L D E I A D E Y Q G K L T V A K L N I D Q N 130             140             150
P G T A P K Y G I R G I P T L L F K N G E V A A T K V G A 160             170
L S K G Q L K E F L D A N L A G S G H H H H H H STOP
```

H H H H H H STOP
```

```
             10                    20                    30
M  S  D  K  I  I  H  L  T  D  D  S  F  D  T  D  V  L  K  A  D  G  A  I  L  V  D  F  W  A
             40                    50                    60
E  W  C  G  P  G  S  G  S  G  R  N  S  F  E  V  ▓  V  C  A  G  S  G  N  L  L  G  R  N  S
             70                    80                    90
F  E  V  ▓  V  C  A  C  G  S  G  G  R  N  S  F  E  V  ▓  V  C  A  C  P  G  S  G  S  G  P
            100                   110                   120
C  K  M  I  A  P  I  L  D  E  I  A  D  E  Y  Q  G  K  L  T  V  A  K  L  N  I  D  Q  N  P
            130                   140                   150
G  T  A  P  K  Y  G  I  R  G  I  P  T  L  L  F  K  N  G  E  V  A  A  T  K  V  G  A  L
            160                   170
S  K  G  Q  L  K  E  F  L  D  A  N  L  A  G  S  G  H  H  H  H  H  H  STOP
```

R175H

R248Q

Anti-R175H mAbs

10C8

| | |
|---|---|
| WTp53 | QHMTEVVRRCPHHERCSD |
| R175H | QHMTEVVRHCPHHERCSD |
| 6 | ----GGVLHLPHHTRN-- |
| 3 | -----ADNHEPHPLACD- |
| 4 | -------T-RHQPHHSLPPR |
| 8 | -------T-PHQPHHSFTPR |
| 7 | ---VSTGVHYPHHSA----- |
| 2 | ---VDMHHYPHHYKD--- |
| 5 | -------ILASHRPHHYGY- |
| 1 | ---LCTPLLHPIHHL--- |

Consensus: 167QHMTEVVRHCPHHERCSD184

10C8, 7B9, 4H5 epitope

Anti-R248Q mAbs

4H2

```
WTp53     GMNRRPILTIITLEDS
R248Q     GMNQRPILTIITLEDS
1         ------ELWQNVRPFLWV--------------
2         ---------------SRPADHWPRHNE----
3         ---------------SSRPMAHWPIKV-----
4         --------------VSSRPSSHWPI---------
5         ---SNTPHWPGRPGI------------------
6         -------------INTPRDWAYGGL---------
7         ------------FNQPPRSGRVI-----------
```

Consensus: 245 GMNQ<u>RP</u> ILTIITLEDS 260
4H2 epitope

Figure 7B

Anti-R273H mAb

13E4

```
WTp53    ----GRNSFEVRVCAC----------
R273H    ----GRNSFEVHVCAC----------
4        ------GK-TYSYHMQLYT-------
3        --------------YHVGGILGRLFM
5        ------YNTFPYHLGYTL---------
2        ---DNASSSKVHHGH-----------
1        -------------TFVHGNTWTIVN-
6        ---TNTMHAVHHPL------------
```

Consensus: 267RNSFE<u>VH</u>VCACPGR280
13E4 epitope

Figure 7C

Anti-R175H mAbs

7B9

|  | WTp53 | QHMTEVVRRCPHHERCSD |
|---|---|---|
|  | R175H | QHMTEVVRHCPHHERCSD |
| 4 |  | ---YNQTHHPHHQEY---- |
| 9 |  | ---GAPEVHHPAHQA---- |
| 7 |  | ---KTLS-HAPHHSKE--- |
| 8 |  | ---HSPV-HTPHGSGK--- |
| 5 |  | ----TPHQPHHSFTPR--- |
| 6 |  | ---DSHFLHYPHHSN---- |
| 2 |  | ---ESTGHSPHQHN----- |
| 3 |  | ---STPVHTPHHAHY---- |
| 1 |  | ---SGSLQHRPHPRN---- |

4H5

|  | WTp53 | QHMTEVVRRCPHHERCSD |
|---|---|---|
|  | R175H | QHMTEVVRHCPHHERCSD |
| 8 |  | ---VGSPQHWPHHSN---- |
| 9 |  | ---VGSPQHWPHHCN---- |
| 2 |  | ---VGSPQHWPHHSN---- |
| 7 |  | ---VGSPQHWPHHSN---- |
| 1 |  | ---VGSPQHWPHHSK---- |
| 3 |  | ----LEVN-HWGHHYRT-- |
| 5 |  | ---GGSG-HQSGHRP---- |
| 6 |  | ----SLG-HKSHHFIAA-- |
| 10 |  | ---FDLRDYMHMPHH---- |

Consensus: 167QHMTEVVRHCPHHERCSD184

10C8, 7B9, 4H5 epitope

Figure 8A

Anti-R248Q mAbs

3G11

| | |
|---|---|
| WTp53 | GMNRRPILTIITLEDS |
| R248Q | GMNQRPILTIITLEDS |
| 1 | ------------ SSTHYSWSLMDA |
| 2 | ---------- GPSCHYCFTGLP ---- |
| 3 | ------------ GPSCHYCFTGLP ---- |
| 4 | WSVPPGRHIHYS-------------- |
| 5 | WSVPPGRHIHYS-------------- |
| 10 | ------ FSVPSGHYIRAN -------- |
| 8 | ------ FSVRPFHYAQDN -------- |
| 7 | ------ FSVPFDRIQETP ---------- |
| 9 | ------ FSVRPYDPQIEN -------- |
| 6 | ----- HSVWYANGSVKT ------ |

Consensus: 215SVVVPYEPPEVGSDCTTIHYN 235
3G11 epitope

Figure 8B

MEEPQSDPSV EPPLSQETFS DLWKLLPENN VLSPLPSQAM DDLMLSPDDI EQWFTEDPGP DEAPRMPEAA PPVAPAPAAP TPAAPAPAPS WPLSSSVPSQ 100

KTYQGSYGFR LGFLHSGTAK SVTCTYSPAL NKMFCQLAKT CPVQLWVDST PPPGTRVRAM AIYKQSQHMT EVVRRCPHH R175H RCSDSDGLAP PQHLIRVEGN 200

ERVEYLDDRN TFRHSVVVPY EPPEVGSDCT THYNYMCNS SCMGGMNRRP R248Q ILTIITLEDS SGNLLGRNSF EVR R273H CACPGR DRRTEEENLR KKGEPHHELP 300

PGSTKRALPN NTSSSPQPKK KPLDGEYFTL QIRGRERFEM FRELNEALEL KDAQAGKEPG GSRAHSSHLK SKKGQSTSRH KKLMFKTEGP DSD 393

Figure 10

| Cell lines used in study | p53 status |
|---|---|
| A549, MCF-7, HCT116, MRC5, RKO, U2OS | Wild-type |
| AU565 | R175H |
| SKBR3 | R175H |
| HEC-1A | R248Q |
| RD | R248W |
| 786-O | R248W |
| PLC-PRF/15 | R249S |
| KNS-62 | R249S |
| SW480 | R273H |
| A431 | R273H |

Figure 13

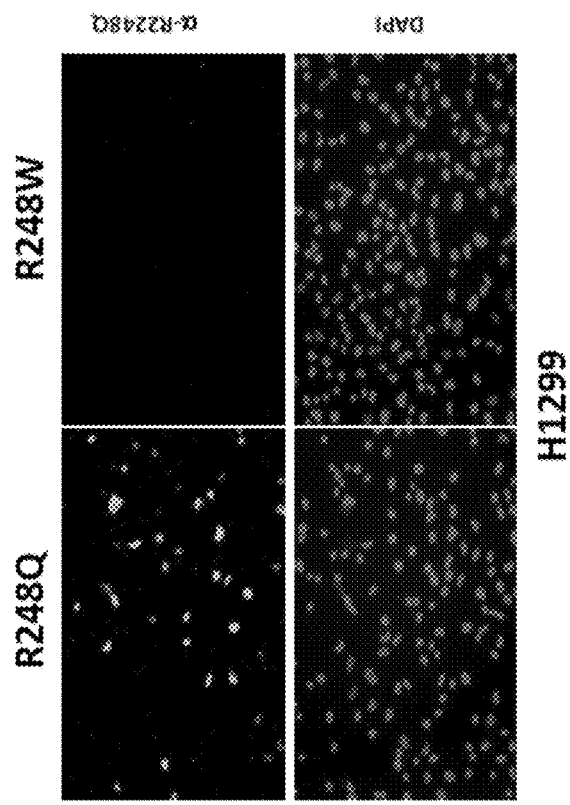

Combined data from analysis of human tumor microarrays by immunohistochemistry

| TMAs * used in study | Total samples = n | α-pan-P53+ (DO7) n (%) | α-R175H+ n (%) |
|---|---|---|---|
| Colon | 99 | 60 (60) | 5 |
| Breast | 102 | 72 (70) | 5 |
| Lung | 169 | 114 (67) | 8 |
| Prostate | 231 | 27 (11) | 0 |
| Renal | 196 | 68 (34) | 3 |

*: TMA: tumor microarray

Figure 21

```
        R175
         ↓
IP53_HUMAN  MTEVVRRCPHHERCSD-SDG-LAPPQHLIRVEGNLRVEYLDDRNTFRHSVVVPYEPPEVG 226
IP53_CERAE  MTEVVRRCPHHERCSD-SDG-LAPPQHLIRVEGNLRVEYSDDRNTFRHSVVVPYEPPEVG 226
IP53_MACMU  MTEVVRRCPHHERCSD-SDG-LAPPQHLIRVEGNLRVEYSDDRNTFRHSVVVPYEPPEVG 226
IP53_MACFU  MTEVVRRCPHHERCSD-SDG-LAPPQHLIRVEGNLRVEYSDDRNTFRHSVVVPYEPPEVG 226
IP53_MACFA  MTEVVRRCPHHERCSD-SDG-LAPPQHLIRVEGNLRVEYSDDRNTFRHSVVVPYEPPEVG 226
IP53_TUPGB  VTEVVRRCPHHERCSD-SDG-LAPPQHLIRVEGNLRVEYSDDRNTFRHSVVVPYEPPEVG 226
IP53_MARMO  MTEVVRRCPHHERCSD-SDG-LAPPQHLIRVEGNLHAEYSDDRNTFRHSVVVPYEPPEVG 226
IP53_RABIT  MTEVVRRCPHHERCSD-SDG-LAPPQHLIRVEGNLRAEYLDDRNTFRHSVVVPYEPPEVG 224
IP53_DELLE  MTEVVRRCPHHERCSD-SDG-LAPPQHLIRVEGNLRAEYLDDRNTFRHSVVVPYEPPEVG 223
IP53_PIG    MTEVVRRCPHHERCSDYSDG-LAPPQHLIRVEGNLRAEYLDDRNTFRHSVVVPYEPPEVG 220
IP53_CANFA  VTEVVRRCPHHERCSDSSDG-LAPPQHLIRVEGNLRAKYLDDRNTFRHSVVVPYEPPEVG 219
IP53_FELCA  MTEVVRRCPHHERCPDSSDG-LAPPQHLIRVEGNLHAKYLDDRNTFRHSVVVPYEPPEVG 214
IP53_CAVPO  MTEVVRRCPHHERCSD-SDG-LAPPQHLIRVEGNLHAEYLDDRTTFRHSVVVPYEPPEVG 219
IP53_SHEEP  MTEVVRRCPHHERCSDYSDG-LAPPQHLIRVEGNLRAEYFDDRNTFRHSVVVPYESPEIE 215
IP53_MESAU  MTEVVRRCPHHERSSE-GDG-LAPPQHLIRVEGNMHAEYLDDKQTFRHSVVVPYEPPEVG 229
IP53_CRIGR  MTEVVRRCPHHERSSE-GDS-LAPPQHLIRVEGNLHAEYLDDKQTFRHSVVVPYEPPEVG 226
IP53_BOVIN  MTEVVRRCPHHERSSDYSDG-LAPPQHLIRVEGNLRAEYLDDRNTFRHSVVVPYESPEID 219
IP53_BOSIN  MTEVVRRCPHHERSSDYSDG-LAPPQHLIRVEGNLRAEYLDDRQTFRHSVVVPYESPEID 219
IP53_RAT    MTEVVRRCPHHERCSD-GDG-LAPPQHLIRVEGNPYAEYLDDRQTFRHSVVVPYEPPEVG 224
IP53_MOUSE  MTEVVRRCPHHERCSD-GDG-LAPPQHLIRVEGNLYPEYLEDRQTFRHSVVVPYEPPEAG 220
IP53_HORSE  MTEVVRRCPHHERCSDSSDG-LAPPQHLIRVEGNLRAEYLDDRNTFRHSVVVPYEPPEVG 177
IP53_EQUAS  MTEVVRRCPHHERCSDSSDG-LAPPQHLIRVEGNLRAEYLDDRNTLRHSVVVPYEPPEVG 102
IP53_CHICK  VAEVVRRCPHHERCPHHERCGGGTDG-LAPAQHLIRVEGNPQARYHDDETTKRHSVVVPYEPPEVG 212
IP53_XENLA  VAEVVRRCPHHERSVEPGED-AAPPSHLMRVEGNLQAYYMEDVNSGRHSVCVPYEGPQVG 201
IP53_ONCMY  VADVVRRCPHHQSTSENNEG-PAPRGHLVRVEGNQRSEYMEDGNTLRHSVLVPYEPPQVG 215
IP53_DANRE  VAEVVRRCPHHERTPDG-DN-LAPAGHLIRVEGNQRANYREDNITLRHSVFVPYEAPQLG 194
IP53_ICTPU  VAEVVRRCPHHERSNDSSDG-PAPPGHLLRVEGNSRAVYQEDGNTQAHSVVVPYEPPQVG 202
IP53_XIPMA  VGEVVKRCPHHQ-SEDLSDN-KS---HLIRVEGSQLAQYFEDPNTRRHSVTVPYERPQLG 189
IP53_XIPHE  VGEVVKRCPHHQ-SEDLSDN-KS---HLIRVEGSQLAQYFEDPNTRRHSVTVPYERPQLG 189
```

Figure 22

```
                          R273
                           ↓
P53_HUMAN   SDCTTIHYNYMCNSSCMGGMNRRPILTIITLEDSSGNLLGRNSFEVRVCACPGRDRRTEE 286
P53_CERAE   SDCTTIHYNYMCNSSCMGGMNRRPILTIITLEDSSGNLLGRNSFEVRVCACPGRDRRTEE 286
P53_MACMU   SDCTTIHYNYMCNSSCMGGMNRRPILTIITLEDSSGNLLGRNSFEVRVCACPGRDRRTEE 286
P53_MACFU   SDCTTIHYNYMCNSSCMGGMNRRPILTIITLEDSSGNLLGRNSFEVRVCACPGRDRRTEE 286
P53_MACFA   SDCTTIHYNYMCNSSCMGGMNRRPILTIITLEDSSGNLLGRNSFEVRVCACPGRDRRTEE 286
P53_TUPGB   SDCTTIHYNYMCNSSCMGGMNRRPILTIITLEDSSGNLLGRNSFEVRICACPGRDRRTEE 286
P53_MARMO   SDCTTIHYNYMCNSSCMGGMNRRPILTIITLEDSSGKLLGRNSFEVRVCACPGRDRRTEE 286
P53_RABIT   SECTTIHYNYMCNSSCMGGMNRRPILTIITLEGSSGNLLGRNSFEVRVCACPGRDRRTEE 284
P53_DELLE   SDCTTIHYNYMCNSSCMGGMNRRPILTIITLEDSSGNLLGRNSFEVRVCACPGRDRRTEE 283
P53_PIG     SDCTTIHYNFMCNSSCMGGMNRRPILTIITLEDASGNLLGRNSFEVRVCACPGRDRRTEE 280
P53_CANFA   SDYTTIHYNYMCNSSCMGGMNRRPILTIITLEDSSGNVLGRNSFEVRVCACPGRDRRTEE 279
P53_FELCA   SDCTTIHYNYMCNSSCMGGMNRRPILTITTLEDSNGKLLGRNSFEVRVCACPGRDRRTEE 274
P53_CAVPO   SDCTTIHYNFMCNSSCMGGMNRRPILTIITLEDSGKLLGRDSFEVRVCACPGRDRRTEE 279
P53_SHEEP   SECTTIHYNFMCNSSCMGGMNRRPILTIITLEDSRGNLLGRSSFEVRICACPGRDRRTEE 284
P53_MESAU   SDCTTIHYNYMCNSSCMGGMNRRPILTIITLEDPSGNLLGRNSFEVRICACPGRDRRTEE 275
P53_CRIGR   SDCTTIHYNYMCNSSCMGGMNRRPILTIITLEDPSGNLLGRNSFEVRICACPGRDRRTEE 289
P53_BOVIN   SECTTIHYNFMCNSSCMGGMNRRPILTIITLEDSCGNLLGRNSFEVRVCACPGRDRRTEE 286
P53_BOSIN   SECTTIHYNFMCNSSCMGGMNRRPILTIITLEDSCGNLLGRDSFEVRVCACPGRDRRTEE 279
P53_RAT     SDYTTIHYKYMCNSSCMGGMNRRPILTIITLEDSSGNLLGRDSFEVRVCACPGRDRRTEE 279
P53_MOUSE   SEYTTIHYKYMCNSSCMGGMNRRPILTIITLEDSSGNLLGRDSFEVRVCACPGRDRRTEE 284
P53_HORSE   SDCTTIHYNFMCNSSCMGGMNRRPILTIITLEDSSGNLLGRNSFEVRVCACPGRDRRTEE 280
P53_EQUAS   SDCTTIHYNFMCNSSCMGGMNRRPILTIITLEDSSGNLLGRNSFEVRVCACPGRDRRTEE 237
P53_CHICK   SDCTTVLYNFMCNSSCMGGMNRRPILTILTLEGPGGQLLGRRCFEVRVCACPGRDRKIEE 162
P53_XENLA   TECTTVLYNYMCNSSCMGGMNRRPILTITTLETPQGLLLGRRCFEVRVCACPGRDRRTEE 272
P53_ONCMY   SECTTVLYNFMCNSSCMGGMNRRPILTITTLETQEGQLLGRRSFEVRVCACPGRDRRTEE 261
P53_DANRE   AEWTTVLLANYMCNSSCMGGMNRRPILTITTLETQEGQLLGRRSFEVRVCACPGRDKTEE 275
P53_ICTPU   SQSTTVLYNYMCNSSCMGGMNRRPILTITTLETQDGHLLGRRTFEVRCFEVRVCACPGRDKTEE 254
P53_XIPMA   SEMTTILLSFMCNSSCMGGMNRRPILTILTLETTEGEVLGRRCFEVRCACPGRDKTEE 262
P53_XIPHE   SEMTTILLSFMCNSSCMGGMNRRPILTILTLETTEGEVLGRRCFEVRCACPGRDKTEE 249
```

Figure 22 (cont.)

```
                     R248
                      ↓
!P53_HUMAN  SDCTTIHYNYMCNSSCMGGMNRRPILTIITLEDSSGNLLGRNSFEVRVCACPGRDRRTEE  286
!P53_CERAE  SDCTTIHYNYMCNSSCMGGMNRRPILTIITLEDSSGNLLGRNSFEVRVCACPGRDRRTEE  286
!P53_MACMU  SDCTTTHYNYMCNSSCMGGMNRRPILTIITLEDSSGNLLGRNSFEVRVCACPGRDRRTEE  286
!P53_MACFU  SDCTTIHYNYMCNSSCMGGMNRRPILTIITLEDSSGNLLGRNSFEVRVCACPGRDRRTEE  286
!P53_MACFA  SDCTTIHYNYMCNSSCMGGMNRRPILTIITLEDSSGNLLGRNSFEVRVCACPGRDRRTEE  286
!P53_TUPGB  SDCTTIHYNYMCNSSCMGGMNRRPILTIITLEDSSGKLLGRNSFEVRVCACPGRDRRTEE  286
!P53_MARMO  SDCTTIHYNYMCNSSCMGGMNRRPILTIITLEGSSGNLLGRNSFEVRVCACPGRDRRTEE  284
!P53_RABIT  SECTTIHYNYMCNSSCMGGMNRRPILTIITLEDSSGNLLGRNSFEVRVCACPGRDRRTEE  283
!P53_DELLE  SDCTTIHYNYMFMCNSSCMGGMNRRPILTIITLEDSNGNLLGRNSFEVRVCACPGRDRRTEE  280
!P53_PIG    SDCTTIHYNFMCNSSCMGGMNRRPILTIITLEDASGNLLGRNSFEVRVCACPGRDRRTEE  279
!P53_CANFA  SDYTTIHYNYMCNSSCMGGMNRRPILTIITLEDSNGKLLGRNVLGRNSFEVRVCACPGRDRRTEE  274
!P53_FELCA  SDCTTIHYNFMCNSSCMGGMNRRPILTIITLEDSSGKLLGRDSFEVRVCACPGRDRRTEE  279
!P53_CAVPO  SDCTTIHYNFMCNSSCMGGMNRRPILTIITLEDSRGNLLGRSSFEVRVCACPGRDRRTEE  284
!P53_SHEEP  SECTTIHYNFMCNSSCMGGMNRRPILTIITLEDPSGNLLGRNSFEVRICACPGRDRRTEE  275
!P53_MESAU  SDCTTIHYNYMCNSSCMGGMNRRPILTIITLEDPSGNLLGRNSFEVRICACPGRDRRTEE  289
!P53_CRIGR  SDCTTIHYNYMCNSSCMGGMNRRPILTIITLEDSCGNLLGRNSFEVRVCACPGRDRRTEE  286
!P53_BOVIN  SECTTIHYNFMCNSSCMGGMNRRPILTIITLEDSCGNLLGRNSFEVRVCACPGRDRRTEE  279
!P53_BOSIN  SECTTIHYNFMCNSSCMGGMNRRPILTIITLEDSSGNLLGRDSFEVRVCACPGRDRRTEE  279
!P53_RAT    SDYTTIHYKYMCNSSCMGGMNRRPILTIITLEDSSGNLLGRDSFEVRVCACPGRDRRTEE  284
!P53_MOUSE  SEYTTIHYKYMCNSSCMGGMNRRPILTIITLEDSSGNLLGRNSFEVRVCACPGRDRRTEE  280
!P53_HORSE  SDCTTIHYNFMCNSSCMGGMNRRPILTIITLEDSSGNLLGRNSFEVRVCACPGRDRRTEE  237
!P53_EQUAS  SDCTTIHYNFMCNSSCMGGMNRRPILTIITLEDSSGNLLGRNSFEVRVCACPGRDRRTEE  162
!P53_CHICK  SDCTTVLYNFMCNSSCMGGMNRRPILTILTLEGPGQLLGRRCFEVRVCACPGRDRKIEE  272
!P53_XENLA  TECTTVLYNYMCNSSCMGGMNRRPILTIITLETPQGLLLGRRCFEVRVCACPGRDRRTEE  261
!P53_ONCMY  SECTTVLYNFMCNSSCMGGMNRRPILTIITLETQEGQLLGRRSFEVRVCACPGRDRKTEE  275
!P53_DANRE  AEWTTVLLNYMCNSSCMGGMNRRPILTIITLETQEGQLLGRRSFEVRVCACPGRDRKTEE  254
!P53_ICTPU  SQSTTVLYNYMCNSSCMGGMNRRPILTIITLEQDGHLLGRRTFEVRVCACPGRDRKTEE  262
!P53_XIPMA  SEMTTILLSFMCNSSCMGGMNRRPILTILTLETTEGEVLGRRCFEVRVCACPGRDRKTEE  249
!P53_XIPHE  SEMTTILLSFMCNSSCMGGMNRRPILTILTLETTEGEVLGRRCFEVRVCACPGRDRKTEE  249
```

Figure 22 (cont.)

Anti-R175H clone 4H5

DIVLTQSTSSLSVSAGERVTLSCKSS<u>QSLLNSGNQKSY</u>LAWYQQKPGQPPKLLIY<u>GAS</u>TRE
SGVPDRFTGSGSETDFTLTISSVQPEDLAVYYC<u>QNDHSYPLT</u>FGAGTKLELK (SEQ ID
NO:18)

|  |  |  |
|---|---|---|
| LC-CDR1: | QSLLNSGNQKSY | (SEQ ID NO:19) |
| LC-CDR2: | GAS | (SEQ ID NO:20) |
| LC-CDR3: | QNDHSYPLT | (SEQ ID NO:21) |

Anti-R175H clone 7B9

DIVMTQSPSSLSVSGGEKVTMSCKSS<u>QSLLNSGNQKSN</u>LAWYQQKPGQPPKLLIY<u>GAS</u>TR
ESGVPDRFAGSGSGTDFTLTISSVQAEDLAVYYC<u>QNDHSYPLT</u>FGGGTKLELK (SEQ ID
NO:22)

|  |  |  |
|---|---|---|
| LC-CDR1: | QSLLNSGNQKSN | (SEQ ID NO:23) |
| LC-CDR2: | GAS | (SEQ ID NO:20) |
| LC-CDR3: | QNDHSYPLT | (SEQ ID NO:21) |

Anti-R175H clone 10C8

DIVMTQSPSSLSVSGGEKVTMSCKSS<u>QSLLNSGNQKSN</u>LAWYQQKPGQPPKLLIY<u>GAS</u>TR
ESGVPDRFAGSGSGTDFTLTISSVQAEDLAVYYC<u>QNDHSYPLT</u>FGGGTKLELK (SEQ ID
NO:22)

|  |  |  |
|---|---|---|
| LC-CDR1: | QSLLNSGNQKSN | (SEQ ID NO:23) |
| LC-CDR2: | GAS | (SEQ ID NO:20) |
| LC-CDR3: | QNDHSYPLT | (SEQ ID NO:21) |

Figure 24

Anti-R175H clone 4H5

EVQLQQSGPELVKPGASVKISCKTS<u>GFTFTEYT</u>MHWMKQSHGRSLEWIGR<u>IDPNNGVT</u>VY
NQKFKVKATLTVDRSSSTAYLELRSLTSEDSAVYYC<u>ARWGGDYV</u>TGGGTTLTVSS (SEQ ID NO:24)

HC-CDR1:    GFTFTEYT    (SEQ ID NO:25)
    HC-CDR2:    IDPNNGVT    (SEQ ID NO:26)
    HC-CDR3:    ARWGGDYV    (SEQ ID NO:27)

Anti-R175H clone 7B9

EVQLQQSGPELVKPGASVKISCKTS<u>GYTFTEYT</u>MHWMKQSHGKSLEWIGR<u>INPYSGGT</u>VY
NQKFKGKATLTVDKSSSTAYMELRSLTSDDSAVYYC<u>ARWGGDYV</u>TGGGTTLTVSS (SEQ ID NO:28)

HC-CDR1:    GYTFTEYT    (SEQ ID NO:29)
    HC-CDR2:    INPYSGGT    (SEQ ID NO:30)
    HC-CDR3:    ARWGGDYV    (SEQ ID NO:27)

Anti-R175H clone 10C8

EVQLQQSGPELVKPGASVKISCKTS<u>GYTFTEYT</u>MHWMKQSHGKSLEWIGR<u>INPYSGGT</u>VY
NQKFKGKATLTVDKSSSTAYMELRSLTSDDSAVYYC<u>ARWGGDYV</u>TGGGTTLTVSS (SEQ ID NO:28)

HC-CDR1:    GYTFTEYT    (SEQ ID NO:29)
    HC-CDR2:    INPYSGGT    (SEQ ID NO:30)
    HC-CDR3:    ARWGGDYV    (SEQ ID NO:27)

Figure 25

| Anti R175H Clone | CDR 1 | CDR 2 | CDR 3 |
|---|---|---|---|
| | | Light Chain | |
| 4H5 | QSLLNSGNQKSY (SEQ ID NO:19) | GAS (SEQ ID NO:20) | QNDHSYPLT (SEQ ID NO:21) |
| 7B9 | QSLLNSGNQKSN (SEQ ID NO:23) | GAS (SEQ ID NO:20) | QNDHSYPLT (SEQ ID NO:21) |
| 10C8 | QSLLNSGNQKSN (SEQ ID NO:23) | GAS (SEQ ID NO:20) | QNDHSYPLT (SEQ ID NO:21) |
| Consensus | QSLLNSGNQKSX$_1$ (SEQ ID NO:31)<br><br>where X$_1$ = Y or N | GAS (SEQ ID NO:20) | QNDHSYPLT (SEQ ID NO:21) |
| | | Heavy Chain | |
| 4H5 | GFTFTEYT (SEQ ID NO:25) | IDPNNGVT (SEQ ID NO:26) | ARWGGDYV (SEQ ID NO:27) |
| 7B9 | GYTFTEYT (SEQ ID NO:29) | INPYSGGT (SEQ ID NO:30) | ARWGGDYV (SEQ ID NO:27) |
| 10C8 | GYTFTEYT (SEQ ID NO:29) | INPYSGGT (SEQ ID NO:30) | ARWGGDYV (SEQ ID NO:27) |
| Consensus | GX$_2$TFTEYT (SEQ ID NO:32)<br><br>where X$_2$ = F or Y | IX$_3$PX$_4$X$_5$GX$_6$T (SEQ ID NO:33)<br><br>where X$_3$ = D or N; X$_4$ = N or Y; X$_5$ = N or S; and X$_6$ = V or G | ARWGGDYV (SEQ ID NO:27) |

Figure 26

Light chain variable domains

Anti-R175H clone 4H5

>4H5_aa_L
DIVLTQSTSSLSVSAGERVTLSCKSS<u>QSLLNSGNQKSY</u>LAWYQQKPGQPPKLLIY<u>GAS</u>TRE
SGVPDRFTGSGSETDFTLTISSVQPEDLAVYYC<u>QNDHSYPLT</u>FGAGTKLELK [SEQ ID
NO:18]

>4H5_ntd_L
GATATTGTGCTCACCCAATCTACATCCTCCCTGAGTGTGTCAGCTGGAGAGAGGGTCA
CTTTGAGCTGCAAGTCCAGTCAGAGTCTGTTAAACAGTGGAAATCAAAAGAGTTACTTG
GCCTGGTACCAGCAGAAACCAGGGCAGCCTCCTAAACTGTTGATCTACGGGGCATCCA
CTAGGGAATCTGGGGTCCCTGATCGCTTCACAGGCAGTGGATCTGAAACCGATTTCAC
TCTTACCATCAGCAGTGTGCAGCCTGAAGACCTGGCAGTTTATTATTGTCAGAATGATC
ATAGTTATCCGCTCACGTTCGGTGCTGGGACCAAGCTGGAGCTGAAA [SEQ ID NO: 34]

Anti-R175H clone 7B9

>7B9_aa_L
DIVMTQSPSSLSVSGGEKVTMSCKSSQSLLNSGNQKSNLAWYQQKPGQPPKLLIYGASTR
ESGVPDRFAGSGSGTDFTLTISSVQAEDLAVYYCQNDHSYPLTFGGGTKLELK [SEQ ID
NO:22]

>7B9_ntd_L
GATATTGTGATGACCCAGTCTCCATCCTCCCTGAGTGTGTCAGGAGGAGAGAAGGTCA
CTATGAGCTGCAAGTCCAGTCAGAGTCTGTTAAACAGTGGAAATCAAAAGAGCAACTTG
GCCTGGTACCAGCAGAAACCAGGGCAGCCTCCTAAATTGTTGATCTATGGGCATCCA
CTAGGGAATCTGGGGTCCCTGATCGCTTCGCAGGCAGTGGATCTGGAACCGATTTCAC
TCTTACCATCAGCAGTGTGCAGGCTGAAGACCTGGCAGTTTATTACTGTCAAAATGATC
ATAGTTATCCGCTCACGTTCGGTGGTGGGACCAAGCTGGAGCTGAAA [SEQ ID NO: 35]

Anti-R175H clone 10C8

>10C8_aa_L
DIVMTQSPSSLSVSGGEKVTMSCKSS<u>QSLLNSGNQKSN</u>LAWYQQKPGQPPKLLIY<u>GAS</u>TR
ESGVPDRFAGSGSGTDFTLTISSVQAEDLAVYYC<u>QNDHSYPLT</u>FGGGTKLELK [SEQ ID
NO: 22]

>10C8_ntd_L
GATATTGTGATGACCCAGTCTCCATCCTCCCTGAGTGTGTCAGGAGGAGAGAAGGTCA
CTATGAGCTGCAAGTCCAGTCAGAGTCTGTTAAACAGTGGAAATCAAAAGAGCAACTTG
GCCTGGTACCAGCAGAAACCAGGGCAGCCTCCTAAATTGTTGATCTATGGGCATCCA
CTAGGGAATCTGGGGTCCCTGATCGCTTCGCAGGCAGTGGATCTGGAACCGATTTCAC
TCTTACCATCAGCAGTGTGCAGGCTGAAGACCTGGCAGTTTATTACTGTCAAAATGATC
ATAGTTATCCGCTCACGTTCGGTGGTGGGACCAAGCTGGAGCTGAAA [SEQ ID NO: 36]

Figure 27

Heavy chain variable domains

Anti-R175H clone 4H5

>4H5_aa_H
EVQLQQSGPELVKPGASVKISCKTS<u>GFTFTEYT</u>MHWMKQSHGRSLEWIGR<u>IDPNNGVT</u>VY
NQKFKVKATLTVDRSSSTAYLELRSLTSEDSAVYYC<u>ARWGGDYV</u>TGGGTTLTVSS [SEQ ID
NO: 24]

>4H5_ntd_H
GAGGTTCAGCTGCAGCAGTCTGGACCTGAACTGGTGAAGCCTGGGGCTTCAGTGAAGA
TATCTTGCAAGACTTCCGGATTCACATTCACTGAATACACCATGCACTGGATGAAACAG
AGCCATGGAAGGAGCCTTGAGTGGATCGGACGTATTGATCCTAACAATGGTGTTACTGT
TTATAACCAGAAGTTCAAGGTCAAGGCCACATTGACTGTGGACAGGTCCTCCAGCACA
GCCTATCTGGAGCTCCGCAGTCTGACGTCTGAGGACTCTGCAGTCTATTACTGTGCAA
GATGGGGTGGTGACTACGTCACGGGGGGAGGCACCACTCTCACAGTCTCCTCA [SEQ
ID NO: 37]

Anti-R175H clone 7B9

>7B9_aa_H
EVQLQQSGPELVKPGASVKISCKTS<u>GYTFTEYT</u>MHWMKQSHGKSLEWIGR<u>INPYSGGT</u>VY
NQKFKGKATLTVDKSSSTAYMELRSLTSDDSAVYYC<u>ARWGGDYV</u>TGGGTTLTVSS [SEQ
ID NO: 28]

>7B9_ntd_H
GAGGTCCAGCTGCAGCAGTCTGGACCTGAGCTGGTGAAGCCTGGGGCTTCAGTGAAG
ATATCCTGCAAGACTTCTGGCTACACTTTCACTGAATACACCATGCACTGGATGAAGCA
GAGCCATGGAAAGAGCCTTGAGTGGATTGGACGTATTAATCCTTATAGTGGTGGTACTG
TCTACAACCAGAAGTTCAAGGGCAAGGCCACATTGACTGTGGACAAGTCCTCCAGCAC
AGCCTATATGGAGCTCCGCAGCCTGACATCTGATGATTCTGCAGTCTATTACTGTGCAA
GATGGGGTGGTGACTACGTCACGGGGGGAGGCACCACTCTCACAGTCTCCTCA [SEQ
ID NO: 38]

Anti-R175H clone 10C8

>10C8_aa_H
EVQLQQSGPELVKPGASVKISCKTS<u>GYTFTEYT</u>MHWMKQSHGKSLEWIGR<u>INPYSGGT</u>VY
NQKFKGKATLTVDKSSSTAYMELRSLTSDDSAVYYC<u>ARWGGDYV</u>TGGGTTLTVSS [SEQ
ID NO: 28]

>10C8_ntd_H
GAGGTGCAGCTTCAGCAGTCGGGACCTGAGCTGGTGAAGCCTGGGGCTTCAGTGAAG
ATATCCTGCAAGACTTCTGGCTACACTTTCACTGAATACACCATGCACTGGATGAAGCA
GAGCCATGGAAAGAGCCTTGAGTGGATTGGACGTATTAATCCTTATAGTGGTGGTACTG
TCTACAACCAGAAGTTCAAGGGCAAGGCCACATTGACTGTGGACAAGTCCTCCAGCAC
AGCCTATATGGAGCTCCGCAGCCTGACATCTGATGATTCTGCAGTCTATTACTGTGCAA
GATGGGGTGGTGACTACGTCACGGGGGGAGGCACCACTCTCACAGTCTCCTCA [SEQ
ID NO: 39]

Figure 27 (cont.)

Anti-R248Q clone 3G11

DIVLTQTPLTLSVTIGQPASISCKSN<u>QSLLYSDGKTY</u>LNWLLQRPGQSPKRLIY<u>LVS</u>KLDSGV
PDRFTGSGSGTDFTLKISRVEAEDLGLYYC<u>WQGTHFPLT</u>FGAGTKLELK (SEQ ID NO:40)

LC-CDR1:    QSLLYSDGKTY    (SEQ ID NO:41)
      LC-CDR2:    LVS    (SEQ ID NO:42)
      LC-CDR3:    WQGTHFPLT    (SEQ ID NO:43)

Anti-R248Q clone 4H2

DIVITQSPLTLSVTIGQPASISCKSD<u>QSLLYSDGKTY</u>LNWLLQRPGQSPKRLIY<u>LVS</u>ELDSGV
PDRFTGSGSGTDFTLKISRVEAEDLGLYYCWQGTHFPLTFGAGTKLELK (SEQ ID NO:44)

LC-CDR1:    QSLLYSDGKTY    (SEQ ID NO:41)
      LC-CDR2:    LVS    (SEQ ID NO:42)
      LC-CDR3:    WQGTHFPLT    (SEQ ID NO:43)

Figure 28

Anti-R248Q clone 3G11

DVQLQQSGPELVKPGASVKMSCKAS<u>GYTFTDYY</u>VKWVKQSPGQSLEWIGD<u>IHPKNGGT</u>N
YNQKFKGKAALTVDKSSSTAYMQLNSLTSEDSAVYFC<u>AKMGGYDDY</u>WGQGTTLTVSS
(SEQ ID NO:45)

HC-CDR1:    GYTFTDYY   (SEQ ID NO:46)
    HC-CDR2:    IHPKNGGT   (SEQ ID NO:47)
    HC-CDR3:    AKMGGYDDY(SEQ ID NO:48)

Anti-R248Q clone 4H2

QVQLKQSGPELVKPGASVKMSCKAS<u>GYTFTDYY</u>LKWVRQSHGKSLEWIGD<u>IDPKNGGT</u>NY
NQKFKGKATLTVDKSSSTAYMQLNSLTSEDSAVYYC<u>AKQGGFDDY</u>WGQGTTLTVSS (SEQ
ID NO:49)

HC-CDR1:    GYTFTDYY   (SEQ ID NO:46)
    HC-CDR2:    IDPKNGGT   (SEQ ID NO:50)
    HC-CDR3:    AKQGGFDDY(SEQ ID NO:51)

Figure 29

| Anti-R248Q Clone | CDR 1 | CDR 2 | CDR 3 |
|---|---|---|---|
| Light Chain | | | |
| 3G11 | QSLLYSDGKTY (SEQ ID NO:41) | LVS (SEQ ID NO:42) | WQGTHFPLT (SEQ ID NO:43) |
| 4H2 | QSLLYSDGKTY (SEQ ID NO:41) | LVS (SEQ ID NO:42) | WQGTHFPLT (SEQ ID NO:43) |
| Consensus | QSLLYSDGKTY (SEQ ID NO:41) | LVS (SEQ ID NO:42) | WQGTHFPLT (SEQ ID NO:43) |
| Heavy Chain | | | |
| 3G11 | GYTFTDYY (SEQ ID NO:46) | IHPKNGGT (SEQ ID NO:47) | AKMGGYDDY (SEQ ID NO:48) |
| 4H2 | GYTFTDYY (SEQ ID NO:46) | IDPKNGGT (SEQ ID NO:50) | AKQGGFDDY (SEQ ID NO:51) |
| Consensus | GYTFTDYY (SEQ ID NO:46) | IX$_7$PKNGGT (SEQ ID NO:52) where X$_7$ = H or D | AKX$_8$GGX$_9$DDY (SEQ ID NO:53) where X$_8$ = M or Q; and X$_9$ = Y or F |

Figure 30

Light chain variable domains

Anti-R248Q clone 3G11

>3G11_aa_L
DIVLTQTPLTLSVTIGQPASISCKSNQSLLYSDGKTYLNWLLQRPGQSPKRLIYLVSKLDSGV
PDRFTGSGSGTDFTLKISRVEAEDLGLYYCWQGTHFPLTFGAGTKLELK [SEQ ID NO:40]

>3G11_ntd_L
GATATTGTGCTGACACAGACTCCACTCACTTTGTCGGTTACCATTGGACAACCAGCCTC
CATCTCTTGCAAGTCAAATCAGAGCCTCTTATATAGTGATGGAAAGACATATTTGAATTG
GTTATTACAGAGGCCAGGCCAGTCTCCAAAGCGCCTAATCTATCTGGTGTCTAAACTGG
ACTCTGGAGTCCCTGACAGGTTCACTGGCAGTGGATCAGGGACAGATTTCACACTGAA
AATCAGCAGAGTGGAGGCTGAGGATTTGGGACTTTATTATTGCTGGCAAGGTACACATT
TTCCTCTCACGTTCGGTGCTGGGACCAAGCTGGAGCTGAAA [SEQ ID NO: 54]

Anti-R248Q clone 4H2

>4H2_aa_L
DIVITQSPLTLSVTIGQPASISCKSDQSLLYSDGKTYLNWLLQRPGQSPKRLIYLVSELDSGV
PDRFTGSGSGTDFTLKISRVEAEDLGLYYCWQGTHFPLTFGAGTKLELK [SEQ ID NO:44]

>4H2_ntd_L
GACATTGTGATCACACAGTCTCCACTCACTTTGTCGGTTACCATTGGACAACCAGCCTC
CATCTCTTGCAAGTCAGATCAGAGCCTCTTATATAGTGATGGAAAGACATATTTGAATTG
GCTATTACAGAGGCCAGGCCAGTCTCCAAAGCGCCTAATCTATCTGGTGTCTGAACTG
GACTCTGGAGTCCCTGACAGGTTCACTGGCAGTGGATCAGGGACAGATTTCACACTGA
AAATCAGCAGAGTGGAGGCTGAGGATTTGGGACTTTATTATTGCTGGCAAGGTACACAT
TTTCCTCTCACGTTCGGTGCTGGGACCAAGCTGGAGCTGAAA [SEQ ID NO: 55]

Figure 31

Heavy chain variable domains

Anti-R248Q clone 3G11

>3G11_aa_H
DVQLQQSGPELVKPGASVKMSCKAS<u>GYTFTDYY</u>VKWVKQSPGQSLEWIGD<u>IHPKNGGTN</u>YNQKFKGKAALTVDKSSSTAYMQLNSLTSEDSAVYFC<u>AKMGGYDDY</u>WGQGTTLTVSS
[SEQ ID NO:45]

>3G11_ntd_H
GATGTGCAGCTTCAGCAGTCAGGACCTGAGCTGGTGAAGCCTGGGGCTTCAGTGAAGA
TGTCCTGTAAGGCTTCTGGATACACATTCACTGACTACTATGTGAAGTGGGTGAAGCAG
AGTCCTGGACAGAGCCTTGAGTGGATTGGAGATATTCATCCTAAGAACGGTGGTACTAA
CTACAACCAGAAGTTCAAGGGCAAGGCCGCATTGACTGTGGACAAATCCTCCAGCACA
GCCTACATGCAGCTCAACAGCCTGACATCTGAGGACTCTGCAGTCTATTTCTGTGCAAA
AATGGGAGGCTACGACGACTACTGGGGCCAAGGCACCACTCTCACAGTCTCCTCA
[SEQ ID NO: 56]

Anti-R248Q clone 4H2

>4H2_aa_H
QVQLKQSGPELVKPGASVKMSCKAS<u>GYTFTDYY</u>LKWVRQSHGKSLEWIGD<u>IDPKNGGTNY</u>NQKFKGKATLTVDKSSSTAYMQLNSLTSEDSAVYYC<u>AKQGGFDDY</u>WGQGTTLTVSS [SEQ ID NO:49]

>4H2_ntd_H
CAGGTGCAGCTGAAGCAGTCAGGACCTGAGCTGGTGAAGCCTGGGGCTTCAGTGAAG
ATGTCCTGTAAGGCTTCTGGATACACATTCACTGACTACTATCTGAAGTGGGTGAGGCA
GAGTCATGGAAAGAGCCTTGAGTGGATTGGAGATATAGATCCCAAGAATGGTGGTACT
AATTACAACCAGAAGTTTAAGGGCAAGGCCACATTGACTGTGGACAAATCCTCCAGCAC
AGCCTACATGCAGCTCAACAGCCTGACATCTGAGGACTCTGCAGTCTATTACTGTGCAA
AACAGGGGGGGTTCGACGACTACTGGGGCCAAGGCACCACTCTCACAGTCTCCTCA
[SEQ ID NO: 57]

Figure 31 (cont.)

Anti-R273H clone 13E4

DIVMTQSPLSLPVNLGDQVSLSCRSSQSIVHNNGDTYLEWYLQKPGQSPKLLIYKVSNRFS
GVPDRFSGSGSGTDFTLKISRVEAEDLGIYYCFQGSHLPLTFGSGTKLELK (SEQ ID NO:58)

| | | |
|---|---|---|
| LC-CDR1: | QSIVHNNGDTY | (SEQ ID NO:59) |
| LC-CDR2: | KVS | (SEQ ID NO:60) |
| LC-CDR3: | FQGSHLPLT | (SEQ ID NO:61) |

Figure 32

Anti-R273H clone 13E4

EVQLLETGGDLVTPGGSLKLSCAASGFSFSDYYMYWVRQTPEKRLEWVATISVGGTYTFY
SDNVKGRFVISRDNARKNLHLEMNSLKSEDAAMYYCVRDGNDGKFLGYWGQGTFVTVTV
S (SEQ ID NO:62)

| | | |
|---|---|---|
| HC-CDR1: | GFSFSDYY | (SEQ ID NO:63) |
| HC-CDR2: | ISVGGTYT | (SEQ ID NO:64) |
| HC-CDR3: | VRDGNDGKFLG | (SEQ ID NO:65) |

Figure 33

Anti-R273H clone 13E4

Light chain variable domain

>13E4_aa_L
DIVMTQSPLSLPVNLGDQVSLSCRSSQSIVHNNGDTYLEWYLQKPGQSPKLLIYKVSNRFS
GVPDRFSGSGSGTDFTLKISRVEAEDLGIYYCFQGSHLPLTFGSGTKLELK [SEQ ID NO:58]

>13E4_ntd_L
GATATTGTGATGACACAATCTCCACTCTCCCTGCCTGTCAATCTTGGAGATCAAGTCTC
CCTCTCTTGCAGATCTAGTCAGAGCATTGTACATAATAATGGAGACACCTATTTAGAATG
GTACCTACAGAAACCAGGCCAGTCTCCAAAGCTCCTGATCTACAAAGTTTCCAACCGAT
TTTCTGGGGTCCCAGACAGGTTCAGTGGCAGTGGATCAGGGACAGATTTCACACTCAA
GATCAGCAGAGTGGAGGCTGAGGATCTGGGAATTTATTACTGCTTTCAAGGTTCACATC
TTCCGCTCACGTTCGGTTCTGGGACCAAGCTGGAGCTGAAA [SEQ ID NO: 66]

Heavy chain variable domain

>13E4_aa_H
EVQLLETGGDLVTPGGSLKLSCAASGFSFSDYYMYWVRQTPEKRLEWVATISVGGTYTFY
SDNVKGRFVISRDNARKNLHLEMNSLKSEDAAMYYCVRDGNDGKFLGYWGQGTFVTVTV
S [SEQ ID NO:62]

>13E4_ntd_H
GAAGTGCAGCTGTTGGAGACTGGGGGAGACTTAGTGACGCCTGGAGGGTCCCTGAAA
CTCTCCTGTGCAGCCTCTGGATTCAGCTTCAGTGACTATTATATGTATTGGGTTCGCCA
GACTCCGGAAAAGAGGCTGGAGTGGGTCGCAACTATTAGTGTTGGTGGTACATACACC
TTCTATTCAGACAATGTGAAGGGGAGATTCGTCATCTCCAGAGACAATGCCAGGAAAAA
TCTGCATCTGGAAATGAACAGTCTGAAGTCTGAGGACGCAGCCATGTATTACTGTGTAA
GAGATGGCAACGATGGAAAATTTCTTGGGTACTGGGGCCAGGGGACTTTCGTCACTGT
CACT [SEQ ID NO: 67]

Figure 34

Clone: 4H5

Clone: 7B9

Clone: 10C8

R175H
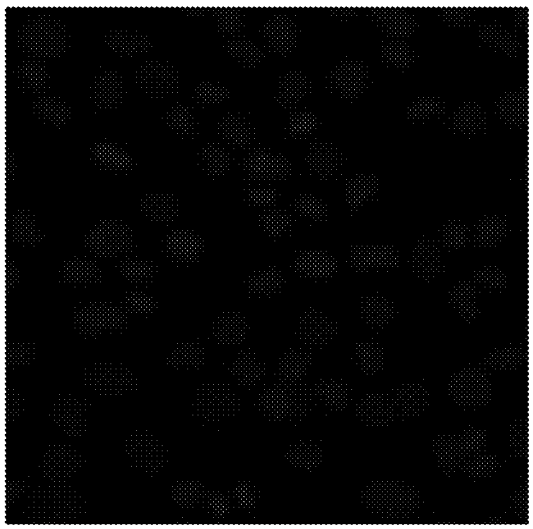
Normal mouse serum on R175H positive cells
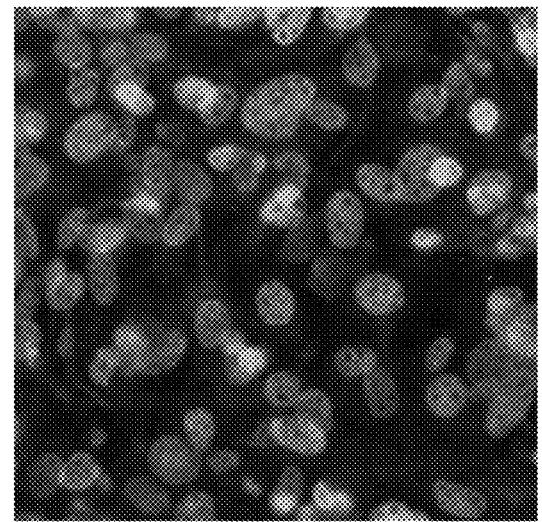
R175H Mouse serum on R175H positive cells
Figure 47A
R248Q
Normal mouse serum on R248Q positive cells
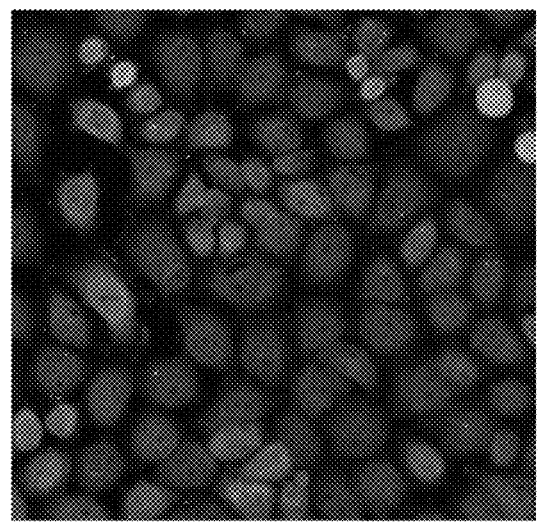
R248Q Mouse serum on R248Q positive cells
Figure 47B

R273H
 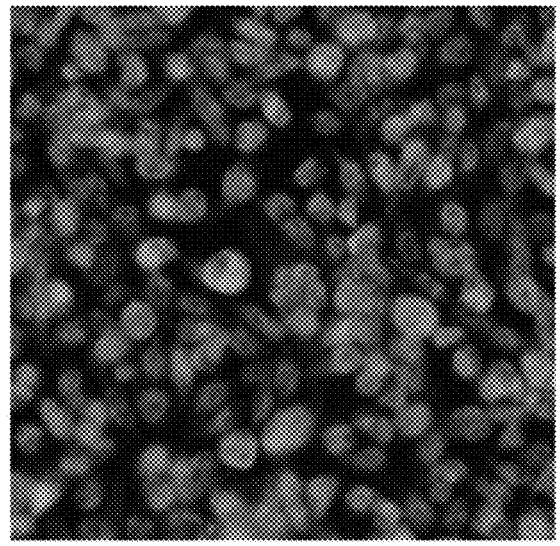
Normal mouse serum on R273H positive cells    R273H Mouse serum on R273H positive cells
Figure 47C

Mouse-human chimeric anti-R175H clone 4H5
DIVLTQSTSSLSVSAGERVTLSCKSS<u>QSLLNSGNQKSY</u>LAWYQQKPGQPPKLLIY<u>GAS</u>TRE
SGVPDRFTGSGSETDFTLTISSVQPEDLAVYYC<u>QNDHSYPLT</u>FGAGTKLELK (SEQ ID
NO:237)

LC-CDR1:    QSLLNSGNQKSY    (SEQ ID NO:19)
        LC-CDR2:    GAS    (SEQ ID NO:20)
        LC-CDR3:    QNDHSYPLT    (SEQ ID NO:21)

Mouse-human chimeric anti-R175H clone 7B9
DIVMTQSPSSLSVSGGEKVTMSCKSS<u>QSLLNSGNQKSN</u>LAWYQQKPGQPPKLLIY<u>GAS</u>TR
ESGVPDRFAGSGSGTDFTLTISSVQAEDLAVYYC<u>QNDHSYPLT</u>FGGGTKLELK (SEQ ID
NO:238)

LC-CDR1:    QSLLNSGNQKSN    (SEQ ID NO:23)
        LC-CDR2:    GAS    (SEQ ID NO:20)
        LC-CDR3:    QNDHSYPLT    (SEQ ID NO:21)

Mouse-human chimeric anti-R175H clone 10C8
DIVMTQSPSSLSVSGGEKVTMSCKSS<u>QSLLNSGNQKSN</u>LAWYQQKPGQPPKLLIY<u>GAS</u>TR
ESGVPDRFAGSGSGTDFTLTISSVQAEDLAVYYC<u>QNDHSYPLT</u>FGGGTKLELK (SEQ ID
NO:238)

LC-CDR1:    QSLLNSGNQKSN    (SEQ ID NO:23)
        LC-CDR2:    GAS    (SEQ ID NO:20)
        LC-CDR3:    QNDHSYPLT    (SEQ ID NO:21)

Figure 49

Mouse-human chimeric anti-R175H clone 4H5

EVQLQQSGPELVKPGASVKISCKTS<u>GFTFTEYT</u>MHWMKQSHGRSLEWIGR<u>IDPNNGVT</u>VY
NQKFKVKATLTVDRSSSTAYLELRSLTSEDSAVYYC<u>ARWGGDYV</u>TGGGTTLTVSS (SEQ ID
NO:239)

HC-CDR1: GFTFTEYT (SEQ ID NO:25)
   HC-CDR2: IDPNNGVT (SEQ ID NO:26)
   HC-CDR3: ARWGGDYV (SEQ ID NO:27)

Mouse-human chimeric anti-R175H clone 7B9

EVQLQQSGPELVKPGASVKISCKTS<u>GYTFTEYT</u>MHWMKQSHGKSLEWIGR<u>INPYSGGT</u>VY
NQKFKGKATLTVDKSSSTAYMELRSLTSDDSAVYYC<u>ARWGGDYV</u>TGGGTTLTVSS (SEQ
ID NO:240)

HC-CDR1: GYTFTEYT (SEQ ID NO:29)
   HC-CDR2: INPYSGGT (SEQ ID NO:30)
   HC-CDR3: ARWGGDYV (SEQ ID NO:27)

Mouse-human chimeric anti-R175H clone 10C8

EVQLQQSGPELVKPGASVKISCKTS<u>GYTFTEYT</u>MHWMKQSHGKSLEWIGR<u>INPYSGGT</u>VY
NQKFKGKATLTVDKSSSTAYMELRSLTSDDSAVYYC<u>ARWGGDYV</u>TGGGTTLTVSS (SEQ
ID NO:241)

HC-CDR1: GYTFTEYT (SEQ ID NO:29)
   HC-CDR2: INPYSGGT (SEQ ID NO:30)
   HC-CDR3: ARWGGDYV (SEQ ID NO:27)

Figure 50

Light chain variable domains

Mouse-human chimeric anti-R175H clone 4H5

>MH 4H5_aa_L
DIVLTQSTSSLSVSAGERVTLSCKSSQSLLNSGNQKSYLAWYQQKPGQPPKLLIYGASTRE
SGVPDRFTGSGSETDFTLTISSVQPEDLAVYYCQNDHSYPLTFGAGTKLELK [SEQ ID NO:237]

>MH 4H5_ntd_L
GATATTGTGcTCaCCCaATCTACATCCTCCCTGAGTGTGTCAGCTGGAGAGAGGGTCAC
TTTGAGCTGCAAGTCCAGTCAGAGTCTGTTAAACAGTGGAAATCAAAAGAGTTACTTGG
CCTGGTACCAGCAGAAACCAGGGCAGCCTCCTAAACTGTTGATCTACGGGGCATCCAC
TAGGGAATCTGGGGTCCCTGATCGCTTCACAGGCAGTGGATCTGAAACCGATTTCACT
CTTACCATCAGCAGTGTGCAGCCTGAAGACCTGGCAGTTTATTATTGTCAGAATGATCA
TAGTTATCCGCTCACGTTCGGTGCTGGGACCAAGCTGGAGCTGAAA [SEQ ID NO:242]

Mouse-human chimeric anti-R175H clone 7B9

>MH 7B9_aa_L
DIVMTQSPSSLSVSGGEKVTMSCKSSQSLLNSGNQKSNLAWYQQKPGQPPKLLIYGASTR
ESGVPDRFAGSGSGTDFTLTISSVQAEDLAVYYCQNDHSYPLTFGGGTKLELK [SEQ ID NO:238]

>MH 7B9_ntd_L
GATATTGTGATGACCCAGTCTCCATCCTCCCTGAGTGTGTCAGGAGGAGAGAAGGTCA
CTATGAGCTGCAAGTCCAGTCAGAGTCTGTTAAACAGTGGAAATCAAAAGAGCAACTTG
GCCTGGTACCAGCAGAAACCAGGGCAGCCTCCTAAATTGTTGATCTATGGGGCATCCA
CTAGGGAATCTGGGGTCCCTGATCGCTTCGCAGGCAGTGGATCTGGAACCGATTTCAC
TCTTACCATCAGCAGTGTGCAGGCTGAAGACCTGGCAGTTTATTACTGTCAAAATGATC
ATAGTTATCCGCTCACGTTCGGTGGTGGGACCAAGCTGGAGCTGAAA [SEQ ID NO:243]

Mouse-human chimeric anti-R175H clone 10C8

>MH 10C8_aa_L
DIVMTQSPSSLSVSGGEKVTMSCKSSQSLLNSGNQKSNLAWYQQKPGQPPKLLIYGASTR
ESGVPDRFAGSGSGTDFTLTISSVQAEDLAVYYCQNDHSYPLTFGGGTKLELK [SEQ ID NO:238]

>MH 10C8_ntd_L
GATATTGTGATGACCCAGTCTCCATCCTCCCTGAGTGTGTCAGGAGGAGAGAAGGTCA
CTATGAGCTGCAAGTCCAGTCAGAGTCTGTTAAACAGTGGAAATCAAAAGAGCAACTTG
GCCTGGTACCAGCAGAAACCAGGGCAGCCTCCTAAATTGTTGATCTATGGGGCATCCA
CTAGGGAATCTGGGGTCCCTGATCGCTTCGCAGGCAGTGGATCTGGAACCGATTTCAC
TCTTACCATCAGCAGTGTGCAGGCTGAAGACCTGGCAGTTTATTACTGTCAAAATGATC
ATAGTTATCCGCTCACGTTCGGTGGTGGGACCAAGCTGGAGCTGAAA [SEQ ID NO:243]

Figure 51

Heavy chain variable domains

Mouse-human chimeric anti-R175H clone 4H5

>MH 4H5_aa_H
EVQLQQSGPELVKPGASVKISCKTSGFTFTEYTMHWMKQSHGRSLEWIGRIDPNNGVTVY
NQKFKVKATLTVDRSSSTAYLELRSLTSEDSAVYYCARWGGDYVTGGGTTLTVSS [SEQ ID
NO:239]

>MH 4H5_ntd_H
GAGGTTCAGCTGCAGCAGTCTGGACCTGAACTGGTGAAGCCTGGGGCTTCAGTGAAGA
TATCTTGCAAGACTTCCGGATTCACATTCACTGAATACACCATGCACTGGATGAAACAG
AGCCATGGAAGGAGCCTTGAGTGGATCGGACGTATTGATCCTAACAATGGTGTTACTGT
TTATAACCAGAAGTTCAAGGTCAAGGCCACATTGACTGTGGACAGGTCCTCCAGCACA
GCCTATCTGGAGCTCCGCAGTCTGACGTCTGAGGACTCTGCAGTCTATTACTGTGCAA
GATGGGGTGGTGACTACGTCACGGGGGGAGGCACCACTCTCACAGTCTCCTCA  [SEQ
ID NO:244]

Mouse-human chimeric anti-R175H clone 7B9

>MH 7B9_aa_H
EVQLQQSGPELVKPGASVKISCKTSGYTFTEYTMHWMKQSHGKSLEWIGRINPYSGGTVY
NQKFKGKATLTVDKSSSTAYMELRSLTSDDSAVYYCARWGGDYVTGGGTTLTVSS [SEQ
ID NO:240]

>MH 7B9_ntd_H
GAGGTCCAGCTGCAGCAGTCTGGACCTGAGCTGGTGAAGCCTGGGGCTTCAGTGAAG
ATATCCTGCAAGACTTCTGGCTACACTTTCACTGAATACACCATGCACTGGATGAAGCA
GAGCCATGGAAAGAGCCTTGAGTGGATTGGACGTATTAATCCTTATAGTGGTGGTACTG
TCTACAACCAGAAGTTCAAGGGCAAGGCCACATTGACTGTGGACAAGTCCTCCAGCAC
AGCCTATATGGAGCTCCGCAGCCTGACATCTGATGATTCTGCAGTCTATTACTGTGCAA
GATGGGGTGGTGACTACGTCACGGGGGGAGGCACCACTCTCACAGTCTCCTCA  [SEQ
ID NO:245]

Mouse-human chimeric anti-R175H clone 10C8

>MH 10C8_aa_H
EVQLQQSGPELVKPGASVKISCKTSGYTFTEYTMHWMKQSHGKSLEWIGRINPYSGGTVY
NQKFKGKATLTVDKSSSTAYMELRSLTSDDSAVYYCARWGGDYVTGGGTTLTVSS [SEQ
ID NO:241]

>MH 10C8_ntd_H
GAGGTGCAGCTTCaGCAGTCGGGACCTGAGCTGGTGAAGCCTGGGGCTTCAGTGAAG
ATATCCTGCAAGACTTCTGGCTACACTTTCACTGAATACACCATGCACTGGATGAAGCA
GAGCCATGGAAAGAGCCTTGAGTGGATTGGACGTATTAATCCTTATAGTGGTGGTACTG
TCTACAACCAGAAGTTCAAGGGCAAGGCCACATTGACTGTGGACAAGTCCTCCAGCAC
AGCCTATATGGAGCTCCGCAGCCTGACATCTGATGATTCTGCAGTCTATTACTGTGCAA
GATGGGGTGGTGACTACGTCACGGGGGGAGGCACCACTCTCACAGTCTCCTCA  [SEQ
ID NO:246]

Figure 52

Mouse-human chimeric anti-R273H clone 13E4

DIVMTQSPLSLPVNLGDQVSLSCRSS<u>QSIVHNNGDTY</u>LEWYLQKPGQSPKLLIY<u>KVS</u>NRFS
GVPDRFSGSGSGTDFTLKISRVEAEDLGIYYC<u>FQGSHLPLT</u>FGSGTKLELK (SEQ ID
NO:247)

| | | |
|---|---|---|
| LC-CDR1: | QSIVHNNGDTY | (SEQ ID NO:59) |
| LC-CDR2: | KVS | (SEQ ID NO:60) |
| LC-CDR3: | FQGSHLPLT | (SEQ ID NO:61) |

Figure 53

Mouse-human chimeric anti-R273H clone 13E4

EVQLLETGGDLVTPGGSLKLSCAAS<u>GFSFSDYY</u>MYWVRQTPEKRLEWVAT<u>ISVGGTYT</u>FY
SDNVKGRFVISRDNARKNLHLEMNSLKSEDAAMYYC<u>VRDGNDGKFLG</u>YWGQGTFVTVTV
S (SEQ ID NO:248)

| | | |
|---|---|---|
| HC-CDR1: | GFSFSDYY | (SEQ ID NO:63) |
| HC-CDR2: | ISVGGTYT | (SEQ ID NO:64) |
| HC-CDR3: | VRDGNDGKFLG | (SEQ ID NO:65) |

Figure 54

Mouse-human chimeric anti-R273H clone 13E4 light chain variable domain

>MH 13E4_aa_L
DIVMTQSPLSLPVNLGDQVSLSCRSSQSIVHNNGDTYLEWYLQKPGQSPKLLIYKVSNRFS
GVPDRFSGSGSGTDFTLKISRVEAEDLGIYYCFQGSHLPLTFGSGTKLELK [SEQ ID
NO:247]

>MH 13E4_ntd_L
GATATTGTGATGACACAATCTCCACTCTCCCTGCCTGTCAATCTTGGAGATCAAGTCTC
CCTCTCTTGCAGATCTAGTCAGAGCATTGTACATAATAATGGAGACACCTATTTAGAATG
GTACCTACAGAAACCAGGCCAGTCTCCAAAGCTCCTGATCTACAAAGTTTCCAACCGAT
TTTCTGGGGTCCCAGACAGGTTCAGTGGCAGTGGATCAGGGACAGATTTCACACTCAA
GATCAGCAGAGTGGAGGCTGAGGATCTGGGAATTTATTACTGCTTTCAAGGTTCACATC
TTCCGCTCACGTTCGGTTCTGGGACCAAGCTGGAGCTGAAA [SEQ ID NO:249]

Figure 55

Mouse-human chimeric anti-R273H clone 13E4 heavy chain variable domain

>MH 13E4_aa_H
EVQLLETGGDLVTPGGSLKLSCAASGFSFSDYYMYWVRQTPEKRLEWVATISVGGTYTFY
SDNVKGRFVISRDNARKNLHLEMNSLKSEDAAMYYCVRDGNDGKFLGYWGQGTFVTVTV
S [SEQ ID NO:248]

>MH 13E4_ntd_H
GAAGTGCAGCTGTTGGAGACTGGGGGAGACTTAGTGACGCCTGGAGGGTCCCTGAAA
CTCTCCTGTGCAGCCTCTGGATTCAGCTTCAGTGACTATTATGTATTGGGTTCGCCA
GACTCCGGAAAAGAGGCTGGAGTGGGTCGCAACTATTAGTGTTGGTGGTACATACACC
TTCTATTCAGACAATGTGAAGGGGAGATTCGTCATCTCCAGAGACAATGCCAGGAAAAA
TCTGCATCTGGAAATGAACAGTCTGAAGTCTGAGGACGCAGCCATGTATTACTGTGTAA
GAGATGGCAACGATGGAAAATTTCTTGGGTACTGGGGCCAGGGGACTTTCGTCACTGT
CACTGTCTCT [SEQ ID NO:250]

Figure 56

Mouse-human chimeric anti-R248Q clone 3G11

DIVLTQTPLTLSVTIGQPASISCKSN<u>QSLLYSDGKTY</u>LNWLLQRPGQSPKRLIY<u>LVS</u>KLDSGV
PDRFTGSGSGTDFTLKISRVEAEDLGLYYC<u>WQGTHFPLT</u>FGAGTKLELK (SEQ ID NO:251)

LC-CDR1:  QSLLYSDGKTY  (SEQ ID NO:41)
   LC-CDR2:  LVS  (SEQ ID NO:42)
   LC-CDR3:  WQGTHFPLT  (SEQ ID NO:43)

Mouse-human chimeric anti-R248Q clone 4H2

DIVITQSPLTLSVTIGQPASISCKSD<u>QSLLYSDGKTY</u>LNWLLQRPGQSPKRLIY<u>LVS</u>ELDSGV
PDRFTGSGSGTDFTLKISRVEAEDLGLYYC<u>WQGTHFPLT</u>FGAGTKLELK (SEQ ID NO:252)

LC-CDR1:  QSLLYSDGKTY  (SEQ ID NO:41)
   LC-CDR2:  LVS  (SEQ ID NO:42)
   LC-CDR3:  WQGTHFPLT  (SEQ ID NO:43)

Figure 57

Mouse-human chimeric anti-R248Q clone 3G11

DVQLQQSGPELVKPGASVKMSCKAS<u>GYTFTDYY</u>VKWVKQSPGQSLEWIGD<u>IHPKNGGTN</u>
YNQKFKGKAALTVDKSSSTAYMQLNSLTSEDSAVYFC<u>AKMGGYDDY</u>WGQGTTLTVSS
(SEQ ID NO:253)

HC-CDR1:    GYTFTDYY    (SEQ ID NO:46)
    HC-CDR2:    IHPKNGGT    (SEQ ID NO:47)
    HC-CDR3:    AKMGGYDDY(SEQ ID NO:48)

Mouse-human chimeric anti-R248Q clone 4H2

QVQLKQSGPELVKPGASVKMSCKAS<u>GYTFTDYY</u>LKWVRQSHGKSLEWIGD<u>IDPKNGGTNY</u>
NQKFKGKATLTVDKSSSTAYMQLNSLTSEDSAVYYC<u>AKQGGFDDY</u>WGQGTTLTVSS (SEQ
ID NO:254)

HC-CDR1:    GYTFTDYY    (SEQ ID NO:46)
    HC-CDR2:    IDPKNGGT    (SEQ ID NO:50)
    HC-CDR3:    AKQGGFDDY(SEQ ID NO:51)

Figure 58

Mouse-human chimeric anti-R248Q clone 3G11 light chain variable domain

\>MH 3G11_aa_L
DIVLTQTPLTLSVTIGQPASISCKSNQSLLYSDGKTYLNWLLQRPGQSPKRLIYLVSKLDSGV
PDRFTGSGSGTDFTLKISRVEAEDLGLYYCWQGTHFPLTFGAGTKLELK [SEQ ID NO:251]

\>MH 3G11_ntd_L
GATATTGTGCTGACACAGACTCCACTCACTTTGTCGGTTACCATTGGACAACCAGCCTC
CATCTCTTGCAAGTCAAATCAGAGCCTCTTATATAGTGATGGAAAGACATATTTGAATTG
GTTATTACAGAGGCCAGGCCAGTCTCCAAAGCGCCTAATCTATCTGGTGTCTAAACTGG
ACTCTGGAGTCCCTGACAGGTTCACTGGCAGTGGATCAGGGACAGATTTCACACTGAA
AATCAGCAGAGTGGAGGCTGAGGATTTGGGACTTTATTATTGCTGGCAAGGTACACATT
TTCCTCTCACGTTCGGTGCTGGGACCAAGCTGGAGCTGAAA [SEQ ID NO:255]

Mouse-human chimeric anti-R248Q clone 4H2 light chain variable domain

\>MH 4H2_aa_L
DIVITQSPLTLSVTIGQPASISCKSDQSLLYSDGKTYLNWLLQRPGQSPKRLIYLVSELDSGV
PDRFTGSGSGTDFTLKISRVEAEDLGLYYCWQGTHFPLTFGAGTKLELK [SEQ ID NO:252]

\>MH 4H2_ntd_L
GACATTGTGATCACACAGTCTCCACTCACTTTGTCGGTTACCATTGGACAACCAGCCTC
CATCTCTTGCAAGTCAGATCAGAGCCTCTTATATAGTGATGGAAAGACATATTTGAATTG
GCTATTACAGAGGCCAGGCCAGTCTCCAAAGCGCCTAATCTATCTGGTGTCTGAACTG
GACTCTGGAGTCCCTGACAGGTTCACTGGCAGTGGATCAGGGACAGATTTCACACTGA
AAATCAGCAGAGTGGAGGCTGAGGATTTGGGACTTTATTATTGCTGGCAAGGTACACAT
TTTCCTCTCACGTTCGGTGCTGGGACCAAGCTGGAGCTGAAA [SEQ ID NO:256]

Figure 59

Mouse-human chimeric anti-R248Q clone 3G11 heavy chain variable domain

>MH 3G11_aa_H
DVQLQQSGPELVKPGASVKMSCKASGYTFTDYYVKWVKQSPGQSLEWIGDIHPKNGGTN
YNQKFKGKAALTVDKSSSTAYMQLNSLTSEDSAVYFCAKMGGYDDYWGQGTTLTVSS
[SEQ ID NO:253]

>MH 3G11_ntd_H
GATGTGCAGCTTCAGCAGTCAGGACCTGAGCTGGTGAAGCCTGGGGCTTCAGTGAAGA
TGTCCTGTAAGGCTTCTGGATACACATTCACTGACTACTATGTGAAGTGGGTGAAGCAG
AGTCCTGGACAGAGCCTTGAGTGGATTGGAGATATTCATCCTAAGAACGGTGGTACTAA
CTACAACCAGAAGTTCAAGGGCAAGGCCGCATTGACTGTGGACAAATCCTCCAGCACA
GCCTACATGCAGCTCAACAGCCTGACATCTGAGGACTCTGCAGTCTATTTCTGTGCAAA
AATGGGAGGCTACGACGACTACTGGGGCCAAGGCACCACTCTCACAGTCTCCTCA
[SEQ ID NO:257]

Mouse-human chimeric anti-R248Q clone 4H2 heavy chain variable domain

>MH 4H2_aa_H
QVQLKQSGPELVKPGASVKMSCKASGYTFTDYYLKWVRQSHGKSLEWIGDIDPKNGGTNY
NQKFKGKATLTVDKSSSTAYMQLNSLTSEDSAVYYCAKQGGFDDYWGQGTTLTVSS [SEQ
ID NO:254]

>MH 4H2_ntd_H
CAGGTGCAGCTGAAGCAGTCAGGACCTGAGCTGGTGAAGCCTGGGGCTTCAGTGAAG
ATGTCCTGTAAGGCTTCTGGATACACATTCACTGACTACTATCTGAAGTGGGTGAGGCA
GAGTCATGGAAAGAGCCTTGAGTGGATTGGAGATATAGATCCCAAGAATGGTGGTACT
AATTACAACCAGAAGTTTAAGGGCAAGGCCACATTGACTGTGGACAAATCCTCCAGCAC
AGCCTACATGCAGCTCAACAGCCTGACATCTGAGGACTCTGCAGTCTATTACTGTGCAA
AACAGGGGGGGTTCGACGACTACTGGGGCCAAGGCACCACTCTCACAGTCTCCTCA
[SEQ ID NO:258]

Figure 60

Note: "MH 3G11" refers to chimeric 3G11 antibody, "MH 4H2" refers to chimeric 4H2 antibody Day 21

Control    Pt/s: 1.50 X 10^10 ± 0.60
           Inhibition (%): 0.00

13E4
R273H mAb  Pt/s: 2.76 X 10^9 ± 2.01
           Inhibition (%): 81.62 mAb treatment; 100 ug of ascites was i.v. injected into mouse on Day 3, 6, 9, 12, 15, 18, 21 and Day 24. Mice were sacrificed on Day 25 and tumor weight was measured.

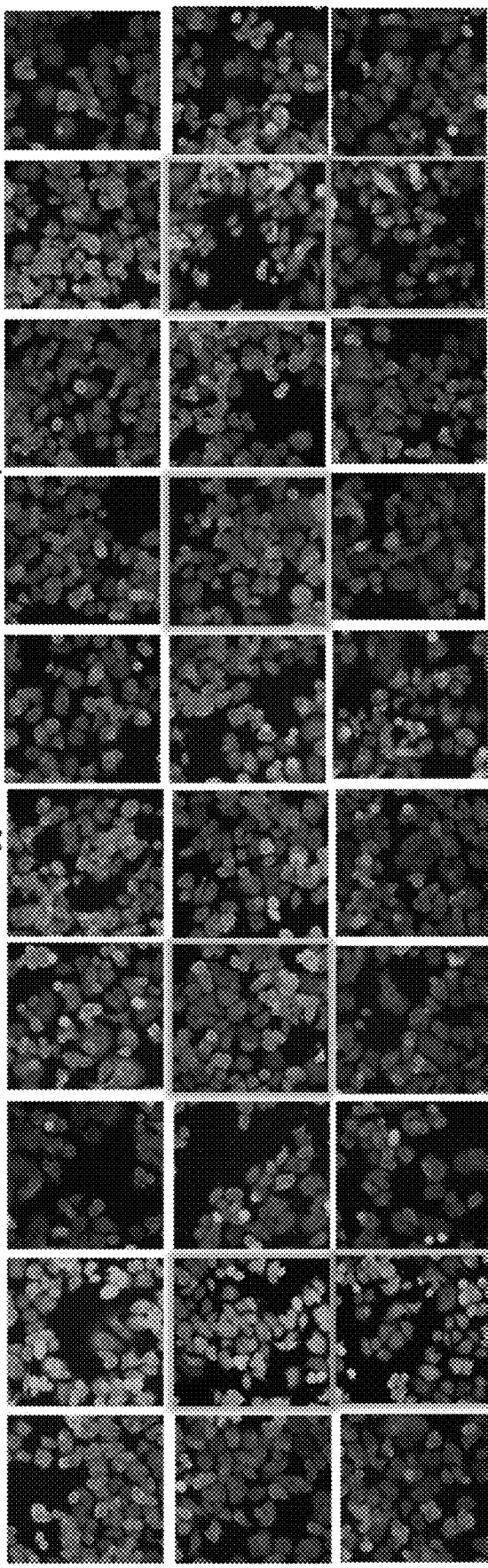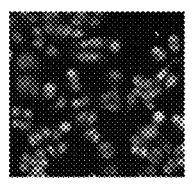
Figure 74C

ANTI-p53 ANTIBODIES

CROSS REFERENCE TO RELATED APPLICATIONS

This application is a Continuation of U.S. patent application Ser. No. 16/342,763, filed on Apr. 17, 2019, which is a U.S. National Stage Application filed under 35 U.S.C. 371 of PCT Application No. PCT/SG2017/050522, filed on Oct. 17, 2017, which claims the benefit under U.S.C. § 119 (e) of United Kingdom Patent Application Serial No. 1617564.8, filed on Oct. 17, 2016, each of which is incorporated herein by reference in its entirety.

FIELD OF THE INVENTION

The present invention relates to antibodies directed against mutant p53 polypeptides and methods for producing the same.

SEQUENCE LISTING

The instant application contains a Sequence Listing that has been submitted in XML format and is hereby incorporated by reference in its entirety. The XML copy, created on Feb. 22, 2023, is named "091404-753186.xml", and is 304 kilobytes in size.

BACKGROUND TO THE INVENTION

Evolutionary processes have resulted in the perfection of the immune response, in order for highly specific recognition events that can be surmounted to combat evading almost all types of exogenous antigens (Flajnik and Kasahara, Nat Rev Gene (2010) 11 (1): 47-59). In vertebrates, both T- and B-lymphocytes have developed receptors that undergo antigen-induced selective rearrangements to detect the slightest of variabilities that may occur in highly related antigenic proteins from similar species (Cooper and Alder, Cell (2006) 124(4):815-822), thereby establishing a barrier against foreign invasion. This innate ability has been exploited to generate a large number of antibodies against highly similar proteins with subtle structural variations (Lo et al., 2014 Microbiol. Spectr. 2, AID-0007-2012). Moreover, antibodies have also been made to detect subtle post-translational modifications such as phosphorylation, ubiquitination and acetylation on target amino-acid residues, which has led to the mechanistic understanding of a wide variety of physiological and pathological processes. However, detection of single amino acid changes, often noted due to missense mutations in the cancer genomes, represent a significant challenge to the generation of selective antibodies, due to the high homology of the flanking regions on the parent proteins. Whilst attempts have been made to make mutation-specific antibodies that do not cross-react with the unmutated native protein, most efforts have been thus far been unsuccessful (Bondgaard et al., Modern Pathology (2014) 27:1590-1598).

While mAbs against surface antigens such as EGFR, PD-1, etc. have been successfully used in the clinical setting for treatment (Martinelli et al., 2009 Clinical and Experimental Immunology 158 (1): 1-9; Philips and Atkins 2014, Int Immunol 27 (1): 39-46), mAbs against nuclear antigens generally face a challenge in getting past the cell membrane to be effective. However, recent studies have shown that antibodies against nuclear antigens can indeed be therapeutically effective (Hong and Zeng, 2012 Cancer Res 72 (11): 3715), providing promise that the approach may be successful in the future.

p53 is the most mutated gene across all cancer types, with over 50% of all tumors exhibiting some form of genetic alterations in it (Forbes et al. 2015 Nucleic Acids Res 43, D805-D811). Most mutations in p53 are found in the central DNA-binding domain (DBD) that spans around 200 amino-acids, and account for about 90% of all p53 mutations identified. Almost all DBD mutations lead to the loss of wild-type p53 functions, which are essential for tumor suppression and effective response to therapy, due to p53's multi-functional role in guarding the genome (Vousden and Lu, Nat Rev Cancer (2002) 2 (8): 594-604; Freed-Pastor and Prives, Genes Dev (2012) 26 (12): 1268-1286). Besides loss of wild-type functions, mutations in p53 also leads to two major phenomena that aid the development of cancers and also inhibit effective response against therapy. One is the dominant-negative (DN) effect that occurs when a mutant allele of p53 co-exists with the wild-type allele, thereby forming hetero-oligomers that result in the attenuation of the remaining wild-type p53 function (Kern et al., Science (1992) 256:827-830). In addition, the presence of mutant p53 allele alone, especially during the later stages of cancers when the wild-type p53 allele is lost due to loss-of-heterozygozity, results in cancer cells becoming addicted to the mutant p53 protein for survival, due to the gain of novel oncogenic functions (GOF) by mutant p53 that promotes survival and invasive properties (Sabapathy, Front Oncol (2015) 5:276). A causal role for mutant p53 in these processes has been demonstrated by reducing its expression or inactivating its function, where both the DN and GOF functions can be rescued, allowing cancer cells to become more sensitive to therapeutic treatment (Lee et al. Cancer Cell (2012) 22:751-764). While these data opens up the exciting possibility of targeting mutant p53, several challenge for successful inactivation of mutant p53 exist. Most importantly, it is to be noted that while all mutations in p53 unequivocally lead to loss of its wild-type activities and in most cases the DN effect, the GOF property appears to be selective for some mutants and not all (Lee et al. Cancer Cell (2012) 22:751-764; Hanel et al., Cell Death Diff (2013) 20:898-909), highlighting that targeting mutant p53 needs a more sophisticated approach to selectively detect and inactivate each individual p53 mutant.

Understanding the biology of mutant p53 has been fundamental to uncovering mutant p53's role in carcinogenesis and response to therapy. While significant progress has been made in our knowledge of how mutant p53 exerts its pro-survival functions, there are limitations. For example, not all mutations are functionally similar (Sabapathy, 2015 Front. Oncol. 5:276), and the mutations found in the transactivation and oligomerization domains of p53—which are quite common in certain populations (Achatz et al., 2007 Cancer Lett. 245:96-102)—require further evaluation.

Current technologies have utilized knock-in mouse models or human tumor cell lines that express only the mutant protein without the wildtype protein, which may not entirely reflect the role of the mutant protein in co-existence with the wildtype protein.

Attempts to generate antibodies against mutant p53 have been made over the decades, and monoclonal antibodies (mAb) against the mutant (PAb240) or the wild-type (PAb246) conformation of p53 are available (Gannon et al., EMBO J (1990) 9 (5): 1595-1602). However, these antibodies are not sufficiently specific and exhibit cross reactivity, and require very selective conditions for the detection of the correct conformations that have thus limited their use.

Vojtesek and Lane, J Cell Sci (1993), 105 (3): 607-612 describes an antibody designated DO-1 against the amino-terminal region of human p53, which shows a high level of specificity for human p53 without any cross-reactivity with mouse p53.

SUMMARY OF THE INVENTION

In a first aspect, the present invention provides a method for producing an antibody which is specific for a mutant p53 polypeptide over wildtype p53 polypeptide, comprising using as an immunogen a peptide or polypeptide comprising: (i) an antigen sequence, comprising an amino acid sequence of the mutant p53 polypeptide including the mutation and at least one amino acid immediately adjacent to the mutation, and (ii) a scaffold sequence for providing the antigen sequence in a solvent-accessible configuration.

In some embodiments, the scaffold sequence is derived from a peptide or polypeptide comprising a solvent-accessible sequence, and wherein the antigen sequence is inserted in, or substituted for all or part of, the solvent-accessible sequence of the peptide or polypeptide. In some embodiments, the peptide or polypeptide comprising a solvent-accessible sequence is a thioredoxin, and wherein the solvent-accessible sequence is the active site sequence of the thioredoxin. In some embodiments, the peptide or polypeptide used as an immunogen additionally comprises one or more linker sequences between the antigen sequence and the scaffold sequence. In some embodiments, the peptide or polypeptide used as an immunogen comprises at least two amino acid sequences of the mutant p53 polypeptide. In some embodiments, the peptide or polypeptide used as an immunogen additionally comprises linker sequences between the at least two amino acid sequences of the mutant p53 polypeptide. In some embodiments, the at least two amino acid sequences of the mutant p53 polypeptide are non-identical. In some embodiments, the amino acid sequence of the mutant p53 polypeptide comprises at least 5 amino acids. In some embodiments, the mutant p53 polypeptide comprises a mutation in the DNA-binding domain (DBD). In some embodiments, the mutant p53 polypeptide comprises a mutation selected from one of R175H, R248Q, R273H, R248W, G245S, R273C, R282W, R249S, G245D, C176F, H179Y, H179R, Y220C, and R337H. In some embodiments, the mutant p53 polypeptide comprises, or consists of, the amino acid sequence of one of SEQ ID NOs: 3 to 16.

In another aspect, the present invention provides an antibody, or antigen binding fragment, obtained or obtainable by a method for producing an antibody according to the invention.

In another aspect, the present invention provides an antibody, or antigen binding fragment, which is specific for a mutant p53 polypeptide over wildtype p53 polypeptide.

In some embodiments, the mutant p53 polypeptide comprises a mutation in the DNA-binding domain (DBD). In some embodiments, the mutant p53 polypeptide comprises a mutation selected from one of R175H, R248Q, R273H, R248W, G245S, R273C, R282W, R249S, G245D, C176F, H179Y, H179R, Y220C and R337H. In some embodiments, the mutant p53 polypeptide comprises, or consists of, the amino acid sequence of one of SEQ ID NOs: 3 to 16.

In another aspect, the present invention provides an antibody, or antigen binding fragment, which is capable of binding to R175H p53 polypeptide, optionally isolated, having the amino acid sequences i) to vi):

i) LC-CDR1:
                                    (SEQ ID NO: 31)
QSLLNSGNQKSX$_1$;

ii) LC-CDR2:
                                    (SEQ ID NO: 20)
GAS;

iii) LC-CDR3:
                                    (SEQ ID NO: 21)
QNDHSYPLT;

iv) HC-CDR1:
                                    (SEQ ID NO: 32)
GX$_2$TFTEYT;

v) HC-CDR2:
                                    (SEQ ID NO: 33)
IX$_3$PX$_4$X$_5$GX$_6$T;

vi) HC-CDR3:
                                    (SEQ ID NO: 27)
ARWGGDYV;

or a variant thereof in which one or two or three amino acids in one or more of the sequences i) to vi) are replaced with another amino acid, where $X_1$=Y or N; $X_2$=F or Y; $X_3$=D or N; $X_4$=N or Y; $X_5$=N or S; and $X_6$=V or G.

In some embodiments, LC-CDR1 is one of QSLLNSGNQKSY (SEQ ID NO:19) or QSLLNSGNQKSN (SEQ ID NO:23). In some embodiments, HC-CDR1 is one of GFTFTEYT (SEQ ID NO:25) or GYTFTEYT (SEQ ID NO:29). In some embodiments, HC-CDR2 is one of IDPNNGVT (SEQ ID NO:26) or INPYSGGT (SEQ ID NO:30).

In some embodiments, the antibody, or antigen binding fragment, has at least one light chain variable region incorporating the following CDRs:

LC-CDR1:
                                    (SEQ ID NO: 31)
QSLLNSGNQKSX$_1$;

LC-CDR2:
GAS;

LC-CDR3:
                                    (SEQ ID NO: 21)
QNDHSYPLT;

where $X_1$=Y or N.

In some embodiments, the antibody, or antigen binding fragment has at least one light chain variable region incorporating the following CDRs:

LC-CDR1:
                                    (SEQ ID NO: 19)
QSLLNSGNQKSY;

LC-CDR2:
GAS;

LC-CDR3:
                                    (SEQ ID NO: 21)
QNDHSYPLT.

In some embodiments, the antibody, or antigen binding fragment has at least one light chain variable region incorporating the following CDRs:

```
LC-CDR1:
                            (SEQ ID NO: 23)
QSLLNSGNQKSN;

LC-CDR2:
GAS;

LC-CDR3:
                            (SEQ ID NO: 21)
QNDHSYPLT.
```

In some embodiments, the antibody, or antigen binding fragment has at least one heavy chain variable region incorporating the following CDRs:

```
HC-CDR1:
                            (SEQ ID NO: 32)
GX₂TFTEYT;

HC-CDR2:
                            (SEQ ID NO: 33)
IX₃PX₄X₅GX₆T;

HC-CDR3:
                            (SEQ ID NO: 27)
ARWGGDYV;
``` where $X_2$=F or Y; $X_3$=D or N; $X_4$=N or Y; $X_5$=N or S; and $X_6$=V or G.

In some embodiments, the antibody, or antigen binding fragment has at least one heavy chain variable region incorporating the following CDRs:

```
HC-CDR1:
                            (SEQ ID NO: 25)
GFTFTEYT;

HC-CDR2:
                            (SEQ ID NO: 26)
IDPNNGVT;

HC-CDR3:
                            (SEQ ID NO: 27)
ARWGGDYV.
```

In some embodiments, the antibody, or antigen binding fragment has at least one heavy chain variable region incorporating the following CDRs:

```
HC-CDR1:
                            (SEQ ID NO: 29)
GYTFTEYT;

HC-CDR2:
                            (SEQ ID NO: 30)
INPYSGGT;

HC-CDR3:
                            (SEQ ID NO: 27)
ARWGGDYV.
```

In another aspect, the present invention provides an isolated light chain variable region polypeptide, comprising the following the following CDRs:

```
LC-CDR1:
                            (SEQ ID NO: 31)
QSLLNSGNQKSX₁;

LC-CDR2:
GAS;

LC-CDR3:
                            (SEQ ID NO: 21)
QNDHSYPLT;
``` where $X_1$=Y or N.

In some embodiments, LC-CDR1 is one of QSLLNSGNQKSY (SEQ ID NO:19) or QSLLNSGNQKSN (SEQ ID NO:23).

In another aspect, the present invention provides an isolated heavy chain variable region polypeptide, comprising the following the following CDRs:

```
HC-CDR1:
                            (SEQ ID NO: 32)
GX₂TFTEYT;

HC-CDR2:
                            (SEQ ID NO: 33)
IX₃PX₄X₅GX₆T;

HC-CDR3:
                            (SEQ ID NO: 27)
ARWGGDYV;
``` where $X_2$=F or Y; $X_3$=D or N; $X_4$=N or Y; $X_5$=N or S; and $X_6$=V or G.

In some embodiments, HC-CDR1 is one of GFTFTEYT (SEQ ID NO:25) or GYTFTEYT (SEQ ID NO:29). In some embodiments, HC-CDR2 is one of IDPNNGVT (SEQ ID NO:26) or INPYSGGT (SEQ ID NO:30).

In another aspect, the present invention provides an isolated light chain variable region polypeptide as described herein in combination with a heavy chain variable region polypeptide as described herein.

In another aspect, the present invention provides an antibody, or antigen binding fragment, which is capable of binding to R175H p53 polypeptide, comprising a light chain and a heavy chain variable region sequence, wherein:
the light chain comprises a LC-CDR1, LC-CDR2, LC-CDR3, having at least 85% overall sequence identity to LC-CDR1: one of QSLLNSGNQKSX1 (SEQ ID NO:31), QSLLNSGNQKSY (SEQ ID NO:19) or QSLLNSGNQKSN (SEQ ID NO:23); LC-CDR2: GAS; LC-CDR3: QNDHSYPLT (SEQ ID NO:21); and
the heavy chain comprises a HC-CDR1, HC-CDR2, HC-CDR3, having at least 85% overall sequence identity to HC-CDR1: one of GX₂TFTEYT (SEQ ID NO:32), GFTFTEYT (SEQ ID NO:25) or GYTFTEYT (SEQ ID NO:29); HC-CDR2: one of IX₃PX₄X₅GX₆T (SEQ ID NO:33), IDPNNGVT (SEQ ID NO:26) or INPYSGGT (SEQ ID NO:30); HC-CDR3: ARWGGDYV (SEQ ID NO:27); where $X_1$=Y or N; $X_2$=F or Y; $X_3$=D or N; $X_4$=N or Y; $X_5$=N or S; and $X_6$=V or G.

In another aspect, the present invention provides an antibody, or antigen binding fragment, which is capable of binding to R175H p53 polypeptide, comprising a light chain and a heavy chain variable region sequence, wherein:
the light chain sequence has at least 85% sequence identity to the light chain sequence of SEQ ID NO:18 or 22 (FIG. 24), or SEQ ID NO:237 or 94 (FIG. 49), and;
the heavy chain sequence has at least 85% sequence identity to the heavy chain sequence of SEQ ID NO:24 or 28 (FIG. 25), or SEQ ID NO:239, 240 or 241 (FIG. 50).

In another aspect, the present invention provides an antibody, or antigen binding fragment, optionally isolated, which is capable of binding to R175H p53 polypeptide, which is a bispecific antibody or a bispecific antigen binding fragment comprising (i) an antigen binding fragment or polypeptide as described herein, and (ii) an antigen binding fragment capable of binding to a polypeptide other than R175H p53 polypeptide.

In another aspect, the present invention provides an in vitro complex, optionally isolated, comprising an antibody, antigen binding fragment, or polypeptide as described herein bound to R175H p53 polypeptide or a fragment thereof.

In another aspect, the present invention provides an antibody, or antigen binding fragment, which is capable of binding to R248Q p53 polypeptide, optionally isolated, having the amino acid sequences i) to vi):

```
i) LC-CDR1:
                                      (SEQ ID NO: 41)
   QSLLYSDGKTY;

ii) LC-CDR2:
                                      (SEQ ID NO: 42)
   LVS;

iii) LC-CDR3:
                                      (SEQ ID NO: 43)
   WQGTHFPLT;

iv) HC-CDR1:
                                      (SEQ ID NO: 46)
   GYTFTDYY;

v) HC-CDR2:
                                      (SEQ ID NO: 52)
   IX7PKNGGT;

vi) HC-CDR3:
                                      (SEQ ID NO: 53)
   AKX8GGX9DDY;
``` or a variant thereof in which one or two or three amino acids in one or more of the sequences i) to vi) are replaced with another amino acid, where $X_7$=H or D; $X_8$=M or Q; and $X_9$=Y or F.

In some embodiments, HC-CDR2 is one of IHPKNGGT (SEQ ID NO:47) or IDPKNGGT (SEQ ID NO:50). In some embodiments, HC-CDR3 is one of AKMGGYDDY (SEQ ID NO:48) or AKQGGFDDY (SEQ ID NO:51).

In some embodiments, the antibody, or antigen binding fragment, has at least one light chain variable region incorporating the following CDRs:

```
LC-CDR1:
                                      (SEQ ID NO: 41)
   QSLLYSDGKTY

LC-CDR2:
                                      (SEQ ID NO: 42)
   LVS

LC-CDR3:
                                      (SEQ ID NO: 43)
   WQGTHFPLT.
```

In some embodiments, the antibody, or antigen binding fragment, has at least one heavy chain variable region incorporating the following CDRs:

```
HC-CDR1:
                                      (SEQ ID NO: 46)
   GYTFTDYY;

HC-CDR2:
                                      (SEQ ID NO: 52)
   IX7PKNGGT;

HC-CDR3:
                                      (SEQ ID NO: 53)
   AKX8GGX9DDY;
``` where $X_7$=H or D; $X_8$=M or Q; and $X_9$=Y or F.

In some embodiments, the antibody, or antigen binding fragment, has at least one heavy chain variable region incorporating the following CDRs:

```
HC-CDR1:
                                      (SEQ ID NO: 46)
   GYTFTDYY;

HC-CDR2:
                                      (SEQ ID NO: 47)
   IHPKNGGT;

HC-CDR3:
                                      (SEQ ID NO: 48)
   AKMGGYDDY.
```

In some embodiments, the antibody, or antigen binding fragment, has at least one heavy chain variable region incorporating the following CDRs:

```
HC-CDR1:
                                      (SEQ ID NO: 46)
   GYTFTDYY;

HC-CDR2:
                                      (SEQ ID NO: 50)
   IDPKNGGT;

HC-CDR3:
                                      (SEQ ID NO: 51)
   AKQGGFDDY.
```

In another aspect, the present invention provides an isolated light chain variable region polypeptide, comprising the following the following CDRs:

```
LC-CDR1:
                                      (SEQ ID NO: 41)
   QSLLYSDGKTY

LC-CDR2:
                                      (SEQ ID NO: 42)
   LVS

LC-CDR3:
                                      (SEQ ID NO: 43)
   WQGTHFPLT.
```

In another aspect, the present invention provides an isolated heavy chain variable region polypeptide, comprising the following the following CDRs:

```
HC-CDR1:
                                      (SEQ ID NO: 46)
   GYTFTDYY;

HC-CDR2:
                                      (SEQ ID NO: 52)
   IX7PKNGGT;

HC-CDR3:
                                      (SEQ ID NO: 53)
   AKX8GGX9DDY;
``` where $X_7$=H or D; $X_8$=M or Q; and $X_9$=Y or F.

In some embodiments, HC-CDR2 is one of IHPKNGGT (SEQ ID NO:47) or IDPKNGGT (SEQ ID NO:50). In some embodiments, HC-CDR3 is one of AKMGGYDDY (SEQ ID NO:48) or AKQGGFDDY (SEQ ID NO:51).

In another aspect, the present invention provides an isolated light chain variable region polypeptide as described herein in combination with a heavy chain variable region polypeptide as described herein.

In another aspect, the present invention provides an antibody, or antigen binding fragment, which is capable of binding to R248Q p53 polypeptide, comprising a light chain and a heavy chain variable region sequence, wherein:
- the light chain comprises a LC-CDR1, LC-CDR2, LC-CDR3, having at least 85% overall sequence identity to LC-CDR1: QSLLYSDGKTY (SEQ ID NO:41); LC-CDR2: LVS (SEQ ID NO:42); LC-CDR3: WQGTHFPLT (SEQ ID NO:43); and
- the heavy chain comprises a HC-CDR1, HC-CDR2, HC-CDR3, having at least 85% overall sequence identity to HC-CDR1: GYTFTDYY (SEQ ID NO:46); HC-CDR2: one of $IX_7PKNGGT$ (SEQ ID NO:52), IHPKNGGT (SEQ ID NO:47) or IDPKNGGT (SEQ ID NO: 50); HC-CDR3: one of $AKX_8GGX_9DDY$ (SEQ ID NO:53), AKMGGYDDY (SEQ ID NO: 48) or AKQGGFDDY (SEQ ID NO:51); where $X_7$=H or D; $X_8$=M or Q; and $X_9$=Y or F.

In another aspect, the present invention provides an antibody, or antigen binding fragment, which is capable of binding to R248Q p53 polypeptide, comprising a light chain and a heavy chain variable region sequence, wherein:
- the light chain sequence has at least 85% sequence identity to the light chain sequence of SEQ ID NO:40 or 44 (FIG. 28), or SEQ ID NO:251 or 252 (FIG. 57), and;
- the heavy chain sequence has at least 85% sequence identity to the heavy chain sequence of SEQ ID NO:45 or 49 (FIG. 29), or SEQ ID NO:253 or 254 (FIG. 58).

In another aspect, the present invention provides an antibody, or antigen binding fragment, optionally isolated, which is capable of binding to R248Q p53 polypeptide, which is a bispecific antibody or a bispecific antigen binding fragment comprising (i) an antigen binding fragment or polypeptide as described herein, and (ii) an antigen binding fragment capable of binding to a polypeptide other than R248Q p53 polypeptide.

In another aspect, the present invention provides an in vitro complex, optionally isolated, comprising an antibody, antigen binding fragment, or polypeptide as described herein bound to R248Q p53 polypeptide or a fragment thereof.

In another aspect, the present invention provides an antibody, or antigen binding fragment, which is capable of binding to R273H p53 polypeptide, optionally isolated, having the amino acid sequences i) to vi):

i)
LC-CDR1:
(SEQ ID NO: 59)
QSIVHNNGDTY;

ii)
LC-CDR2:
(SEQ ID NO: 60)
KVS;

iii) LC-CDR3:
(SEQ ID NO: 61)
FQGSHLPLT;

iv) HC-CDR1:
(SEQ ID NO: 63)
GFSFSDYY;

v) HC-CDR2:
(SEQ ID NO: 64)
ISVGGTYT;

vi) HC-CDR3:
(SEQ ID NO: 65)
VRDGNDGKFLG;

or a variant thereof in which one or two or three amino acids in one or more of the sequences i) to vi) are replaced with another amino acid.

In some embodiments, the antibody, or antigen binding fragment, has at least one light chain variable region incorporating the following CDRs:

LC-CDR1:
(SEQ ID NO: 59)
QSIVHNNGDTY

LC-CDR2:
(SEQ ID NO: 60)
KVS

LC-CDR3:
(SEQ ID NO: 61)
FQGSHLPLT.

In some embodiments, the antibody, or antigen binding fragment, has at least one heavy chain variable region incorporating the following CDRs:

HC-CDR1:
(SEQ ID NO: 63)
GFSFSDYY

HC-CDR2:
(SEQ ID NO: 64)
ISVGGTYT

HC-CDR3:
(SEQ ID NO: 65)
VRDGNDGKFLG.

In another aspect, the present invention provides an isolated light chain variable region polypeptide, comprising the following following CDRs:

LC-CDR1:
(SEQ ID NO: 59)
QSIVHNNGDTY

LC-CDR2:
(SEQ ID NO: 60)
KVS

LC-CDR3:
(SEQ ID NO: 61)
FQGSHLPLT.

In another aspect, the present invention provides an isolated heavy chain variable region polypeptide, comprising the following following CDRs:

HC-CDR1:
(SEQ ID NO: 63)
GFSFSDYY

```
-continued
HC-CDR2:
                                        (SEQ ID NO: 64)
   ISVGGTYT HC-CDR3:
                                        (SEQ ID NO: 65)
   VRDGNDGKFLG.
```

In another aspect, the present invention provides an isolated light chain variable region polypeptide as described herein in combination with a heavy chain variable region polypeptide as described herein.

In another aspect, the present invention provides an antibody, or antigen binding fragment, which is capable of binding to R273H p53 polypeptide, comprising a light chain and a heavy chain variable region sequence, wherein:
- the light chain comprises a LC-CDR1, LC-CDR2, LC-CDR3, having at least 85% overall sequence identity to LC-CDR1: QSIVHNNGDTY (SEQ ID NO:59); LC-CDR2: KVS (SEQ ID NO:60); LC-CDR3: FQGSHLPLT (SEQ ID NO:61); and
- the heavy chain comprises a HC-CDR1, HC-CDR2, HC-CDR3, having at least 85% overall sequence identity to HC-CDR1: GFSFSDYY (SEQ ID NO:63); HC-CDR2: ISVGGTYT (SEQ ID NO:64); HC-CDR3: VRDGNDGKFLG (SEQ ID NO:65).

In another aspect, the present invention provides an antibody, or antigen binding fragment, which is capable of binding to R273H p53 polypeptide, comprising a light chain and a heavy chain variable region sequence, wherein:
- the light chain sequence has at least 85% sequence identity to the light chain sequence of SEQ ID NO:58 (FIG. 32) or SEQ ID NO:247 (FIG. 53), and;
- the heavy chain sequence has at least 85% sequence identity to the heavy chain sequence of SEQ ID NO:62 (FIG. 33) or SEQ ID NO:248 (FIG. 54).

In another aspect, the present invention provides an antibody, or antigen binding fragment, optionally isolated, which is capable of binding to R273H p53 polypeptide, which is a bispecific antibody or a bispecific antigen binding fragment comprising (i) an antigen binding fragment or polypeptide as described herein, and (ii) an antigen binding fragment capable of binding to a polypeptide other than R273H p53 polypeptide.

In another aspect, the present invention provides an in vitro complex, optionally isolated, comprising an antibody, antigen binding fragment, or polypeptide as described herein bound to R273H p53 polypeptide or a fragment thereof.

In another aspect, the present invention provides an antibody, antigen binding fragment, or polypeptide as described herein conjugated to a drug moiety or a detectable moiety.

In another aspect, the present invention provides a chimeric antigen receptor (CAR) comprising an antigen binding fragment or polypeptide as described herein.

In another aspect, the present invention provides a cell comprising a chimeric antigen receptor (CAR) as described herein.

In another aspect, the present invention provides a composition comprising the antibody, antigen binding fragment, polypeptide, conjugate, chimeric antigen receptor (CAR) or cell as described herein and at least one pharmaceutically-acceptable carrier.

In another aspect, the present invention provides an isolated nucleic acid encoding the antibody, antigen binding fragment, polypeptide, conjugate, or chimeric antigen receptor (CAR) as described herein.

In another aspect, the present invention provides a vector comprising the nucleic acid as described herein.

In another aspect, the present invention provides a host cell comprising the vector as described herein.

In another aspect, the present invention provides a method for making an antibody, antigen binding fragment, polypeptide, conjugate, or chimeric antigen receptor (CAR) as described herein, comprising culturing the host cell under conditions suitable for the expression of a vector encoding the antibody, antigen binding fragment, polypeptide or conjugate, and recovering the antibody, antigen binding fragment, polypeptide or conjugate In another aspect, the present invention provides an antibody, antigen binding fragment, polypeptide, conjugate, chimeric antigen receptor (CAR) or cell as described herein for use in therapy, or in a method of medical treatment.

In another aspect, the present invention provides an antibody, antigen binding fragment, polypeptide, conjugate, chimeric antigen receptor (CAR) or cell as described herein in the manufacture of a medicament for use in a method of medical treatment.

In another aspect, the present invention provides a method of treating a disease, the method comprising administering an antibody, antigen binding fragment, polypeptide, conjugate, chimeric antigen receptor (CAR) or cell as described herein to a patient suffering from a disease.

In another aspect, the present invention provides an antibody, antigen binding fragment, polypeptide, conjugate, chimeric antigen receptor (CAR) or cell as described herein for use in the treatment or prevention of cancer.

In another aspect, the present invention provides an antibody, antigen binding fragment, polypeptide, conjugate, chimeric antigen receptor (CAR) or cell as described herein in the manufacture of a medicament for use in the treatment or prevention of cancer.

In another aspect, the present invention provides a method of treating cancer comprising administering an antibody, antigen binding fragment, polypeptide, conjugate, chimeric antigen receptor (CAR) or cell as described herein to a patient suffering from a cancer.

In another aspect, the present invention provides a method of preventing cancer or preventing a recurrence of cancer, the method comprising administering an antibody, antigen binding fragment, polypeptide, conjugate, chimeric antigen receptor (CAR) or cell as described herein to a patient considered to be at risk of cancer or at risk of recurrence of cancer.

In another aspect, the present invention provides a method, optionally an in vitro method, comprising contacting a sample containing, or suspected to contain, a mutant p53 polypeptide with an antibody, antigen binding fragment, polypeptide, conjugate, chimeric antigen receptor (CAR) or cell as described herein and detecting the formation of a complex of the antibody, antigen binding fragment, polypeptide, conjugate, CAR or cell with the mutant p53 polypeptide.

In another aspect, the present invention provides a method of diagnosing a disease or condition in a subject, the method comprising contacting, in vitro, a sample from the subject with an antibody, antigen binding fragment, polypeptide, conjugate, chimeric antigen receptor (CAR) or cell as described herein and detecting the formation of a complex of the antibody, antigen binding fragment, polypeptide, conjugate, CAR or cell with the mutant p53 polypeptide.

In another aspect, the present invention provides a method of selecting or stratifying a subject for treatment with a mutant p53 polypeptide-targeted agent, the method comprising contacting, in vitro, a sample from the subject with an antibody, antigen binding fragment, polypeptide, conjugate, chimeric antigen receptor (CAR) or cell as described herein and detecting the formation of a complex of the antibody, antigen binding fragment, polypeptide, conjugate, CAR or cell with the mutant p53 polypeptide.

In another aspect, the present invention provides the use of an antibody, antigen binding fragment, polypeptide, conjugate, chimeric antigen receptor (CAR) or cell as described herein for the detection of a mutant p53 polypeptide in vitro or in vivo.

In another aspect, the present invention provides the use of an antibody, antigen binding fragment, polypeptide, conjugate, chimeric antigen receptor (CAR) or cell as described herein as an in vitro or in vivo diagnostic or prognostic agent.

In another aspect, the present invention provides the use of an antibody, antigen binding fragment, polypeptide, conjugate, chimeric antigen receptor (CAR) or cell as described herein in a method for detecting, localizing or imaging a cancer in vivo.

In another aspect, the present invention provides a method for detecting, localizing or imaging a cancer in vivo, comprising administering an antibody, antigen binding fragment, polypeptide, conjugate, chimeric antigen receptor (CAR) or cell as described herein to a subject, and detecting the antibody, antigen binding fragment, polypeptide, conjugate, chimeric antigen receptor (CAR) or cell.

In another aspect, the present invention provides a vaccine, optionally a cancer vaccine, comprising an immunogen as described herein.

In another aspect, the present invention provides an immunogen as described herein for use in a method of vaccination, optionally against a cancer.

In another aspect, the present invention provides the use of an immunogen as described herein in the manufacture of a medicament for use in the vaccination of a subject, optionally against a cancer.

In another aspect, the present invention provides a method for vaccinating a subject, optionally against a cancer, comprising administering to the subject an immunogen as described herein, thereby vaccinating the subject against a cancer.

In some embodiments in accordance with various aspects of the present invention, the cancer is a cancer comprising a cell or cells expressing a mutant p53 polypeptide, or comprising nucleic acid encoding a mutant p53 polypeptide. The mutant p53 polypeptide may correspond to the selected antibody, antigen binding fragment, polypeptide, conjugate, chimeric antigen receptor (CAR), cell or immunogen.

DESCRIPTION

Mutant p53 Polypeptides and Wildtype p53 Polypeptides

The p53 tumour suppressor is a protein which is encoded in humans by the TP53 gene. p53 plays a crucial role in cellular response to DNA damage and other genomic aberrations. Activation of p53 leads to cell cycle arrest, DNA repair or apoptosis. Mutations of the gene encoding p53 have been implicated in the development and progression of a variety of cancers (Muller and Vousden, Cancer Cell (2014) 25:304-317).

Certain p53 mutations, including the hotspot mutations (R175H, R248W and R273H), not only result in the loss of p53-dependent tumor suppressor activity, but also result in the acquisition of oncogenic activity.

A wildtype p53 polypeptide as referred to herein may comprise or consist of a reference amino acid sequence for p53 for a given animal. Reference amino acid sequences for p53 can be retrieved from databases known to the person skilled in the art. Such databases include GenBank, EMBL, DDBJ, UniProt, Swiss-Prot, TrEMBL, Protein Information Resource, Protein Data Bank, Ensembl and InterPro.

The animal may be a mammal. In some embodiments, the animal may be a human. In some embodiments, the animal may be a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

In some embodiments a wildtype p53 polypeptide may comprise or consist of the amino acid sequence of UniProtKB-P04637 (P53_HUMAN):

```
                                          (SEQ ID NO: 1)
MEEPQSDPSVEPPLSQETFSDLWKLLPENNVLSPL

PSQAMDDLMLSPDDIEQWFTEDPGPDEAPRMPEAA

PPVAPAPAAPTPAAPAPAPSWPLSSSVPSQKTYQG

SYGFRLGFLHSGTAKSVTCTYSPALNKMFCQLAKT

CPVQLWVDSTPPPGTRVRAMAIYKQSQHMTEVVRR

CPHHERCSDSDGLAPPQHLIRVEGNLRVEYLDDRN

TFRHSVVVPYEPPEVGSDCTTIHYNYMCNSSCMGG

MNRRPILTIITLEDSSGNLLGRNSFEVRVCACPGR

DRRTEEENLRKKGEPHHELPPGSTKRALPNNTSSS

PQPKKKPLDGEYFTLQIRGRERFEMFRELNEALEL

KDAQAGKEPGGSRAHSSHLKSKKGQSTSRHKKLMF

KTEGPDSD
```

A mutant p53 polypeptide is a polypeptide having an amino acid sequence which is different to the amino acid sequence of the wildtype p53 polypeptide, e.g. as a result of insertion, deletion or substitution of one or more amino acids of the wildtype p53 polypeptide amino acid sequence.

Mutant p53 polypeptides may occur as a result of genetic mutation of the DNA encoding a p53 polypeptide causing a change in the amino acid sequence of the polypeptide. Mutations of p53 are known in the art, and are described for example in Muller and Vousden, Cancer Cell (2014) 25:304-317, which is hereby incorporated by reference in its entirety-see e.g. Table 1 spanning pages 305-308.

The present invention is concerned in particular with antibodies which are capable of binding to mutant p53 polypeptides which are only very subtly different from wildtype p53 polypeptide, and which do not exhibit significant binding to wildtype p53 polypeptide.

In some embodiments, the antibodies are capable of binding to a mutant p53 polypeptide which differs from wildtype p53 polypeptide by 10 amino acids or fewer, e.g. 5, 4, 3 or 2 amino acids or fewer. In some embodiments, an antibody is capable of binding to a mutant p53 polypeptide which differs from wildtype p53 polypeptide by one amino acid.

That is, the present invention provides antibodies capable of recognising single amino acid mutant variants of p53.

In some embodiments, the amino acid(s) of the mutant p53 polypeptide which differ from the amino acid sequence of wildtype p53 are in the sequence of the DNA-binding domain.

The DNA-binding domain of p53 is evolutionarily conserved, and the skilled person is able to identify the DNA-binding domain for a given wildtype p53 polypeptide by reference to the DNA-binding domain sequence of e.g. human wildtype p53 polypeptide. The DNA-binding domain for human wildtype p53 polypeptide corresponds to positions 101-306 of SEQ ID NO: 1 (see e.g. Freed-Pastor and Prives, Genes and Development (2012) 26:1268-1286), having the following sequence:

(SEQ ID NO: 2)
KTYQGSYGFRLGFLHSGTAKSVTCTYSPALNKMFC

QLAKTCPVQLWDSTPPPGTRVRAMAIYKQSQHMTE

VVRRCPHHERCSDSDGLAPPQHLIRVEGNLRVEYL

DDRNTFRHSVVVPYEPPEVGSDCTTIHYNYMCNSS

CMGGMNRRPILTIITLEDSSGNLLGRNSFEVRVCA

CPGRDRRTEEENLRKKGEPHHELPPGSTKR

Nine hot spots for mutation of p53 within the DNA binding domain of p53 have been identified, corresponding to positions 248, 273, 175, 176, 179, 220, 245, 249, 282 numbered relative to SEQ ID NO:1, and a further hotspot has been identified at position 337. In some embodiments, the mutant p53 polypeptide to which an antibody according to the present invention specifically binds comprises an amino acid difference relative to the wildtype p53 sequence at one or more of positions 248, 273, 175, 176, 179, 220, 245, 249, 282 and 337. In some embodiments, the mutant p53 polypeptide comprises an amino acid difference relative to the wildtype p53 sequence at one of position 248, 273, 175, 176, 179, 220, 245, 249, 282, or 337.

In some embodiments, an antibody according to the invention is capable of binding to a specific, known mutant p53 polypeptide. In some embodiments an antibody according to the present invention may be capable of binding to a p53 polypeptide comprising one of the following amino acid substitutions numbered relative to SEQ ID NO:1: R175H, R248Q, R273H, R248W, G245S, R273C, R282W, R249S, G245D, C176F, H179Y, H179R, Y220C, R337H.

In some embodiments, an antibody according to the invention may be capable of binding to mutant p53 polypeptide comprising or consisting of one of the following sequences:

| Mutation | Sequence (mutated residue relative to wildtype p53 shown bold, underlined) | SEQ ID NO: |
|---|---|---|
| R175H | MEEPQSDPSVEPPLSQETFSDLWKLLPENNVLSPLPSQAMDDLMLSPD DIEQWFTEDPGPDEAPRMPEAAPPVAPAPAAPTPAAPAPAPSWPLSSS VPSQKTYQGSYGFRLGFLHSGTAKSVTCTYSPALNKMFCQLAKTCPVQ LWWDSTPPPGTRVRAMAIYKQSQHMTEVVRHCPHHERCSDSDGLAPPQ HLIRVEGNLRVEYLDDRNTFRHSVVVPYEPPEVGSDCTTIHYNYMCNS SCMGGMNRRPILTIITLEDSSGNLLGRNSFEVRVCACPGRDRRTEEENL RKKGEPHHELPPGSTKRALPNNTSSSPQPKKKPLDGEYFTLQIRGRERF EMFRELNEALELKDAQAGKEPGGSRAHSSHLKSKKGQSTSRHKKLMFK TEGPDSD | SEQ ID NO: 3 |
| R248Q | MEEPQSDPSVEPPLSQETFSDLWKLLPENNVLSPLPSQAMDDLMLSPD DIEQWFTEDPGPDEAPRMPEAAPPVAPAPAAPTPAAPAPAPSWPLSSS VPSQKTYQGSYGFRLGFLHSGTAKSVTCTYSPALNKMFCQLAKTCPVQ LWVDSTPPPGTRVRAMAIYKQSQHMTEVVRRCPHHERCSDSDGLAPPQ HLIRVEGNLRVEYLDDRNTFRHSVVVPYEPPEVGSDCTTIHYNYMCNS SCMGGMNQRPILTIITLEDSSGNLLGRNSFEVRVCACPGRDRRTEEENL RKKGEPHHELPPGSTKRALPNNTSSSPQPKKKPLDGEYFTLQIRGRERF EMFRELNEALELKDAQAGKEPGGSRAHSSHLKSKKGQSTSRHKKLMFK TEGPDSD | SEQ ID NO: 4 |
| R273H | MEEPQSDPSVEPPLSQETFSDLWKLLPENNVLSPLPSQAMDDLMLSPD DIEQWFTEDPGPDEAPRMPEAAPPVAPAPAAPTPAAPAPAPSWPLSSS VPSQKTYQGSYGFRLGFLHSGTAKSVTCTYSPALNKMFCQLAKTCPVQ LWWDSTPPPGTRVRAMAIYKQSQHMTEVVRRCPHHERCSDSDGLAPPQ HLIRVEGNLRVEYLDDRNTFRHSVVVPYEPPEVGSDCTTIHYNYMCNS SCMGGMNRRPILTIITLEDSSGNLLGRNSFEVHVCACPGRDRRTEEENL RKKGEPHHELPPGSTKRALPNNTSSSPQPKKKPLDGEYFTLQIRGRERF EMFRELNEALELKDAQAGKEPGGSRAHSSHLKSKKGQSTSRHKKLMFK TEGPDSD | SEQ ID NO: 5 |
| R248W | MEEPQSDPSVEPPLSQETFSDLWKLLPENNVLSPLPSQAMDDLMLSPD DIEQWFTEDPGPDEAPRMPEAAPPVAPAPAAPTPAAPAPAPSWPLSSS VPSQKTYQGSYGFRLGFLHSGTAKSVTCTYSPALNKMFCQLAKTCPVQ LWWVDSTPPPGTRVRAMAIYKQSQHMTEVVRRCPHHERCSDSDGLAPP QHLIRVEGNLRVEYLDDRNTFRHSVVVPYEPPEVGSDCTTIHYNYMCNS SCMGGMNWRPILTIITLEDSSGNLLGRNSFEVRVCACPGRDRRTEEENL RKKGEPHHELPPGSTKRALPNNTSSSPQPKKKPLDGEYFTLQIRGRERF EMFRELNEALELKDAQAGKEPGGSRAHSSHLKSKKGQSTSRHKKLMFK TEGPDSD | SEQ ID NO: 6 |
| G245S | MEEPQSDPSVEPPLSQETFSDLWKLLPENNVLSPLPSQAMDDLMLSPD DIEQWFTEDPGPDEAPRMPEAAPPVAPAPAAPTPAAPAPAPSWPLSSS VPSQKTYQGSYGFRLGFLHSGTAKSVTCTYSPALNKMFCQLAKTCPVQ LWDSTPPPGTRVRAMAIYKQSQHMTEVVRRCPHHERCSDSDGLAPP QHLIRVEGNLRVEYLDDRNTFRHSVVVPYEPPEVGSDCTTIHYNYMCNS | SEQ ID NO: 7 |

-continued

| Mutation | Sequence (mutated residue relative to wildtype p53 shown bold, underlined) | SEQ ID NO: |
|---|---|---|
| | SCMGSMNRRPILTIITLEDSSGNLLGRNSFEVRVCACPGRDRRTEEENL<br>RKKGEPHHELPPGSTKRALPNNTSSSPQPKKKPLDGEYFTLQIRGRERF<br>EMFRELNEALELKDAQAGKEPGGSRAHSSHLKSKKGQSTSRHKKLMFK<br>TEGPDSD | |
| R273C | MEEPQSDPSVEPPLSQETFSDLWKLLPENNVLSPLPSQAMDDLMLSPD<br>DIEQWFTEDPGPDEAPRMPEAAPPVAPAPAAPTPAAPAPAPSWPLSSS<br>VPSQKTYQGSYGFRLGFLHSGTAKSVTCTYSPALNKMFCQLAKTCPVQ<br>LWDSTPPPGTRVRAMAIYKQSQHMTEVVRRCPHHERCSDSDGLAPP<br>QHLIRVEGNLRVEYLDDRNTFRHSVVVPYEPPEVGSDCTTIHYNYMCNS<br>SCMGGMNRRPILTIITLEDSSGNLLGRNSFEVCVCACPGRDRRTEEENL<br>RKKGEPHHELPPGSTKRALPNNTSSSPQPKKKPLDGEYFTLQIRGRERF<br>EMFRELNEALELKDAQAGKEPGGSRAHSSHLKSKKGQSTSRHKKLMFK<br>TEGPDSD | SEQ ID NO: 8 |
| R282W | MEEPQSDPSVEPPLSQETFSDLWKLLPENNVLSPLPSQAMDDLMLSPD<br>DIEQWFTEDPGPDEAPRMPEAAPPVAPAPAAPTPAAPAPAPSWPLSSS<br>VPSQKTYQGSYGFRLGFLHSGTAKSVTCTYSPALNKMFCQLAKTCPVQ<br>LWDSTPPPGTRVRAMAIYKQSQHMTEVVRRCPHHERCSDSDGLAPP<br>QHLIRVEGNLRVEYLDDRNTFRHSVVVPYEPPEVGSDCTTIHYNYMCNS<br>SCMGGMNRRPILTIITLEDSSGNLLGRNSFEVRVCACPGRDWRTEEENL<br>RKKGEPHHELPPGSTKRALPNNTSSSPQPKKKPLDGEYFTLQIRGRERF<br>EMFRELNEALELKDAQAGKEPGGSRAHSSHLKSKKGQSTSRHKKLMFK<br>TEGPDSD | SEQ ID NO: 9 |
| R249S | MEEPQSDPSVEPPLSQETFSDLWKLLPENNVLSPLPSQAMDDLMLSPD<br>DIEQWFTEDPGPDEAPRMPEAAPPVAPAPAAPTPAAPAPAPSWPLSSS<br>VPSQKTYQGSYGFRLGFLHSGTAKSVTCTYSPALNKMFCQLAKTCPVQ<br>LWDSTPPPGTRVRAMAIYKQSQHMTEVVRRCPHHERCSDSDGLAPP<br>QHLIRVEGNLRVEYLDDRNTFRHSVVVPYEPPEVGSDCTTIHYNYMCNS<br>SCMGGMNRSPILTIITLEDSSGNLLGRNSFEVRVCACPGRDRRTEEENL<br>RKKGEPHHELPPGSTKRALPNNTSSSPQPKKKPLDGEYFTLQIRGRERF<br>EMFRELNEALELKDAQAGKEPGGSRAHSSHLKSKKGQSTSRHKKLMFK<br>TEGPDSD | SEQ ID NO: 10 |
| G245D | MEEPQSDPSVEPPLSQETFSDLWKLLPENNVLSPLPSQAMDDLMLSPD<br>DIEQWFTEDPGPDEAPRMPEAAPPVAPAPAAPTPAAPAPAPSWPLSSS<br>VPSQKTYQGSYGFRLGFLHSGTAKSVTCTYSPALNKMFCQLAKTCPVQ<br>LWWDSTPPPGTRVRAMAIYKQSQHMTEVVRRCPHHERCSDSDGLAPP<br>QHLIRVEGNLRVEYLDDRNTFRHSVVVPYEPPEVGSDCTTIHYNYMCNS<br>SCMGDMNRRPILTIITLEDSSGNLLGRNSFEVRVCACPGRDRRTEEENL<br>RKKGEPHHELPPGSTKRALPNNTSSSPQPKKKPLDGEYFTLQIRGRERF<br>EMFRELNEALELKDAQAGKEPGGSRAHSSHLKSKKGQSTSRHKKLMFK<br>TEGPDSD | SEQ ID NO: 11 |
| C176F | MEEPQSDPSVEPPLSQETFSDLWKLLPENNVLSPLPSQAMDDLMLSPD<br>DIEQWFTEDPGPDEAPRMPEAAPPVAPAPAAPTPAAPAPAPSWPLSSS<br>VPSQKTYQGSYGFRLGFLHSGTAKSVTCTYSPALNKMFCQLAKTCPVQ<br>LWDSTPPPGTRVRAMAIYKQSQHMTEVVRRFPHHERCSDSDGLAPP<br>QHLIRVEGNLRVEYLDDRNTFRHSVVVPYEPPEVGSDCTTIHYNYMCNS<br>SCMGGMNRRPILTIITLEDSSGNLLGRNSFEVRVCACPGRDRRTEEENL<br>RKKGEPHHELPPGSTKRALPNNTSSSPQPKKKPLDGEYFTLQIRGRERF<br>EMFRELNEALELKDAQAGKEPGGSRAHSSHLKSKKGQSTSRHKKLMFK<br>TEGPDSD | SEQ ID NO: 12 |
| H179Y | MEEPQSDPSVEPPLSQETFSDLWKLLPENNVLSPLPSQAMDDLMLSPD<br>DIEQWFTEDPGPDEAPRMPEAAPPVAPAPAAPTPAAPAPAPSWPLSSS<br>VPSQKTYQGSYGFRLGFLHSGTAKSVTCTYSPALNKMFCQLAKTCPVQ<br>LWDSTPPPGTRVRAMAIYKQSQHMTEVVRRCPHYERCSDSDGLAPPQ<br>HLIRVEGNLRVEYLDDRNTFRHSVVVPYEPPEVGSDCTTIHYNYMCNS<br>SCMGGMNRRPILTIITLEDSSGNLLGRNSFEVRVCACPGRDRRTEEENL<br>RKKGEPHHELPPGSTKRALPNNTSSSPQPKKKPLDGEYFTLQIRGRERF<br>EMFRELNEALELKDAQAGKEPGGSRAHSSHLKSKKGQSTSRHKKLMFK<br>TEGPDSD | SEQ ID NO: 13 |
| H179R | MEEPQSDPSVEPPLSQETFSDLWKLLPENNVLSPLPSQAMDDLMLSPD<br>DIEQWFTEDPGPDEAPRMPEAAPPVAPAPAAPTPAAPAPAPSWPLSSS<br>VPSQKTYQGSYGFRLGFLHSGTAKSVTCTYSPALNKMFCQLAKTCPVQ<br>LWDSTPPPGTRVRAMAIYKQSQHMTEVVRRCPHRERCSDSDGLAPPQ<br>HLIRVEGNLRVEYLDDRNTFRHSVVVPYEPPEVGSDCTTIHYNYMCNS<br>SCMGGMNRRPILTIITLEDSSGNLLGRNSFEVRVCACPGRDRRTEEENL<br>RKKGEPHHELPPGSTKRALPNNTSSSPQPKKKPLDGEYFTLQIRGRERF<br>EMFRELNEALELKDAQAGKEPGGSRAHSSHLKSKKGQSTSRHKKLMFK<br>TEGPDSD | SEQ ID NO: 14 |

-continued

| Mutation | Sequence (mutated residue relative to wildtype p53 shown bold, underlined) | SEQ ID NO: |
|---|---|---|
| Y220C | MEEPQSDPSVEPPLSQETFSDLWKLLPENNVLSPLPSQAMDDLMLSPD DIEQWFTEDPGPDEAPRMPEAAPPVAPAPAAPTPAAPAPAPSWPLSSS VPSQKTYQGSYGFRLGFLHSGTAKSVTCTYSPALNKMFCQLAKTCPVQ LWVDSTPPPGTRVRAMAIYKQSQHMTEVVRRCPHHERCSDSDGLAPP QHLIRVEGNLRVEYLDDRNTFRHSVVVPCEPPEVGSDCTTIHYNYMCNS SCMGGMNRRPILTIITLEDSSGNLLGRNSFEVRVCACPGRDRRTEEENL RKKGEPHHELPPGSTKRALPNNTSSSPQPKKKPLDGEYFTLQIRGRERF EMFRELNEALELKDAQAGKEPGGSRAHSSHLKSKKGQSTSRHKKLMFK TEGPDSD | SEQ ID NO: 15 |
| R337H | MEEPQSDPSVEPPLSQETFSDLWKLLPENNVLSPLPSQAMDDLMLSPD DIEQWFTEDPGPDEAPRMPEAAPPVAPAPAAPTPAAPAPAPSWPLSSS VPSQKTYQGSYGFRLGFLHSGTAKSVTCTYSPALNKMFCQLAKTCPVQ LWWDSTPPPGTRVRAMAIYKQSQHMTEVVRRCPHHERCSDSDGLAPP QHLIRVEGNLRVEYLDDRNTFRHSVVVPYEPPEVGSDCTTIHYNYMCNS SCMGGMNRRPILTIITLEDSSGNLLGRNSFEVRVCACPGRDRRTEEENL RKKGEPHHELPPGSTKRALPNNTSSSPQPKKKPLDGEYFTLQIRGREHF EMFRELNEALELKDAQAGKEPGGSRAHSSHLKSKKGQSTSRHKKLMFK TEGPDSD | SEQ ID NO: 16 |

The skilled person is readily able to determine equivalent mutations of the p53 polypeptide in the amino acid sequence of p53 polypeptides of other species, e.g. by sequence alignment.

Reference to a given p53 mutation numbered according to the amino acid sequence of the human wildtype p53 polypeptide (SEQ ID NO:1) includes equivalent mutations in homologous proteins to p53 in other species, e.g. mouse or rat.

For example, reference to "R175H" herein encompasses the equivalent arginine to histidine mutation at position 172 of the amino acid sequence for the mouse homologue of p53 (i.e. R172H)—see e.g. Olive et al, 2004 Cell 119, 847-860, which is hereby incorporated by reference in its entirety. Similarly, reference to "R175H p53 polypeptide" herein encompasses the polypeptide comprising the equivalent R172H mutant polypeptide of the mouse homologue of p53

Immunogens

The antibodies according to the present invention are produced according to methods described herein, raised using immunogens.

In the present invention, an immunogen is a peptide or polypeptide molecule. As used herein, a "peptide" is a chain of two or more amino acid monomers linked by peptide bonds. A peptide typically has a length in the region of about 2 to 50 amino acids. A "polypeptide" is a polymer chain of two or more peptides. Polypeptides typically have a length greater than about 50 amino acids.

In the methods of the present invention antibodies are raised by a method using as an immunogen a peptide or polypeptide comprising: (i) an antigen sequence, comprising an amino acid sequence of the mutant p53 polypeptide including the mutation and at least one amino acid either side of the mutation, and (ii) a scaffold sequence for providing the antigen sequence in a solvent-accessible configuration.

Antigen Sequence

The antigen sequence comprises, or consists of, an amino acid sequence of the mutant p53 polypeptide to which the antibody produced by the method is capable of binding.

The amino acid sequence of the mutant p53 polypeptide of the antigen sequence comprises the mutation; that is, the antigen sequence includes the mutated position of the mutant p53 polypeptide relative to the amino acid sequence of the wildtype p53 polypeptide.

The amino acid sequence of the mutant p53 polypeptide of the antigen sequence additionally comprises at least one amino acid immediately adjacent to the mutation. That is, the sequence includes at least one amino acid residue immediately upstream of (i.e. N-terminal to) or immediately downstream of (i.e. C-terminal to) the mutated position in the amino acid sequence of the mutated p53 polypeptide. The mutation is thereby presented in the context of the immediate sequence of amino acids in which it occurs in the mutant p53 polypeptide.

By way of illustration, with reference to R175H mutant p53 represented by SEQ ID NO:1 above, the amino acid sequence of the mutant p53 polypeptide comprises at least "RH", or "HC".

In some embodiments, the amino acid sequence of the mutant p53 polypeptide of the antigen sequence may comprise one of at least 1, 2, 3, 4, 5, 6, 7, 8, 9, or 10 amino acids immediately upstream of the mutated position. In some embodiments, the amino acid sequence of the mutant p53 polypeptide of the antigen sequence may comprise one of at least 1, 2, 3, 4, 5, 6, 7, 8, 9, or 10 amino acids immediately downstream of the mutated position. In some embodiments, the amino acid sequence of the mutant p53 polypeptide of the antigen sequence may comprise one of at least 1, 2, 3, 4, 5, 6, 7, 8, 9, or 10 amino acids immediately upstream of the mutated position, and one of at least 1, 2, 3, 4, 5, 6, 7, 8, 9, or 10 amino acids immediately upstream of the mutated position.

In some embodiments, the amino acid sequence of the mutant p53 polypeptide of the antigen sequence may comprise or consist of one of not more than 25, 20, 19, 18, 17, 16, 15, 14, 13, 12, 11, 12, 11, or 10 amino acids immediately upstream of the mutated position. In some embodiments, the amino acid sequence of the mutant p53 polypeptide of the antigen sequence may comprise or consist of one of not more than 25, 20, 19, 18, 17, 16, 15, 14, 13, 12, 11, 12, 11, or 10 amino acids immediately downstream of the mutated position. In some embodiments, the amino acid sequence of the mutant p53 polypeptide of the antigen sequence may comprise or consist of one of not more than 25, 20, 19, 18, 17, 16, 15, 14, 13, 12, 11, 12, 11, or 10 amino acids immediately upstream of the mutated position, and one of not more than 25, 20, 19, 18, 17, 16, 15, 14, 13, 12, 11, 12, 11, or 10 amino acids immediately upstream of the mutated position.

In some embodiments, the amino acid sequence of the mutant p53 polypeptide of the antigen sequence may comprise or consist of one of 1-2, 1-3, 1-4, 1-5, 1-6, 1-7, 1-8, 1-9, 1-10, 1-11, 1-12, 1-13, 1-14, 1-15, or 1-20 amino acids immediately upstream of the mutated position. In some embodiments, the amino acid sequence of the mutant p53 polypeptide of the antigen sequence may comprise or consist of one of 1-2, 1-3, 1-4, 1-5, 1-6, 1-7, 1-8, 1-9, 1-10, 1-11, 1-12, 1-13, 1-14, 1-15, or 1-20 amino acids immediately downstream of the mutated position. In some embodiments, the amino acid sequence of the mutant p53 polypeptide of the antigen sequence may comprise or consist of one of 1-2, 1-3, 1-4, 1-5, 1-6, 1-7, 1-8, 1-9, 1-10, 1-11, 1-12, 1-13, 1-14, 1-15, or 1-20 amino acids immediately upstream of the mutated position and one of 1-2, 1-3, 1-4, 1-5, 1-6, 1-7, 1-8, 1-9, 1-10, 1-11, 1-12, 1-13, 1-14, 1-15, or 1-20 amino acids immediately downstream of the mutated position.

In some embodiments, the amino the amino acid sequence of the mutant p53 polypeptide of the antigen sequence may comprise or consist of one of 7-11, 3-7, or 2-5 amino acids immediately upstream and downstream of the mutated position.

The amino acid sequence of the mutant p53 polypeptide (including the mutation and upstream/downstream amino acids) may comprise or consist of one of at least 2, 3, 4, 5, 6, 7, 8, 9, 10, 11, 12, 13, 14, 15, 16, 17, 18, 19, 20, 25, or 30 amino acids. In some embodiments, the amino acid sequence of the mutant p53 polypeptide may comprise or consist of not more than 50, 45, 40, 35, 30, 20, 19, 18, 17, 16, 15, 14, 13, 12, 11, 12, 11, or 10 amino acids. In some embodiments, the amino acid sequence of the mutant p53 polypeptide may be 2-50, 5-40, 5-30, 5-25, 5-20, 5-15, 8-30, 8-25, 8-20, 8-15, 10-30, 10-25, 10-20, or 10-15 amino acids in length. In some preferred embodiments the amino acid sequence of the mutant p53 polypeptide may be 5-20 or 8-20 amino acids in length.

In some embodiments, the antigen sequence of the immunogen comprises more than a single copy of the mutation. That is, in some embodiments, the antigen sequence comprises two or more amino acid sequences of the mutant p53 polypeptide. In embodiments wherein the antigen sequence comprises multiple amino acid sequences of the mutant p53 polypeptide, each amino acid sequence of the mutant p53 polypeptide may independently be defined according to an embodiment described herein.

By way of example, with reference to R175H mutant p53 represented by SEQ ID NO:1 above, an antigen sequence comprising more than one amino acid sequence of the R175H mutant p53 polypeptide may comprise the sequence "QHMTEVVRHCPHHERCSDgsgTEVVRHCPHHER" (SEQ ID NO:90) (lower case indicates a flexible serine/glycine linker sequence). It will be clear that this sequence comprises two amino acid sequences of the mutant p53 polypeptide; (1) QHMTEVVRHCPHHERCSD and (2) TEVVRHCPHHER.

In some embodiments, the antigen sequence comprises one of 1, 2, 3, 4, 5 or 6 amino acid sequences of the mutant p53 polypeptide. In some embodiments, the antigen sequence comprises at least 2, 3 or 4 amino acid sequences of the mutant p53 polypeptide. In some embodiments, the antigen sequence comprises not more than 6, 5, 4 or 3 amino acid sequences of the mutant p53 polypeptide. In some embodiments, the antigen sequence comprises or consists of 2 or 3 amino acid sequences of the mutant p53 polypeptide.

In embodiments where the antigen sequence comprises more than one amino acid sequence of the mutant p53 polypeptide, each amino acid sequence of the mutant p53 polypeptide may be identical. In some embodiments, an antigen sequence may comprise non-identical amino acid sequences of the mutant p53 polypeptide. In some embodiments, each amino acid sequence of the mutant p53 polypeptide may be non-identical.

In some embodiments wherein the antigen sequence comprises more than one amino acid sequence of the mutant p53 polypeptide, the antigen sequence additionally comprises linker sequence(s) between amino acid sequences of the mutant p53 polypeptide. Linker sequences are described hereinbelow.

Scaffold Sequence

The immunogen also comprises a scaffold sequence for providing the antigen sequence in a solvent-accessible configuration.

By providing the antigen sequence in a solvent-accessible configuration, the scaffold sequence provides the opportunity to raise antibodies directed against the antigen sequence of the immunogen. Specifically, such configuration allows antibody to physically contact the antigen sequence.

Whether a scaffold sequence provides the antigen sequence in a solvent accessible configuration can be determined or predicted based on the amino acid sequence of the immunogen.

Solvent accessible and/or inaccessible amino acids or sequences of amino acids may be predicted based on the sequence of amino acids, or based on the three-dimensional structure of an amino acid sequence. Solvent accessibility can, for example, be predicted by calculating the accessible surface area (ASA), as reviewed in Ali et al., Current protein and Peptide Science, 2014, 15 (3), which is hereby incorporated by reference in its entirety. ASA may be calculated, for example, using the Shrake-Rupley (rolling probe) algorithm, Z-layer integration, intersection, linear combinations of pairwise overlaps (LCPO), or power diagram. Tools for predicting ASA for an amino acid sequence include artificial neural networks (ANN), support vector machines (SVM), and the Markov chain model (MCM). Software which can be used to predict solvent accessibility includes ASAview, ACCpro, PDBePISA, CCP4, GETAREA, DSSP, ProtSA, NACCESS, ACCESS, POPS-R, SERF, NetSurfP, ASAP, SANN and SABLE. ACCPro5.1 implements a 1D-recursive neural network algorithm.

In some embodiments, the scaffold sequence is derived from a peptide or polypeptide comprising a solvent-accessible sequence.

In some embodiments, the antigen sequence is provided in a solvent accessible configuration by being inserted in, or substituted for all or part of, the solvent accessible sequence of the peptide or polypeptide. It will be appreciated that in such embodiments, the scaffold sequence is interrupted by the antigen sequence.

In some embodiments, the antigen sequence may be inserted between two amino acids within a solvent-accessible sequence of the peptide or polypeptide from which the scaffold sequence is derived. In some embodiments, the antigen sequence may be inserted in place of one or more residues of the solvent accessible sequence.

Solvent accessible and/or inaccessible amino acids or sequences of amino acids are known or predicted for some peptides/polypeptides, and can be identified by the skilled person with reference to databases known to the skilled person, including ASAview. Solvent accessible and/or inaccessible amino acids or sequences of amino acids may also be predicted based on the sequence of amino acids for a peptide/polypeptide, or based on the three-dimensional structure of an amino acid sequence for a peptide/polypeptide, using the tools described hereinabove.

Any suitable scaffold sequence may be used in the immunogen according to the present invention. In some embodiments, the scaffold sequence may be selected such that:
a) the antigen sequence inserted in the scaffold sequence is presented on the surface of the folded scaffold sequence; and/or
b) the folding and/or the three-dimensional structure of the scaffold sequence is not substantially changed or disrupted by the antigen sequence; and/or
c) the scaffold sequence provides for high expression and/or easy purification of the immunogen; and/or
d) the scaffold sequence is immunogenic.

The skilled person is able to readily identify scaffold sequences possessing the above recited properties, e.g. by analysis of scaffold/immunogen sequences using algorithm-based predictions from amino acid sequences/protein structures, reference to databases, or empirical analysis.

In some embodiments, the peptide/polypeptide comprising a solvent-accessible sequence from which the scaffold sequence is derived is a thioredoxin. Thioredoxin structure and function is described in Collet and Messens, Antioxid Redox Signal (2010) 13:1205-1216, which is hereby incorporated by reference in its entirety. Barrell et al. Protein Expr Purif (2004) 33 (1): 153-159 (hereby incorporated by reference in entirety) describes insertion of an amino acid sequence into the active site of a bacterial thioredoxin for the production of antibodies specific to the inserted amino acid sequence.

In some embodiments the thioredoxin comprises the amino acid sequence according to SEQ ID NO: 17, or an fragment thereof having at least 20 amino acids (optionally one of at least 30, 40, 50, 60, 70, 80, 90 or 100 amino acids), having at least 70%, 75%, 80%, 85%, 90%, 91%, 92%, 93%, 94%, 95%, 96%, 97%, 98% or 99% sequence identity thereto (e.g. following alignment), and having the active site motif Cys-Gly-Pro-Cys (SEQ ID NO:91):

```
                                        (SEQ ID NO: 17)
MSDKIIHLTDDSFDTDVLKADGAILVDFWAEWC

GPCKMIAPILDEIADEYQGKLTVAKLNIDQNPG

TAPKYGIRGIPTLLLFKNGEVAATKVGALSKGQ

LKEFLDANLA
```

In some embodiments, the solvent-accessible sequence of the thioredoxin is the active site sequence. The active site sequence of thioredoxin corresponds to the motif Cys-Gly-Pro-Cys, which is conserved in thioredoxins of diverse origin. In some embodiments, the antigen sequence is inserted into, or substituted for all or part of, this sequence. In some embodiments the antigen sequence is inserted after the N-terminal Cys residue of the active site sequence, or after the Gly residue, or after the Pro residue. In some embodiments, the antigen sequence is inserted immediately upstream of the N-terminal Cys residue of the active site sequence in the amino acid sequence of the thioredoxin. In some embodiments, the antigen sequence is inserted immediately downstream of the C-terminal Cys residue of the active site sequence in the amino acid sequence of the thioredoxin.

In some embodiments the scaffold sequence comprises, or consists of, SEQ ID NO:17. In some embodiments the scaffold sequence comprises, or consists of, an amino acid sequence having at least 70%, 75%, 80%, 85%, 90%, 91%, 92%, 93%, 94%, 95%, 96%, 97%, 98% or 99% sequence identity to SEQ ID NO:17, or a fragment thereof having at least 20 amino acids (optionally one of at least 30, 40, 50, 60, 70, 80, 90 or 100 amino acids).

In some embodiments, the scaffold sequence may comprise one or more additional amino acids to facilitate surface orientation and/or solvent exposure of the antigen sequence of the immunogen. In some embodiments, the scaffold may comprise amino acid residues at one of each end of the antigen sequence to facilitate surface orientation and/or solvent exposure of the antigen sequence provided in the sequence of the immunogen.

By way of illustration, with reference to the R175H immunogen shown in FIG. 1A (i.e. SEQ ID NO: 80), the scaffold (positions 1 to 35 and positions 91 to 165 of SEQ ID NO:80) of the immunogen comprises an additional proline residue adjacent to the antigen sequence insert, so that the antigen sequence is flanked in the sequence of the immunogen by proline residues (positions 35 and 91 of SEQ ID NO:80).

Linker Sequence

The immunogen may comprise one or more linker sequences between amino acid sequences. As explained above, the immunogen may comprise linker sequences between amino acid sequences of a mutant p53 polypeptide within the antigen sequence.

In some embodiments, the immunogen may additionally comprise one or more linker sequences between the antigen sequence and scaffold sequence. In embodiments wherein the antigen sequence is inserted in, or substituted for all or part of, a scaffold sequence, a linker sequence may be provided at one or both 'ends' of the antigen sequence. By way of illustration, the immunogen may comprise the following structure:

[scaffold sequence]-{linker}-[antigen sequence]-{linker}-[scaffold sequence]

Linker sequences are known to the skilled person, and are described, for example in Chen et al., Adv Drug Deliv Rev (2013) 65 (10): 1357-1369, which is hereby incorporated by reference in its entirety.

In some embodiments, a linker sequence may be a flexible linker sequence. Advantageously, flexible linker sequences allow for relative movement of the amino acid sequences which are linked by the linker sequence, enhancing accessibility of the sequence to antigen binding molecules. Flexible linkers are known to the skilled person, and several are identified in Chen et al., Adv Drug Deliv Rev (2013) 65 (10): 1357-1369, incorporated by reference hereinabove. Flexible linker sequences often comprise high proportions of glycine and/or serine residues.

In some embodiments, the linker sequence comprises at least one glycine residue and/or at least one serine residue. In some embodiments the linker sequence consists of glycine and serine residues. In some embodiments the linker sequence comprises or consists of alternating glycine and serine residues (i.e. "GSGS" (SEQ ID NO:92) . . . etc.). In some embodiments, the linker sequence has a length of 1-2, 1-3, 1-4, 1-5, 1-6, 1-7, 1-8, 1-9, 1-10, 1-15 or 1-20 amino acids.

Flexible linker sequences provided between plural sequences of a mutant p53 polypeptide within an antigen sequence according to the invention allows flexible relative arrangement of the mutant p53 polypeptide sequences. In some embodiments, linker sequence(s) between mutant p53 polypeptide sequences comprise or consist of glycine and serine residues. In some embodiments, the linker sequences comprise or consist of alternating glycine and serine residues. In some embodiments, the linker sequences comprise or consist of alternating glycine and serine residues of 1-2, 1-3, 1-4 or 1-5 amino acids in length. In some embodiments, linker sequences between mutant p53 polypeptide sequences comprise or consist of the sequence GSG (SEQ ID NO:89).

The immunogen may in addition to the antigen sequence, scaffold sequence and any linker sequence(s) comprise further amino acids or amino acid sequences. For example, the immunogen may comprise amino acid sequence(s) to facilitate expression, folding, trafficking, processing or purification of the immunogen. For example, the immunogen may comprise a sequence encoding a His, (e.g. 6×His), Myc GST, MBP, FLAG, HA, E, or Biotin tag, optionally at the N- or C-terminus.

Exemplary Embodiments of Immunogens

The present invention provides an immunogen comprising: (i) an antigen sequence, comprising an amino acid sequence of the R175H mutant p53 polypeptide including the R175H mutation and at least one amino acid either side of the mutation, and (ii) a scaffold sequence for providing the antigen sequence in a solvent-accessible configuration. In some embodiments, the immunogen comprises more than sequence of the R175H mutant p53 polypeptide; in some embodiments the immunogen comprises e.g. 2, 3, 4 or 5 such sequences. In some embodiments, the immunogen comprises an antigen sequence comprising sequences of the R175H mutant p53 polypeptide (including the R175H mutation) of different lengths. In some embodiments, the antigen sequence comprises sequence(s) of the R175H mutant p53 polypeptide of from 5 to 22, 7 to 20 or 9 to 18 amino acids in length. In some embodiments, the immunogen comprises an antigen sequence comprising one or more of: QHMTEVVRHCPHHERCSD (SEQ ID NO:77), TEVVRHCPHHER (SEQ ID NO:78) and VRHCPHHER (SEQ ID NO:79). In some embodiments the immunogen comprises an antigen sequence comprising SEQ ID NOs: 77, 78 and 79. In some embodiments, the immunogen comprises an antigen sequence comprising SEQ ID NOs: 77, 78 and 79, and comprising linker sequences as described hereinabove between SEQ ID NOs: 77, 78 and 79. In some embodiments, the immunogen comprises an antigen sequence comprising SEQ ID NOs: 77, 78 and 79 and linker sequences between the between the antigen sequence and scaffold sequence. In some embodiments the immunogen comprises, or consists of the following sequence:

```
                                    (SEQ ID NO: 80)
MSDKIIHLTDDSFDTDVLKADGAILVDFWAEWC

GPGSGSGQHMTEVVRHCPHHERCSDGSGTEVVR

HCPHHERGSGVRHCPHHERGSGSGPCKMIAPIL

DEIADEYQGKLTVAKLNIDQNPGTAPKYGIRGI

PTLLLFKNGEVAATKVGALSKGQLKEFLDANLA

GSGHHHHHH
```

The present invention provides an immunogen comprising: (i) an antigen sequence, comprising an amino acid sequence of the R248Q mutant p53 polypeptide including the R248Q mutation and at least one amino acid either side of the mutation, and (ii) a scaffold sequence for providing the antigen sequence in a solvent-accessible configuration. In some embodiments, the immunogen comprises more than sequence of the R248Q mutant p53 polypeptide; in some embodiments the immunogen comprises e.g. 2, 3, 4 or 5 such sequences. In some embodiments, the immunogen comprises an antigen sequence comprising sequences of the R248Q mutant p53 polypeptide (including the R248Q mutation) of different lengths. In some embodiments, the antigen sequence comprises sequence(s) of the R248Q mutant p53 polypeptide of from 10 to 22, 12 to 20 or 15 to 18 amino acids in length. In some embodiments, the immunogen comprises an antigen sequence comprising one or more of: SCMGGMNQRPILTIITLED (SEQ ID NO:81), MGGMNQRPILTIITLED (SEQ ID NO: 82) and NSSCMGGMNQRPILT (SEQ ID NO:83). In some embodiments the immunogen comprises an antigen sequence comprising SEQ ID NOs: 81, 82 and 83. In some embodiments, the immunogen comprises an antigen sequence comprising SEQ ID NOs: 81, 82 and 83, and comprising linker sequences as described hereinabove between SEQ ID NOs: 81, 82 and 83. In some embodiments, the immunogen comprises an antigen sequence comprising SEQ ID NOs: 81, 82 and 83 and linker sequences between the between the antigen sequence and scaffold sequence. In some embodiments the immunogen comprises, or consists of the following sequence:

```
                                    (SEQ ID NO: 84)
MSDKIIHLTDDSFDTDVLKADGAILVDFWAEWC

GPGSGSGSCMGGMNQRPILTIITLEDGSGMGGM

NQRPILTIITLEDGSGNSSCMGGMNQRPILTGS

GSGPCKMIAPILDEIADEYQGKLTVAKLNIDQN

PGTAPKYGIRGIPTLLLFKNGEVAATKVGALSK

GQLKEFLDANLAGSGHHHHHH
```

The present invention provides an immunogen comprising: (i) an antigen sequence, comprising an amino acid sequence of the R273H mutant p53 polypeptide including the R273H mutation and at least one amino acid either side of the mutation, and (ii) a scaffold sequence for providing the antigen sequence in a solvent-accessible configuration. In some embodiments, the immunogen comprises more than sequence of the R273H mutant p53 polypeptide; in some embodiments the immunogen comprises e.g. 2, 3, 4 or 5 such sequences. In some embodiments, the immunogen comprises an antigen sequence comprising sequences of the R273H mutant p53 polypeptide (including the R273H mutation) of different lengths. In some embodiments, the antigen sequence comprises sequence(s) of the R273H mutant p53 polypeptide of from 5 to 20, 6 to 18 or 10 to 15 amino acids in length. In some embodiments, the immunogen comprises an antigen sequence comprising one or more of: RNSFEVHVCA (SEQ ID NO:85), NLLGRNSFEVHVCAC (SEQ ID NO:86) and GRNSFEVHVCACP (SEQ ID NO:87). In some embodiments the immunogen comprises an antigen sequence comprising SEQ ID NOs: 85, 86 and 87. In some embodiments, the immunogen comprises an antigen sequence comprising SEQ ID NOs: 85, 86 and 87, and comprising linker sequences as described hereinabove between SEQ ID NOs: 85, 86 and 87. In some embodiments, the immunogen comprises an antigen sequence comprising SEQ ID NOs: 85, 86 and 87 and linker sequences between the between the antigen sequence and scaffold sequence. In some embodiments the immunogen comprises, or consists of the following sequence:

(SEQ ID NO: 88)
MSDKIIHLTDDSFDTDVLKADGAILVDFWAEWC

GPGSGSGRNSFEVHVCAGSGNLLGRNSFEVHVC

ACGSGGRNSFEVHVCACPGSGSGPCKMIAPILD

EIADEYQGKLTVAKLNIDQNPGTAPKYGIRGIP

TLLLFKNGEVAATKVGALSKGQLKEFLDANLAG

SGHHHHHH

Methods for Producing an Antibody

The present invention provides methods for producing an antibody. The methods typically involve introducing material into an animal which is recognised by the immune system of the animal to be foreign (i.e. non-host), resulting in the selective production by the animal of antibodies capable of binding to the material.

The material used to provoke an immune response is referred to herein as an immunogen. The immunogen may comprise or consist of, or may be processed to, an antigen. As used herein, "antigen" refers to a molecule capable of stimulating the production of an antibody by stimulating an adaptive immune response, in particular the B lymphocyte mediated (humoral) adaptive immune response. The term "antigenic" as used herein refers to the ability of a molecule to stimulate the production of antibodies by stimulating an adaptive immune response, in particular a B lymphocyte mediated adaptive immune response.

In the present invention, an immunogen may be a peptide or polypeptide molecule. The ability of animal immune system to produce antibodies capable of binding specifically to antigens can be used to generate antibodies for detecting molecules of interest in various research, diagnostic and therapeutic applications.

Methods for producing antibodies by immunization of animals are well known in the art, and are described, for example, in Antibodies: A Laboratory Manual, Second Edition, 2014; Edward A. Greenfield, Cold Spring Harbor Laboratory Press, which is hereby incorporated by reference in its entirety. In particular, Chapter 6 provides detailed description of the immunization of animals for the production of antibodies.

Antibody production involves challenging an animal with an immunogen to stimulate production of antigen-specific antibodies which can then be recovered from the animal.

As used herein, "producing" an antibody refers to the process of creating an antibody, which may include one or more of, for example: preparing immunogen for immunization, immunizing an animal, hybridoma formation, collecting antibody, screening for binding to target, isotyping antibody, purifying antibody, or labelling antibody.

In the methods of the present invention antibodies are produced by immunizing an animal with an immunogen. Any animal capable of producing antibody in response to immunization with immunogen is useful in accordance with the present methods. It will be appreciated that the methods of the invention are not methods for the diagnosis or treatment of diseases, nor methods of surgery. In some embodiments, the animal may be a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate). In particular, the animal may be a mouse (e.g. *Mus musculus*), rat (e.g. *Rattus norvegicus*), or rhesus macaque (*Macaca mulatta*). In particular embodiments of the animal is a mouse. In the present methods, immunogen is administered to animals by way of immunization.

Immunization of an animal with an immunogen according to the present invention can be by any suitable means, such as those described, for example, in Antibodies: A Laboratory Manual, Second Edition, 2014; Edward A. Greenfield, Cold Spring Harbor Laboratory Press (hereby incorporated by reference in entirety), in particular at Chapter 6. Materials for immunizations may be formulated as appropriate. For example, immunogen peptide/polypeptide may be diluted in sterile saline, and may combined with an adjuvant (e.g. Complete or Incomplete Freund's Adjuvant and/or CpG) to form a stable emulsion. Appropriate amounts of immunogen for an individual immunization can be readily determined by the skilled person, e.g. by reference to Antibodies: A Laboratory Manual, Second Edition, 2014; Edward A. Greenfield, Cold Spring Harbor Laboratory Press (incorporated by reference herein above). Appropriate volumes and concentrations for immunizations can also be determined by the skilled person.

The method for producing an antibody according to the present invention may comprise a step of screening for the production of antibody; for example, at an appropriate period of time following administration, a sample (e.g. a blood sample) may be obtained from the animal and analysed for antibody production. Immunoassays for the detection and quantification of antibody production are well known to the skilled person, and are described, for example, in Antibodies: A Laboratory Manual, Second Edition, 2014; Edward A. Greenfield, Cold Spring Harbor Laboratory Press, 2014 (incorporated by reference herein above), in particular at Chapter 15. For example, a blood, plasma, serum or ascites sample may be collected from the animal, and analysed e.g. by ELISA or flow cytometry.

Antibodies produced by the methods according to the invention can be analysed for binding to mutant p53 polypeptide and/or wildtype p53 polypeptide by methods known to the skilled person. For example, analysis may be performed by ELISA, immunoblot (e.g. western blot), flow cytometry, immunohistochemistry, immunoprecipitation, surface plasmon resonance (BIAcore), biolayer interferometry.

Analysis may also include analysis of epitopes for antibodies produced by the methods, and may include analysis to determine the identity (e.g. the sequence) of antibodies. Such analysis may include antibody sequencing, e.g. by mass spectrometry.

In some embodiments the methods for producing an antibody may include isolating antibodies capable of binding to the mutant p53 polypeptide. In some embodiments, the one or more antibodies are isolated from an animal. The antibodies may be recovered from e.g. the blood, plasma, serum, or ascites of the animal. In some embodiments, antibodies may be isolated from cells obtained from an animal which has been immunized with immunogen in accordance with the invention. In some embodiments, the cells are B lymphocytes. In some embodiments, the antibodies may be isolated from cell culture supernatant from B lymphocytes cultured in vitro.

Polyclonal antibodies may be recovered directly from blood or serum obtained from the animal at an appropriate time following administration according to the invention.

In some embodiments, antibodies are obtained from a hybridoma producing one or more antibodies capable of binding to a mutant p53 polypeptide. In some embodiments, the antibodies are obtained from cell culture supernatant of a culture of a hybridoma. In some embodiments, the antibodies are obtained from the blood, plasma, serum, or ascites of an animal immunized with a hybridoma producing one or more antibodies capable of binding to the mutant p53 polypeptide of interest.

Methods for isolating (i.e. purifying) antibodies from an antibody containing sample (e.g. cell, cell extract, cell culture medium, blood, plasma, serum, ascites) are well known to the skilled person, and are described in detail in Antibodies: A Laboratory Manual, Second Edition, 2014; Edward A. Greenfield, Cold Spring Harbor Laboratory Press (incorporated by reference herein above), in particular at Chapter 10. The methods include, for example, ion exchange chromatography, protein A or protein G based purification, gel electrophoresis, dialysis, and affinity purification based on target binding.

In some embodiments, the methods of the present invention comprise producing a hybridoma producing one or more antibodies capable of binding to the mutant p53 polypeptide of interest. The methods comprise fusing a cell capable of producing one more antibodies capable of binding to the mutant p53 polypeptide of interest isolated from the animal with a myeloma cell, to produce a hybridoma.

In particular, the methods of the present invention are for producing monoclonal antibodies capable of binding to a mutant p53 polypeptide. This is achieved by immunizing an animal with immunogen according to the invention, and subsequently generating monoclonal hybridomas from cells isolated from the animals, the hybridomas producing antibodies of a single type (i.e. of a single specificity), which are capable of binding to the mutant p53 polypeptide.

Methods for hybridoma formation are well known to the skilled person, and are described, for example, in Antibodies: A Laboratory Manual, Second Edition, 2014; Edward A. Greenfield, Cold Spring Harbor Laboratory Press (incorporated by reference herein above); in particular at Chapter 7. Briefly, an animal is immunized in accordance with the invention, stimulating an adaptive immune response, and B lymphocytes are isolated from the animal and fused with a suitable myeloma cell line to produce a hybridoma. B lymphocytes and myeloma cells may be fused using methods known to the skilled person. For example, cells may be fused by co-centrifugation in polyethylene glycol (PEG). Following fusion, cells are plated-out by limiting dilution in tissue culture plates to roughly a single cell per well, and cultured in vitro. Hybridomas may be selected by culture using selective media known in the art (e.g. media containing hypoxanthine-aminopterin-thymidine (HAT)), which unfused lymphocytes and myeloma cells are unable to grow or survive in.

Antibodies produced by the methods of the invention may be produced on a large scale using methods known to the skilled person. Hybridomas can be propagated either in in vitro culture using standard methods of cell culture, or in vivo, e.g. as ascites in a host animal. In some embodiments, the methods of the present invention comprise propagating the hybridoma by in vitro cell culture. In some embodiments, the methods comprise propagating the hybridoma in vivo by injecting a host animal with the hybridoma.

Antibodies according to the invention can also be produced recombinantly, as described hereinbelow. For example, a polynucleotide encoding a monoclonal antibody can be isolated from a B cell or hybridoma cell producing an antibody, e.g., by reverse transcription PCR (RT-PCR) using oligonucleotide primers that specifically amplify the genes encoding the heavy and light chains of the antibody, and the sequence of the polynucleotide can be determined. Isolated polynucleotides encoding the heavy and light chains can be cloned into suitable expression vectors which produce the monoclonal antibodies when transfected into host cells such as *E. coli*, simian COS cells, Chinese hamster ovary (CHO) cells, or myeloma cells that do not otherwise produce immunoglobulin proteins.

Antibodies

The antibodies of the present invention are specific for mutant p53 polypeptides over wildtype p53 polypeptide.

The antibodies may be capable of binding to particular mutant p53 polypeptides, and may not be capable of binding to wildtype p53 polypeptide. By "not capable of binding", we mean that the antibodies exhibit substantially no binding to the peptide/polypeptide, or do not exhibit significant binding to the peptide/polypeptide, e.g. above non-specific binding levels.

As used herein, an antibody which is "specific for" a given polypeptide/peptide displays specific binding to the polypeptide/peptide. "Specific binding" is interaction which is not non-specific. Specific binding is mediated by non-covalent interactions such as Van der Waals forces, electrostatic interactions, hydrogen bonding, and hydrophobic interactions. An antibody of the present invention preferably displays specific binding to the mutant p53 polypeptide for which the antibody is specific over wildtype p53 and/or other, different, mutants of p53.

An antibody which is specific for a given peptide/polypeptide over another, reference peptide/polypeptide may bind to the given peptide/polypeptide with greater affinity than the affinity of binding of the antibody to the reference peptide/polypeptide. An antibody displaying 'greater affinity' for a given peptide/polypeptide binds to that peptide/polypeptide with greater strength as compared to the strength of binding to the reference peptide/polypeptide. An antibody of the present invention may bind to the mutant p53 polypeptide for which the antibody is specific with greater affinity as compared to the affinity of binding by the antibody to wildtype p53 and/or other, different, mutants of p53.

The affinity of an antibody for its antigen refers to the strength with which an antibody binds to the antigen. Antibody affinity can be determined by methods well known to the person skilled in the art. Such methods include, for example, in vitro analysis by SPR assay with purified antigen. Binding can be expressed in the following terms: "on rate" $k_{on}$, a constant representing how quickly the antibody/antigen complex forms; "off rate" $k_{off}$, a constant representing how quickly the antibody/antigen complex dissociates; and the equilibrium dissociation constant $K_D$, calculated according to the formula $K_D=(K_{off}/K_{on})$.

The affinity of binding of an antibody for a peptide/polypeptide can be determined quantitatively. In some embodiments, an antibody displaying greater affinity for a given peptide/polypeptide as compared to a reference peptide/polypeptide binds to the given peptide/polypeptide with a Kp value or an EC50 value which is less than the value for binding of the antibody to the reference peptide/polypeptide.

"Cross-reactivity" refers to the ability of an antibody to bind to more than one peptide/polypeptide. That is, an antibody displaying binding to two or more peptide/polypeptides is said to be "cross-reactive" for those peptides/polypeptides. An antibody according to the present invention preferably displays low or no cross-reactivity to wildtype p53 and/or mutants of p53 other than the mutant p53 polypeptide for which the antibody is specific. By "not cross-reactive" we mean that an antibody exhibits low cross-reactivity, no cross-reactivity or substantially no binding to the respective peptide/polypeptide.

The antibodies according to the present invention display greater affinity for a given mutant p53 polypeptide as compared to affinity for wildtype p53 polypeptide. In some embodiments, the antibodies display greater affinity for a given mutant of human p53 polypeptide as compared to affinity for wildtype human p53 polypeptide. In some embodiments the antibodies display greater affinity for a p53 peptide/polypeptide comprising a mutation corresponding to one of R175H, R248Q, R273H, R248W, G245S, R273C, R282W, R249S, G245D, C176F, H179Y, H179R, Y220C or R337H as compared to affinity for a p53 peptide/polypeptide not comprising said mutation. In some embodiments, an antibody may display greater affinity for a peptide/polypeptide comprising the amino acid sequence of one of SEQ ID NOs: 3, 4, 5, 6, 7, 8, 9, 10, 11, 12, 13, 14, 15, or 16 or a fragment thereof comprising the mutation, as compared to affinity for a peptide/polypeptide comprising the amino acid sequence of SEQ ID NO:1, or a fragment thereof.

The antibodies according to the present invention may display greater affinity for a given mutant p53 polypeptide as compared to other mutant p53 polypeptides. In some embodiments, the antibodies display greater affinity for a given mutant of human p53 polypeptide as compared to affinity for other mutants of human p53 polypeptide.

In some embodiments the antibodies display greater affinity for a p53 peptide/polypeptide comprising a mutation corresponding to R175H as compared to affinity for a p53 peptide/polypeptide not comprising said mutation, or comprising a mutation corresponding to one or more of R248Q, R273H, R248W, G245S, R273C, R282W, R249S, G245D, C176F, H179Y, H179R, Y220C or R337H.

In some embodiments, an antibody may display greater affinity for a polypeptide/peptide comprising or consisting of the amino acid sequence of SEQ ID NO:3, or a fragment thereof comprising the R175H mutation, as compared to a polypeptide/peptide comprising or consisting of the amino acid sequence of one of SEQ ID NO:1, 4, 5, 6, 7, 8, 9, 10, 11, 12, 13, 14, 15 or 16.

In some embodiments the antibodies display greater affinity for a p53 peptide/polypeptide comprising a mutation corresponding to R248Q as compared to affinity for a p53 peptide/polypeptide not comprising said mutation, or comprising a mutation corresponding to one or more of R175H, R273H, R248W, G245S, R273C, R282W, R249S, G245D, C176F, H179Y, H179R, Y220C or R337H.

In some embodiments, an antibody may display greater affinity for a polypeptide/peptide comprising or consisting of the amino acid sequence of SEQ ID NO:4, or a fragment thereof comprising the R248Q mutation, as compared to a polypeptide/peptide comprising or consisting of the amino acid sequence of one of SEQ ID NO:1, 3, 5, 6, 7, 8, 9, 10, 11, 12, 13, 14, 15 or 16.

In some embodiments the antibodies display greater affinity for a p53 peptide/polypeptide comprising a mutation corresponding to R273H as compared to affinity for a p53 peptide/polypeptide not comprising said mutation, or comprising a mutation corresponding to one or more of R175H, R248Q, R248W, G245S, R273C, R282W, R249S G245D, C176F, H179Y, H179R, Y220C or R337H.

In some embodiments, an antibody may display greater affinity for a polypeptide/peptide comprising or consisting of the amino acid sequence of SEQ ID NO:5, or a fragment thereof comprising the R273H mutation, as compared to a polypeptide/peptide comprising or consisting of the amino acid sequence of one of SEQ ID NO:1, 3, 4, 6, 7, 8, 9, 10, 11, 12, 13, 14, 15, or 16.

In some embodiments the antibodies display greater affinity for a p53 peptide/polypeptide comprising a mutation corresponding to R248W as compared to affinity for a p53 peptide/polypeptide not comprising said mutation, or comprising a mutation corresponding to one or more of R175H, R248Q, R273H, G245S, R273C, R282W, R249S, G245D, C176F, H179Y, H179R, Y220C or R337H.

In some embodiments, an antibody may display greater affinity for a polypeptide/peptide comprising or consisting of the amino acid sequence of SEQ ID NO:6, or a fragment thereof comprising the R248W mutation, as compared to a polypeptide/peptide comprising or consisting of the amino acid sequence of one of SEQ ID NO:1, 3, 4, 5, 7, 8, 9, 10, 11, 12, 13, 14, 15 or 16.

In some embodiments the antibodies display greater affinity for a p53 peptide/polypeptide comprising a mutation corresponding to G245S as compared to affinity for a p53 peptide/polypeptide not comprising said mutation, or comprising a mutation corresponding to one or more of R175H, R248Q, R273H, R248W, R273C, R282W, R249S, G245D, C176F, H179Y, H179R, Y220C or R337H.

In some embodiments, an antibody may display greater affinity for a polypeptide/peptide comprising or consisting of the amino acid sequence of SEQ ID NO:7, or a fragment thereof comprising the G245S mutation, as compared to a polypeptide/peptide comprising or consisting of the amino acid sequence of one of SEQ ID NO:1, 3, 4, 5, 6, 8, 9, 10, 11, 12, 13, 14, 15 or 16.

In some embodiments the antibodies display greater affinity for a p53 peptide/polypeptide comprising a mutation corresponding to R273C as compared to affinity for a p53 peptide/polypeptide not comprising said mutation, or comprising a mutation corresponding to one or more of R175H, R248Q, R273H, R248W, G245S, R282W, R249S, G245D, C176F, H179Y, H179R, Y220C or R337H.

In some embodiments, an antibody may display greater affinity for a polypeptide/peptide comprising or consisting of the amino acid sequence of SEQ ID NO:8, or a fragment thereof comprising the R273C mutation, as compared to a polypeptide/peptide comprising or consisting of the amino acid sequence of one of SEQ ID NO:1, 3, 4, 5, 6, 7, 9, 10, 11, 12, 13, 14, 15 or 16.

In some embodiments the antibodies display greater affinity for a p53 peptide/polypeptide comprising a mutation corresponding to R282W as compared to affinity for a p53 peptide/polypeptide not comprising said mutation, or comprising a mutation corresponding to one or more of R175H, R248Q, R273H, R248W, G245S, R273C, R249S, G245D, C176F, H179Y, H179R, Y220C or R337H.

In some embodiments, an antibody may display greater affinity for a polypeptide/peptide comprising or consisting of the amino acid sequence of SEQ ID NO:9, or a fragment thereof comprising the R282W mutation, as compared to a polypeptide/peptide comprising or consisting of the amino acid sequence of one of SEQ ID NO:1, 3, 4, 5, 6, 7, 8, 10, 11, 12, 13, 14, 15 or 16.

In some embodiments the antibodies display greater affinity for a p53 peptide/polypeptide comprising a mutation corresponding to R249S as compared to affinity for a p53 peptide/polypeptide not comprising said mutation, or comprising a mutation corresponding to one or more of R175H, R248Q, R273H, R248W, G245S, R273C, R282W, G245D, C176F, H179Y, H179R, Y220C or R337H.

In some embodiments, an antibody may display greater affinity for a polypeptide/peptide comprising or consisting of the amino acid sequence of SEQ ID NO:10, or a fragment thereof comprising the R249S mutation, as compared to a polypeptide/peptide comprising or consisting of the amino acid sequence of one of SEQ ID NO:1, 3, 4, 5, 6, 7, 8, 9, 11, 12, 13, 14, 15 or 16.

In some embodiments the antibodies display greater affinity for a p53 peptide/polypeptide comprising a mutation corresponding to G245D as compared to affinity for a p53 peptide/polypeptide not comprising said mutation, or comprising a mutation corresponding to one or more of R175H, R248Q, R273H, R248W, G245S, R273C, R282W, R249S, C176F, H179Y, H179R, Y220C or R337H.

In some embodiments, an antibody may display greater affinity for a polypeptide/peptide comprising or consisting of the amino acid sequence of SEQ ID NO:11, or a fragment thereof comprising the G245D mutation, as compared to a polypeptide/peptide comprising or consisting of the amino acid sequence of one of SEQ ID NO:1, 3, 4, 5, 6, 7, 8, 9, 10, 12, 13, 14, 15 or 16.

In some embodiments the antibodies display greater affinity for a p53 peptide/polypeptide comprising a mutation corresponding to C176F as compared to affinity for a p53 peptide/polypeptide not comprising said mutation, or comprising a mutation corresponding to one or more of R175H, R248Q, R273H, R248W, G245S, R273C, R282W, R249S, G245D, H179Y, H179R, Y220C or R337H.

In some embodiments, an antibody may display greater affinity for a polypeptide/peptide comprising or consisting of the amino acid sequence of SEQ ID NO:12, or a fragment thereof comprising the C176F mutation, as compared to a polypeptide/peptide comprising or consisting of the amino acid sequence of one of SEQ ID NO:1, 3, 4, 5, 6, 7, 8, 9, 10, 11, 13, 14, 15 or 16.

In some embodiments the antibodies display greater affinity for a p53 peptide/polypeptide comprising a mutation corresponding to H179Y as compared to affinity for a p53 peptide/polypeptide not comprising said mutation, or comprising a mutation corresponding to one or more of R175H, R248Q, R273H, R248W, G245S, R273C, R282W, R249S, G245D, C176F, H179R, Y220C or R337H.

In some embodiments, an antibody may display greater affinity for a polypeptide/peptide comprising or consisting of the amino acid sequence of SEQ ID NO:13, or a fragment thereof comprising the H179Y mutation, as compared to a polypeptide/peptide comprising or consisting of the amino acid sequence of one of SEQ ID NO:1, 3, 4, 5, 6, 7, 8, 9, 10, 11, 12, 14, 15 or 16.

In some embodiments the antibodies display greater affinity for a p53 peptide/polypeptide comprising a mutation corresponding to H179R as compared to affinity for a p53 peptide/polypeptide not comprising said mutation, or comprising a mutation corresponding to one or more of R175H, R248Q, R273H, R248W, G245S, R273C, R282W, R249S, G245D, C176F, H179Y, Y220C or R337H.

In some embodiments, an antibody may display greater affinity for a polypeptide/peptide comprising or consisting of the amino acid sequence of SEQ ID NO:14, or a fragment thereof comprising the H179R mutation, as compared to a polypeptide/peptide comprising or consisting of the amino acid sequence of one of SEQ ID NO:1, 3, 4, 5, 6, 7, 8, 9, 10, 11, 12, 13, 15 or 16.

In some embodiments the antibodies display greater affinity for a p53 peptide/polypeptide comprising a mutation corresponding to Y220C as compared to affinity for a p53 peptide/polypeptide not comprising said mutation, or comprising a mutation corresponding to one or more of R175H, R248Q, R273H, R248W, G245S, R273C, R282W, R249S, G245D, C176F, H179Y, H179R or R337H.

In some embodiments, an antibody may display greater affinity for a polypeptide/peptide comprising or consisting of the amino acid sequence of SEQ ID NO:15, or a fragment thereof comprising the Y220C mutation, as compared to a polypeptide/peptide comprising or consisting of the amino acid sequence of one of SEQ ID NO:1, 3, 4, 5, 6, 7, 8, 9, 10, 11, 12, 13, 14 or 16.

In some embodiments the antibodies display greater affinity for a p53 peptide/polypeptide comprising a mutation corresponding to R337H as compared to affinity for a p53 peptide/polypeptide not comprising said mutation, or comprising a mutation corresponding to one or more of R175H, R248Q, R273H, R248W, G245S, R273C, R282W, R249S, G245D, C176F, H179Y, H179R or Y220C.

In some embodiments, an antibody may display greater affinity for a polypeptide/peptide comprising or consisting of the amino acid sequence of SEQ ID NO:16, or a fragment thereof comprising the R337H mutation, as compared to a polypeptide/peptide comprising or consisting of the amino acid sequence of one of SEQ ID NO:1, 3, 4, 5, 6, 7, 8, 9, 10, 11, 12, 13, 14 or 15.

The present invention is concerned in particular with antibodies which are capable of binding to mutant p53 polypeptides, which are not capable of binding to wildtype p53 polypeptide. That is, the invention is concerned with antibodies which bind specifically to mutant p53 polypeptides, and which are not cross-reactive with (i.e. do not also bind to) wildtype p53 polypeptide.

The present invention is also concerned with antibodies which are capable of binding to a given, particular p53 mutant and which are not capable of binding to other, different mutants of p53. That is, the invention is concerned with antibodies which bind specifically to a given, particular p53 mutant, and which are not cross-reactive with (i.e. do not also bind to) other, different mutants of p53.

In some embodiments, an antibody may be capable of binding to a given mutant p53 polypeptide, and may not be capable of binding to another mutant p53 polypeptide.

Whether an antibody is capable of binding to a given molecule can be determined by methods well known to the skilled person. For example, the methods include analysis by immunoassay such as enzyme linked immunosorbent assay (ELISA), immunoprecipitation, western blot, immunofluorescence methods etc., and other methods such as surface plasmon resonance (SPR) assay and fluorescence resonance energy transfer (FRET).

The ability of an antibody to bind to a given peptide or polypeptide can be determined by detection of interaction between the antibody and peptide/polypeptide which is of greater affinity than non-specific interaction between the antibody and a control peptide/polypeptide. A control peptide/polypeptide may be a peptide or polypeptide to which it is known, or to which is has been determined, the antibody does not specifically bind.

In some embodiments, the capability of an antibody to bind to a given peptide or protein can be determined by observation of interaction between the antibody and peptide/polypeptide which is stronger than, more stable than, lasts longer than, or has a lower equilibrium dissociation constant ($K_D$) than non-specific interaction between the antibody and a negative control peptide/polypeptide.

In some embodiments, the extent of binding of an antibody to an unrelated target is less than about 10% of the binding of the antibody to the target as measured, e.g., by ELISA, SPR, Bio-Layer Interferometry or by RIA. Alternatively, the binding specificity may be reflected in terms of binding affinity where an antibody according to the present invention binds to its cognate mutant p53 polypeptide with a $K_D$ that is at least 0.1 order of magnitude (i.e. $0.1 \times 10^n$, where n is an integer representing the order of magnitude) greater than the $K_D$ of the antibody towards another target molecule (e.g. other mutant p53 polypeptide and/or wildtype p53 polypeptide). This may optionally be one of at least 0.2, 0.3, 0.4, 0.5, 0.6, 0.7, 0.8, 0.9, 1.0, 1.5, or 2.0.

In some embodiments of the present invention, the methods produce an antibody capable of binding to an antigen sequence in the context of the full-length amino acid sequence of a mutant p53 polypeptide. That is, in some embodiments, the methods produce an antibody which can bind to the mutant p53 polypeptide through binding to the antigen sequence.

The site within a peptide/polypeptide to which an antibody binds can be determined by the skilled person using various methods well known in the art, including X-ray co-crystallography analysis of antibody-antigen complexes, peptide scanning, mutagenesis mapping, hydrogen-deuterium exchange analysis by mass spectrometry, phage display, competition ELISA and proteolysis-based 'protection' methods. Such methods are described, for example, in Gershoni et al., BioDrugs, 2007, 21 (3): 145-156, which is hereby incorporated by reference in its entirety.

Preferably, the antibodies bind to the mutant p53 polypeptide for which they are specific with a KD of 1 µM or less, preferably one of ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM≤3 nM, ≤2 nM, ≤1 nM, ≤500 pM. Binding affinity of an antibody for its target is often described in terms of its dissociation constant ($K_D$). Binding affinity can be measured by methods known in the art, such as by ELISA, Surface Plasmon Resonance (SPR; see e.g. Hearty et al., Methods Mol Biol (2012) 907:411-442), Bio-Layer Interferometry (see e.g. Lad et al., (2015) J Biomol Screen 20 (4): 498-507), or by a radiolabeled antigen binding assay (RIA) performed with the Fab version of the antibody and antigen molecule.

Antibodies according to the present invention may be provided in isolated and/or purified form.

By "antibody" we include a fragment or derivative thereof, or a synthetic antibody or synthetic antibody fragment.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen.

Polyclonal antibodies are useful in the methods of the invention. Monospecific polyclonal antibodies are preferred. Suitable polyclonal antibodies can be prepared using methods well known in the art.

Antigen binding fragments of antibodies, such as Fab and $Fab_2$ fragments may also be used/provided as can genetically engineered antibodies and antibody fragments. The variable heavy ($V_H$) and variable light ($V_L$) domains of the antibody/fragment are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parent antibody (Morrison et al (1984) Proc. Natl. Acad. Sd. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. by a flexible oligopeptide.

Fab, Fv, ScFv and dAb antibody fragments can all be expressed in and secreted from E. coli, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site. Synthetic antibodies may also be made using phage display technology as is well known in the art.

The present application also provides antibodies, or antigen binding fragments, optionally isolated, which are capable of binding to a given mutant p53 polypeptide, which are bispecific antibodies/antigen binding fragments comprising (i) an antigen binding fragment or polypeptide according to the invention, and (ii) an antigen binding fragment capable of binding to a polypeptide other than the given mutant p53 polypeptide.

In some embodiments, the antigen binding fragment capable of binding to a polypeptide other than the given mutant p53 polypeptide may be capable of binding to another, different mutant p53 polypeptide.

An antigen binding fragment of a bispecific antibody or bispecific antigen binding fragment according to the present invention may be any fragment of a polypeptide which is capable of binding to an antigen. In some embodiments, an antigen binding fragment comprises at least the three light chain CDRs (i.e. LC-CDR1, LC-CDR2 and LC-CDR3) and three heavy chain CDRs (i.e. HC-CDR1, HC-CDR2 and HC-CDR3) which together define the antigen binding region of an antibody or antigen binding fragment. In some embodiments, an antigen binding fragment may comprise the light chain variable domain and heavy chain variable domain of an antibody or antigen binding fragment. In some embodiments, an antigen binding fragment may comprise the light chain polypeptide and heavy chain polypeptide of an antibody or antigen binding fragment.

Bispecific antibodies and bispecific antigen binding fragments according to the invention may be provided in any suitable format, such as those formats described in Kontermann MAbs 2012, 4 (2): 182-197, which is hereby incorporated by reference in its entirety. For example, a bispecific antibody or bispecific antigen binding fragment may be a bispecific antibody conjugate (e.g. an IgG2, F(ab')$_2$ or CovX-Body), a bispecific IgG or IgG-like molecule (e.g. an IgG, scFV$_4$-Ig, IgG-scFv, scFv-IgG, DVD-Ig, IgG-sVD, sVD-IgG, 2 in 1-IgG, mAb$^2$, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (Db), dsDb, DART, scDb, tand-Abs, tandem scFv (taFv), tandem dAb/VHH, triple body, triple head, Fab-scFv, or F(ab')$_2$-scFv$_2$), a bispecific Fc and C$_H$3 fusion protein (e.g. a taFv-Fc, Di-diabody, scDb-C$_H$3, scFv-Fc-scFv, HCAb-VHH, scFv-kih-Fc, or scFv-kih-C$_H$3), or a bispecific fusion protein (e.g. a scFv$_2$-albumin, scDb-albumin, taFv-toxin, DNL-Fab$_3$, DNL-Fab$_4$-IgG, DNL-Fab$_4$-IgG-cytokine$_2$). See in particular FIG. 2 of Kontermann MAbs 2012, 4 (2): 182-19.

The skilled person is able to design and prepare bispecific antibodies and bispecific antigen binding fragments according to the present invention. Methods for producing bispecific antibodies include chemically crosslinking of antibodies or antibody fragments, e.g. with reducible disulphide or non-reducible thioether bonds, for example as described in Segal and Bast, 2001. Production of Bispecific Antibodies. Current Protocols in Immunology. 14: IV: 2.13:2.13.1-2.13.16, which is hereby incorporated by reference in its entirety. For example, N-succinimidyl-3-(2-pyridyldithio)-propionate (SPDP) can be used to chemically crosslink e.g. Fab fragments via hinge region SH— groups, to create disulfide-linked bispecific F (ab) 2 heterodimers. Other methods for producing bispecific antibodies include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16.

Bispecific antibodies and bispecific antigen binding fragments according to the present invention can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies: Diabodies and Tandem scFv (Hornig and Färber-Schwarz), or French, How to make bispecific antibodies, Methods Mol. Med. 2000; 40:333-339, the entire contents of both of which are hereby incorporated by reference. For example, a DNA construct encoding the light and heavy chain variable domains for the two antigen binding fragments (i.e. the light and heavy chain variable domains for the antigen binding fragment capable of binding to a mutant p53 polypeptide, and the light and heavy chain variable domains for the antigen binding fragment capable of binding to another target protein), and including sequences encoding a suitable linker or dimerization domain between the antigen binding fragments can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., Rio/Technology 10:779-783 (1992); Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154 (7): 331 0-15 9 (1995); and Hawkins et al, J. Mol. Biol. 226:889-896 (1992).

Antibodies according to the present invention preferably exhibit specific binding to a given mutant p53 polypeptide. An antibody that specifically binds to a target molecule preferably binds the target with greater affinity, and/or with greater duration than it binds to other targets. The present antibodies may bind with greater affinity to a given mutant p53 polypeptide than to other mutant p53 polypeptides and wildtype p53 polypeptide.

The antibodies, fragments or polypeptides may display substantially no binding to wildtype p53 polypeptide, e.g. human p53 polypeptide. This is an unexpected feature for antibodies directed against mutant p53 polypeptides as described herein, which may differ from wildtype p53 polypeptide amino acid sequence by only a single amino acid residue. That is, it would be expected that an antibody capable of binding to a polypeptide would display cross-reactivity for another polypeptide differing by only a single amino acid. The present antibodies which are specific for single acid mutants of p53 are useful to discriminate mutant from wildtype p53, and therefore have wide range of uses, such as in research, therapy and diagnostic applications.

'Substantially no binding' as used herein refers to binding which is not significantly greater than the level of binding by a negative control antibody (e.g. an antibody directed against a target unrelated to wildtype p53 polypeptide, or an antibody known not to bind to wildtype p53 polypeptide). In some embodiments, an antibody according to the present invention may exhibit binding to wildtype p53 polypeptide (e.g. human wildtype p53 polypeptide) which is ≤500%, ≤400%, ≤300%, ≤250%, ≤200%, ≤150%, or ≤100% of the binding to wildtype p53 polypeptide displayed by a negative control antibody (e.g. an antibody directed against a target unrelated to wildtype p53 polypeptide, or an antibody known not to bind to wildtype p53 polypeptide), in a given assay or at a given concentration. Binding can be measured by techniques well known to the person skilled in the art, including ELISA, SPR, Bio-Layer Interferometry, flow cytometry or by a radioimmunoassay (RIA).

In some embodiments, an antibody according to the invention may be capable of inhibiting tumour growth or cancer progression. In some embodiments an antibody according to the invention may display anti-cancer activity. In some embodiments, inhibition of tumour growth or cancer progression may be in vivo. 'Inhibition' may be reduction or control of tumour growth, or reduction or control of the number of cancer cells. Inhibition of tumour growth or cancer progression can be evaluated in vivo, for example in an animal model of a cancer as described herein.

Anti-cancer activity may be determined by detection of a reduced number of tumor cells and/or reduced tumor volume following treatment with an antibody/fragment according to the invention, as compared to the number of tumor cells and/or tumor volume in the absence of treatment, or treatment with a negative control antibody.

In some embodiments, the antibody according to the invention is capable of binding to R175H p53 polypeptide, e.g. as shown in SEQ ID NO:3, or a fragment thereof comprising the R175H mutation. In some embodiments, the antibody according to the invention is capable of binding to R248Q p53 polypeptide, e.g. as shown in SEQ ID NO:4, or a fragment thereof comprising the R248Q mutation. In some embodiments, the antibody according to the invention is capable of binding to R273H p53 polypeptide, e.g. as shown in SEQ ID NO: 5, or a fragment thereof comprising the R273H mutation. In some embodiments, the antibody according to the invention is capable of binding to R248W p53 polypeptide, e.g. as shown in SEQ ID NO:6, or a fragment thereof comprising the R248W mutation. In some embodiments, the antibody according to the invention is capable of binding to G245S p53 polypeptide, e.g. as shown in SEQ ID NO:7, or a fragment thereof comprising the G245S mutation. In some embodiments, the antibody according to the invention is capable of binding to R273C p53 polypeptide, e.g. as shown in SEQ ID NO:8, or a fragment thereof comprising the R273C mutation. In some embodiments, the antibody according to the invention is capable of binding to R282W p53 polypeptide, e.g. as shown in SEQ ID NO:9, or a fragment thereof comprising the R282W mutation. In some embodiments, the antibody according to the invention is capable of binding to R249S p53 polypeptide, e.g. as shown in SEQ ID NO:10, or a fragment thereof comprising the R249S mutation. In some embodiments, the antibody according to the invention is capable of binding to G245D p53 polypeptide, e.g. as shown in SEQ ID NO:11, or a fragment thereof comprising the G245D mutation. In some embodiments, the antibody according to the invention is capable of binding to C176F p53 polypeptide, e.g. as shown in SEQ ID NO:12, or a fragment thereof comprising the C176F mutation. In some embodiments, the antibody according to the invention is capable of binding to H179Y p53 polypeptide, e.g. as shown in SEQ ID NO:13, or a fragment thereof comprising the H179Y mutation. In some embodiments, the antibody according to the invention is capable of binding to H179R p53 polypeptide, e.g. as shown in SEQ ID NO:14, or a fragment thereof comprising the H179R mutation. In some embodiments, the antibody according to the invention is capable of binding to Y220C p53 polypeptide, e.g. as shown in SEQ ID NO:15, or a fragment thereof comprising the Y220C mutation. In some embodiments, the antibody according to the invention is capable of binding to R337H p53 polypeptide, e.g. as shown in SEQ ID NO:16, or a fragment thereof comprising the R337H mutation.

In some embodiments, an antibody according to the invention is specific for a particular mutant p53 polypeptide. That is, in some embodiments an antibody is capable of binding only to a particular mutant p53 polypeptide and is not capable of binding to a p53 polypeptide other than said mutant p53 polypeptide such as wildtype p53 polypeptide or other mutant p53 polypeptide.

In some embodiments, the antibodies of the present invention are capable of binding to a given mutant of human p53 polypeptide and are not capable of binding to wildtype human p53 polypeptide. In some embodiments the antibodies are capable of binding to a p53 peptide/polypeptide comprising a mutation corresponding to one of R175H, R248Q, R273H, R248W, G245S, R273C, R282W, R249S, G245D, C176F, H179Y, H179R, Y220C, or R337H, and are not capable of binding to a p53 peptide/polypeptide not comprising said mutation. In some embodiments, an antibody may be capable of binding to a peptide/polypeptide comprising the amino acid sequence of one of SEQ ID NOs: 3, 4, 5, 6, 7, 8, 9, 10, 11, 12, 13, 14, 15 or 16, or a fragment thereof comprising the mutation, and not capable of binding to peptide/polypeptide comprising the amino acid sequence of SEQ ID NO: 1, or a fragment thereof.

The antibodies according to the present invention may be capable of binding to a given mutant p53 polypeptide, and may not be capable of binding to other mutant p53 polypeptides. In some embodiments, the antibodies may be capable of binding to a given mutant of human p53 polypeptide and may not be capable of binding to other mutants of human p53 polypeptide.

In some embodiments the antibodies may be capable of binding to a p53 peptide/polypeptide comprising a mutation corresponding to R175H, and may not be capable of binding to a p53 peptide/polypeptide not comprising said mutation, or comprising a mutation corresponding to one or more of R248Q, R273H, R248W, G245S, R273C, R282W, R249S, G245D, C176F, H179Y, H179R, Y220C, or R337H. In some embodiments, an antibody may be capable of binding to a polypeptide/peptide comprising or consisting of the amino acid sequence of SEQ ID NO:3, or a fragment thereof comprising the mutation, and may not be capable of binding to a polypeptide/peptide comprising or consisting of the amino acid sequence of one of SEQ ID NO:1, 4, 5, 6, 7, 8, 9, 10, 11, 12, 13, 14, 15 or 16.

In some embodiments the antibodies may be capable of binding to a p53 peptide/polypeptide comprising a mutation corresponding to R248Q, and may not be capable of binding to a p53 peptide/polypeptide not comprising said mutation, or comprising a mutation corresponding to one or more of R175H, R273H, R248W, G245S, R273C, R282W, R249S, G245D, C176F, H179Y, H179R, Y220C, or R337H. In some embodiments, an antibody may be capable of binding to a polypeptide/peptide comprising or consisting of the amino acid sequence of SEQ ID NO:4, or a fragment thereof comprising the mutation, and may not be capable of binding to a polypeptide/peptide comprising or consisting of the amino acid sequence of one of SEQ ID NO:1, 3, 5, 6, 7, 8, 9, 10, 11, 12, 13, 14, 15 or 16.

In some embodiments the antibodies may be capable of binding to a p53 peptide/polypeptide comprising a mutation corresponding to R273H, and may not be capable of binding to a p53 peptide/polypeptide not comprising said mutation, or comprising a mutation corresponding to one or more of R175H, R248Q, R248W, G245S, R273C, R282W, R249S, G245D, C176F, H179Y, H179R, Y220C, or R337H. In some embodiments, an antibody may be capable of binding to a polypeptide/peptide comprising or consisting of the amino acid sequence of SEQ ID NO:5, or a fragment thereof comprising the mutation, and may not be capable of binding to a polypeptide/peptide comprising or consisting of the amino acid sequence of one of SEQ ID NO:1, 3, 4, 6, 7, 8, 9, 10, 11, 12, 13, 14, 15 or 16.

In some embodiments the antibodies may be capable of binding to a p53 peptide/polypeptide comprising a mutation corresponding to R248W, and may not be capable of binding to a p53 peptide/polypeptide not comprising said mutation, or comprising a mutation corresponding to one or more of R175H, R248Q, R273H, G245S, R273C, R282W, R249S, G245D, C176F, H179Y, H179R, Y220C, or R337H. In some embodiments, an antibody may be capable of binding to a polypeptide/peptide comprising or consisting of the amino acid sequence of SEQ ID NO:6, or a fragment thereof comprising the mutation, and may not be capable of binding to a polypeptide/peptide comprising or consisting of the amino acid sequence of one of SEQ ID NO:1, 3, 4, 5, 7, 8, 9, 10, 11, 12, 13, 14, 15 or 16.

In some embodiments the antibodies may be capable of binding to a p53 peptide/polypeptide comprising a mutation corresponding to G245S, and may not be capable of binding to a p53 peptide/polypeptide not comprising said mutation, or comprising a mutation corresponding to one or more of R175H, R248Q, R273H, R248W, R273C, R282W, R249S, G245D, C176F, H179Y, H179R, Y220C, or R337H. In some embodiments, an antibody may be capable of binding to a polypeptide/peptide comprising or consisting of the amino acid sequence of SEQ ID NO:7, or a fragment thereof comprising the mutation, and may not be capable of binding to a polypeptide/peptide comprising or consisting of the amino acid sequence of one of SEQ ID NO:1, 3, 4, 5, 6, 8, 9, 10, 11, 12, 13, 14, 15 or 16.

In some embodiments the antibodies may be capable of binding to a p53 peptide/polypeptide comprising a mutation corresponding to R273C, and may not be capable of binding to a p53 peptide/polypeptide not comprising said mutation, or comprising a mutation corresponding to one or more of R175H, R248Q, R273H, R248W, G245S, R282W, R249S, G245D, C176F, H179Y, H179R, Y220C, or R337H. In some embodiments, an antibody may be capable of binding to a polypeptide/peptide comprising or consisting of the amino acid sequence of SEQ ID NO:8, or a fragment thereof comprising the mutation, and may not be capable of binding to a polypeptide/peptide comprising or consisting of the amino acid sequence of one of SEQ ID NO:1, 3, 4, 5, 6, 7, 9, 10, 11, 12, 13, 14, 15 or 16.

In some embodiments the antibodies may be capable of binding to a p53 peptide/polypeptide comprising a mutation corresponding to R282W, and may not be capable of binding a p53 peptide/polypeptide not comprising said mutation, or comprising a mutation corresponding to one or more of R175H, R248Q, R273H, R248W, G245S, R273C, R249S, G245D, C176F, H179Y, H179R, Y220C, or R337H. In some embodiments, an antibody may be capable of binding to a polypeptide/peptide comprising or consisting of the amino acid sequence of SEQ ID NO:9, or a fragment thereof comprising the mutation, and may not be capable of binding to a polypeptide/peptide comprising or consisting of the amino acid sequence of one of SEQ ID NO:1, 3, 4, 5, 6, 7, 8, 10, 11, 12, 13, 14, 15 or 16.

In some embodiments the antibodies may be capable of binding to a p53 peptide/polypeptide comprising a mutation corresponding to G245S, and may not be capable of binding to a p53 peptide/polypeptide not comprising said mutation, or comprising a mutation corresponding to one or more of R175H, R248Q, R273H, R248W, G245S, R273C, R282W, G245D, C176F, H179Y, H179R, Y220C, or R337H. In some embodiments, an antibody may be capable of binding to a polypeptide/peptide comprising or consisting of the amino acid sequence of SEQ ID NO:10, or a fragment thereof comprising the mutation, and may not be capable of binding to a polypeptide/peptide comprising or consisting of the amino acid sequence of one of SEQ ID NO:1, 3, 4, 5, 6, 7, 8, 9, 11, 12, 13, 14, 15 or 16.

In some embodiments the antibodies may be capable of binding to a p53 peptide/polypeptide comprising a mutation corresponding to G245D, and may not be capable of binding to a p53 peptide/polypeptide not comprising said mutation, or comprising a mutation corresponding to one or more of R175H, R248Q, R273H, R248W, G245S, R273C, R282W, R249S, C176F, H179Y, H179R, Y220C, or R337H. In some embodiments, an antibody may be capable of binding to a polypeptide/peptide comprising or consisting of the amino acid sequence of SEQ ID NO:11, or a fragment thereof comprising the mutation, and may not be capable of binding to a polypeptide/peptide comprising or consisting of the amino acid sequence of one of SEQ ID NO:1, 3, 4, 5, 6, 7, 8, 9, 10, 12, 13, 14, 15 or 16.

In some embodiments the antibodies may be capable of binding to a p53 peptide/polypeptide comprising a mutation corresponding to C176F, and may not be capable of binding to a p53 peptide/polypeptide not comprising said mutation, or comprising a mutation corresponding to one or more of R175H, R248Q, R273H, R248W, G245S, R273C, R282W, R249S, G245D, H179Y, H179R, Y220C, or R337H. In some embodiments, an antibody may be capable of binding to a polypeptide/peptide comprising or consisting of the amino acid sequence of SEQ ID NO:12, or a fragment thereof comprising the mutation, and may not be capable of binding to a polypeptide/peptide comprising or consisting of the amino acid sequence of one of SEQ ID NO:1, 3, 4, 5, 6, 7, 8, 9, 10, 11, 13, 14, 15 or 16.

In some embodiments the antibodies may be capable of binding to a p53 peptide/polypeptide comprising a mutation corresponding to H179Y, and may not be capable of binding to a p53 peptide/polypeptide not comprising said mutation, or comprising a mutation corresponding to one or more of R175H, R248Q, R273H, R248W, G245S, R273C, R282W, R249S, G245D, C176F, H179R, Y220C, or R337H. In some embodiments, an antibody may be capable of binding to a polypeptide/peptide comprising or consisting of the amino acid sequence of SEQ ID NO:13, or a fragment thereof comprising the mutation, and may not be capable of binding to a polypeptide/peptide comprising or consisting of the amino acid sequence of one of SEQ ID NO:1, 3, 4, 5, 6, 7, 8, 9, 10, 11, 12, 14, 15 or 16.

In some embodiments the antibodies may be capable of binding to a p53 peptide/polypeptide comprising a mutation corresponding to H179R, and may not be capable of binding to a p53 peptide/polypeptide not comprising said mutation, or comprising a mutation corresponding to one or more of R175H, R248Q, R273H, R248W, G245S, R273C, R282W, R249S, G245D, C176F, H179Y, Y220C, or R337H. In some embodiments, an antibody may be capable of binding to a polypeptide/peptide comprising or consisting of the amino acid sequence of SEQ ID NO:14, or a fragment thereof comprising the mutation, and may not be capable of binding to a polypeptide/peptide comprising or consisting of the amino acid sequence of one of SEQ ID NO:1, 3, 4, 5, 6, 7, 8, 9, 10, 11, 12, 13, 15 or 16.

In some embodiments the antibodies may be capable of binding to a p53 peptide/polypeptide comprising a mutation corresponding to Y220C, and may not be capable of binding to a p53 peptide/polypeptide not comprising said mutation, or comprising a mutation corresponding to one or more of R175H, R248Q, R273H, R248W, G245S, R273C, R282W, R249S, G245D, C176F, H179Y, H179R, or R337H. In some embodiments, an antibody may be capable of binding to a polypeptide/peptide comprising or consisting of the amino acid sequence of SEQ ID NO:15, or a fragment thereof comprising the mutation, and may not be capable of binding to a polypeptide/peptide comprising or consisting of the amino acid sequence of one of SEQ ID NO:1, 3, 4, 5, 6, 7, 8, 9, 10, 11, 12, 13, 14 or 16.

In some embodiments the antibodies may be capable of binding to a p53 peptide/polypeptide comprising a mutation corresponding to R337H, and may not be capable of binding to a p53 peptide/polypeptide not comprising said mutation, or comprising a mutation corresponding to one or more of R175H, R248Q, R273H, R248W, G245S, R273C, R282W, R249S, G245D, C176F, H179Y, H179R, or Y220C. In some embodiments, an antibody may be capable of binding to a polypeptide/peptide comprising or consisting of the amino acid sequence of SEQ ID NO:16, or a fragment thereof comprising the mutation, and may not be capable of binding to a polypeptide/peptide comprising or consisting of the amino acid sequence of one of SEQ ID NO:1, 3, 4, 5, 6, 7, 8, 9, 10, 11, 12, 13, 14 or 15.

A fragment of a mutant p53 polypeptide of the invention to which an antibody according to the invention is capable of binding comprises the mutation. In some embodiments the fragment of a mutant p53 polypeptide of the invention to which an antibody according to the invention is capable of binding may comprise at least 3, 4, 5, 6, 7, 8, 9, 10, 11, 12, 13, 14, 15, 16, 17, 18, 19, 20, 25, 30, 35, 40 or 50 amino acids. In some embodiments the fragment may consist of 5 to 300, 5 to 250, 5 to 200, 5 to 150, 5 to 100, 5 to 75, 5 to 50, 5 to 40, 5 to 30, 5 to 20, or 5 to 10 amino acids of the amino acid sequence of the mutant p53 polypeptide.

In some embodiments, an antibody according to the invention may be defined by reference to the epitope of the mutant p53 polypeptide to which the antibody binds. In some embodiments, the antibody may bind to a linear epitope, consisting of a contiguous sequence of amino acids (i.e. an amino acid primary sequence). In some embodiments, the antibody may bind to a conformational epitope, consisting of a discontinuous sequence of amino acids of the amino acid sequence. The amino acids of the discontinuous sequence of amino acids may be located in different regions of the mutant p53 polypeptide, and be positioned in close proximity when the sequence is folded, e.g. into its native structure.

In some embodiments, the antibody capable of binding to R175H p53 polypeptide may bind to an epitope of the polypeptide comprising, or consisting of, an amino acid sequence corresponding to one of positons 100 to 250, 110 to 240, 120 to 230, 130 to 220, 140 to 210, 150 to 200, 160 to 190, or 170 to 180 of SEQ ID NO:3.

In some embodiments, an antibody capable of binding to R248Q p53 polypeptide may bind to an epitope of the polypeptide comprising, or consisting of, an amino acid sequence corresponding to one of positons to 173 to 323, 183 to 313, 193 to 303, 203 to 293, 213 to 283, 223 to 273, 233 to 263, or 243 to 253 of SEQ ID NO:4.

In some embodiments, an antibody capable of binding to R273H p53 polypeptide may bind to an epitope of the polypeptide comprising, or consisting of, an amino acid sequence corresponding to one of positons to 198 to 348, 208 to 338, 218 to 328, 228 to 318, 238 to 308, 248 to 298, 258 to 288, or 268 to 278 of SEQ ID NO:5.

In some embodiments, an antibody capable of binding to R248W p53 polypeptide may bind to an epitope of the polypeptide comprising, or consisting of, an amino acid sequence corresponding to one of positons to 173 to 323, 183 to 313, 193 to 303, 203 to 293, 213 to 283, 223 to 273, 233 to 263, or 243 to 253 of SEQ ID NO:6.

In some embodiments, an antibody capable of binding to G245S p53 polypeptide may bind to an epitope of the polypeptide comprising, or consisting of, an amino acid sequence corresponding to one of positons to 170 to 320, 180 to 310, 190 to 300, 200 to 290, 210 to 280, 220 to 270, 230 to 260, or 240 to 250 of SEQ ID NO:7.

In some embodiments, an antibody capable of binding to R273C p53 polypeptide may bind to an epitope of the polypeptide comprising, or consisting of, an amino acid sequence corresponding to one of positons to 198 to 348, 208 to 338, 218 to 328, 228 to 318, 238 to 308, 248 to 298, 258 to 288, or 268 to 278 of SEQ ID NO:8.

In some embodiments, an antibody capable of binding to R282W p53 polypeptide may bind to an epitope of the polypeptide comprising, or consisting of, an amino acid sequence corresponding to one of positons to 207 to 357, 217 to 347, 227 to 337, 237 to 327, 247 to 317, 257 to 301, 267 to 297 or 277 to 287 of SEQ ID NO:9.

In some embodiments, an antibody capable of binding to R249S p53 polypeptide may bind to an epitope of the polypeptide comprising, or consisting of, an amino acid sequence corresponding to one of positons to 174 to 324, 184 to 314, 194 to 304, 204 to 294, 214 to 284, 224 to 274, 234 to 264, or 244 to 254 of SEQ ID NO:10.

In some embodiments, an antibody capable of binding to G245D p53 polypeptide may bind to an epitope of the polypeptide comprising, or consisting of, an amino acid sequence corresponding to one of positons to 170 to 320, 180 to 310, 190 to 300, 200 to 290, 210 to 280, 220 to 270, 230 to 260, or 240 to 250 of SEQ ID NO:11.

In some embodiments, an antibody capable of binding to C176F p53 polypeptide may bind to an epitope of the polypeptide comprising, or consisting of, an amino acid sequence corresponding to one of positons to 101 to 251, 111 to 241, 121 to 231, 131 to 221, 141 to 211, 151 to 201, 161 to 191, or 171 to 181 of SEQ ID NO:12.

In some embodiments, an antibody capable of binding to H179Y p53 polypeptide may bind to an epitope of the polypeptide comprising, or consisting of, an amino acid sequence corresponding to one of positons to 104 to 254, 114 to 244, 124 to 234, 134 to 224, 144 to 214, 154 to 204, 164 to 194, or 174 to 184 of SEQ ID NO:13.

In some embodiments, an antibody capable of binding to H179R p53 polypeptide may bind to an epitope of the polypeptide comprising, or consisting of, an amino acid sequence corresponding to one of positons to 104 to 254, 114 to 244, 124 to 234, 134 to 224, 144 to 214, 154 to 204, 164 to 194, or 174 to 184 of SEQ ID NO:14.

In some embodiments, an antibody capable of binding to Y220C p53 polypeptide may bind to an epitope of the polypeptide comprising, or consisting of, an amino acid sequence corresponding to one of positons to 145 to 295, 155 to 285, 165 to 275, 175 to 265, 185 to 255, 195 to 245, 205 to 235, or 215 to 225 of SEQ ID NO:15.

In some embodiments, an antibody capable of binding to R337H p53 polypeptide may bind to an epitope of the polypeptide comprising, or consisting of, an amino acid sequence corresponding to one of positons to 262 to 412, 272 to 402, 282 to 392, 292 to 382, 302 to 372, 312 to 362, 322 to 352, or 332 to 342 of SEQ ID NO:16.

In some embodiments, the antibody capable of binding to R175H p53 polypeptide may bind to an epitope of the polypeptide comprising, or consisting of, amino acid positions corresponding to positons 175 to 179 of SEQ ID NO:3, i.e. HCPHH (SEQ ID NO:68), or amino acid positions corresponding to positons 175 (i.e. H) and 177 to 179 (i.e. PHH (SEQ ID NO: 69)) of SEQ ID NO:3, or amino acid positions corresponding to positons 175 (i.e. H) and 178 to 179 (i.e. HH (SEQ ID NO:70)) of SEQ ID NO:3. That is, in some embodiments, the antibody capable of binding to R175H p53 polypeptide may bind to an epitope as follows:

| Epitope | Corresponding positions of SEQ ID NO: 3 |
|---------|------------------------------------------|
| HCPHH   | 175 to 179                               |
| H . . . PHH | 175 and 177 to 179                   |
| H . . . HH  | 175 and 178 to 179                   |

In some embodiments, an antibody capable of binding to R248Q p53 polypeptide may bind to epitope of the polypeptide comprising, or consisting of, amino acid positions corresponding to positons 247 to 249 of SEQ ID NO:4, i.e. NQR (SEQ ID NO:71), or amino acid positions corresponding to positons 215 to 216 (i.e. SV (SEQ ID NO:72)) and 233 to 234 (i.e. HY (SEQ ID NO:73)) of SEQ ID NO:4, or amino acid positions corresponding to positons 249 to 250 of SEQ ID NO:4, i.e. RP (SEQ ID NO:74). That is, in some embodiments, the antibody capable of binding to R248Q p53 polypeptide may bind to an epitope as follows:

| Epitope | Corresponding positions of SEQ ID NO: 4 |
|---------|------------------------------------------|
| NQR     | 247 to 249                               |
| SV . . . HY | 215 to 216 and 233 to 234             |
| RP      | 249 to 250                               |

In some embodiments, an antibody capable of binding to R273H p53 polypeptide may bind to epitope of the polypeptide comprising, or consisting of, amino acid positions corresponding to positons 272 to 273 of SEQ ID NO:5, i.e. VH (SEQ ID NO:75).

In some aspects, the antibody is clone anti-R175H p53 antibody clone 4H5 or MH 4H5. Anti-R175H p53 antibody clones 4H5 and MH 4H5 comprise the following CDR sequences:
Light Chain:

```
Light chain:
LC-CDR1:
                                  (SEQ ID NO: 19)
QSLLNSGNQKSY

LC-CDR2:
GAS

LC-CDR3:
                                  (SEQ ID NO: 21)
QNDHSYPLT

Heavy chain:
HC-CDR1:
                                  (SEQ ID NO: 25)
GFTFTEYT

HC-CDR2:
                                  (SEQ ID NO: 26)
IDPNNGVT

HC-CDR3:
                                  (SEQ ID NO: 27)
ARWGGDYV
```

For all of the antibodies described herein, the CDRs are defined according to VBASE2 CDR prediction tool (Retter et al. Nucleic Acids Research (2005) 33 (Database issue): D671-674, hereby incorporated by reference in its entirety).

In some aspects, the antibody is clone anti-R175H p53 antibody clone 7B9 or MH 7B9. Anti-R175H p53 antibody clones 7B9 and MH 7B9 comprise the following CDR sequences:

```
Light chain:
LC-CDR1:
                                  (SEQ ID NO: 23)
QSLLNSGNQKSN

LC-CDR2:
GAS

LC-CDR3:
                                  (SEQ ID NO: 21)
QNDHSYPLT

Heavy chain:
HC-CDR1:
                                  (SEQ ID NO: 29)
GYTFTEYT

HC-CDR2:
                                  (SEQ ID NO: 30)
INPYSGGT

HC-CDR3:
                                  (SEQ ID NO: 27)
ARWGGDYV
```

In some aspects, the antibody is clone anti-R175H p53 antibody clone 10C8 or MH 10C8. Anti-R175H p53 antibody clones 10C8 and MH 10C8 comprise the following CDR sequences:

```
Light chain:
LC-CDR1:
                                  (SEQ ID NO: 23)
QSLLNSGNQKSN

LC-CDR2:
GAS

LC-CDR3:
                                  (SEQ ID NO: 21)
QNDHSYPLT

Heavy chain:
HC-CDR1:
                                  (SEQ ID NO: 29)
GYTFTEYT

HC-CDR2:
                                  (SEQ ID NO: 30)
INPYSGGT

HC-CDR3:
                                  (SEQ ID NO: 27)
ARWGGDYV
```

In some embodiments in accordance with the various aspects of the present invention, wherein HC-CDR2 is INPYSGGT (SEQ ID NO: 30), this sequence may be comprised in the sequence INPYSGGTV (SEQ ID NO: 76). In some embodiments, HC-CDR2 is INPYSGGTV (SEQ ID NO: 76).

Anti-R175H p53 antibodies according to the present invention may comprise the CDRs of clone 4H5, 7B9 or 10C8 or one of SEQ ID NOs 18 or 22; and 24 or 28.

Anti-R175H p53 antibodies according to the present invention may comprise the CDRs of clone MH 4H5, MH 7B9 or MH 10C8 or one of SEQ ID NOs 237 or 238; and 239, 240 or 241.

Amino acid sequences of the $V_L$ and $V_H$ chains of anti-R175H p53 antibody clones are shown in FIGS. 24, 25, 49 and 50. The encoding nucleotide sequences are shown in FIGS. 27, 51 and 52.

Anti-R175H p53 antibodies may have $V_L$ and/or $V_H$ chains comprising an amino acid sequence that has a high percentage sequence identity to one or more of the $V_L$ and/or $V_H$ amino acid sequences of SEQ ID NOs 18, 22, 237 and 238; or 24, 28, 239, 240 or 241, or to one of the amino acid sequences shown in FIGS. 24, 25, 49 and 50. For example, antibodies according to the present invention include antibodies that bind to R175H p53 polypeptide and have a $V_L$ or $V_H$ chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the $V_L$ or $V_H$ chain amino acid sequence of one of SEQ ID NOs 18, 22, 237, 238, 24, 28, 239, 240 or 241, or to one or the amino acid sequences shown in FIGS. 24, 25, 49 and 50.

In some aspects, the antibody is clone anti-R248Q p53 antibody clone 3G11 or MH 3G11. Anti-R248Q p53 antibody clones 3G11 and MH 3G11 comprise the following CDR sequences:

```
Light chain:
LC-CDR1:
                              (SEQ ID NO: 41)
QSLLYSDGKTY

LC-CDR2:
                              (SEQ ID NO: 42)
LVS

LC-CDR3:
                              (SEQ ID NO: 43)
WQGTHFPLT

Heavy chain:
HC-CDR1:
                              (SEQ ID NO: 46)
GYTFTDYY

HC-CDR2:
                              (SEQ ID NO: 47)
IHPKNGGT

HC-CDR3:
                              (SEQ ID NO: 48)
AKMGGYDDY
```

In some aspects, the antibody is clone anti-R248Q p53 antibody clone 4H2 or MH 4H2. Anti-R248Q p53 antibody clones 4H2 and MH 4H2 comprise the following CDR sequences:

```
Light chain:
LC-CDR1:
                              (SEQ ID NO: 41)
QSLLYSDGKTY

LC-CDR2:
                              (SEQ ID NO: 42)
LVS

LC-CDR3:
                              (SEQ ID NO: 43)
WQGTHFPLT

Heavy chain:
HC-CDR1:
                              (SEQ ID NO: 46)
GYTFTDYY

HC-CDR2:
                              (SEQ ID NO: 50)
IDPKNGGT

HC-CDR3:
                              (SEQ ID NO: 51)
AKQGGFDDY
```

Anti-R248Q p53 antibodies according to the present invention may comprise the CDRs of clone 3G11 or 4H2, or one of SEQ ID NOs 40 or 44; and 45 or 49.

Anti-R248Q p53 antibodies according to the present invention may comprise the CDRs of clone MH 3G11 or MH 4H2, or one of SEQ ID NOs 251 or 252; and 253 or 254.

Amino acid sequences of the $V_L$ and $V_H$ chains of anti-R248Q p53 antibody clones are shown in FIGS. 28, 29, 57 and 58. The encoding nucleotide sequences are shown in FIGS. 31, 59 and 60.

Anti-R248Q p53 antibodies may have $V_L$ and/or $V_H$ chains comprising an amino acid sequence that has a high percentage sequence identity to one or more of the $V_L$ and/or $V_H$ amino acid sequences of SEQ ID NOs 40, 44, 251 and 252; or 45, 49, 253 or 254 or to one of the amino acid sequences shown in FIGS. 28, 29, 57 and 58. For example, antibodies according to the present invention include antibodies that bind to R248Q p53 polypeptide and have a $V_L$ or $V_H$ chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the $V_L$ or $V_H$ chain amino acid sequence of one of SEQ ID NOs 40, 44, 251, 252, 45, 49, 253 or 254 or to one of the amino acid sequences shown in FIGS. 28, 29, 57 and 58.

In some aspects, the antibody is clone anti-R273H p53 antibody clone 13E4 or MH 13E4. Anti-R273H p53 antibody clones 13E4 and MH 13E4 comprise the following CDR sequences:
Light Chain:

```
Light chain:
LC-CDR1:
                              (SEQ ID NO: 59)
QSIVHNNGDTY

LC-CDR2:
                              (SEQ ID NO: 60)
KVS

LC-CDR3:
                              (SEQ ID NO: 61)
FQGSHLPLT

Heavy chain:
HC-CDR1:
                              (SEQ ID NO: 63)
GFSFSDYY

HC-CDR2:
                              (SEQ ID NO: 64)
ISVGGTYT

HC-CDR3:
                              (SEQ ID NO: 65)
VRDGNDGKFLG
```

Anti-R273H p53 antibodies according to the present invention may comprise the CDRs of clone 13E4, or one of SEQ ID NOs 58 and 62.

Anti-R273H p53 antibodies according to the present invention may comprise the CDRs of clone MH 13E4, or one of SEQ ID NOs 247 and 248.

Amino acid sequences of the $V_L$ and $V_H$ chains of anti-R273H p53 antibody clones are shown in FIGS. 32, 33, 53 and 54. The encoding nucleotide sequences are shown in FIGS. 34, 55 and 56.

Anti-R273H p53 antibodies may have $V_L$ and/or $V_H$ chains comprising an amino acid sequence that has a high percentage sequence identity to one or more of the $V_L$ and/or $V_H$ amino acid sequences of SEQ ID NOs 58, 247, 62 and 248, or to one or the amino acid sequences shown in FIGS. 32, 33, 53 and 54. For example, antibodies according to the present invention include antibodies that bind to R273H p53 polypeptide and have a $V_L$ or $V_H$ chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the $V_L$ or $V_H$ chain amino acid sequence of one of SEQ ID NOs 58, 247, 62 and 248, or to one or the amino acid sequences shown in FIGS. 32, 33, 53 and 54.

In an antibody according to the present invention one or two or three or four of the six CDR sequences may vary. A variant may have one or two amino acid substitutions in one or two of the six CDR sequences.

The light and heavy chain CDRs may also be particularly useful in conjunction with a number of different framework regions. Accordingly, light and/or heavy chains having LC-CDR1-3 or HC-CDR1-3 may possess an alternative framework region. Suitable framework regions are well known in the art and are described for example in M. Lefranc & G. Lefranc (2001) "The Immunoglobulin Facts-Book", Academic Press, incorporated herein by reference.

Antibodies according to the present invention may be detectably labelled or, at least, capable of detection. For example, the antibody may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding moiety may be directly labelled with a detectable label or it may be indirectly labelled. For example, the binding moiety may be an unlabelled antibody which can be detected by another antibody which is itself labelled. Alternatively, the second antibody may have bound to it biotin and binding of labelled streptavidin to the biotin is used to indirectly label the first antibody.

Chimeric Antigen Receptors

The present invention provides a chimeric antigen receptor (CAR) capable of binding to a mutant p53 polypeptide. The CAR comprises an antigen binding fragment or polypeptide according to the present invention.

Chimeric Antigen Receptors (CARs) are recombinant receptors that provide both antigen-binding and T cell activating functions. CAR structure and engineering is reviewed, for example, in Dotti et al., Immunol Rev (2014) 257 (1), hereby incorporated by reference in its entirety.

Antigen-binding fragments according to the present invention are provided herein as the antigen-binding domain of a chimeric antigen receptor (CAR). In some embodiments, the CAR comprises a $V_L$ domain and a $V_H$ domain according to any embodiment of an antibody, antigen binding fragment or polypeptide described herein. Accordingly, the antigen bound by the CAR according to the present invention is a mutant p53 polypeptide as described herein.

CARs may be combined with costimulatory ligands, chimeric costimulatory receptors or cytokines to further enhance T cell potency, specificity and safety (Sadelain et al., The basic principles of chimeric antigen receptor (CAR) design. Cancer Discov. 2013 April; 3 (4): 388-398. doi: 10.1158/2159-8290.CD-12-0548, specifically incorporated herein by reference).

The present invention also provides a cell comprising a CAR according to the invention. The CAR according to the present invention may be used to generate tumor-targeted T cells, e.g. T cells targeted to tumor cells expressing the mutant p53 polypeptide for which the CAR is specific.

Engineering of CARs into T cells may be performed during culture, in vitro, for transduction and expansion, such as happens during expansion of T cells for adoptive T cell therapy. The transduction may utilize a variety of methods, but stable gene transfer is required to enable sustained CAR expression in clonally expanding and persisting T cells.

In addition to the mutant p53 polypeptide specificity determining elements described herein, CAR molecules may be further engineered to express co-stimulatory endodomains such as those derived from CD28 and tumor necrosis factor receptor superfamily member 9 (TNFRSF9; 4-1BB) to promote T cell proliferation and persistence upon encountering tumor cells (Nishio and Dotti., OncoImmunology 4:2, e988098; February 2015).

A CAR typically combines an antigen binding domain with an intracellular domain of the CD3-zeta chain or FcγRI protein in a single chimeric protein. The structural features of a CAR are described by Sjouke et al., (The pharmacology of second-generation chimeric antigen receptors. *Nature Reviews Drug Discovery*, 14, 499 509 (2015) doi: 10.1038/nrd4597). A CAR typically has an extracellular antigen-binding domain linked to a transmembrane domain and endodomain. An optional hinge or spacer domain may provide separation between the binding moiety and transmembrane domain and may act as a flexible linker.

In accordance with the present invention, the antigen recognition domain of the CAR is, or is derived from, an antibody, antigen binding fragment or polypeptide which is capable of binding to a mutant p53 polypeptide, as described herein.

Hinge or spacer regions may be flexible domains allowing the binding moiety to orient in different directions. Hinge or spacer regions may be derived from IgG1 or the $CH_2CH_3$ region of immunoglobulin.

Transmembrane domains may be hydrophobic alpha helix that spans the cell membrane. The transmembrane domain associated with the endodomain is commonly used.

The endodomain is responsible for receptor clustering/dimerization after antigen binding and for initiation of signal transduction to the cell. One commonly used transmembrane domain is the CD3-zeta transmembrane and endodomain. Intracellular domains from one or more co-stimulatory protein receptors, such as CD28 4-1BB, OX40, ICOS, may optionally be incorporated into the cytoplasmic tail of the CAR to provide additional co-stimulatory signaling, which may be beneficial in terms of anti-tumor activity.

In one embodiment, a CAR comprises an extracellular domain having an antigen recognition domain, a transmembrane domain, and a cytoplasmic domain. A transmembrane domain that is naturally associated with one of the domains in the CAR may be used or the transmembrane domain can be selected or modified by amino acid substitution to avoid binding of such domains to the transmembrane domains of the same or different surface membrane proteins to minimize interactions with other members of the receptor complex. The cytoplasmic domain may be designed to comprise the CD28 and/or 4-1BB signaling domain by itself or be combined with any other desired cytoplasmic domain(s). The cytoplasmic domain may be designed to further comprise the signaling domain of CD3-zeta. For example, the cytoplasmic domain of the CAR can include but is not limited to CD3-zeta, 4-1BB and CD28 signaling modules and combinations thereof.

The present invention also provides CAR T cells comprising as a CAR an antigen binding fragment capable of binding to a mutant p53 polypeptide, according to the present invention.

CAR T cells of the invention can be generated by introducing a lentiviral vector in vitro comprising a desired CAR, for example a CAR comprising anti-mutant p53, CD8a hinge and transmembrane domain, and human 4-1BB and CD3zeta signaling domains, into the cells. The CAR T cells of the invention are able to replicate in vivo resulting in long-term persistence that can lead to sustained tumor control.

In one embodiment the invention relates to administering a genetically modified T cell expressing a CAR capable of binding to a mutant p53 polypeptide for the treatment of a patient having cancer or at risk of having cancer using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient.

Methods for Detecting Mutant p53 Polypeptides

Antibodies, antibody fragments, polypeptides, conjugates, CARs or cells described herein may be used in methods that involve the binding of the antibody or antigen binding fragment to a mutant p53 polypeptide. Such methods may involve detection of the bound complex of antibody, antibody fragment, polypeptide, conjugate, CAR or cell, and mutant p53 polypeptide. As such, in one embodiment a method is provided, the method comprising contacting a sample containing, or suspected to contain, a mutant p53 polypeptide with an antibody, antibody fragment, polypeptide, conjugate, CAR or cell as described herein and detecting the formation of a complex of antibody, antibody fragment, polypeptide, conjugate, CAR or cell, and mutant p53 polypeptide.

In aspects of the present invention, an in vitro complex is provided, comprising an antibody, antibody fragment, polypeptide, conjugate, CAR or cell according to the invention bound to (i.e. in complex with) the mutant p53 polypeptide (or a fragment thereof comprising the mutation) for which the antibody, antibody fragment, polypeptide, conjugate, CAR or cell is specific.

Suitable method formats are well known in the art, including immunoassays such as sandwich assays, e.g. ELISA. The method may involve labelling the antibody, antibody fragment, polypeptide, conjugate, CAR or cell, or mutant p53 polypeptide, or both, with a detectable label, e.g. fluorescent, luminescent or radio-label. Expression of a mutant p53 polypeptide may be measured by immunohistochemistry (IHC), for example of a tissue sample obtained by biopsy.

In particular, the anti-mutant p53 antibodies of the present invention are useful in analysis by immunoblot, immunofluorescence, immunoprecipitation, immunohistochemistry and in vivo imaging, as exemplified herein.

Methods of this kind may provide the basis of a method of diagnosis or prognostic evaluation of a disease or condition requiring detection and/or quantitation of a mutant p53 polypeptide. Such methods may be performed in vitro on a patient sample, or following processing of a patient sample. Once the sample is collected, the patient is not required to be present for the in vitro method of diagnosis or prognostic evaluation to be performed and therefore the method may be one which is not practised on the human or animal body.

The methods may involve detecting the presence of a mutant p53 polypeptide present in a patient sample.

The methods may involve determining the amount of a mutant p53 polypeptide present in a patient sample. In some embodiments the methods may further comprise comparing the determined amount against a standard or reference value as part of the process of reaching a diagnosis. Other diagnostic tests may be used in conjunction with those described here to enhance the accuracy of the diagnosis or prognosis or to confirm a result obtained by using the tests described here.

Detection in a sample of a mutant p53 polypeptide may be used for the purpose of diagnosis of a cancerous condition in the patient, diagnosis of a predisposition to a cancerous condition or for providing a prognosis (prognosticating) of a cancerous condition. The diagnosis or prognosis may relate to an existing (previously diagnosed) cancerous condition, which may be benign or malignant, may relate to a suspected cancerous condition or may relate to the screening for cancerous conditions in the patient (which may be previously undiagnosed).

Detection in a sample of a mutant p53 polypeptide may be indicative that a patient may respond to treatment with an anti-mutant p53 antibody, fragment, polypeptide, conjugate, CAR or cell. The presence of a given mutant p53 polypeptide in a sample may be used to select a patient for treatment with a given anti-mutant p53 antibody, fragment, polypeptide, conjugate, CAR or cell. The antibodies, antibody fragments, polypeptides, conjugates, CARs or cells of the present invention may therefore be used to select a patient for treatment with anti-mutant p53 antibody therapy.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; or cells isolated from said individual.

Methods according to the present invention are preferably performed in vitro. The term "in vitro" is intended to encompass experiments with cells in culture whereas the term "in vivo" is intended to encompass experiments with intact multi-cellular organisms.

The invention also provides the antibody, antibody fragment, polypeptide, conjugate, CAR or cell according to the invention for use in methods for detecting, localizing or imaging a cancer (e.g. a tumour), e.g. in vivo.

The antibody, fragment, polypeptide, conjugate, CAR or cell according to the invention may be suitably labeled directly or indirectly with a detectable label (e.g. a signal-generating label), such as a radioactive isotope or non-isotopic entity, for detection. Radioisotopes include Iodine$^{123}$, Iodine$^{125}$, Iodine$^{126}$, Iodine$^{131}$, Iodine$^{133}$, Bromine$^{77}$, Technetium$^{99m}$, Indium$^{111}$, Indium$^{113m}$, Gallium$^{67}$, Gallium$^{68}$, Ruthenium$^{95}$, Ruthenium$^{97}$, Ruthenium$^{103}$, Ruthenium$^{105}$, Mercury$^{207}$, Mercury$^{203}$, Rhenium$^{99m}$, Rhenium$^{101}$, Rhenium$^{105}$, Scandium$^{47}$, Tellurium$^{121m}$, Tellurium$^{122m}$, Tellurium$^{125m}$, Thulium$^{165}$, Thulium$^{167}$, Thulium$^{168}$, Copper$^{67}$, Fluorine$^{18}$, Yttrium$^{90}$, Palladium$^{100}$, Bismuth$^{217}$ and Antimony$^{211}$. Nonisotopic entities may be selected from enzymes (e.g. peroxidase, alkaline phosphatase, glucose oxidase, beta-galactosidase, luciferase), dyes, haptens, luminescent agents such as radioluminescent, chemiluminescent (e.g. acridinium ester, luminol, isoluminol), bioluminescent, fluorescent (e.g. fluorescein, rhodamine, eosine and NDB, green fluorescent protein (GFP) chelates of rare earths such as europium (Eu), terbium (Tb) and samarium (Sm), tetramethyl rhodamine, Texas Red, 4-methyl umbelliferone, 7-amino-4-methyl coumarin, Cy3, Cy5) or phosphorescent agents, antibodies, receptors and ligands such as biotin, avidin, streptavidin or digoxigenin.

Detection techniques are well known to those of skill in the art and can be selected to correspond with the labelling agent. Suitable techniques include PCR amplification of oligonucleotide tags, mass spectrometry, detection of fluorescence or colour, e.g. upon enzymatic conversion of a substrate by a reporter protein, or detection of radioactivity.

In some embodiments, the methods comprising administering the antibody, antibody fragment, polypeptide, conjugate, CAR or cell to a subject, e.g. a patient diagnosed with or suspected of having a cancer and detecting the antibody, antibody fragment, polypeptide, conjugate, CAR or cell. In some embodiments, the methods comprise detecting signal from the antibody, antibody fragment, polypeptide, conjugate, CAR or cell. In some embodiments the method comprises conversion of the signal to an image.

The present invention also provides methods for selecting/stratifying a subject for treatment with a mutant p53 polypeptide-targeted agent using the antibody, fragment, polypeptide, conjugate, CAR, or cell according to the invention. In some embodiments, a subject is selected for treatment in accordance with the invention, or is identified as a subject which would benefit from such treatment, based on detection of the presence of the mutant p53 polypeptide, or nucleic acid encoding the mutant p53 polypeptide, e.g. in a sample obtained from the individual.

Therapeutic Applications

Antibodies, antigen binding fragments, polypeptides, conjugates, CARs and cells according to the present invention and compositions comprising such agents may be provided for use in methods of medical treatment. Treatment may be provided to subjects having a disease or condition in need of treatment. The disease or condition may be a cancer.

In some embodiments, the cancer may comprise cells which express a mutant p53 polypeptide. In some embodiments, the cancer may comprise cells expressing the mutant p53 polypeptide for which the anti-mutant p53 antibody, fragment or polypeptide according to the invention is specific.

For example, such tumor cells expressing mutant p53 polypeptide may be killed directly by treatment with antibodies according to the present invention, by antibody dependent cell-mediated cytotoxicity (ADCC), complement dependent cytotoxicity (CDC), or using antibody-drug conjugates.

The treatment may be aimed at prevention of the development or progression of a cancer. As such, the antibodies, antigen binding fragments, polypeptides or conjugates may be used to formulate pharmaceutical compositions or medicaments and subjects may be prophylactically treated against development of a disease state. This may take place before the onset of symptoms of the disease state, and/or may be given to subjects considered to be at greater risk of development or progression of cancer.

Administration of an antibody, antigen binding fragment or polypeptide is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Antibody Conjugates

The present invention also provides antibody conjugates, comprising an antibody, antigen binding fragment or polypeptide according to the invention conjugated to a chemical moiety.

In some embodiments, the chemical moiety may be a moiety for providing a therapeutic effect. In some embodiments, the chemical moiety may be a drug moiety (e.g. a cytotoxic agent). In some embodiments, the drug moiety may be a chemotherapeutic drug as described hereinbelow.

In some embodiments the chemical moiety may be a detectable moiety. Suitable moieties and means for their detection are well known to those in the art and include the radioactive isotope or non-isotopic entities described hereinabove.

Formulating Pharmaceutically Useful Compositions and Medicaments

Antibodies, antigen binding fragments, polypeptides, conjugates, CARs and cells according to the present invention may be formulated as pharmaceutical compositions for clinical use and may comprise a pharmaceutically acceptable carrier, diluent, excipient or adjuvant.

In accordance with the present invention methods are also provided for the production of pharmaceutically useful compositions, such methods of production may comprise one or more steps selected from: isolating an antibody, antigen binding fragment, polypeptide, CAR, or cell as described herein; and/or mixing an isolated antibody, antigen binding fragment, polypeptide, CAR, or cell as described herein with a pharmaceutically acceptable carrier, adjuvant, excipient or diluent.

For example, a further aspect of the present invention relates to a method of formulating or producing a medicament or pharmaceutical composition for use in the treatment of a cancer, the method comprising formulating a pharmaceutical composition or medicament by mixing an antibody, antigen binding fragment, polypeptide, CAR, or cell as described herein with a pharmaceutically acceptable carrier, adjuvant, excipient or diluent.

Compositions may be administered alone or in combination with other treatments, either simultaneously or sequentially dependent upon the condition to be treated.

In this specification an antibody, antigen binding fragment, polypeptide, CAR, or cell of the present invention and a chemotherapeutic agent may be administered simultaneously or sequentially.

In some embodiments, treatment with an antibody, antigen binding fragment, polypeptide, CAR, or cell of the present invention may be accompanied by chemotherapy.

Simultaneous administration refers to administration of the antibody, antigen binding fragment, polypeptide, CAR, or cell and therapeutic agent together, for example as a pharmaceutical composition containing both agents (combined preparation), or immediately after each other and optionally via the same route of administration, e.g. to the same artery, vein or other blood vessel.

Sequential administration refers to administration of one of the antibody, antigen binding fragment, polypeptide, CAR, or cell or therapeutic agent followed after a given time interval by separate administration of the other agent. It is not required that the two agents are administered by the same route, although this is the case in some embodiments. The time interval may be any time interval.

Cancer

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma. In some embodiments, the cancer may be breast cancer.

In some embodiments the cancer is a cancer encoding or expressing a mutant p53 peptide or polypeptide. In some embodiments the cancer is a cancer encoding or expressing a mutant p53 peptide/polypeptide comprising a mutation in the DNA-binding domain (DBD).

In some embodiments, the cancer is a cancer encoding or expressing a mutant p53 peptide/polypeptide comprising an amino acid difference relative to the wildtype p53 sequence at one or more of positions 248, 273, 175, 176, 179, 220, 245, 249, 282 or 337.

In some embodiments, the cancer is a cancer encoding or expressing a mutant p53 peptide/polypeptide comprising one or more of the following mutations: R175H, R248Q, R273H, R248W, G245S, R273C, R282W, R249S, G245D, C176F, H179Y, H179R, Y220C, and R337H.

A cancer may be determined to encode or express a mutant p53 peptide/polypeptide by any suitable means, which are well known to the skilled person, e.g. based on analysis of a biological sample.

A cancer encoding a mutant p53 polypeptide may be identified on the basis of detection of nucleic acid encoding the mutation, e.g. by DNA sequencing etc. A cancer expressing a mutant p53 polypeptide may be identified by detection of expression of a mutant p53 peptide/polypeptide. Expression may be gene expression or protein expression. Gene expression can be determined e.g. by detection of mRNA encoding a mutant p53 peptide/polypeptide, for example by quantitative real-time PCR (qRT-PCR). Protein expression can be determined e.g. by detection of mutant p53 peptide/polypeptide, for example by antibody-based methods, for example by western blot, immunohistochemistry, immunocytochemistry, flow cytometry, ELISA.

Herein, "a cancer encoding or expressing a mutant p53 peptide/polypeptide" includes any cell encoding or expressing a mutant p53 peptide/polypeptide. In some embodiments, the cell may be a cell of a tumor.

Chemotherapy/Radiotherapy

Chemotherapy and radiotherapy respectively refer to treatment of a cancer with a drug or with ionising radiation (e.g. radiotherapy using X-rays or γ-rays).

The drug may be a chemical entity, e.g. small molecule pharmaceutical, antibiotic, DNA intercalator, protein inhibitor (e.g. kinase inhibitor), or a biological agent, e.g. antibody, antibody fragment, nucleic acid or peptide aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a predetermined timetable, plan, scheme or schedule of chemotherapy administration which may be prepared by a physician or medical practitioner and may be tailored to suit the patient requiring treatment.

The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs and biologics may be selected from: alkylating agents such as cisplatin, carboplatin, mechlorethamine, cyclophosphamide, chlorambucil, ifosfamide; purine or pyrimidine anti-metabolites such as azathiopurine or mercaptopurine; alkaloids and terpenoids, such as vinca alkaloids (e.g. vincristine, vinblastine, vinorelbine, vindesine), podophyllotoxin, etoposide, teniposide, taxanes such as paclitaxel (Taxol™), docetaxel; topoisomerase inhibitors such as the type I topoisomerase inhibitors camptothecins irinotecan and topotecan, or the type II topoisomerase inhibitors amsacrine, etoposide, etoposide phosphate, teniposide; antitumor antibiotics (e.g. anthracyline antibiotics) such as dactinomycin, doxorubicin (Adriamycin™), epirubicin, bleomycin, rapamycin; antibody based agents, such as anti-PD-1 antibodies, anti-PD-L1 antibodies, anti-TIM-3 antibodies, anti-CTLA-4, anti-4-1BB, anti-GITR, anti-CD27, anti-BLTA, anti-OX43, anti-VEGF, anti-TNFα, anti-IL-2, antiGpIIb/IIIa, anti-CD-52, anti-CD20, anti-RSV, anti-HER2/neu (erbB2), anti-TNF receptor, anti-EGFR antibodies, monoclonal antibodies or antibody fragments, examples include: cetuximab, panitumumab, infliximab, basiliximab, bevacizumab (Avastin®), abciximab, daclizumab, gemtuzumab, alemtuzumab, rituximab (Mabthera®), palivizumab, trastuzumab, etanercept, adalimumab, nimotuzumab; EGFR inhibitors such as erlotinib, cetuximab and gefitinib; anti-angiogenic agents such as bevacizumab (Avastin®); cancer vaccines such as Sipuleucel-T (Provenge®).

Further chemotherapeutic drugs may be selected from: 13-cis-Retinoic Acid, 2-Chlorodeoxyadenosine, 5-Azacitidine 5-Fluorouracil, 6-Mercaptopurine, 6-Thioguanine, Abraxane, Accutane®, Actinomycin-D Adriamycin®, Adrucil®, Afinitor®, Agrylin®, Ala-Cort®, Aldesleukin, Alemtuzumab, ALIMTA, Alitretinoin, Alkaban-AQ®, Alkeran@, All-transretinoic Acid, Alpha Interferon, Altretamine, Amethopterin, Amifostine, Aminoglutethimide, Anagrelide, Anandron®, Anastrozole, Arabinosylcytosine, Aranesp®, Aredia®, Arimidex®, Aromasin®, Arranon@, Arsenic Trioxide, Asparaginase, ATRA Avastin®, Azacitidine, BCG, BCNU, Bendamustine, Bevacizumab, Bexarotene, BEXXAR®, Bicalutamide, BICNU, Blenoxane®, Bleomycin, Bortezomib, Busulfan, Busulfex®, Calcium Leucovorin, Campath®, Camptosar®, Camptothecin-11, Capecitabine, Carac™, Carboplatin, Carmustine, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine Cytosar-U®, Cytoxan®, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eligard™, Ellence™, Eloxatin™, Elspar®, Emcyt®, Epirubicin, Epoetin Alfa, Erbitux, Erlotinib, *Erwinia* L-asparaginase, Estramustine, Ethyol Etopophos®, Etoposide, Etoposide Phosphate, Eulexin®, Everolimus, Evista®, Exemestane, Faslodex®, Femara®, Filgrastim, Floxuridine, Fludara®, Fludarabine, Fluoroplex®, Fluorouracil, Fluoxymesterone, Flutamide, Folinic Acid, FUDR®, Fulvestrant, Gefitinib, Gemcitabine, Gemtuzumab ozogamicin, Gleevec™, Gliadel® Wafer, Goserelin, Granulocyte-Colony Stimulating Factor, Granulocyte Macrophage Colony Stimulating Factor, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant Purinethol®, Raloxifene, Revlimid®, Rheumatrex®, Rituxan®, Rituximab, Roferon-A® (Interferon Alfa-2a), Rubex®, Rubidomycin hydrochloride, Sandostatin® Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERBR, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon@, Xeloda®, Zanosar®, Zevalin™, Zinecard®, Zoladex®, Zoledronic acid, Zolinza, Zometa®.

Routes of Administration

Antibodies, antigen binding fragments, polypeptides, conjugates, CARs, cells and other therapeutic agents, medicaments and pharmaceutical compositions according to aspects of the present invention may be formulated for administration by a number of routes, including but not limited to, parenteral, intravenous, intra-arterial, intramuscular, subcutaneous, intradermal, intratumoral and oral. Antibodies, antigen binding fragments, polypeptides, conjugates, CARs, cells and therapeutic agents may be formulated in fluid or solid form. Fluid formulations may be formulated for administration by injection to a selected region of the human or animal body.

Dosage Regimes

Multiple doses of the antibody, antigen binding fragment, polypeptide, conjugate, CAR or cell may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

Kits

In some aspects of the present invention a kit of parts is provided. In some embodiments the kit may have at least one container having a predetermined quantity of the antibody, antigen binding fragment, polypeptide, conjugate, CAR or cell according to the invention. The kit may provide the antibody, antigen binding fragment, polypeptide, conjugate, CAR or cell in the form of a medicament or pharmaceutical composition, and may be provided together with instructions for administration to a patient in order to treat a specified disease or condition. The antibody, antigen binding fragment or polypeptide may be formulated so as to be suitable for injection or infusion to a tumor or to the blood.

In some embodiments the kit may further comprise at least one container having a predetermined quantity of another therapeutic agent (e.g. chemotherapeutic agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Subjects

The subject to be treated with an antibody, antigen binding fragment, polypeptide, conjugate, CAR or cell according to the invention may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, or be suspected of having such a disease or condition.

Sequence Identity

Alignment for purposes of determining percent amino acid or nucleotide sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

Recombinant Production

The immunogen used in the methods according to the invention and the antibodies, fragments, polypeptides, conjugates and CARs according to the invention may be prepared according to methods for recombinant production known to the skilled person.

The peptide/polypeptide of interest may be prepared by chemical synthesis, e.g. liquid or solid phase synthesis. For example, peptides/polypeptides can by synthesised using the methods described in, for example, Chandrudu et al., Molecules (2013), 18:4373-4388, which is hereby incorporated by reference in its entirety.

The immunogens, antibodies, fragments, polypeptides, conjugates and CARs according the invention may be produced by recombinant expression. Molecular biology techniques suitable for recombinant production are well known in the art, such as those set out in Green and Sambrook, Molecular Cloning: A Laboratory Manual (4th Edition), Cold Spring Harbor Press, 2012, which is hereby incorporated by reference in its entirety.

Expression may be from a nucleotide sequence. The nucleotide sequence may be contained in a vector. A "vector" as used herein is an oligonucleotide molecule (DNA or RNA) used as a vehicle to transfer foreign genetic material into a cell. The vector may be an expression vector for expression of the foreign genetic material in the cell. Such vectors may include a promoter sequence operably linked to the nucleotide sequence encoding the sequence to be expressed. A vector may also include a termination codon and expression enhancers. Any suitable vectors, promoters, enhancers and termination codons known in the art may be used to express a peptide or polypeptide from a vector according to the invention. In some embodiments, the vector may be a plasmid, MAC, virus, etc. In some embodiments, the vector may be a eukaryotic expression vector, e.g. a vector comprising the elements necessary for expression of protein from the vector in a eukaryotic cell. In some embodiments, the vector may be a mammalian expression vector, e.g. comprising a cytomegalovirus (CMV) or SV40 promoter to drive protein expression.

The term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. The resulting transcript may then be translated into a desired peptide or polypeptide.

For recombinant production according to the invention, any cell suitable for the expression of polypeptides may be used. The cell may be a prokaryote or eukaryote. In some embodiments the cell is a prokaryotic cell, such as a cell of archaea or bacteria. In some embodiments the bacteria may be Gram-negative bacteria such as bacteria of the family Enterobacteriaceae, for example *Escherichia coli*.

In some embodiments, the cell is a eukaryotic cell such as a yeast cell, a plant cell, insect cell or a mammalian cell, e.g. CHO, HEK, HeLa or COS cells.

In some cases the cell is not a prokaryotic cell because some prokaryotic cells do not allow for the same folding or post-translational modifications as eukaryotic cells. In addition, very high expression levels are possible in eukaryotes and proteins can be easier to purify from eukaryotes using appropriate tags. Specific plasmids may also be utilised which enhance secretion of the protein into the media.

Production may involve culture or fermentation of a eukaryotic cell modified to express the peptide or polypeptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted peptide or polypeptide. Culture, fermentation and separation techniques are well known to those of skill in the art, and are described, for example, in Green and Sambrook, Molecular Cloning: A Laboratory Manual (4$^{th}$ Edition; incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the immunogen, antibody, fragment, polypeptide, conjugate or CAR, the peptide/polypeptide of interest is preferably isolated. Any suitable method for separating proteins from cell culture known in the art may be used. In order to isolate the peptide/polypeptide from a culture, it may be necessary to first separate the cultured cells from media containing the peptide/polypeptide of interest. If the peptide/polypeptide of interest is secreted from the cells, the cells may be separated from the culture media that contains the secreted peptide/polypeptide of interest by centrifugation. If the peptide/polypeptide of interest collects within the cell it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the peptide/polypeptide of interest.

It may then be desirable to isolate the peptide/polypeptide of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography. These may be used as an alternative to precipitation, or may be performed subsequently to precipitation.

Once the peptide/polypeptide of interest has been isolated from culture it may be desired or necessary to concentrate the peptide or polypeptide. A number of methods for concentrating proteins are known in the art, such as ultrafiltration or lyophilisation.

Vaccination

The immunogens used to raise antibodies against mutant p53 polypeptides in the methods of the present invention are also useful as vaccines. The immunogens can be used to generate immunity to cancer associated with mutation of p53.

Accordingly, the present invention provides a vaccine comprising, methods for vaccination using, and the use as a vaccine of, an immunogen in accordance with any embodiment as described herein.

The immunogen of the vaccine/used in vaccination may comprise a mutation of p53 for generating immunity to a cancer comprising the same mutation. For example, an immunogen comprising an antigen sequence comprising the R175H may be useful in a method for vaccination against a cancer comprising a cell or cells expressing a R175H p53, or comprising nucleic acid encoding a R175H p53.

In some embodiments multiple, different immunogens may be used in a vaccine or vaccination according to the present invention. In some embodiments, vaccines/vaccination may use immunogens comprising different mutations of p53, and may therefore be useful to vaccinate against cancers comprising more than one p53 mutation and/or cancers comprising different p53 mutations.

The skilled person is readily able to determine suitable formulations for vaccines and schedules for vaccination in accordance with the present invention, e.g. by reference to Vaccines (6$^{th}$ Edn.) Plotkin et al. 2012, Elsevier Saunders, which is hereby incorporated by reference in its entirety.

Methods of vaccination and associated uses include prophylactic and/or preventative treatment. For example, subjects considered to be at risk of developing a cancer, or at risk of recurrence or relapse following treatment, may be administered a vaccine as described herein. Such administration may occur whilst the subject is considered cancer free. Assessment of risk status and cancer status may be performed by a suitably qualified medical practitioner. Such methods may reduce the likelihood of the cancer developing, growing, metastasising, or recurring.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures in which:

FIGS. 1A to 1C. Amino acid sequences of immunogens used to raise antibodies specific for p53 mutants. (1A) Sequence for immunogen used to raise antibodies against R175H p53 (SEQ ID NO:80). Three copies of the mutant p53 sequences of variable lengths, each harbouring one of mutation, were inserted into the active site of TrxA. (1B) Sequence for immunogen used to raise antibodies against R248Q p53 (SEQ ID NO:84). (1C) Sequence for immunogen used to raise antibodies against R273H p53 (SEQ ID NO:88). Amino acid sequences of mutant p53 are highlighted (light grey), and the mutant residue is indicated (dark grey). Flexible Gly/Ser linker sequences are underlined. The C-terminal 6-His tag used for purification is shown in italics.

FIGS. 2A to 2C. Predicted Swiss Models for the 3D structure of the immunogens used to raise antibodies specific for p53 mutants. (2A) Predicted structure for immunogen used to raise antibodies against R175H p53. (2B) Predicted structure for immunogen used to raise antibodies against R248Q p53. (2C) Predicted structure for immunogen used to raise antibodies against R273H p53. Structures corresponding to the thioredoxin and antigen sequences are indicated, as are the mutations.

FIGS. 6A to 6C. Bar charts showing the results of ELISA screening of p53 mutant specific antibodies. Cell culture supernatants obtained from individual hybridoma clones generated from spleens of mice immunized with (6A) TrxR175H, (6B) TrxR248Q, and (6C) TrxR273H were screened by ELISA against the indicted whole proteins and peptide fragments.

FIGS. 7A to 7C. Sequence alignments showing the results of phage display experiments for determining the epitope bound by the anti-mutant p53 antibodies. Sequences for the peptides captured by cell culture supernatant of hybridomas producing (7A) anti-R175H antibody (SEQ ID NOs: 77, and 93-101) (7B) anti-R248Q antibody (SEQ ID NOs: 102-110) and (7C) anti-R273H antibody (SEQ ID NOs: 111-119). Consensus sequences are shown.

FIGS. 8A and 8B. Sequence alignments showing the results of phage display experiments for determining the epitope bound by the anti-mutant p53 antibodies. Sequences for the peptides captured by cell culture supernatant of the indicated hybridomas producing (8A) anti-R175H antibody (SEQ ID NOs: 77, 93, and 120-135) and (8B) anti-R248Q antibody (SEQ ID NOs: 102, 103, and 136-144). Consensus sequences are shown.

FIG. 10. Sequence showing the epitopes for the antibodies identified by alanine scan analysis of the critical residues that the antibodies recognise (SEQ ID NO:174).

FIG. 13. Table showing p53 mutation status of cell lines used for analysis of p53-specific antibodies in FIGS. 14 and 15.

FIGS. 17A and 17B. Photographs showing the results of immunofluorescence analyses. (17A) The indicated cell lines were used for immunofluorescence analysis using the indicated antibodies. (17B) R248Q mAb in p53-null H1299 cells expressing either the R248Q or R248W mutant p53 polypeptide. Dapi staining highlights nuclei.

FIG. 21. Table summarising the results of human tumour microarray analysis by immunohistochemistry.

FIG. 22. Amino-acid sequence alignments of p53 from various species are shown, with regions containing the R175 (SEQ ID NOs: 192-214), R248 or R273 (SEQ ID NOs:

215-235) residues (indicated by arrows) and the surrounding residues underlined, which shows strong conservation cross species, indicating that the mutant-specific mAbs could work across all species.

FIGS. 23A to 23D. Photographs showing the results of analysis of the mouse equivalent to the R175H mutation (i.e. R172H). Mouse embryonic fibroblasts from the indicated genotypes were used for (23A) direct immunoblotting (I.B.) or (23B) immunoprecipitation (I.P.), (23C) immunofluorescence, or (23D) Immunohistochemical analysis with the anti-R175H-specific mAb. Polyclonal antibody against mouse p53, CM5, was used for I.B. in immunoprecipitation studies. R246S mutant MEFs are from a different hot-spot mutant knock-in mouse strain.

FIG. 24. Light chain variable domain sequences for anti-R175H p53 antibody clones 4H5, 7B9 and 10C8. CDRs are underlined and shown separately.

FIG. 25. Heavy chain variable domain sequences for anti-R175H p53 antibody clones 4H5, 7B9 and 10C8. CDRs are underlined and shown separately.

FIG. 26. Table summarising light and heavy chain CDRs for anti-R175H p53 antibody clones 4H5, 7B9 and 10C8, and indicating consensus sequences.

FIG. 27. Nucleotide and encoded amino acid sequences of heavy and light chain variable domain sequences for anti-R175H p53 antibody clones 4H5, 7B9 and 10C8.

FIG. 28. Light chain variable domain sequences for anti-R248Q p53 antibody clones 3G11 and 4H2. CDRs are underlined and shown separately.

FIG. 29. Heavy chain variable domain sequences for anti-R248Q p53 antibody clones 3G11 and 4H2. CDRs are underlined and shown separately.

FIG. 30. Table summarising light and heavy chain CDRs for anti-R248Q p53 antibody clones 3G11 and 4H2, and indicating consensus sequences.

FIG. 31. Nucleotide and encoded amino acid sequences of heavy and light chain variable domain sequences for anti-R248Q p53 antibody clones 3G11 and 4H2.

FIG. 32. Light chain variable domain sequence for anti-R273H p53 antibody clone 13E4. CDRs are underlined and shown separately.

FIG. 33. Heavy chain variable domain sequence for anti-R273H p53 antibody clone 13E4. CDRs are underlined and shown separately.

FIG. 34. Nucleotide and encoded amino acid sequences of heavy and light chain variable domain sequences for anti-R273H p53 antibody clone 13E4.

Figure 35:
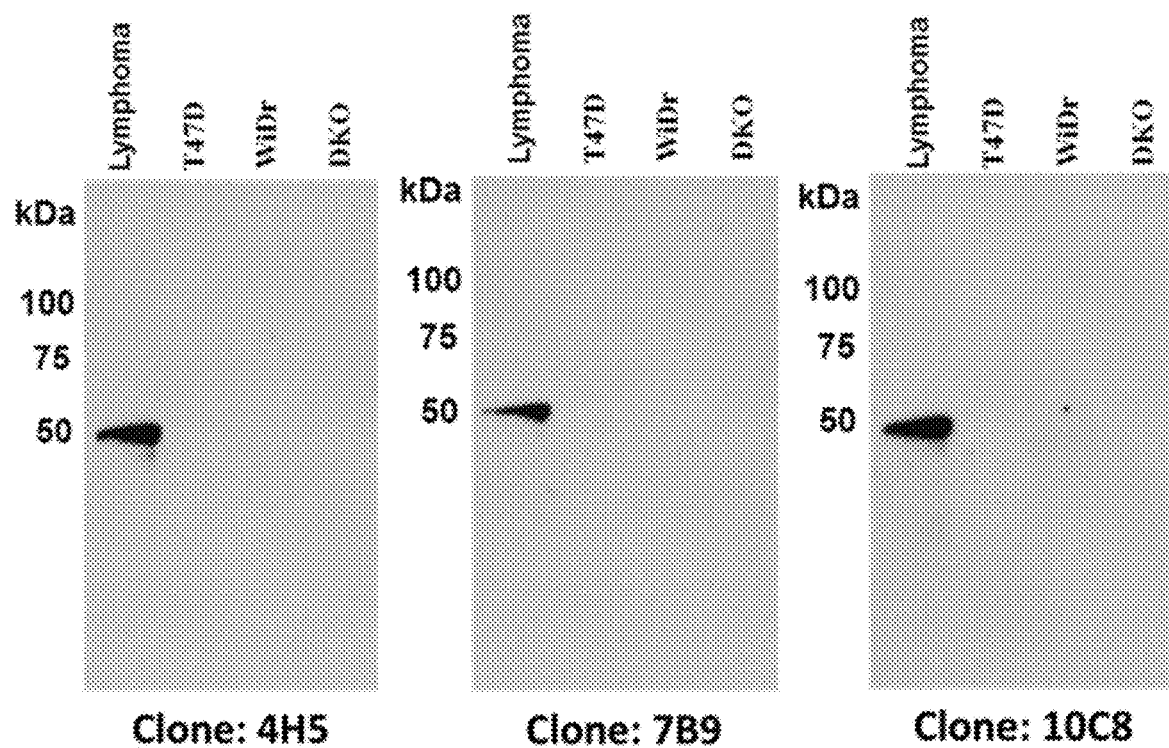

FIG. 35. Photographs showing the results of immunoblots of extracts from R172H mouse thymic lymphoma primary cell line, T47D, WiDr and DKO cells using 4H5, 7B9 and 10C8 hybridoma cell culture supernatant.

Figure 36A:
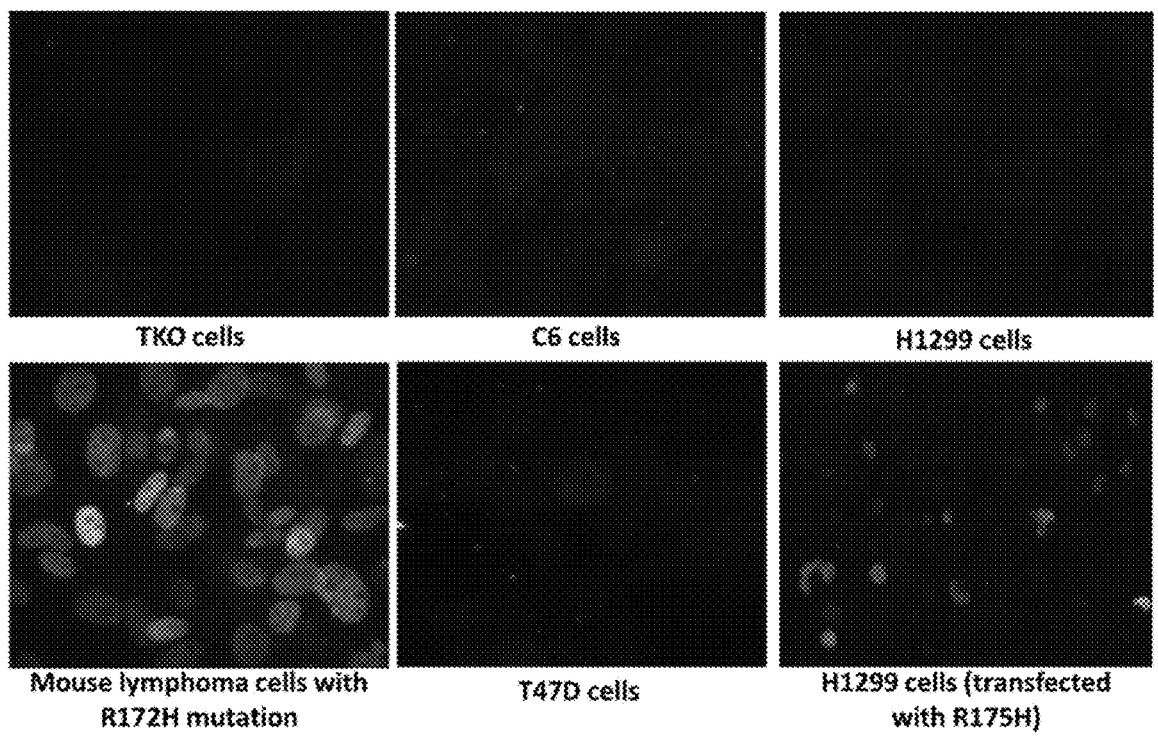
Figure 36B:
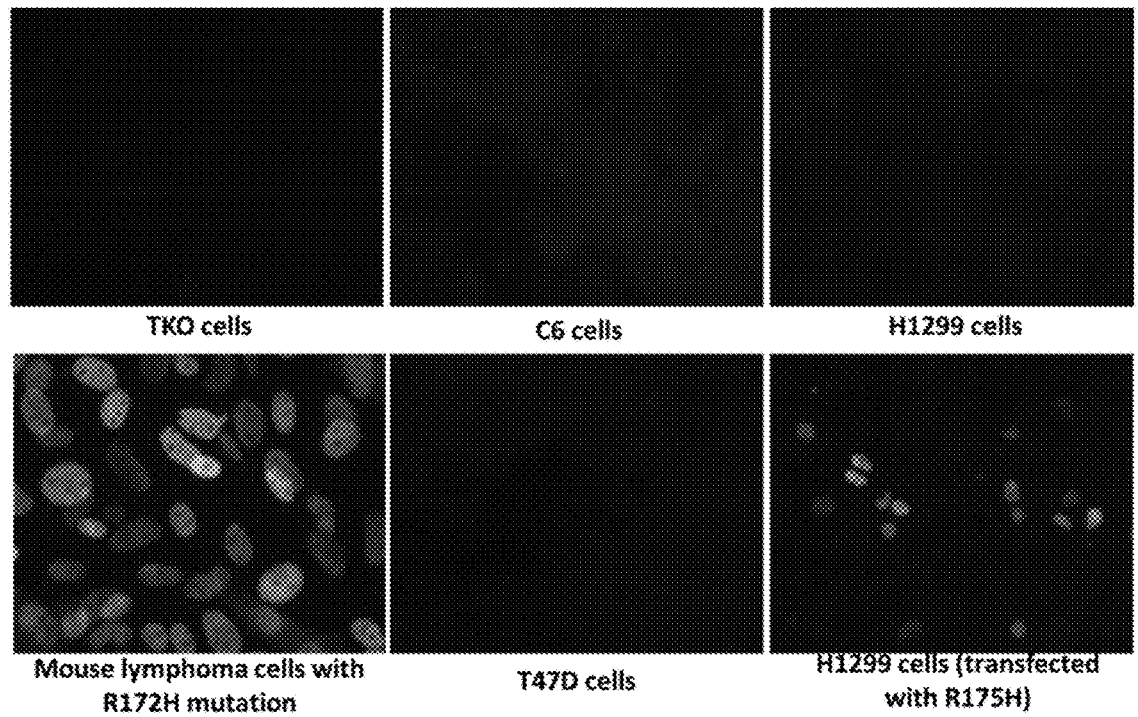
Figure 36C:
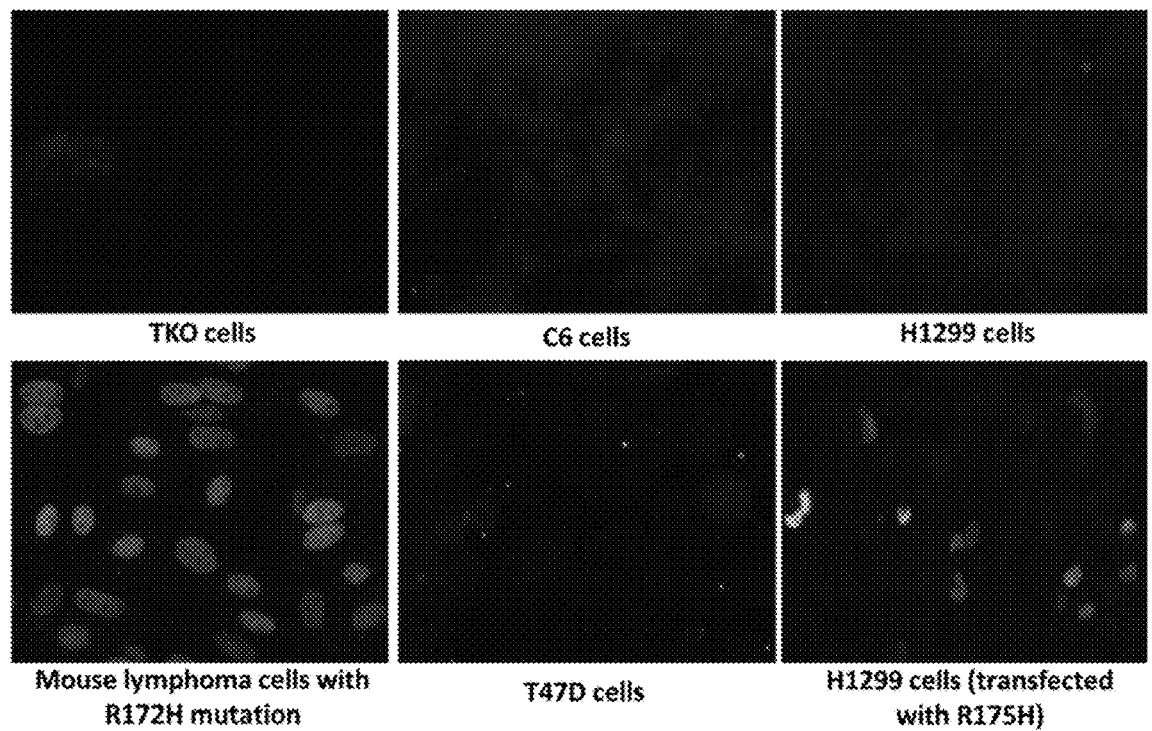

FIGS. 36A to 36C. Photographs showing the results Immunofluorescence analysis of cells expressing and non-expressing R175H mutant p53 proteins with hybridoma cell culture supernatant from clones (36A) 4H5 (36B) 7B9 and (36C) 10C8.

Figure 37:
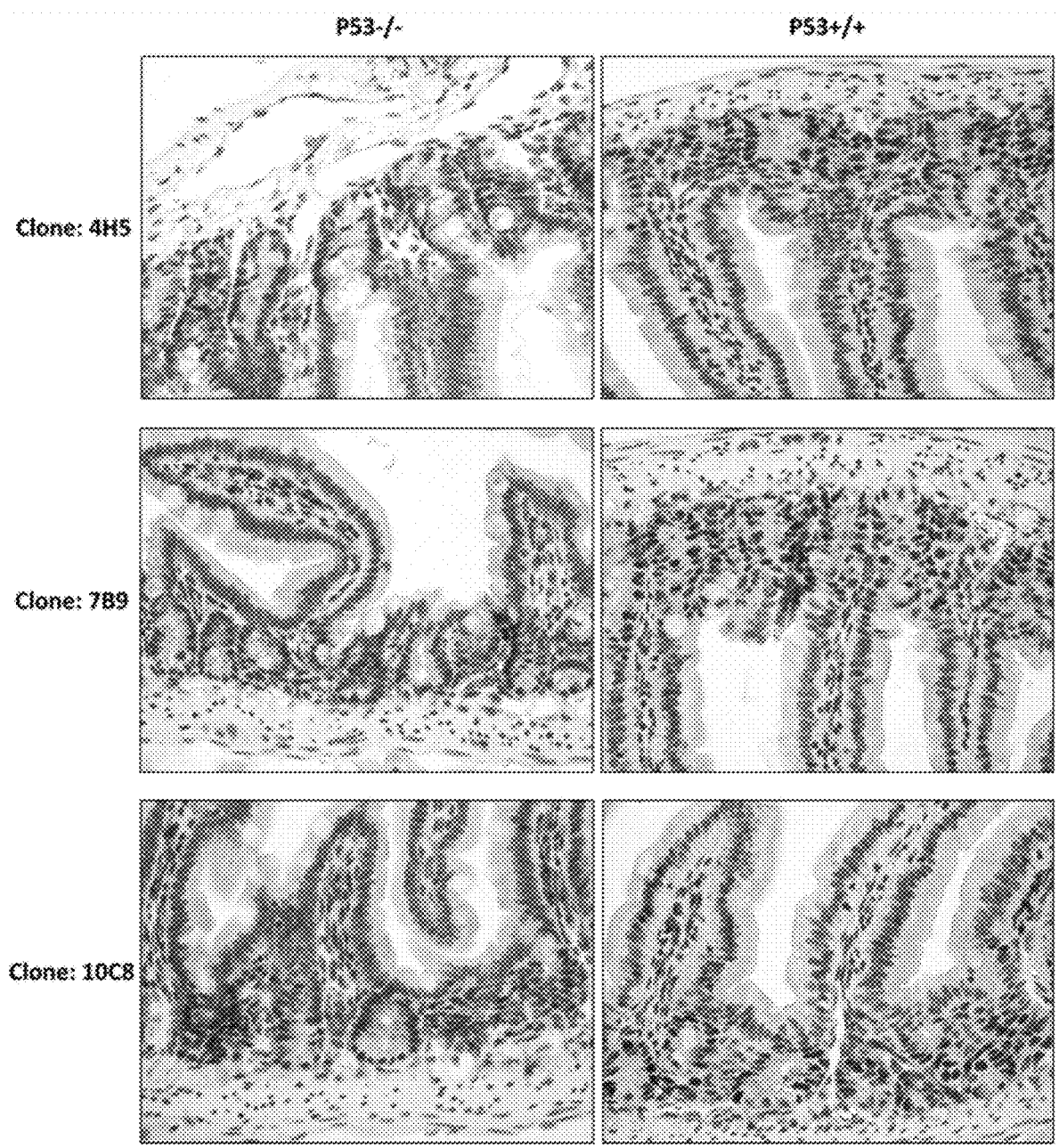

FIG. 37. Photographs showing the results of analysis of mouse intestinal tissue sections (p53 knockout or irradiated, p53 R172H positive) using hybridoma cell culture supernatant from clones 4H5, 7B9 and 10C8.

Figure 38:
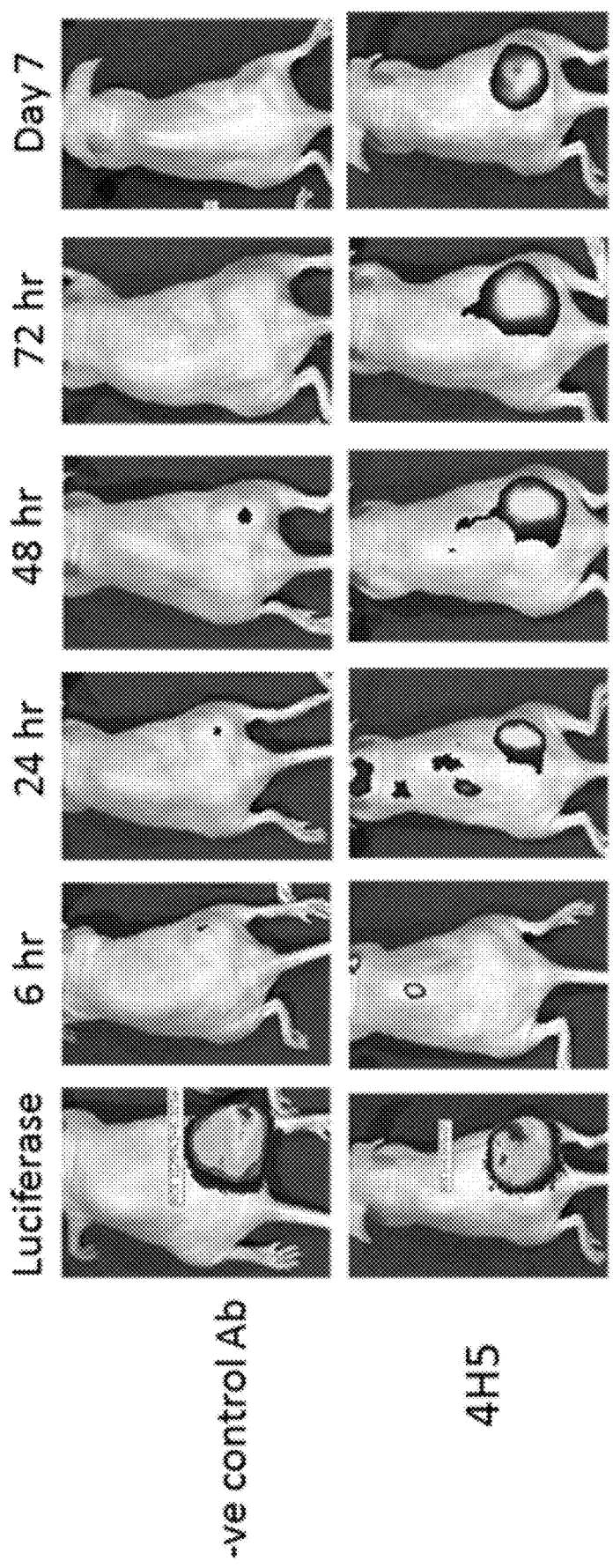

FIG. 38. Photographs showing tumor targeting by the XenoLight CF750 conjugated 4H5 mAb. Mice were imaged at 6, 24, 48, 72 hours and 7 days after i.v. injection of 100 ug XenoLight CF750 labelled 4H5 mAb and imaged by IVIS. Mouse tumor cells derived from P53$^{R172H/R172H}$ mice, were transfected with luciferase gene and used to establish the tumor model.

Figure 39:
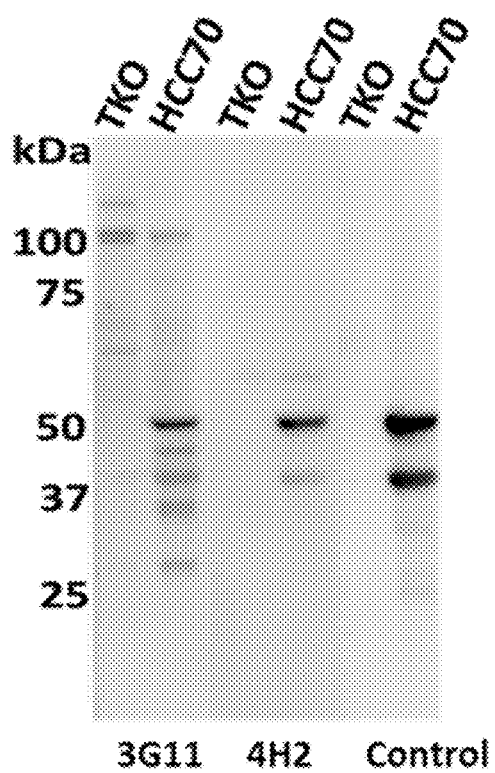

FIG. 39. Photograph showing the results of immunoblots of extracts from TKO and HCC70 cells using 3G11 and 4H2 hybridoma cell culture supernatant.

Figure 40A:
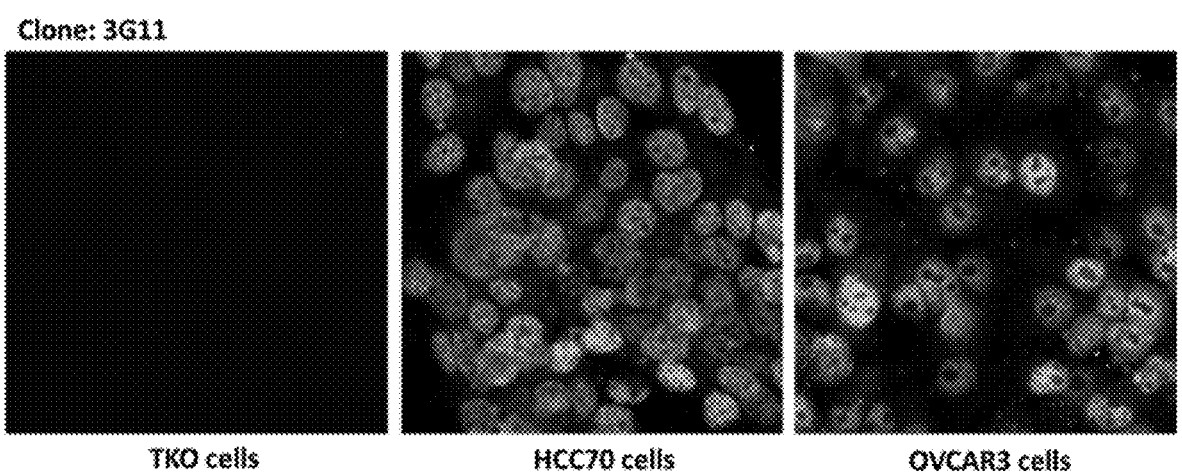
Figure 40B:
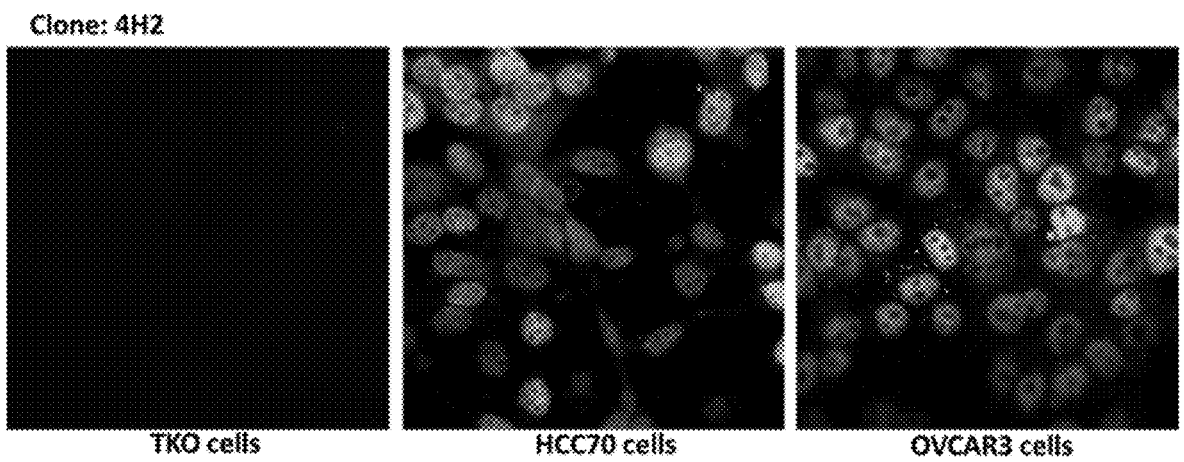

FIGS. 40A and 40B. Photographs showing the results Immunofluorescence analysis of cells expressing R248Q p53, and cells not expressing R248Q p53, with hybridoma cell culture supernatant from clones (40A) 3G11 (40B) 4H2.

Figure 41:
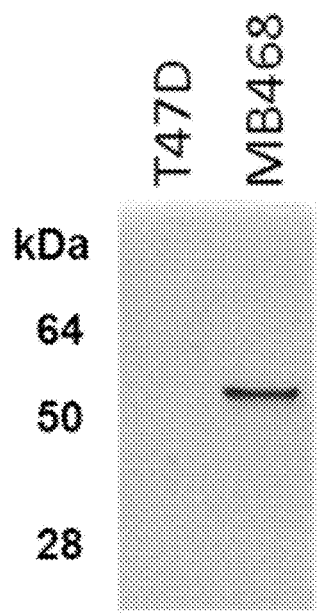

FIG. 41. Photograph showing the results of immunoblots of extracts from T47D and MB468 cells using 13E4 hybridoma cell culture supernatant.

Figure 42:
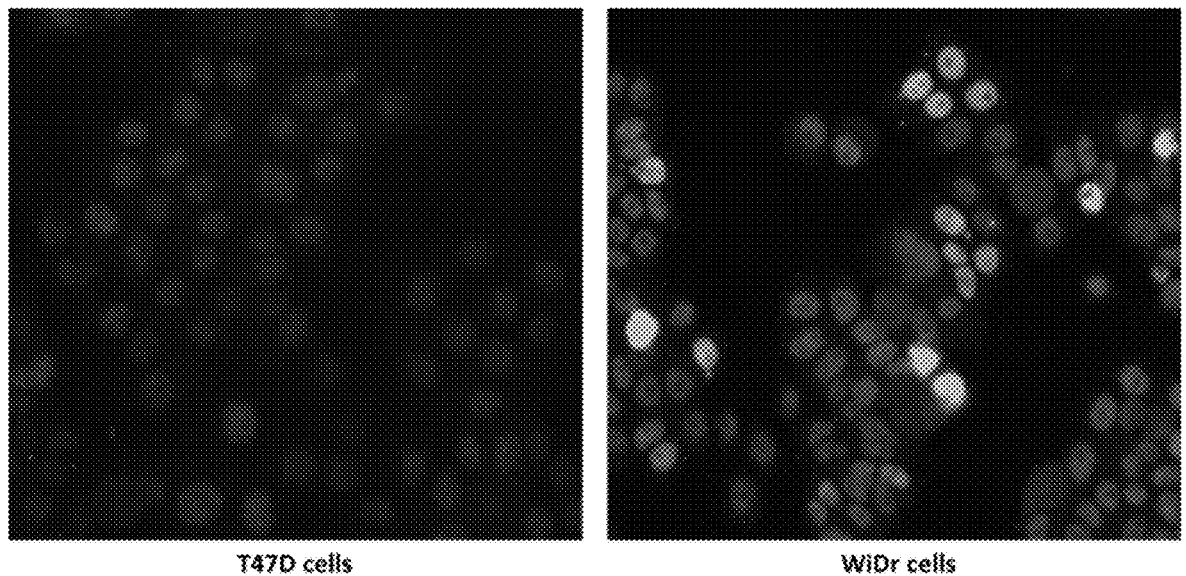

FIG. 42. Photographs showing the results Immunofluorescence analysis of cells expressing R273H p53 (WiDr), and cells not expressing R273H p53 (T47D), with hybridoma cell culture supernatant from clone 13E4.

Figure 43:
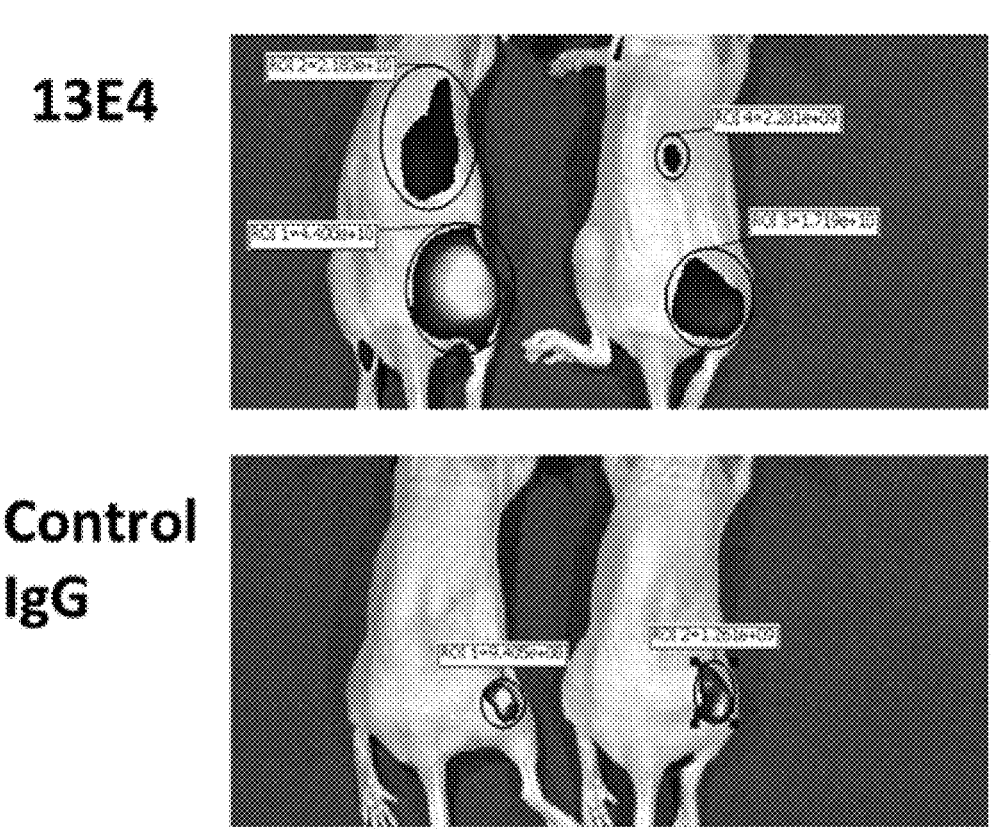

FIG. 43. Photographs showing tumor targeting by the XenoLight CF750 conjugated 13E4 mAb. Mice were imaged at 72 hours after i.v. injection of 100 ug XenoLight CF750 labelled 13E4 mAb and imaged by IVIS. The p53-R273H mutant HT29 tumor cell line transfected with luciferase gene, was used to establish the tumor model.

Figure 44:
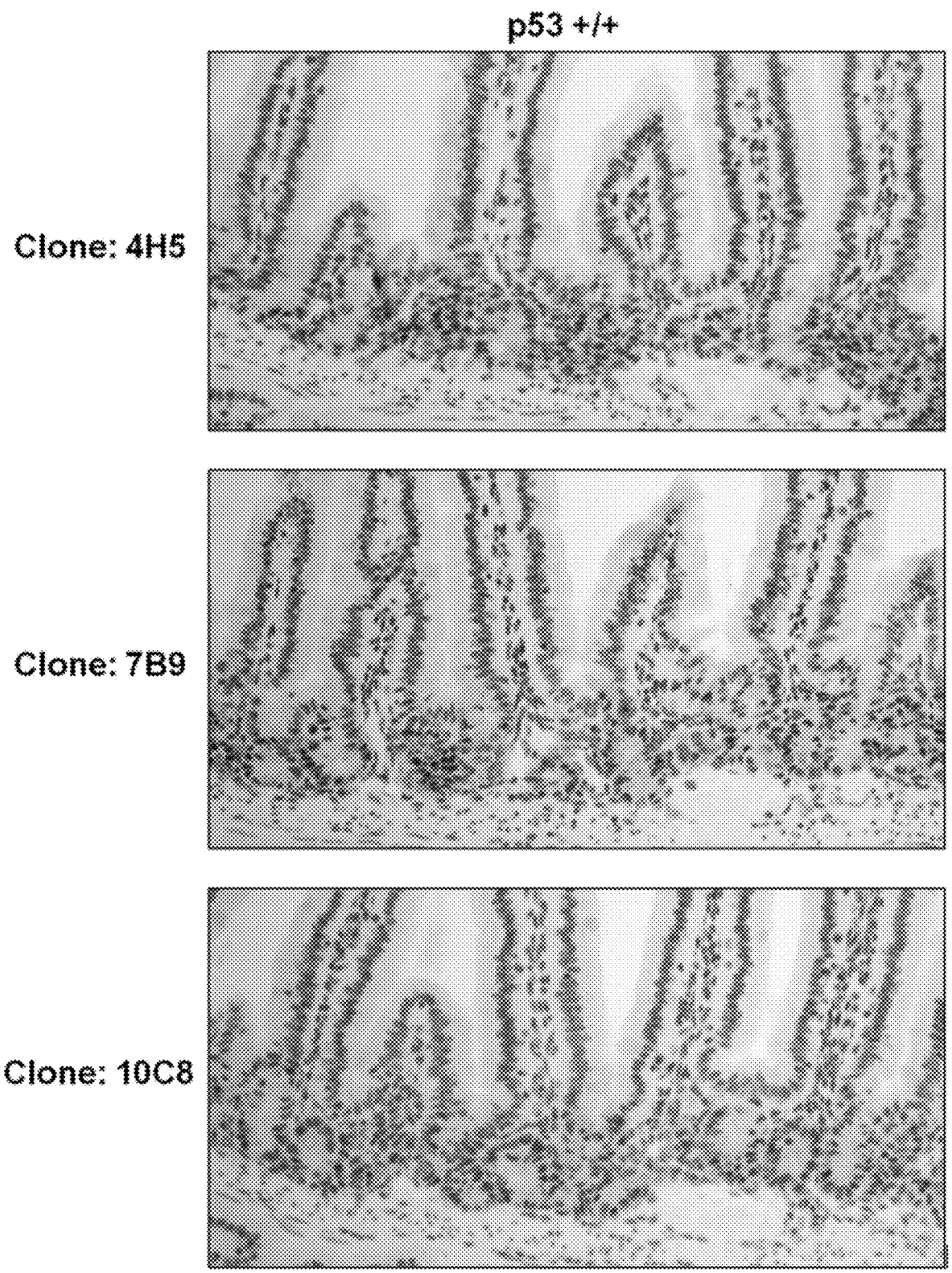

FIG. 44. Photographs showing the results of analysis of mouse intestinal tissue sections (p53 knockout or irradiated, p53 R172H positive) using purified, mouse FV-human IgG1 chimeric 4H5, 7B9 and 10C8 antibodies.

Figure 45:
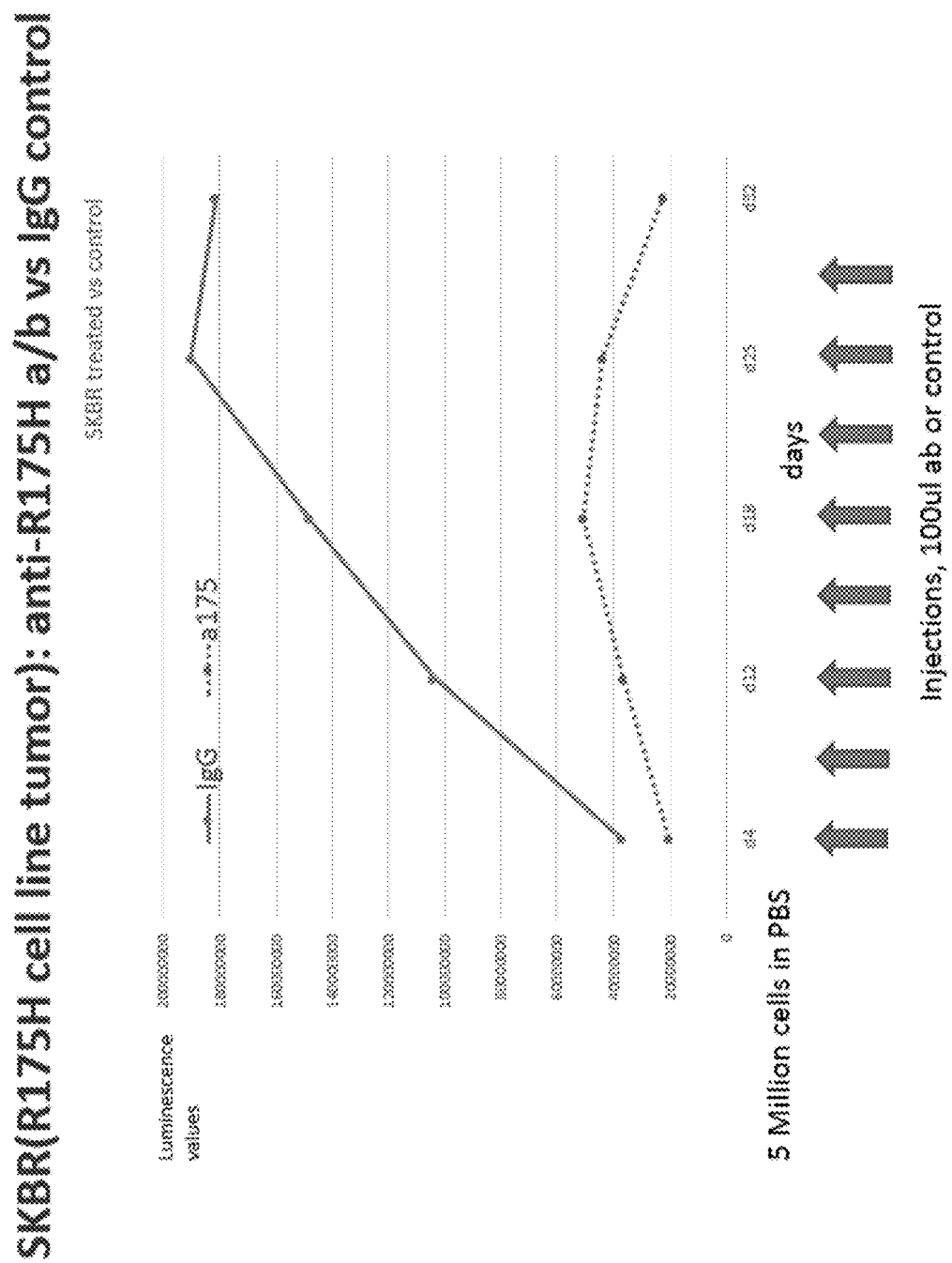

FIG. 45. Graph showing the results of analysis of anti-R175H antibody to control growth of R175H-positive cancer in vivo. SKBR-3 cells carrying luciferase were used to establish a human xenograft cancer model, and the influence on tumor growth of treatment with anti-R175H antibody (a175; dotted line) was compared to IgG control (IgG, solid line).

FIG. 46A to 46E. Graphs showing results of ELISA analysis of antibody response in mice injected with immunogens corresponding to (46A and 46B) R175H, (46C and 46D) R273H or (46E and 46F) R248Q mutants of p53, to peptide corresponding to the p53 mutant or wildtype human p53. Serum from immunized mice was analysed for antibody capable of binding to peptide corresponding to the p53 mutant (46A) R175H, (46C) R273H, or (46E) R248Q, and full-length wildtype human p53 (WT HP53; 46B, 46D and 46E).

FIGS. 47A to 47C. Photographs showing results of immunofluorescence analysis of ability of antibodies produced in response to immunisation with immunogens corresponding to (47A) R175H, (47B) R248Q or (47C) R273H mutants of p53 to recognise cells expressing the corresponding mutant p53 polypeptide.

Figure 48:
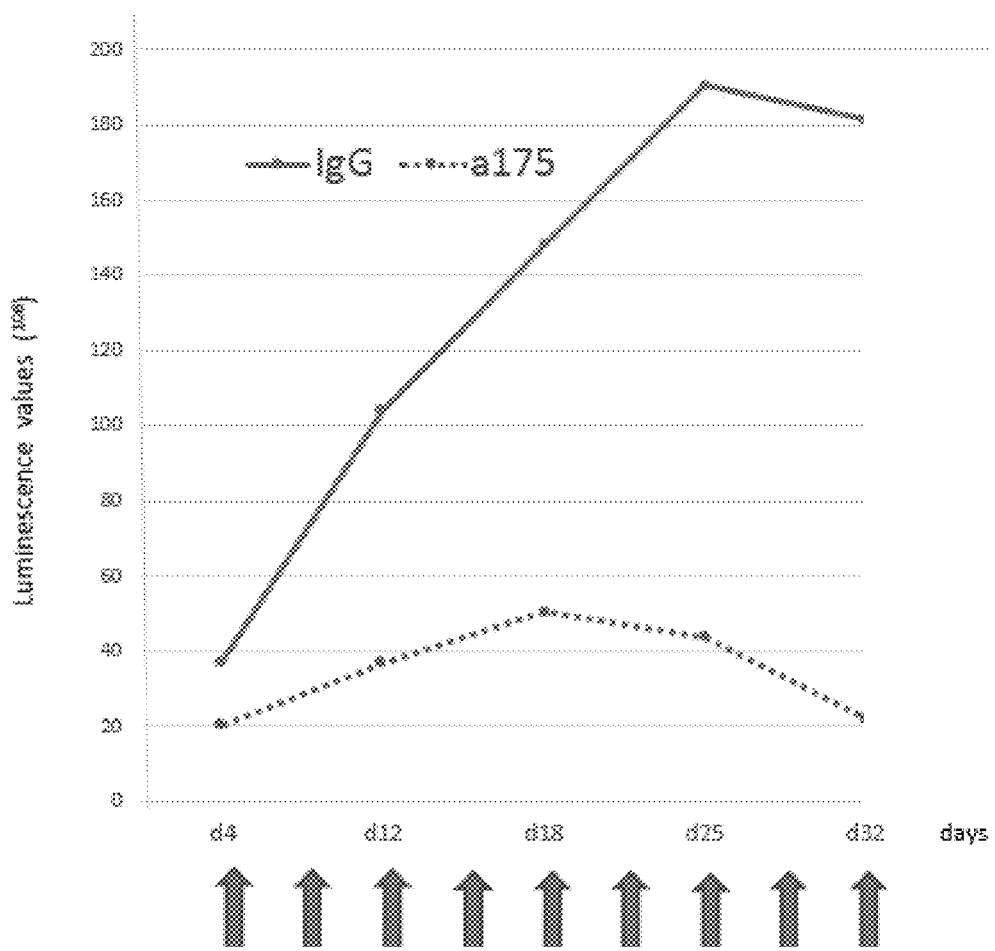

FIG. 48. Graph showing the effect of anti-R175H antibody on growth of SKBR cells. Mice were injected with $5\times10^6$ SKBR luciferase reporter cells, and injected at regular intervals (injections are indicated by arrows) with 100 μl of monoclonal antibody specific for the R175H mutant p53 (a175) or isotype control antibody (IgG). SKBR cell growth was measured by analysis of luciferase activity.

FIG. 49. Light chain variable domain sequence for mouse human chimeric anti-R175H p53 antibody clones MH 4H5, MH 7B9 and MH 10C8. CDRs are underlined and shown separately.

FIG. 50. Heavy chain variable domain sequence for mouse human chimeric anti-R175H p53 antibody clones MH 4H5, MH 7B9 and MH 10C8. CDRs are underlined and shown separately.

FIG. 51. Nucleotide and encoded amino acid sequences of light chain variable domain sequences for mouse human chimeric anti-R175H p53 antibody clones MH 4H5, MH 7B9 and MH 10C8.

FIG. 52. Nucleotide and encoded amino acid sequences of heavy chain variable domain sequences for mouse human chimeric anti-R175H p53 antibody clones MH 4H5, MH 7B9 and MH 10C8.

FIG. 53. Light chain variable domain sequence for mouse human chimeric anti-R273H p53 antibody clone MH 13E4. CDRs are underlined and shown separately.

FIG. 54. Heavy chain variable domain sequence for mouse human chimeric anti-R273H p53 antibody clone MH 13E4. CDRs are underlined and shown separately.

FIG. 55. Nucleotide and encoded amino acid sequences of light chain variable domain sequences for mouse human chimeric anti-R273H p53 antibody clone MH 13E4.

FIG. 56. Nucleotide and encoded amino acid sequences of heavy chain variable domain sequences for mouse human chimeric anti-R273H p53 antibody clone MH 13E4.

FIG. 57. Light chain variable domain sequence for mouse human chimeric anti-R248Q p53 antibody clones MH 3G11 and MH 4H2. CDRs are underlined and shown separately.

FIG. 58. Heavy chain variable domain sequence for mouse human chimeric anti-R248Q p53 antibody clones MH 3G11 and MH 4H2. CDRs are underlined and shown separately.

FIG. 59. Nucleotide and encoded amino acid sequences of light chain variable domain sequences for mouse human chimeric anti-R248Q p53 antibody clones MH 3G11 and MH 4H2.

FIG. 60. Nucleotide and encoded amino acid sequences of heavy chain variable domain sequences for mouse human chimeric anti-R248Q p53 antibody clones MH 3G11 and MH 4H2.

Figure 61:
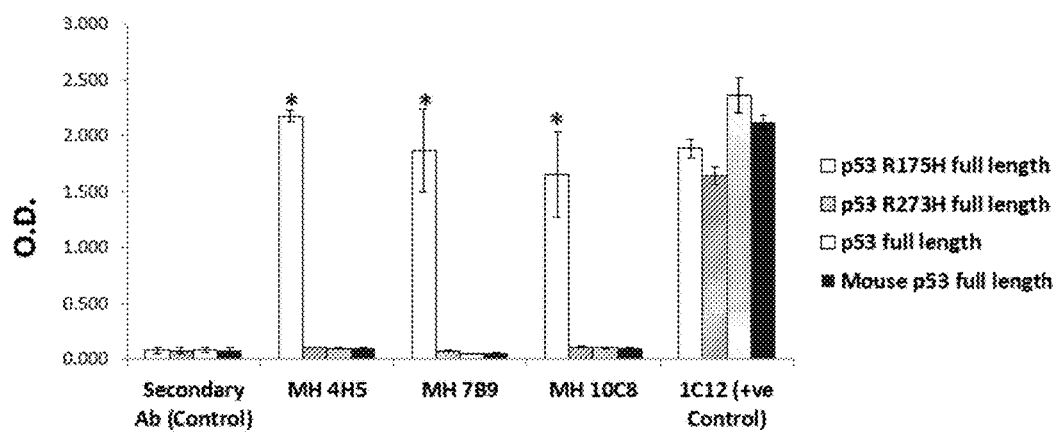

FIG. 61. Bar chart showing the results of ELISA analysis confirming specific binding to R175H p53 by the chimeric mouse human antibody clones MH 4H5, MH7B9 and MH 10C8. Averaged OD450 readings were plotted. The chimeric anti-p53 R175H antibodies (MH 4H5, MH 7B9, MH 10C8) antibodies produced positive signals between 0.1 and 1 ng/µl concentrations. Data shown in this figure was for 1 ng/µl antibody concentration. All chimeric anti-p53 R175H antibodies specifically recognized and detected only human p53 R175H full length protein and not human p53 R273H full length, human p53 wild-type full length, or mouse p53 wild-type full length protein (single asterisks). Commercial anti-p53 antibody (1c12) was included as a positive control antibody. (n=3).

Figure 62:
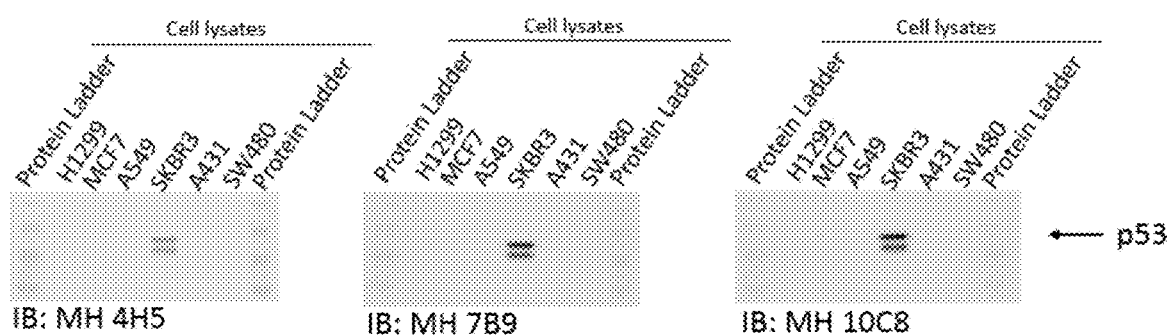

FIG. 62. Western blots showing specific binding to R175H p53 by the chimeric mouse human antibody clones MH 4H5, MH7B9 and MH 10C8. Human cell lines: H1299 (p53-null), MCF7, A549 (both wild-type p53), SKBR3 (p53 R175H), A431, and SW480 (both p53 R273H) were tested in this experiment. All chimeric anti-p53 R175H antibodies recognized and detected only endogenous human p53 R175H protein (SKBR3) and not human p53 R273H, or human p53 wild-type protein (black arrow). All antibodies were tested at 1 ng/µl concentration.

Figure 63:
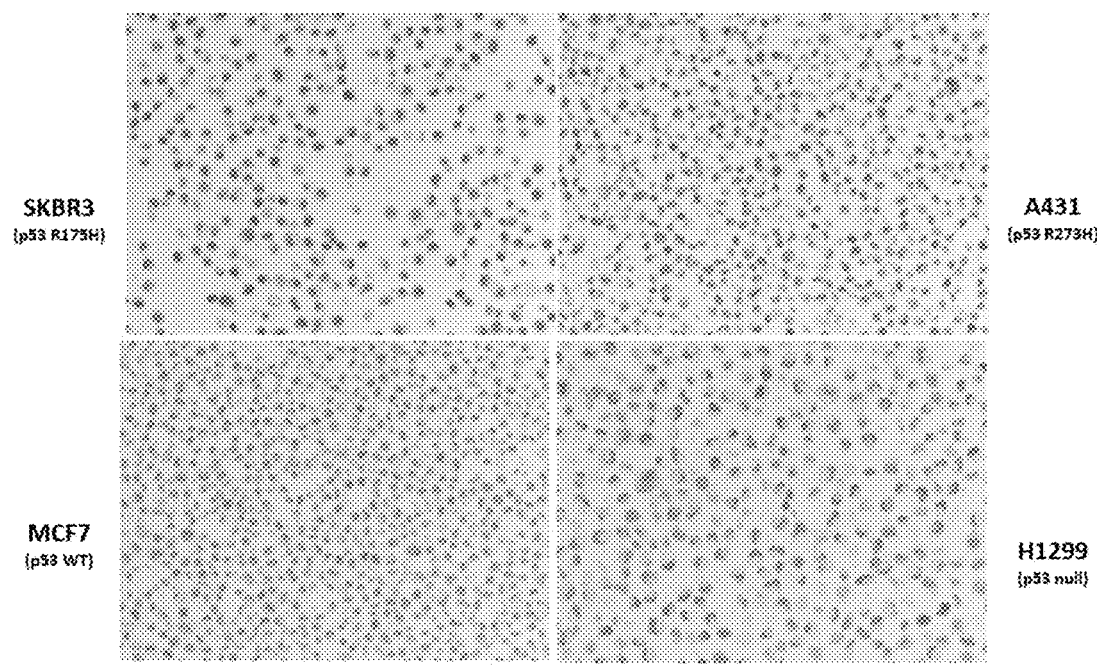

FIG. 63. Representative images showing detection of endogenous p53 proteins in human cell lines by MH 7B9. Cells were fixed in 4% paraformaldehyde then embedded in paraffin. Immunohistochemical assays were performed using the following human cell lines: H1299 (p53-null), MCF7 (wild-type p53), SKBR3 (p53 R175H), and A431 (p53 R273H). The photographs show staining of all cell lines with 1.67 ng/µl of MH 7B9 antibody. All chimeric anti-p53 R175H antibodies specifically recognized and stained only cell nuclei expressing endogenous human p53 R175H protein (SKBR3 (top left panel)).

Figure 64:
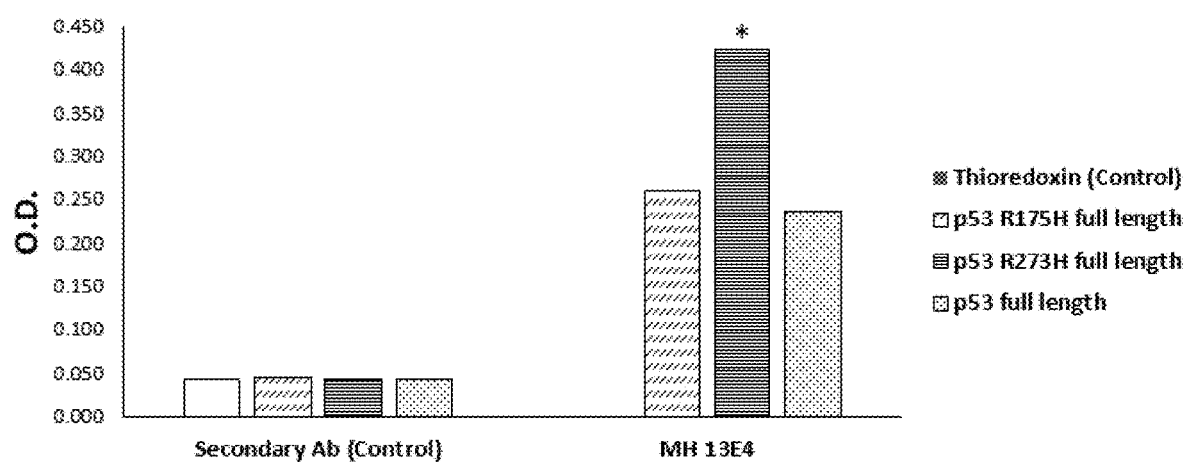

FIG. 64. Bar chart showing the results of ELISA analysis confirming specific binding to R273H p53 by the chimeric mouse human antibody clone MH 13E4. Averaged OD450 readings were plotted. Data shown in this figure was for 1 ng/µl antibody concentration. MH 13E4 specifically recognized and detected only human p53 R273H full length protein and not human p53 R175H full length or human p53 wild-type full length protein (single asterisks).

Figure 65:
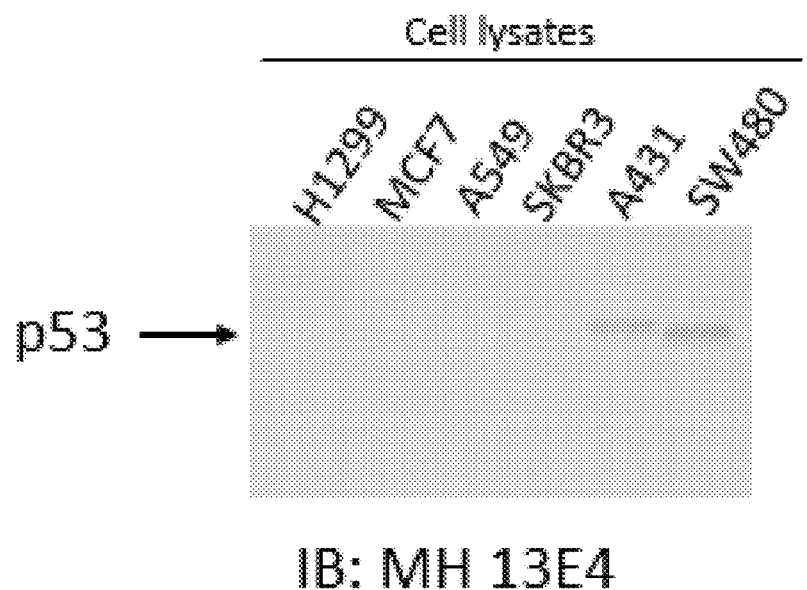

FIG. 65. Western blot showing specific binding to R273H p53 by the chimeric mouse human antibody clone MH 13E4. Human cell lines: H1299 (p53-null), MCF7, A549 (both wild-type p53), SKBR3 (p53 R175H), A431, and SW480 (both p53 R273H) were tested in this experiment. MH 13E4 specifically recognized and detected only endogenous human p53 R273H protein (A431 and SW480) and not human p53 R175H, or human p53 wild-type protein (black arrow). MH 13E4 was tested at 1 ng/µl concentration.

Figure 66:
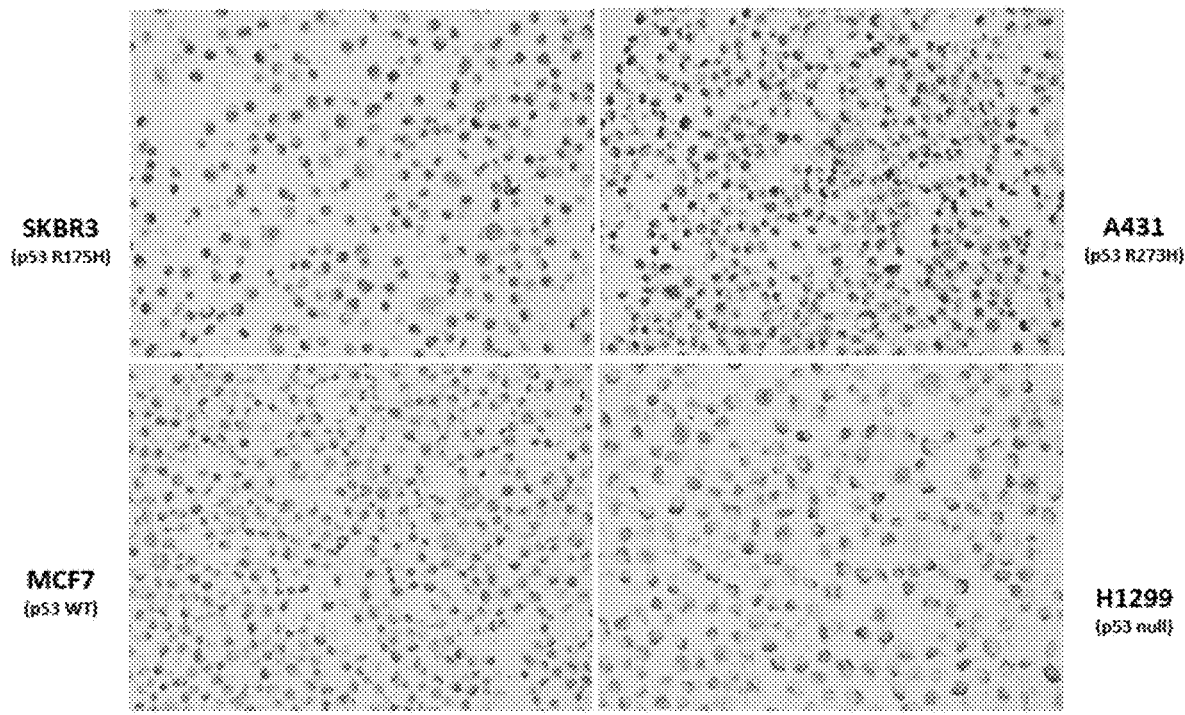

FIG. 66. Representative images showing detection of endogenous p53 proteins in human cell lines by MH 13E4. Cells were fixed in 4% paraformaldehyde then embedded in paraffin. Immunohistochemical assays were performed using the following human cell lines: H1299 (p53-null), MCF7 (wild-type p53), SKBR3 (p53 R175H), and A431 (p53 R273H). The photographs show staining of all cell lines with 5 ng/µl of MH 13E4 antibody. MH 13E4 antibody specifically recognized and stained only cell nuclei expressing endogenous human p53 R273H protein (A431 (top right panel)).

Figure 67:
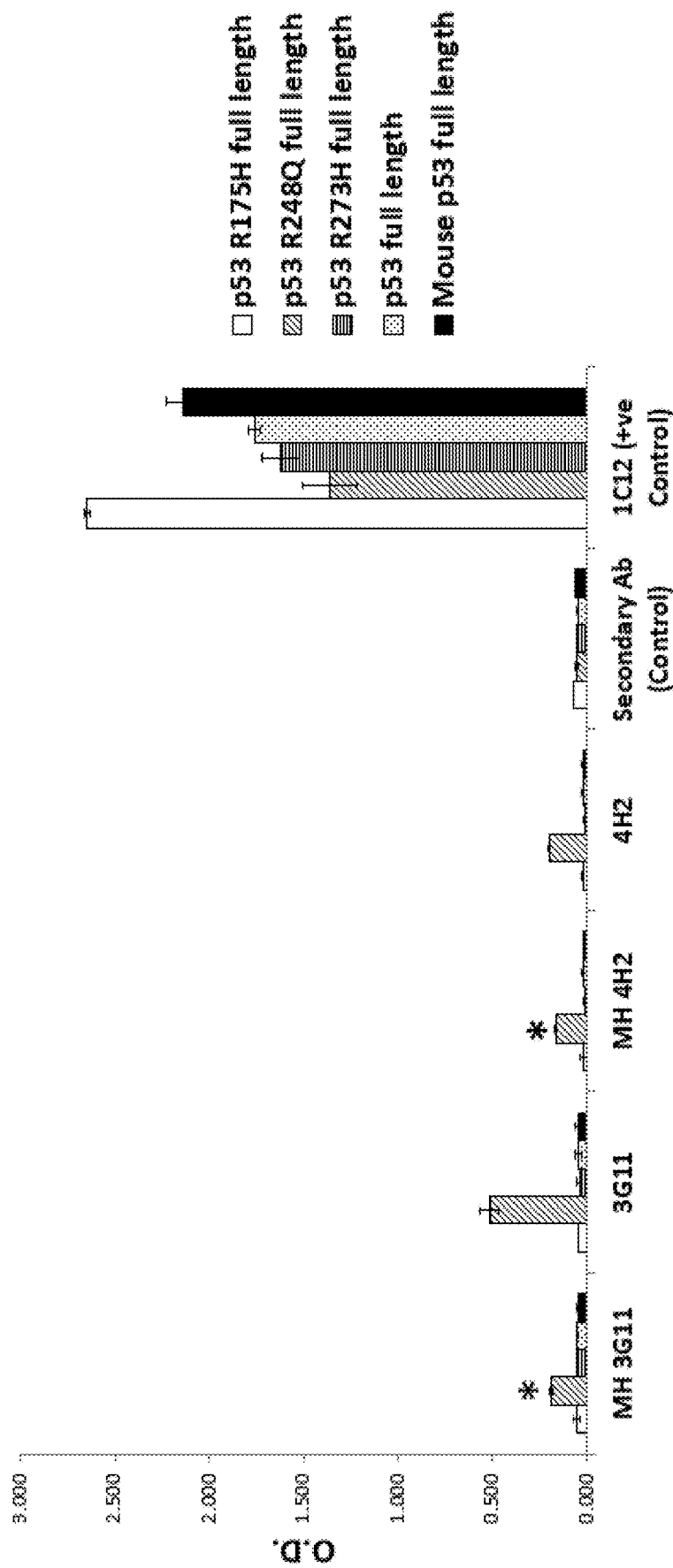

FIG. 67. Bar chart showing the results of ELISA analysis confirming specific binding to R248Q p53 by the chimeric mouse human antibody clones MH 3G11 and MH 4H2. Averaged OD450 readings were plotted. The chimeric anti-p53 R248Q antibodies were used at a concentration of 1 ng/µl, while 3G11 and 4H2 hybridoma supernatants were tested at neat concentration. Both MH 3G11 and MH 4H2 specifically recognized and detected only human p53 R248Q full length protein over human p53 R175H full length, human p53 R273H full length, human p53 wild-type full length, and mouse p53 wild-type full length protein (single asterisks). Hybridoma supernatants and commercial anti-p53 antibody (1C12) were included as positive control antibodies. (n=3).

Figure 68:
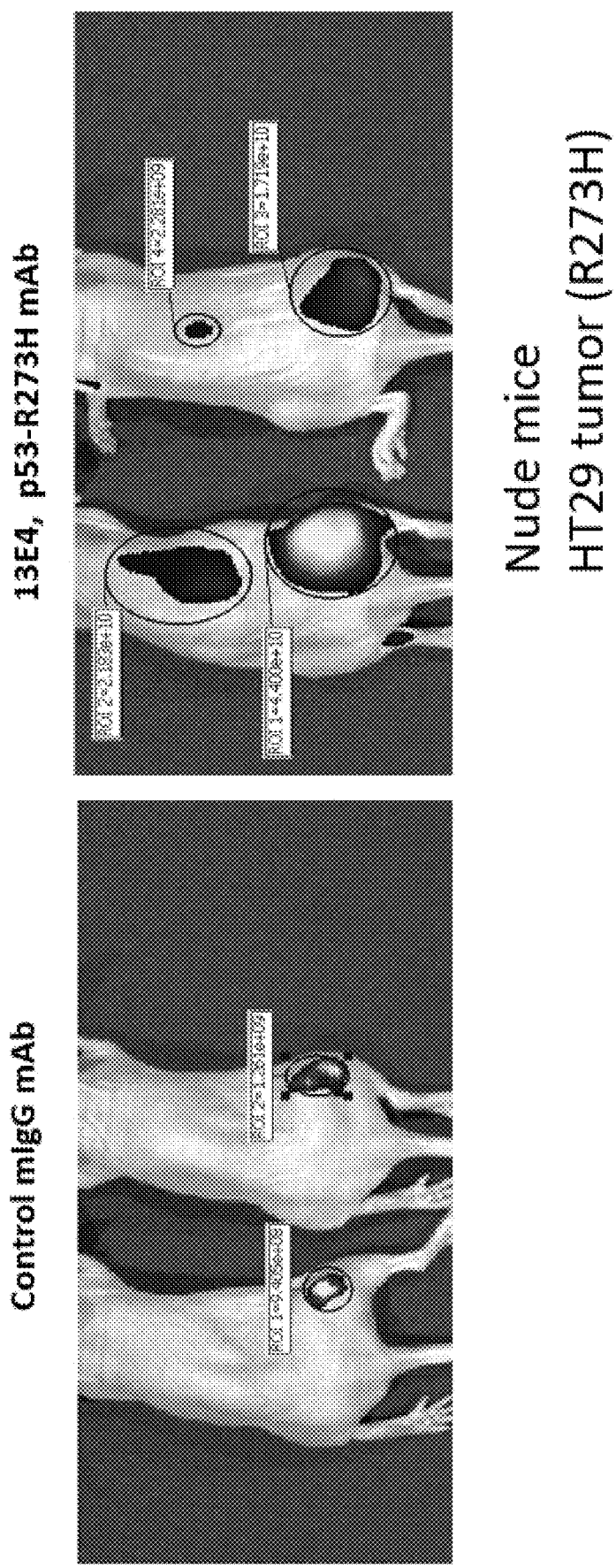

FIG. 68. Images showing detection of R273H mutant p53 in vivo by MH 13E4. 100 µg of fluorescently-labeled R273H specific mAb MH 13E4 or IgG control antibody, was injected i.v. in p53R273H mutant HT29 tumor bearing mice. Mice were imaged by IVIS Sprectrum in vivo imaging system for trafficking mAbs 72 hours following antibody injections.

Figure 69:
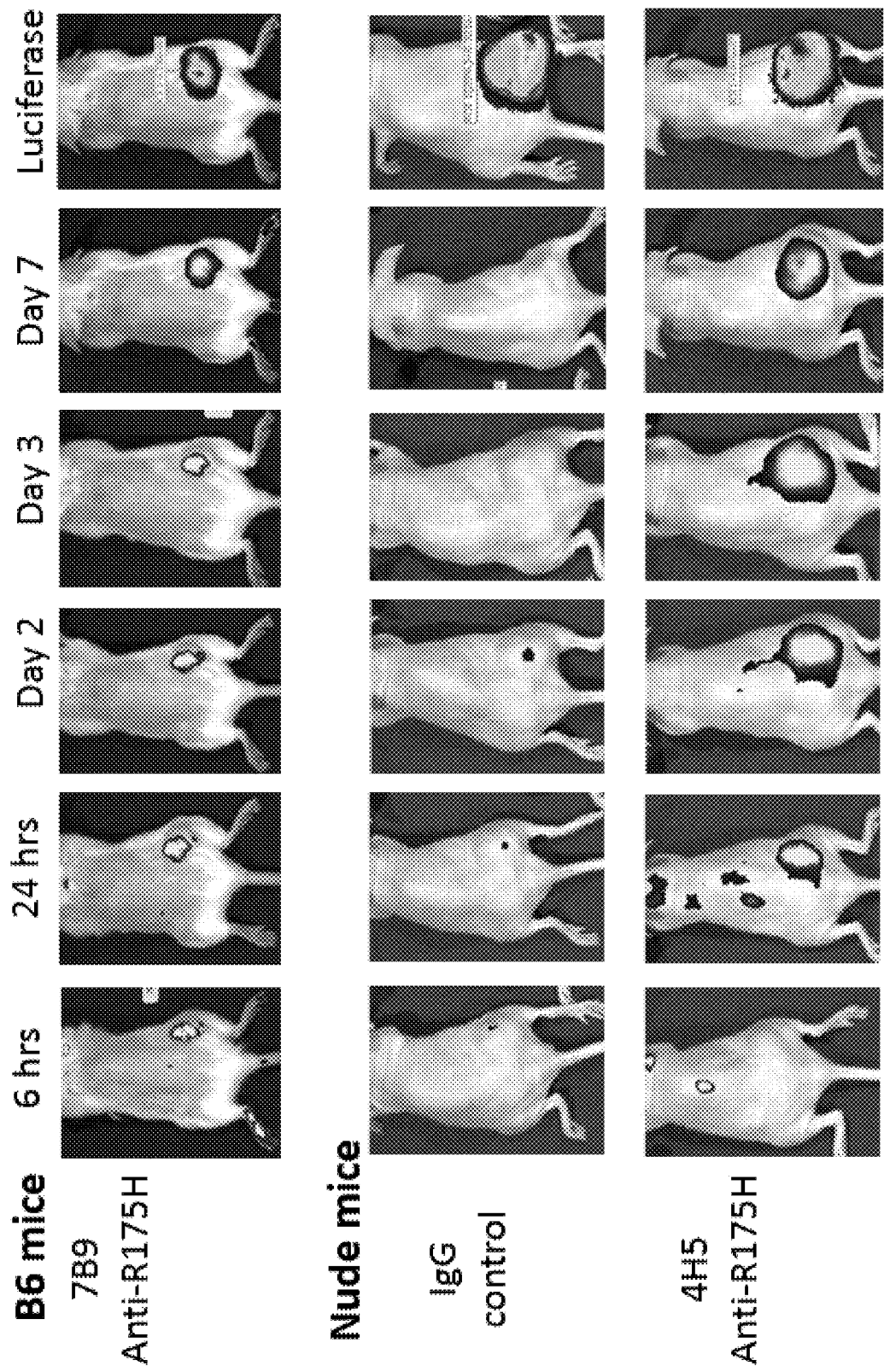

FIG. 69. Images showing detection of R175H mutant p53 in vivo by MH 4H5 and MH 7B9. 100 µg of fluorescently-labeled R175H specific mAb, MH 4H5 or MH 7B9 or IgG control was injected i.v. in p53R175H clone 32 tumor bearing mice. Mice were imaged by IVIS Sprectrum in vivo imaging system for trafficking mAbs at 6 h, 24 h, Day 2, Day 3 and Day 7 following antibody injections. The bioluminescent light indicates the location of the clone32 tumors.

Figure 70:
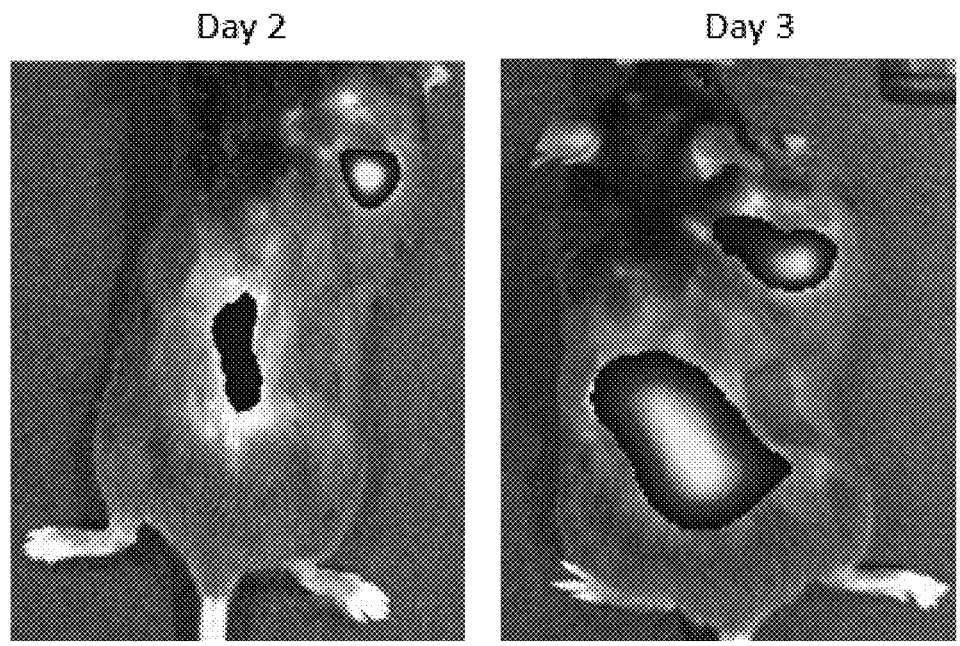

FIG. 70. Images showing detection of spontaneously arising murine R172H mutant p53 in vivo by MH 4H5. 100 µg of fluorescently-labeled R175H specific mAb MH 4H5 was injected i.v. into tumour bearing mutant p53R172H mice. Mice were imaged by IVIS Sprectrum in vivo imaging system on Days 2 and 3 following injection of the antibody.

Figure 71A:
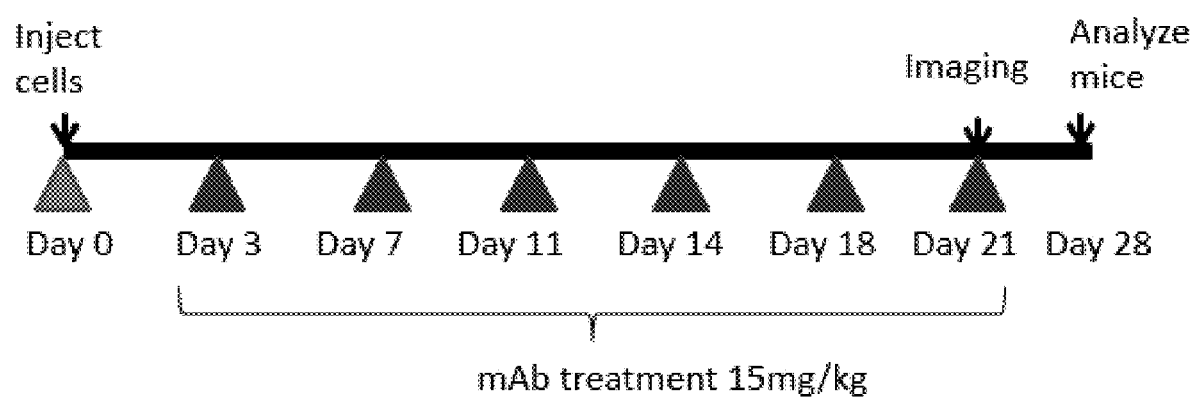
Figure 71B:
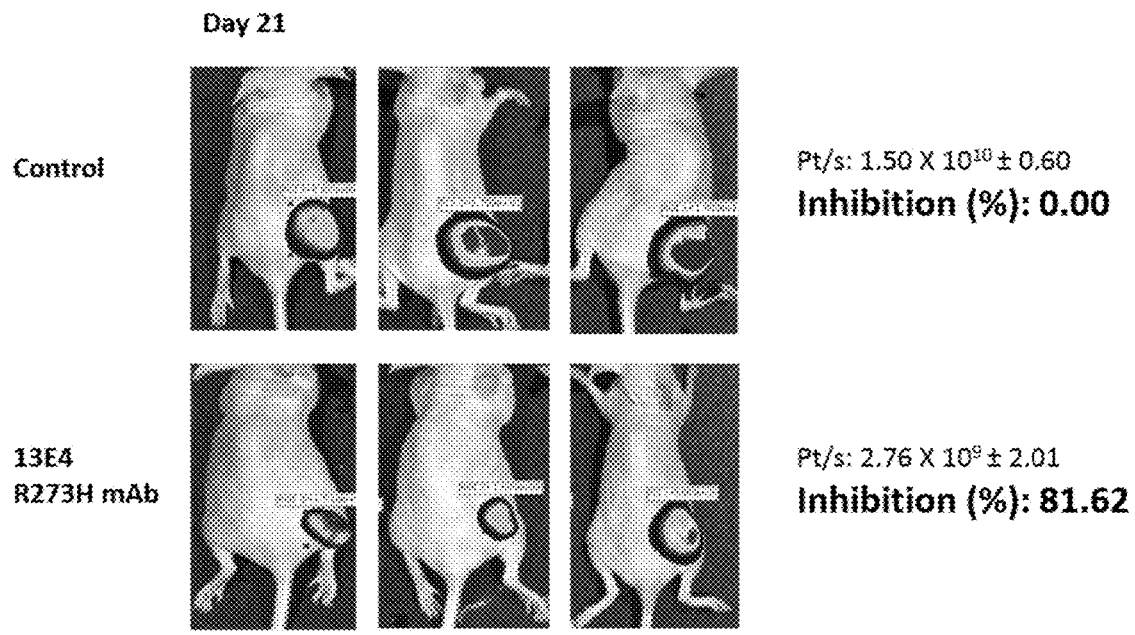

FIGS. 71A and 71B. Schematic and images showing inhibition of HT29 xenograft tumour growth by treatment with mAb 13E4. (71A) Schematic representation of the experimental schedule. (71B) Images showing tumour size as determined by measuring average photon intensity.

FIGS. 72A to 72D. Schematic, bar chart, images and graph showing inhibition of HT29 xenograft tumour growth by treatment with mAb 13E4. (72A) Schematic representation of the experimental schedule. (72B) Bar chart showing tumour mass at the end of the experiment. (71C and 71D) Images and graph showing tumour size as determined by measuring average photon intensity.

Figure 73A:
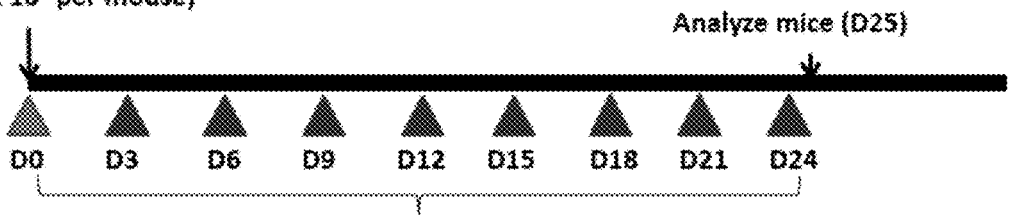
Figure 73B:
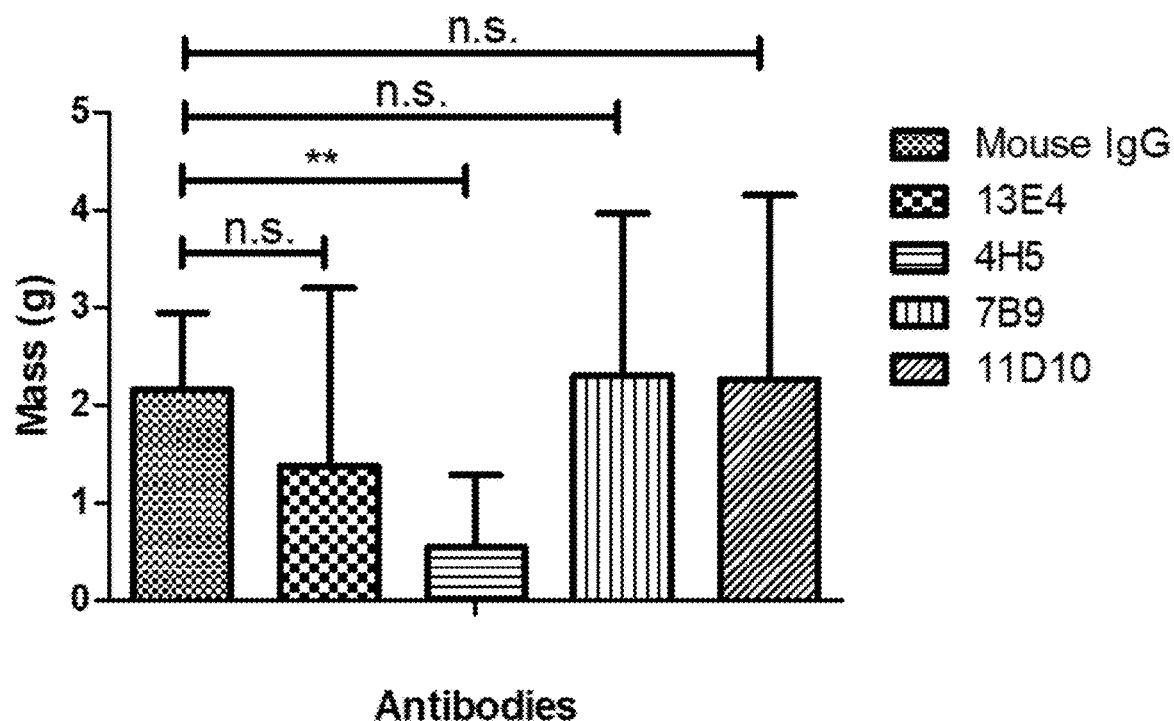

FIGS. 73A and 73B. Schematic and bar chart showing therapeutic effect for anti-p53 mutant R175 antibody against murine p53 R172H-positive cancer. (74A) Schematic representation of the experimental schedule. (74B) Bar chart showing tumour mass at the end of the experiment.

FIGS. 74A to 74F. Schematic, graphs, images and bar chart showing ability of TrxR175H immunisation to raise antibodies capable of binding to mutant p53 R175 protein. (74A) Schematic representation of the experimental schedule. (74B) Graphs showing the ability of the serum from immunised mice to bind to the indicated antigen, as determined by ELISA. (74C and 74D) Images showing ability of the serum from immunised mice to bind to cells expressing p53 mutant R175H (74C), but not p53-negative TKO cells (74D). (74E) Images showing p53 mutant R175H-reactivity of serum obtained from mice immunised with TrxR175H. (74F) Bar chart showing the percentages of different immune cell subsets in the splenocytes of mice immunised with the indicated antigens, as determined by flow cytometry.

EXAMPLES

The inventors describe in the following Examples the generation and characterisation of monoclonal antibodies against DBD region point mutants of P53. The antibodies are shown to be highly specific for the individual p53 hot-spot mutations, and the utility of the antibodies in a variety of biochemical and histological assays is demonstrated.

Example 1: Immunogen Design and Production

Attempts to generate antibodies against specific p53 mutants using a large array of protocols have not been entirely successful, due likely to lack of efficient expression of the mutant epitopes, resulting lack of specificity for the mutant p53 polypeptides.

The inventors therefore utilized the TrxA protein with a protruding body, in which was placed three copies of the mutant p53 mutation (i.e. R175H, R248Q or R273H), with variable lengths of the amino acid sequence flanking the mutation. The mutant p53 polypeptide amino acid sequences were inserted into the active site of TrxA with flanking flexible Gly-Ser-Gly-Ser-Gly (SEQ ID NO:236) linkers separating the antigen sequence and the TrxA sequence. Shorter Gly-Ser-Gly linkers were also inserted between each mutant p53 sequence.

TrxA is a widely-used fusion partner in *Escherichia coli* expression systems for enhancing protein expression levels, solubility and thermal stability, in which the active site (Cys33-Gly34-Pro35-Cys36) (SEQ ID NO:91) protrudes from the protein body into solution (LaVallie et al, 2000 Methods Enzymol 326:322-340; Young et al., 2012 Biotechnol. J. 7:620-634). The presence of a restriction (RsrII) site on the DNA sequence coding for this active site provides an insertion point for internal peptide fusions which can be presented on the surface of TrxA, and has been successfully exploited for production of antibodies by insertion of the antigen within the solvent-accessible loop on the TrxA scaffold (Barrell et al., 2004 Protein Expr. Purif. 33:153-159).

TrxA scaffold harbouring the mutant p53 (R175H, R273H and R248Q) tri-peptide sequences cloned into the pJexpress404 vector, were obtained from DNA2.0 (Menlo Park, CA, USA). The coding sequences were designed with a C-terminus His6-tag to facilitate protein purification by immobilized metal affinity chromatography (IMAC) and custom optimized to *E. coli* preferred codons. Authenticity of the synthetic coding fragments was verified by DNA sequencing.

Figures 1C, 2A:
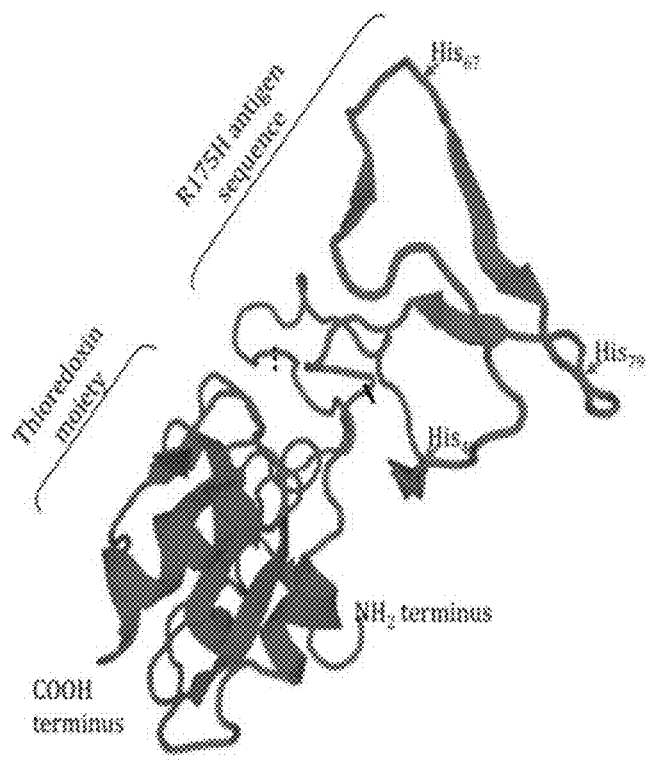

The amino acid sequences for the immunogens used to raise the antibodies are shown in FIG. 1A to 1C.

Figure 2B:
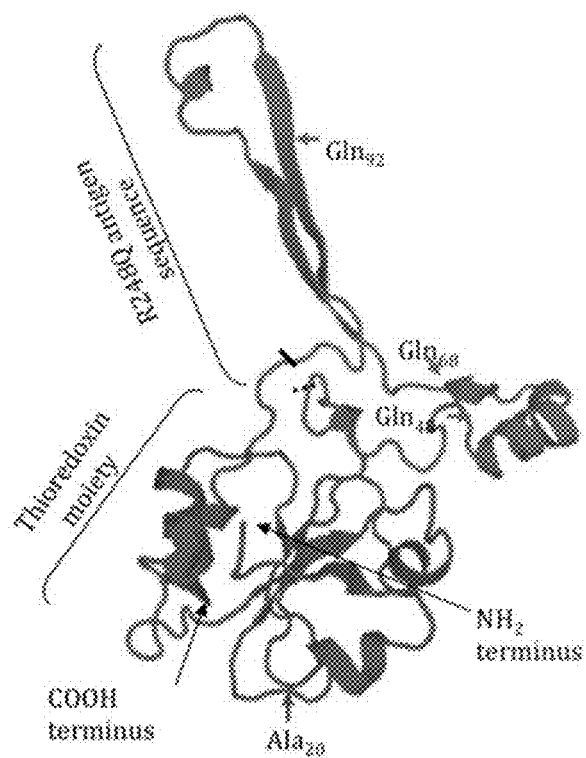
Figure 2C:
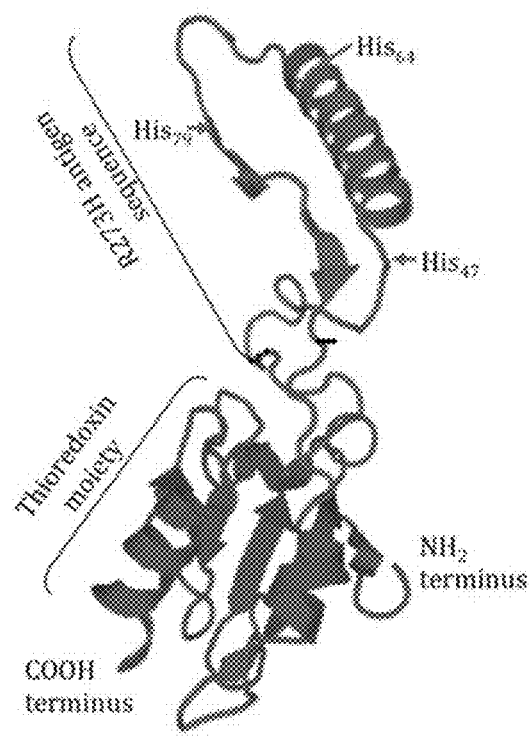

Homology modeling predicted that inserting the mutant p53 antigen sequences into the active site of the TrxA scaffold offers a viable presentation strategy to increase the immunogenicity of the peptide sequence, with the mutant p53 antigen sequence extending away from the TrxA protein, and with the mutated residues exposed in the solvent accessible loop. The predicted 3D structure of the TrxR175H, TrxR248Q and TrxR273H immunogens by Swiss Model are shown (FIG. 2A to 2C), revealing the exposed, solvent accessible mutant p53 antigenic regions.

*E. coli* host strain BL21 (DE3) trxB (Novagen, Merck Millipore, Darmstadt, Germany) was used for the expression of the recombinant Trxp53mutant constructs. Mini-scale expression studies to determine solubility of the protein were performed as described in Liew et al. 2014 Biochimie 89, 21-29. For large scale purification, recovery soluble and insoluble peptides were recovered by native and denaturing IMAC with integrated on-column refolding into phosphate buffer respectively, performed as described in Liew et al. 2014. Protein quantitation was performed using the BCA assay (Pierce, Rockford, IL, USA) and purity was assessed by SDS-PAGE analysis.

Figure 3A:
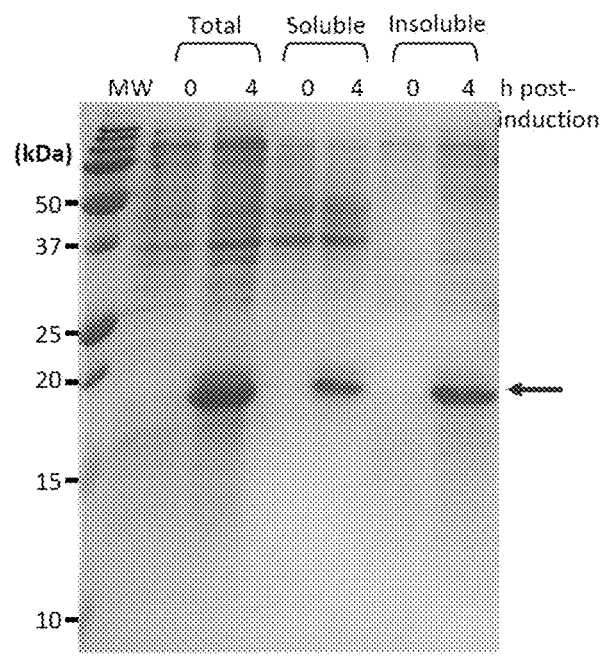
FIGS. 3A to 3C. Photographs of SDS-PAGE (16%) profiles for total, soluble and insoluble proteins isolated from $E.$ $coli$ strain BL21 (DE3) expressing (3A) TrxR175H, (3B) TrxR248Q, and (3C) TrxR273H, before (0 h) and 4 h after IPTG induction. The expected expressed protein is indicated by the arrow. MW=Protein molecular weight ladder (Precision Plus Protein™ All Blue Standards, Bio-Rad).
Figure 3B:
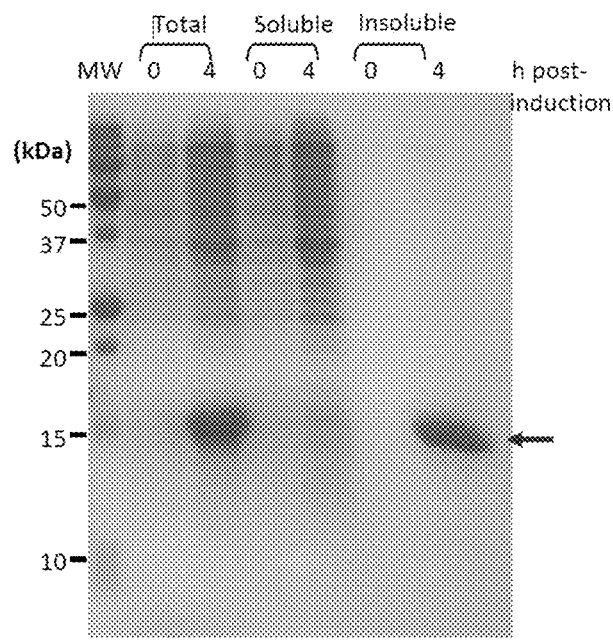
Figure 3C:
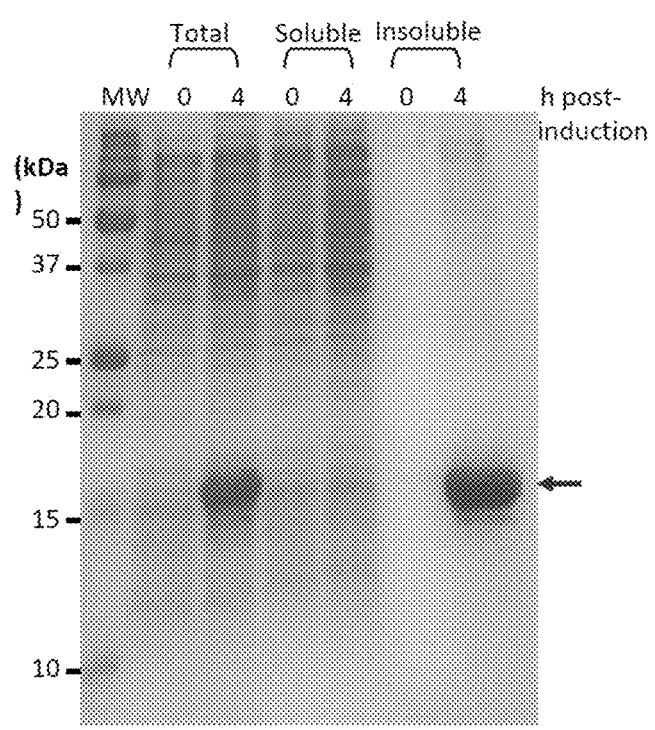
Figure 4A:
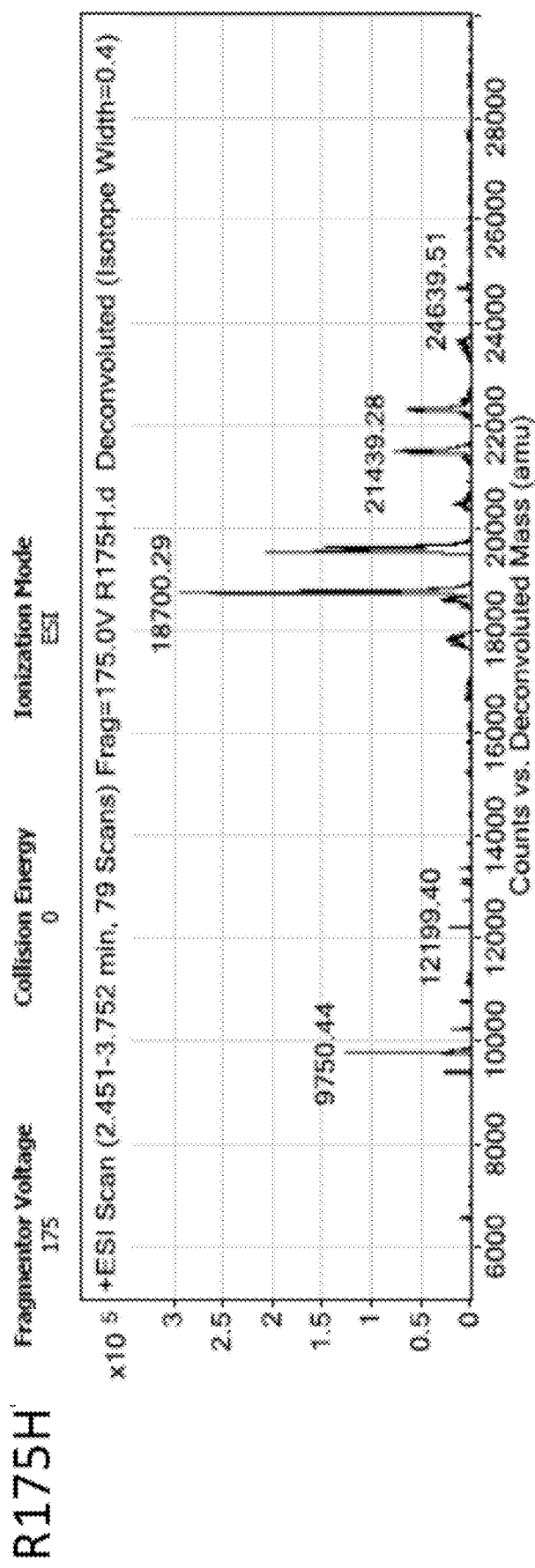
FIGS. 4A and 4B. Mass spectra for purified (4A) TrxR175H and (4B) TrxR248Q, showing primary protein entity of the indicated molecular masses.
Figure 4B:
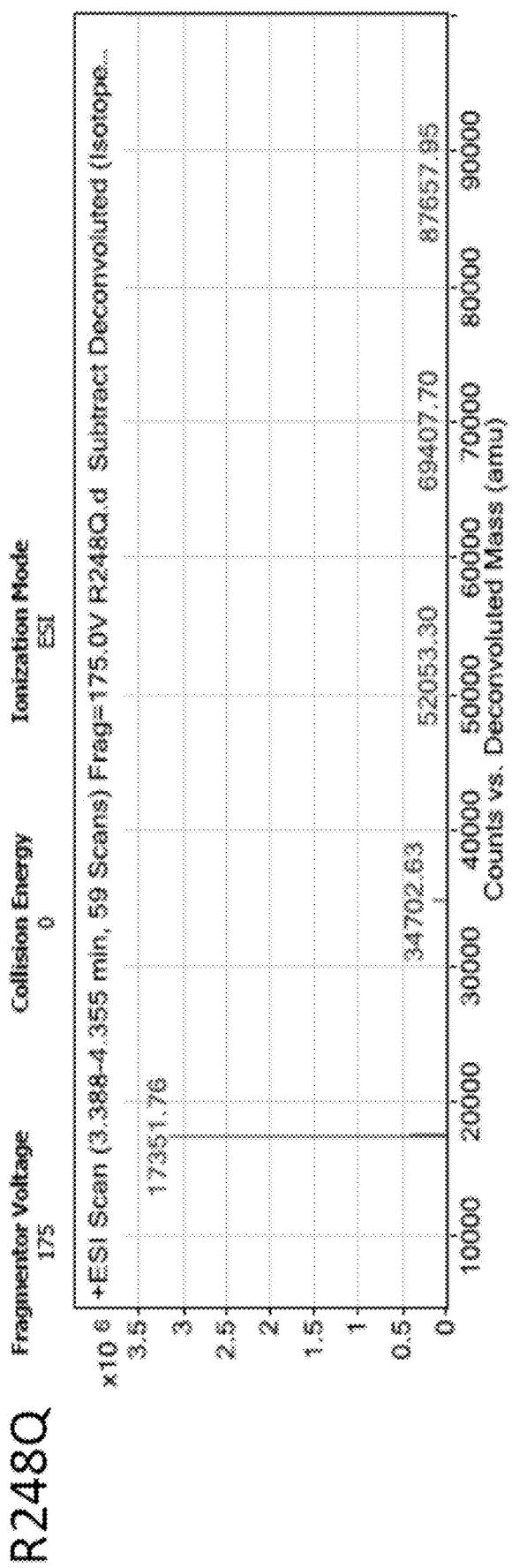

Expression of the TrxR175H immunogen was induced in *E. coli*, and was expected to be of ~18.8 kDa for TrxR175H, which was expressed in both the soluble and insoluble forms (FIG. 3A), with higher partitioning into the insoluble fraction. Analysis by mass spectrometry of purified TrxR175H revealed an actual molecular mass of ~18,700 Da, consistent with loss of the first methionine residue (calculated mass ~18,707 Da) (FIG. 4A). Previous reports have shown that TrxA fusions containing a Ser residue in the second position of its amino acid sequence allowed for efficient cleavage of the first methionine (131 Da), presumably by endogenous methionine aminopeptidase in *E. coli* (Liew et al., 2007). Similarly, TrxR273H was expressed primarily in inclusion bodies in the insoluble fraction, at the expected size of ~18,200 Da (FIG. 3C). The TrxR248Q was found to partition to the insoluble protein fraction, and migrated at an unexpectedly lower molecular weight position of 15 kDa on SDS-PAGE (FIG. 3B), and mass spectrometric analyses revealed a mass of 17,352 Da (FIG. 4B). The coding sequence of the construct was verified by DNA sequencing and the expressed protein could be purified by immobilized metal affinity chromatography (IMAC), which indicated that the His6 tag located at the carboxyl terminus of TrxR248W was intact and that the full length protein was translated, and suggested that the lower molecular mass may be a result of unexpected proteolytic cleavage by *E. coli* proteases, as has been demonstrated (Carrio et al., 1999 Biochim. Biophys. Acta 1434, 170-176; Corchero et al., 1997 Biochem. Biophys. Res. Commun. 237, 325-330), downstream of Ala20 at the N-terminus and corresponds to a 166-residue protein moiety and its sodium form (17,324/17,347 Da). In any case, the unexpected proteolysis by *E. coli* proteases highlights a distinct advantage of nesting the antigen sequence within TrxA instead of the terminal regions of the fusion protein.

Example 2: Initial Screening to Identify p53 Monoclonal Antibodies Against Specific p53 Mutants Three groups of five, 8 week old Balb/c female mice (Biological Resource Center, Singapore) were inoculated with the Trxp53mutant peptides. The first immunisation was performed intraperitoneally with Sigma Adjuvant System (Sigma), followed by five intraperitoneal and subcutaneous injections at 3 week intervals. One week after the fourth immunization, blood was taken from each mouse via cheek bleed using a lancet (MEDIpoint International Inc.). Blood samples were centrifuged for 10 min at 1600 rpm and serum was aspirated and stored at 4° C., for subsequent enzyme-linked immunosorbent assay (ELISA) analyses against the full length R175H, R273H and R248Q mutant p53 proteins.

The mouse with the highest serum antibody titer was selected as the spleen donor for fusion. The selected mice (one for each p53 mutation) received a final boost by intravenous injection of the Trxp53mutant peptide without adjuvant. Mouse myeloma SP2/0 cell line was used as the fusion partner. One week before fusion, cells were cultured in RPMI (Gibco) and 10% FBS until they attained >70% confluency in the logarithmic phase. The spleen cells of the immune mice were removed under sterile conditions. Generation, selection and cloning of hybridoma cells were performed using the ClonaCell-HY Hybridoma Cloning kit (STEMCELL Technologies) according to the manufacturer's protocol.

Hybridoma clones secreting anti-mutant p53 mAbs were selected by ELISA with 96-well plates coated with recombinant full length p53 protein harboring the R175H, R273H and R248Q mutations respectively. Thioredoxin peptide was used as negative control. Supernatant collected from individual hybridoma wells were tested on ELISA plates. 10% fecal bovine serum (FCS) was used for blocking and antibody dilution. PBS with 0.05% Tween 20 was used for washes. After washing, IgGs were detected using 1:5000 goat anti-mouse IgG conjugated to HRP (Biorad) in PBST with 10% FCS. Plates were developed with 1×TMB ELISA substrate solution (Sigma). Absorbance was measured at 650 nm with EnVision Plate Reader (Perkin Elmer).

Figure 5A:
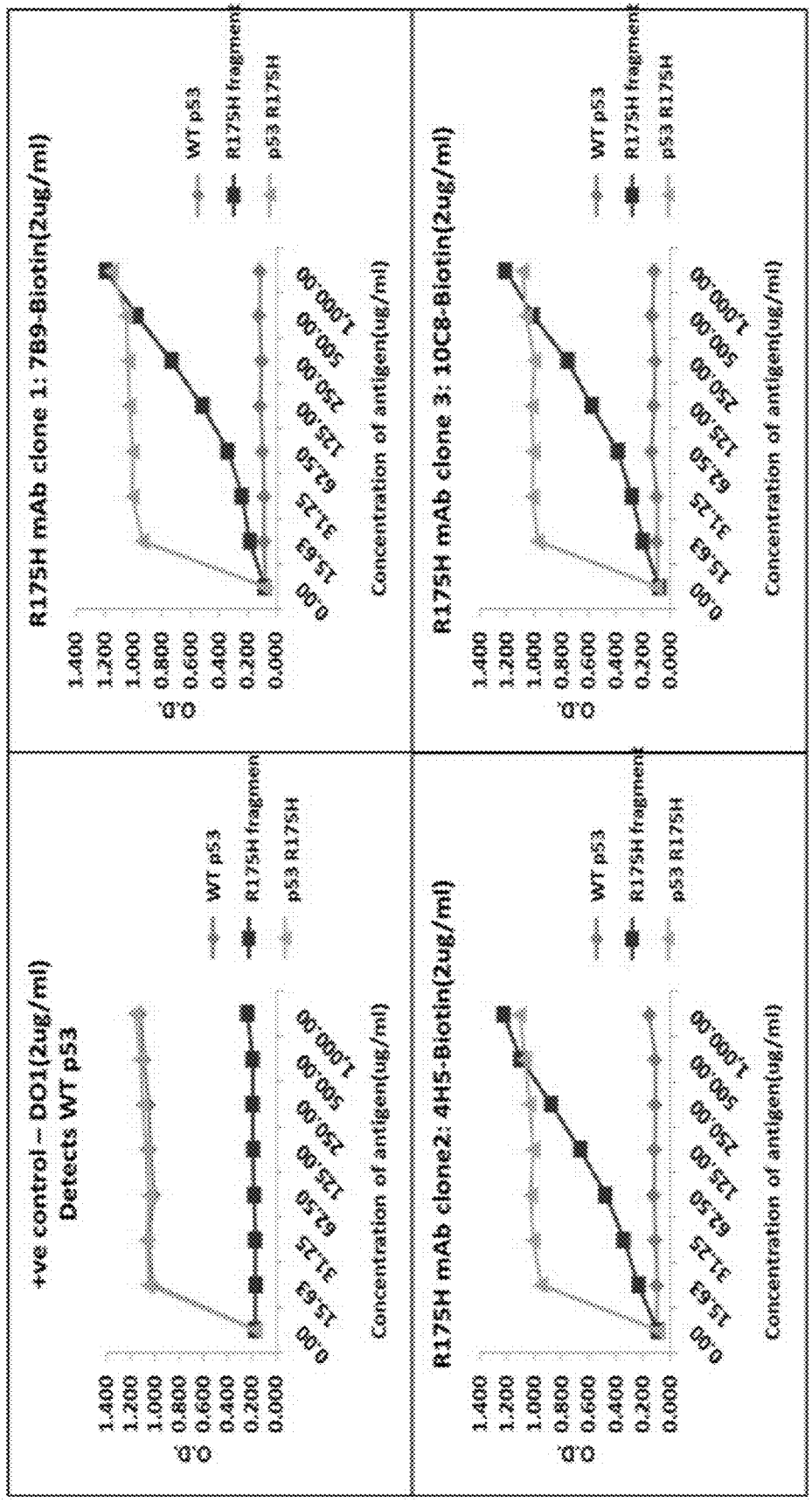
FIGS. 5A to 5C. Graphs showing the results of ELISA screening of p53 mutant specific antibodies. Cell culture supernatants obtained from individual hybridoma clones generated from spleens of mice immunized with (5A) TrxR175H, (5B) TrxR248Q, and (5C) TrxR273H were screened by ELISA against the indicted whole proteins and peptide fragments.
Figure 5B:
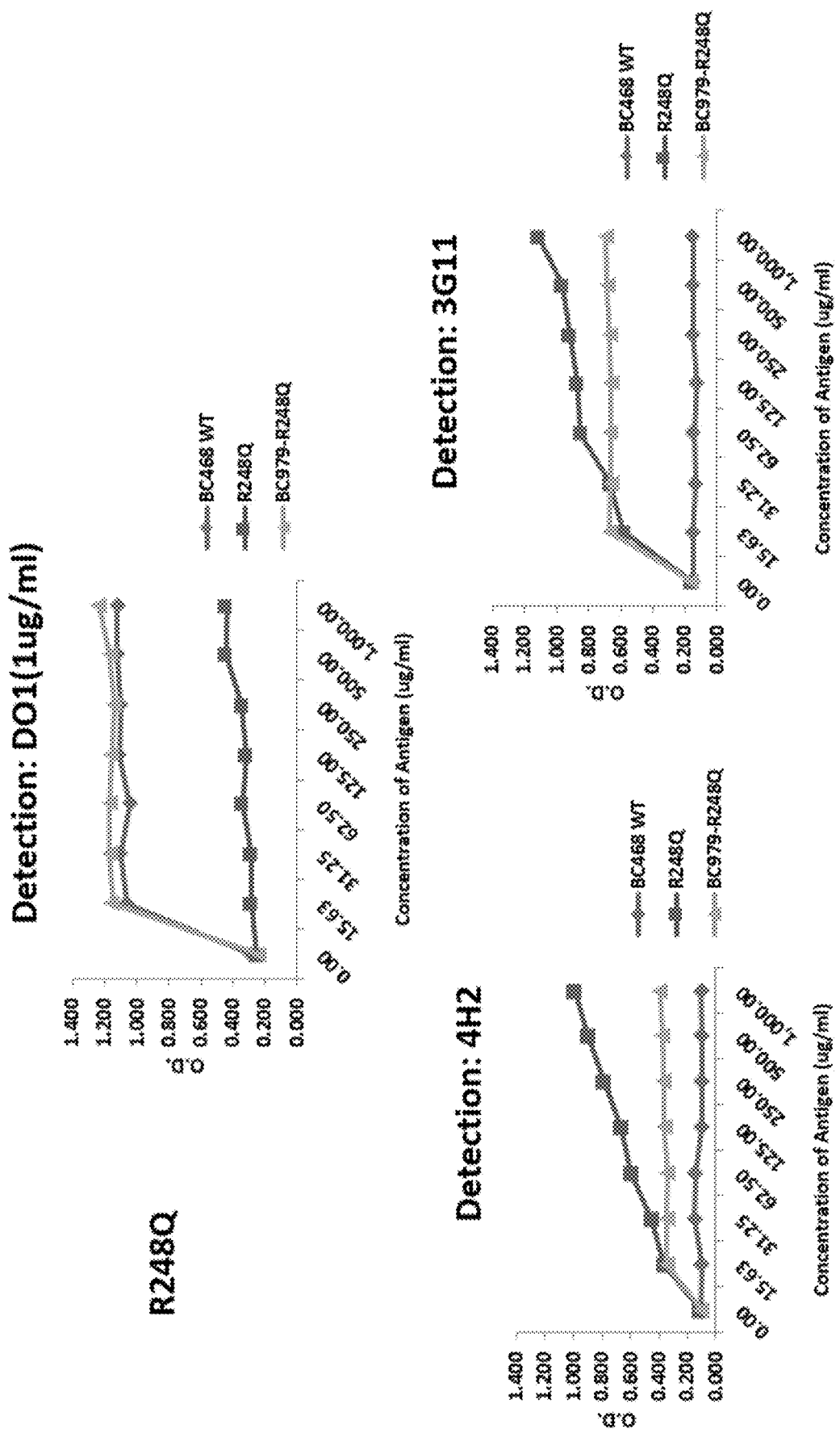
Figure 5C:
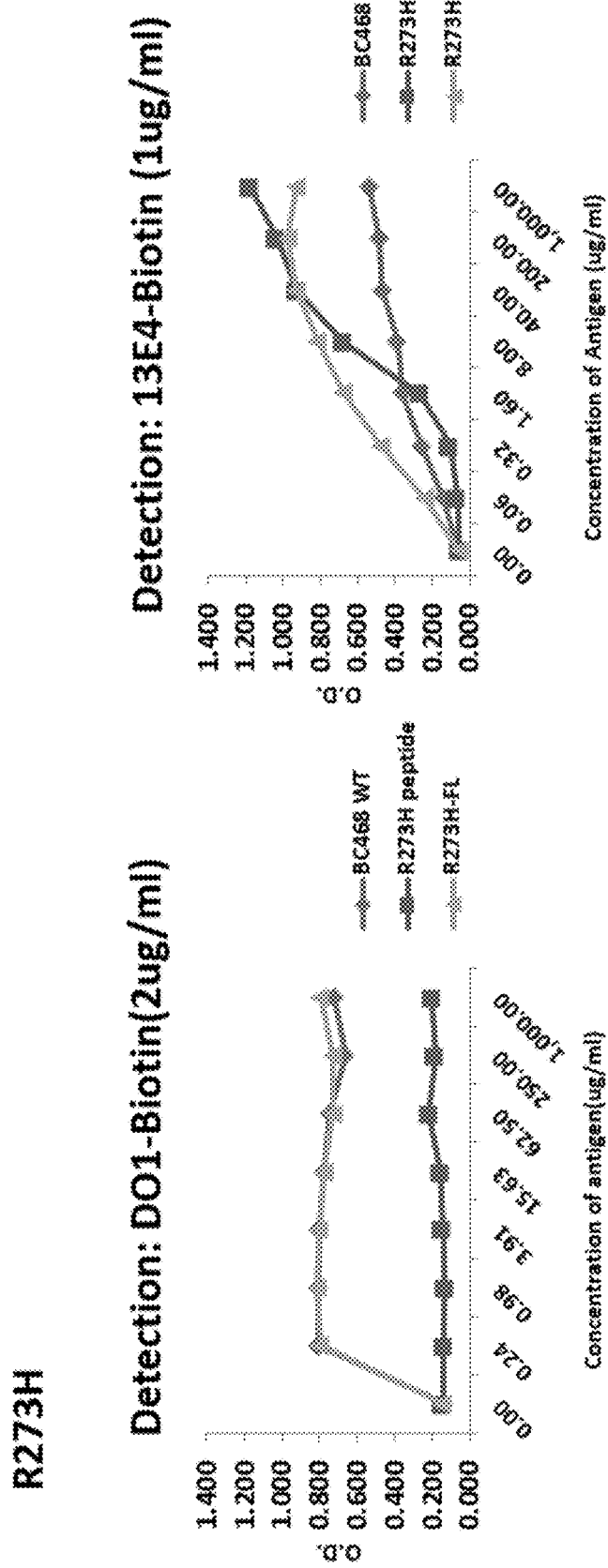

Data from at least three independent mice are presented for each mutation. Initial ELISA screening using the mutant or wild-type p53 protein or the mutant p53 peptide fragment revealed that for each of the hybridomas producing antibody recognising mutant p53, the antibodies were specific for the respective mutations and did not cross-react with the wild-type p53 protein (FIG. 5A-5C). The antibodies were more sensitive to the whole mutant p53 protein as compared to the peptide fragments.

Figure 6A:
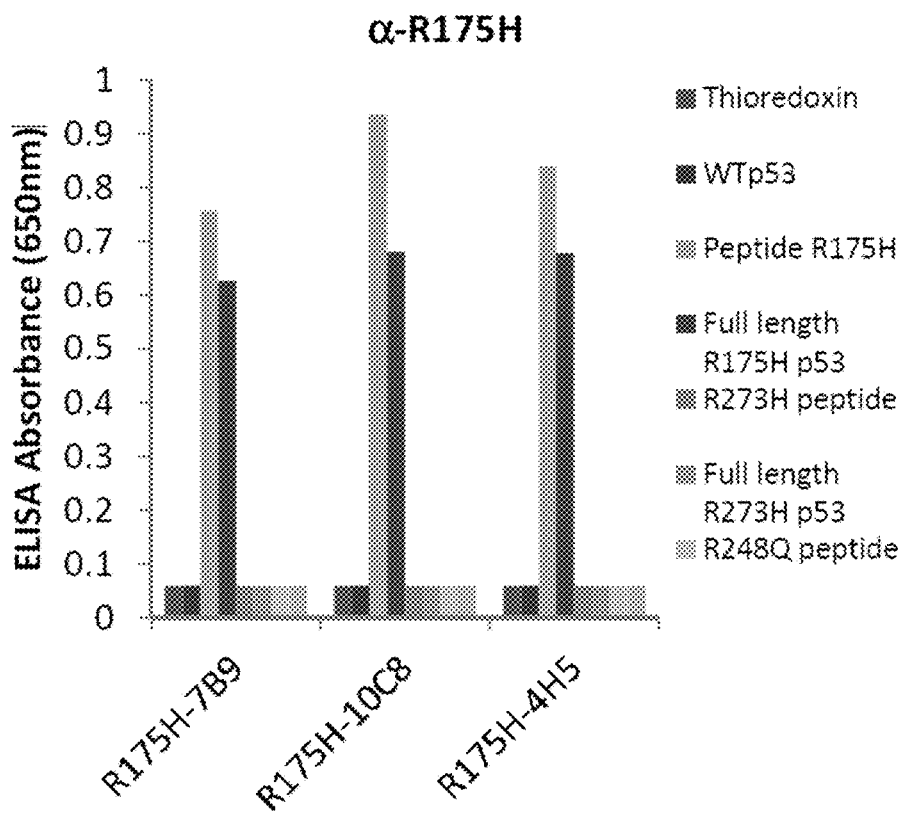
Figure 6B:
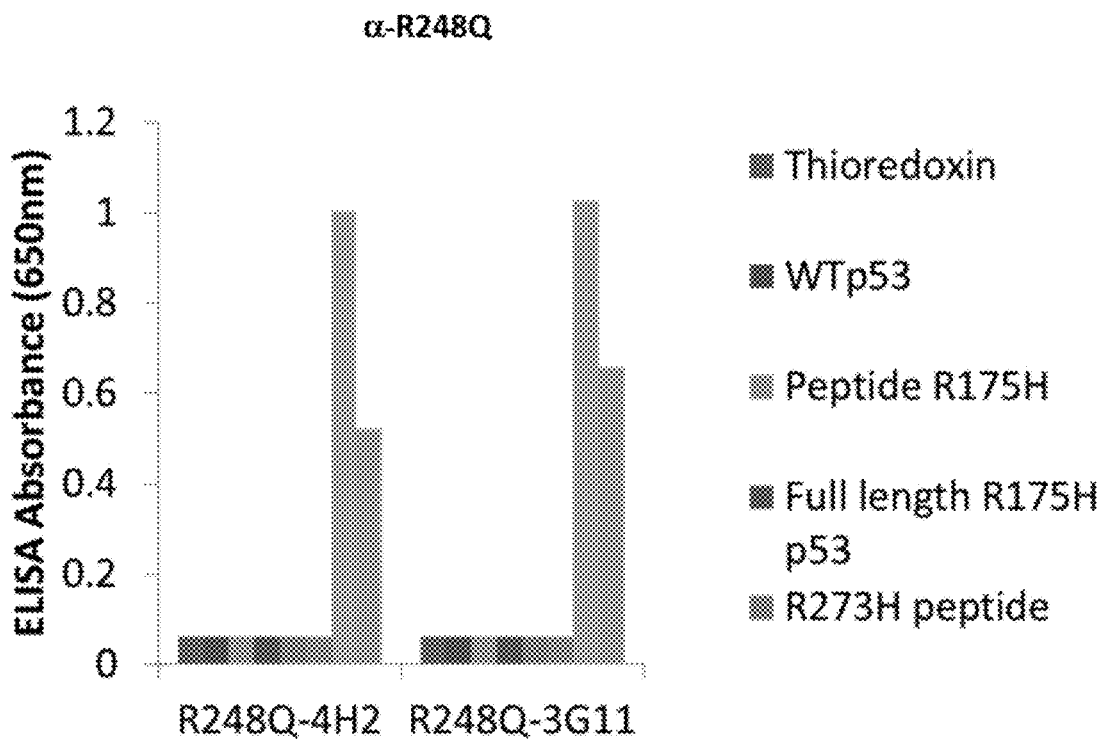
Figures 6C, 7A:
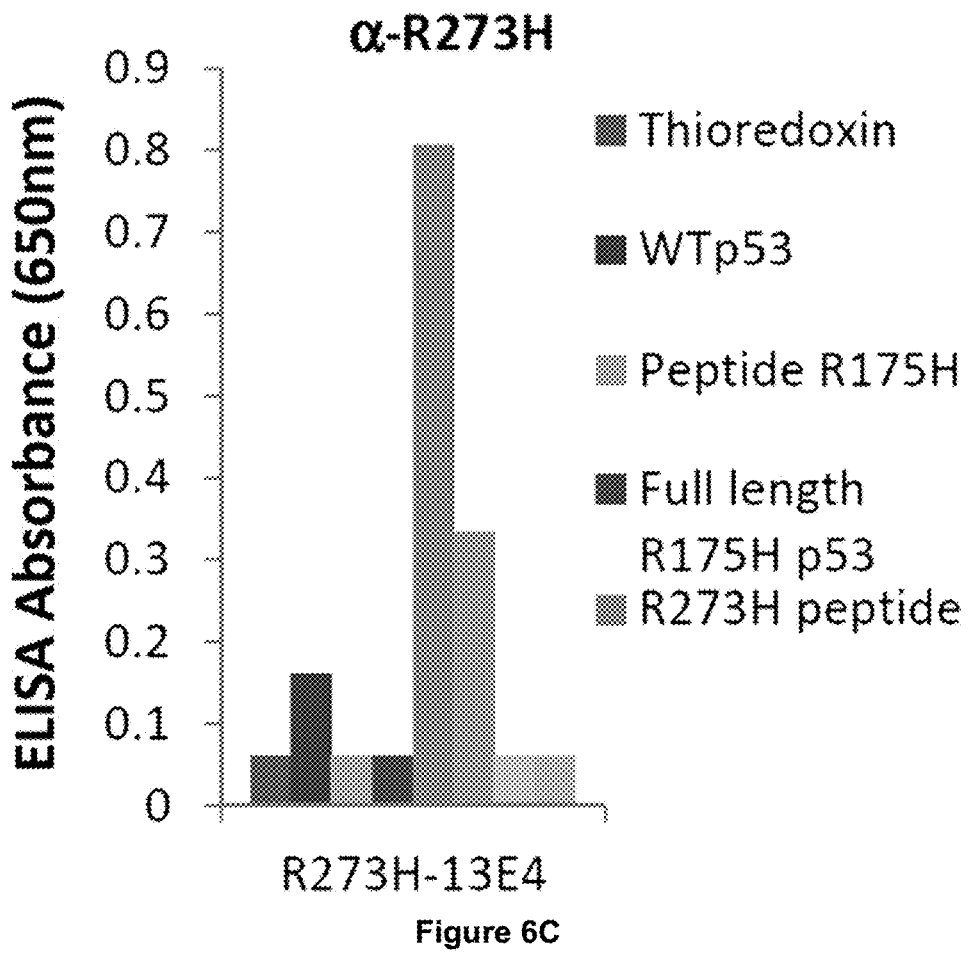

Further analyses using all peptides and mutant proteins to further confirm specificity also showed that the three hybridoma clones producing monoclonal antibody against the R175H mutant p53 were highly specific (clones 7B9, 10C8 and 4H5), and did not cross react with the R248Q or R273H mutant proteins and peptides (FIG. 6A). Similar results were obtained with the clones against the R248Q (clones 4H2 and 3G11) and R273H (clone 13E4) (FIGS. 6B and 6C).

To determine the epitopes targeted by the individual hybridoma clones, peptide phage display analysis was performed using the antibodies against the three p53 mutants.

An M13 phage library (New England Biolabs) encoding random 12-mer peptides at the NH2 terminus of pIII coat protein (2.7×109 sequences) was used. 50 nm purified antibody was coated on 96 well maxisorp plates (Nunc). The wells were incubated with blocking buffer (PBS, 0.5% Tween20, 2% BSA) for 1 h at room temperature, washed with washing buffer (PBS, 1% Tween20, 2% BSA), and incubated in washing buffer at room temperature with $4×10^{10}$ phages. Bound phages were eluted with 0.2 M glycine (pH 2.2) and neutralized with 1 M Tris (pH 9.1). The eluted phages were amplified according to the manufacturer's instructions.

The selection process was repeated for three cycles. Phage plaques from the final round were selected, amplified as described by the manufacturer and sequenced. The peptides displayed on the selected phages were deduced from analysis of results from DNA sequencing. Epitopes targeted by individual antibodies were obtained by determination of consensus sequences from alignment of peptide sequences using Clustal Omega multiple sequence alignment tool.

For the hybridomas against the R175H mutant p53, the consensus sequence was "HCPHH", in which the first Histidine was the mutation that replaces the Arginine residue in the wildtype p53 (FIG. 7A). Almost all clones from all hybridomas against R175H mutant p53 captured this sequence (FIG. 8A). The consensus sequences for the R248Q antibody clones were "SV . . . HY" (positions 215-216 and 233-234; FIG. 8A) for clone 3G11, and "RP" (positions 249-250; FIG. 7B) for clone 4H2. The consensus sequence for anti-R273H clone 13E4 was "VH" (positions 272-273; FIG. 7C).

To determine the crucial amino acids of the epitope, two sets of individually alanine substituted 13 amino acid peptides corresponding from Met169 to Arg181 (MTE-VVRHCPHHER) of R175H mutant p53 protein, and Arg267 to Gly 279 (RNSFEVHVCACP) of R273H mutant p53 protein were chemically synthesised and obtained from Bio Basic Inc. Peptides were conjugated with an N-terminal Biotin and individually incubated on a 96 well Streptavidin coated ELISA plate (Pierce, Thermo Scientific) at 10 ug/ml for 1 hour. After three rounds of washing, the plates were incubated with anti-R175H 10C8, 4H5 and 7B9 and anti-R273H 13E4 respectively at 1 ug/ml for overnight at 4° C. The plates were incubated for an hour at 37° C. with secondary anti-mouse IgG-HRP after washing. After incubation, plates were washed three times prior to application of soluble HRP substrate for 5 minutes and absorbance at 650 nm was determined with Envision plate reader (Perkin Elmer).

Figure 9A:
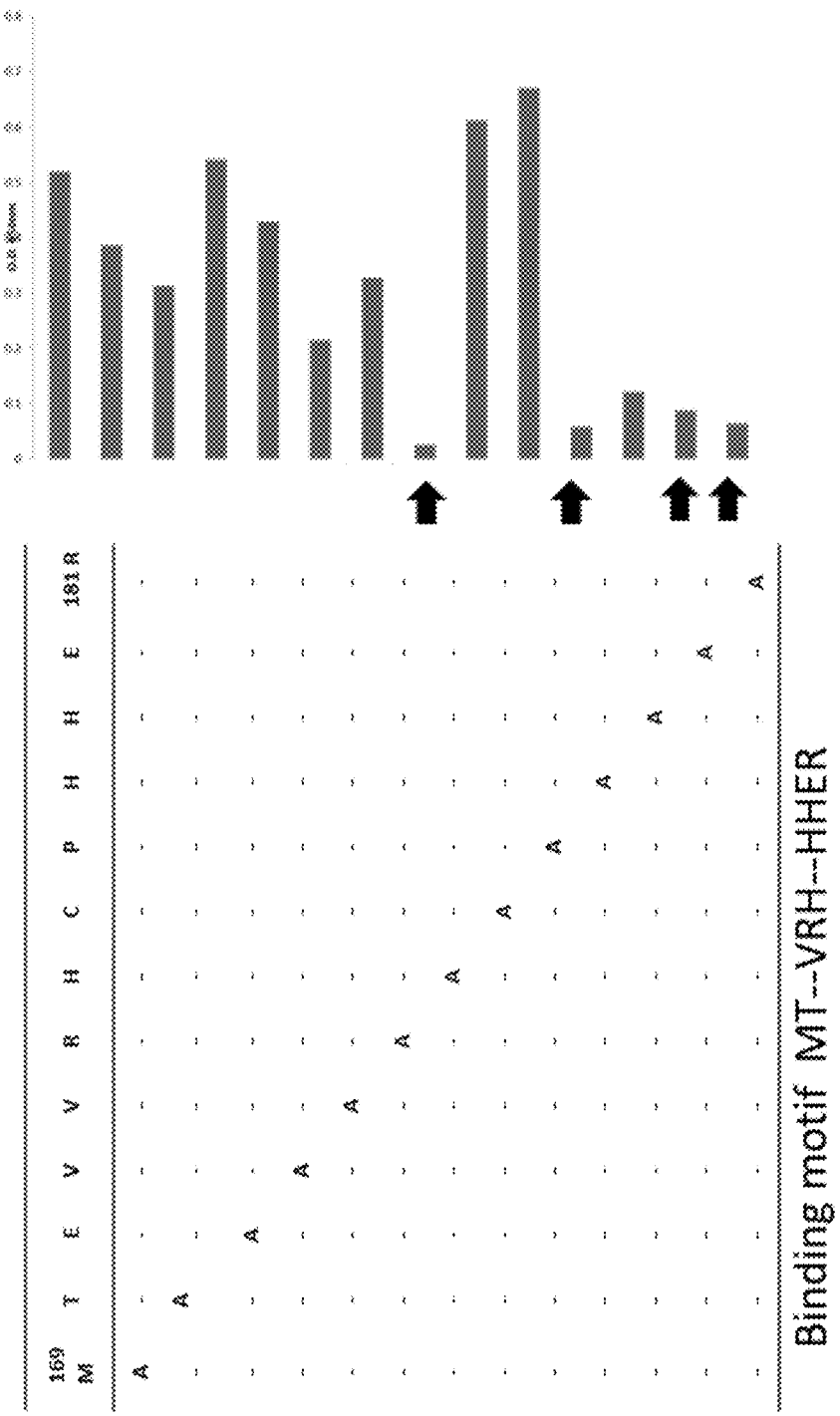
FIG. 9A to 9D. Tables and Bar charts showing results of alanine scan ELISAs for determining the epitope bound by anti-R175H antibody clones (9A) 4H5 (SEQ ID NOs: 145-159), (9B) 7B9 (SEQ ID NOs: 79, and 145-159) and (9C) 10C8 (SEQ ID NOs: 145-159), and (9D) anti-R273H antibody clone 13E4 (SEQ ID NOs: 160-173). Individually alanine substituted 13-mer peptides surrounding the mutated hotspots (His 175 and His 273) were used to determine the critical amino acid residues required for the mutant antibodies binding to mutant p53. Absorbance was measured at 650 nm after 5 minutes' incubation with TMB substrate. Optical density readings of individual alanine substituted peptides are shown. Critical residues for antibody binding are indicated motifs.
Figure 9B:
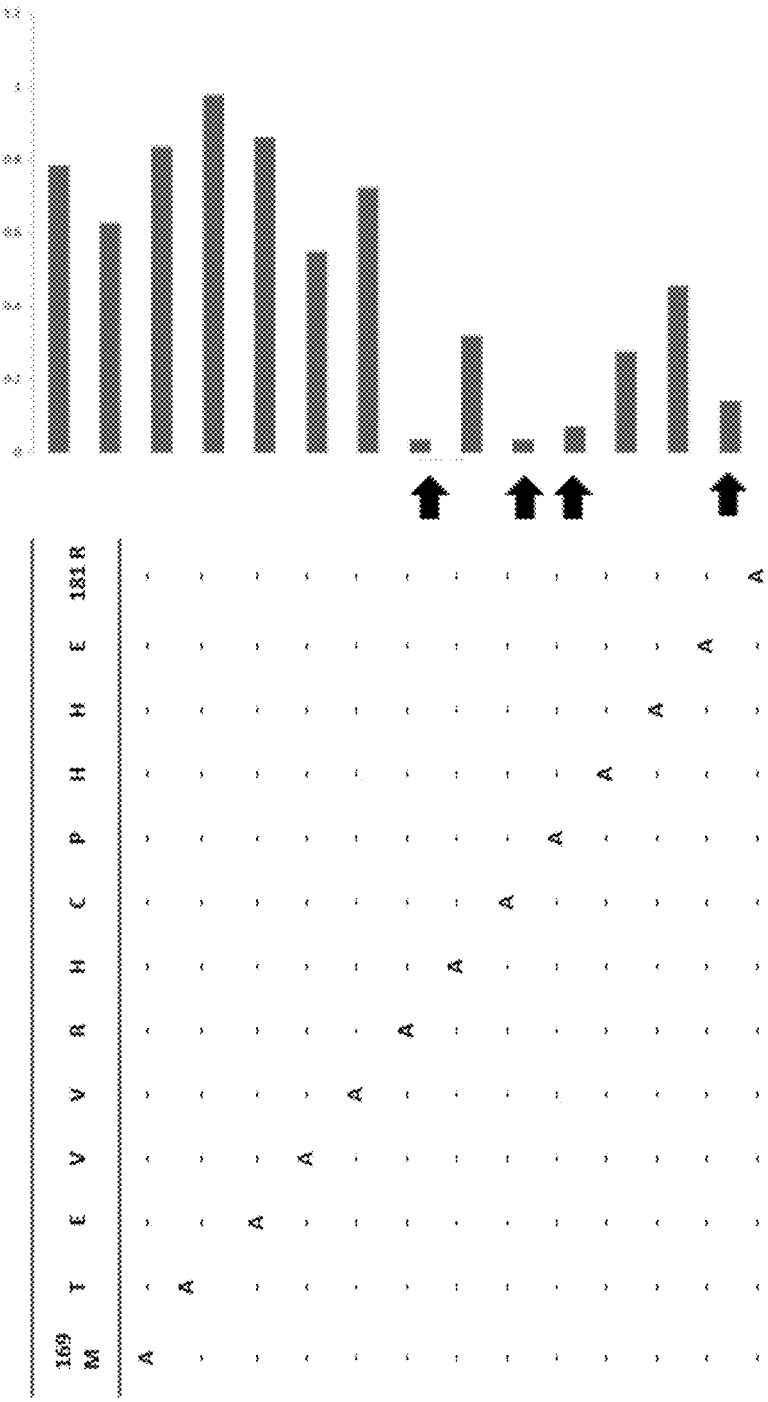
Figure 9C:
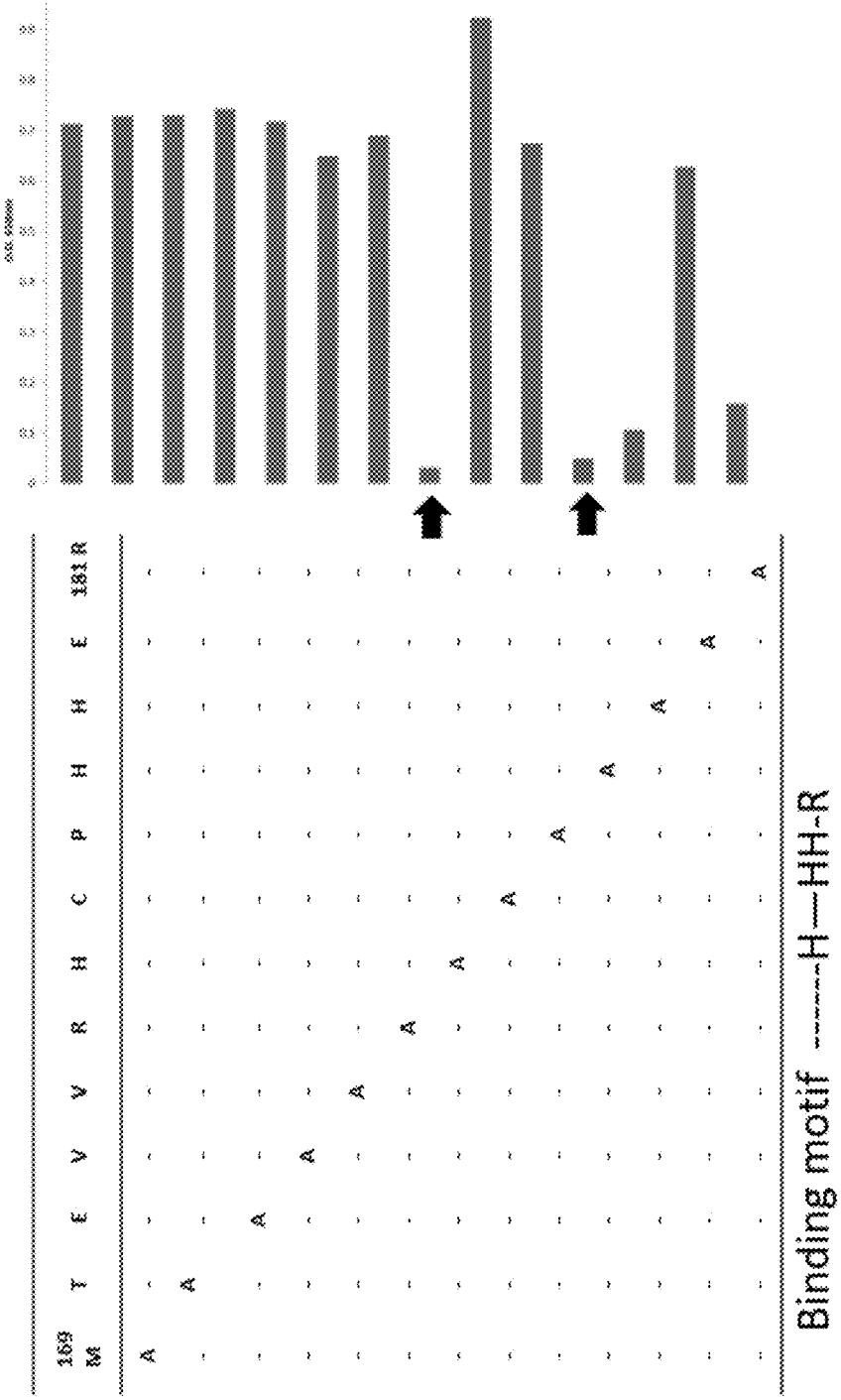
Figure 9D:
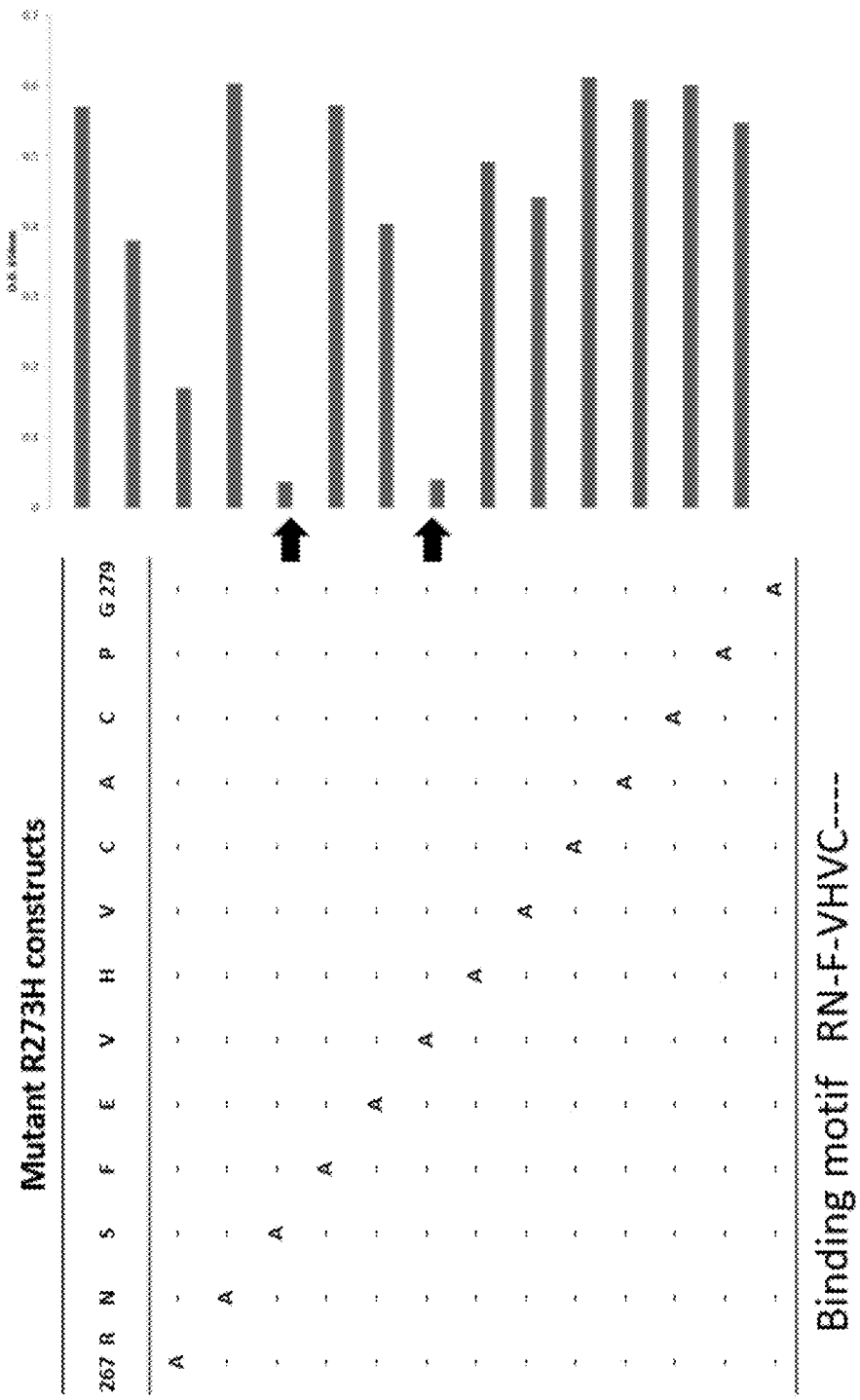

The results for the alanine scans for the R175H antibody clones 4H5, 7B9 and 10C8 are shown in FIGS. 9A-9C, and the results for the R273H antibody clone 13E4 are shown in FIG. 9D. Mutations within p53 peptide sequences were identified as critical to the mAb epitope if they did not support reactivity of the test mAb but did support reactivity of other antibodies.

BALB/c mice were given a single 0.25_mL intraperitoneal (IP) injection of Incomplete Freund's Adjuvant (Sigma Chemical Co.). Fourteen days later, mice were injected with a single IP injection of $4×10^5$ in a volume of 0.5 mL of the hybridoma cells, after which they were examined daily for development of ascites fluid as determined by abdominal distention. Seven to ten days after the injection of hybridoma cells, mice were anesthetized and the ascites fluid was collected aseptically from anesthetized mice by abdominal paracentesis with an 18-22 gauge needle by gravity flow into sterile centrifuge tubes. Digital pressure was gently applied to the abdomen and the position of the mouse was altered as needed to facilitate removal of the ascites fluid. Ascites was pooled for each individual cage of mice. The isotype of the antibody clones was determined from hybridoma supernatant using a mouse mAb isotyping kit (Roche) according to the manufacturer's instructions. The ascitic fluids were diluted at a ratio of 1:10 with PBS and IgGs were purified via Protein G column chromatography (GE Healthcare). Antibody was eluted from the column through 5 ml of elution buffer containing 0.2M Tris-Glycine pH2.7. The eluted fractions were dialyzed against 0.05 mM PBS, pH 7.4. Confirmation of the purified antibodies was performed by SDS-PAGE under reducing conditions.

Example 3: Evaluation of Specificity of mAbs Against Specific p53 Hot-Spot Mutants by Biochemical Approaches The first attempt to determine specificity of the p53 hot-spot mutant-specific antibodies were made by evaluating their effectiveness in immunoblot assays. p53 null H1299-cells stably expressing or transiently transfected with the six common hot-spot p53 mutations (R175H, R245S, R248Q and R248W, R249S, R273H and R282W) were used for the initial analysis.

50 μg of cell lysates were loaded into each well of a 4-12% Bis-Tris SDS polyacrylamide precast gels (Invitrogen). The protein marker used was Precision Plus Protein™ Standards Dual Colour (Bio-Rad, Hercules, CA). SDS-PAGE gels were ran at constant voltage of 60 volts (V) until the protein bands exceeded the stacking gel, after which the gel was continuously ran at 100V until the dye front reaches the bottom. For immunoblotting, protein transfer was carried out on the iBlot™ Drying Blotting system (Invitrogen) for 10 minutes at 20-25V onto nitrocellulose membranes. The membrane was washed three times for 10 minutes each with PBST (phosphate buffered saline (PBS) containing 0.05% Tween20 (Bio-Rad, Hercules, CA), and non-specific binding was blocked using 4% non-fat milk in PBST buffer for 1 hour with gentle agitation. Subsequently, the membrane was washed three times for 10 minutes each with PBST. Excess PBST after the washing step was removed before hybridoma supernatant was added. The primary antibody was incubated under gentle agitation at 4° C. overnight. The membrane was washed three times for 10 minutes each with PBST to remove unbound primary antibodies. 1:5000 goat anti-mouse IgG conjugated to HRP (Biorad) in PBST with 10% FCS was used for detection. The secondary antibody was incubated under gentle agitation for 1 hr at room temperature. Unbound secondary antibodies were washed off in the above mentioned manner before visualization using Clarity western blot ECL substrate (Biorad). Densitometric analysis was performed using Odessey Fc (Licor).

Figure 11:
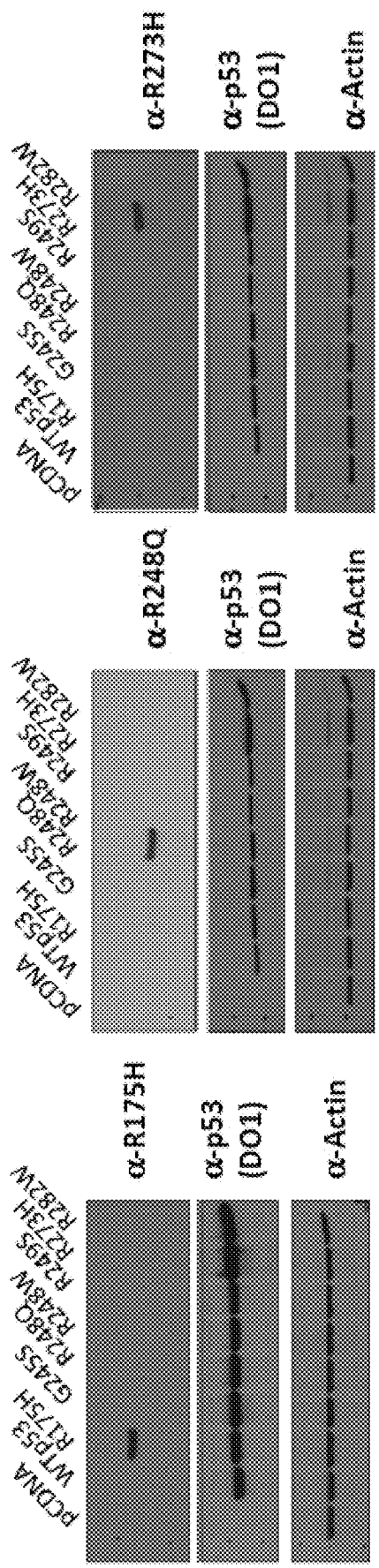
FIG. 11. Photographs showing the results of immunoblots using mutant p53-specific antibodies. p53-null H1299 cells were transiently transfected with plasmids encoding the indicated p53 mutant or wildtype p53 polypeptide, and protein lysates were used for direct immunoblotting with the indicated antibodies. DO1 is a mouse mAb that detects all forms of human p53, and CM1 is a rabbit polyclonal antibody against human p53.

All three mutant-specific antibodies were able to detect their corresponding mutant p53 proteins expressed in H1299 cells, without detecting the other mutants or the wildtype p53 that were abundantly expressed, as determined using the pan-p53 antibody DO1 (FIG. 11).

Of particular significance was the finding that the anti-R248Q antibody was unable to detect the closely related R248W mutant, which comprises a different mutation at the same residue, highlighting the very high specificity of the antibodies.

Figure 12:
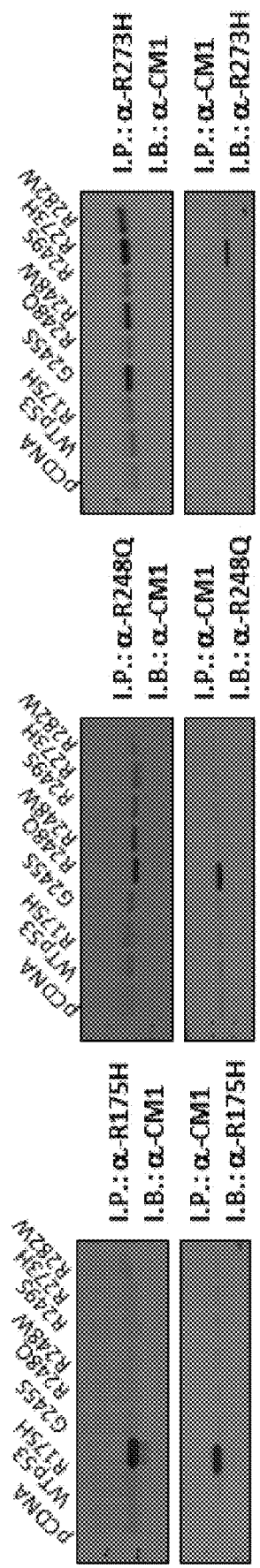
FIG. 12. Photographs showing the results of immunoprecipitation assays using mutant p53-specific antibodies. p53-null H1299 cells were transiently transfected with plasmids encoding the indicated p53 mutant or wildtype p53 polypeptide, and protein lysates were used for immunoprecipitation assays. DO1 is a mouse mAb that detects all forms of human p53, and CM1 is a rabbit polyclonal antibody against human p53. Pull-downs were performed with both the p53-mutant specific mAbs followed by immunoblot with CM1 antibody, and in the reverse order by pull down with CM1 and immunoblotting with the mutant-specific mAbs.

Immunoprecipitation analyses were also performed using the p53 mutant-specific antibodies, followed by detection with the anti-p53 rabbit antibody CM1, which again revealed that the antibodies were specific in bringing down only the respective mutant proteins (FIG. 12). Reverse immunoprecipitation with CM1 antibody followed by immunoblotting with the mutant-specific antibodies also gave similar results, with extreme specificity (FIG. 12).

Figure 14:
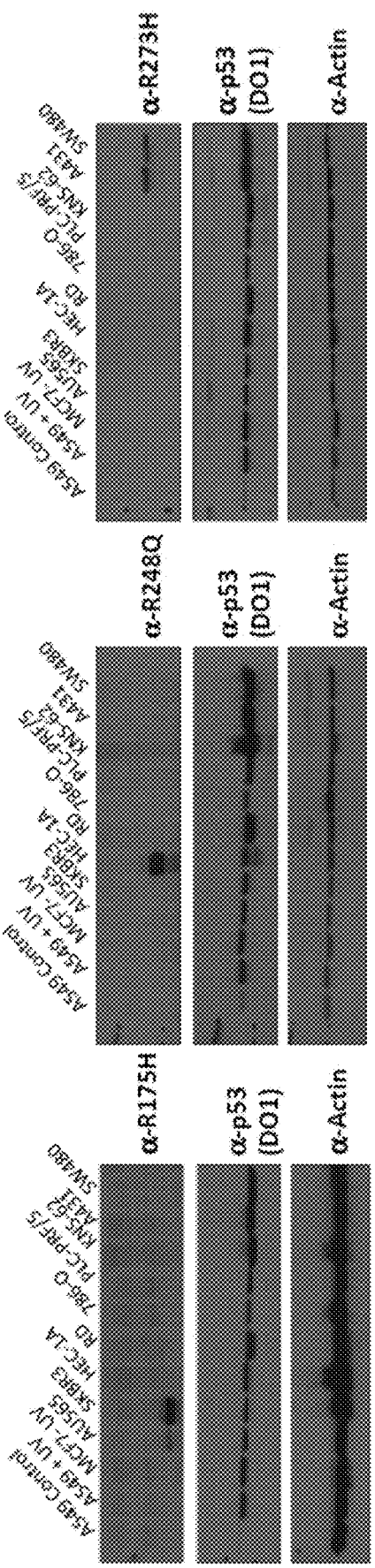
FIG. 14. Photographs showing the results of immunoblots using mutant p53-specific antibodies. Protein lysates of the indicated cell lines were used for direct immunoblotting with the indicated antibodies. A549 and MCF-7 are wild-type p53 carrying cell lines that were used without or with UV irradiation to induce the endogenous p53 expression.

The inventors next determined the ability of these mAbs to recognize endogenous p53 in a large number of human tumor cell lines that express the wild-type protein or the various hot-spot mutants (FIG. 13). Direct immunoblotting with the mutant specific mAbs was able to detect only the respective mutant p53 proteins in the tumor cell lines, though all cell lines expressed large amounts the various mutant p53, or the wild-type p53 that was induced by UV-irradiation and detected by the DO1 antibody (FIG. 14), confirming the specificity of the antibodies.

Figure 15:
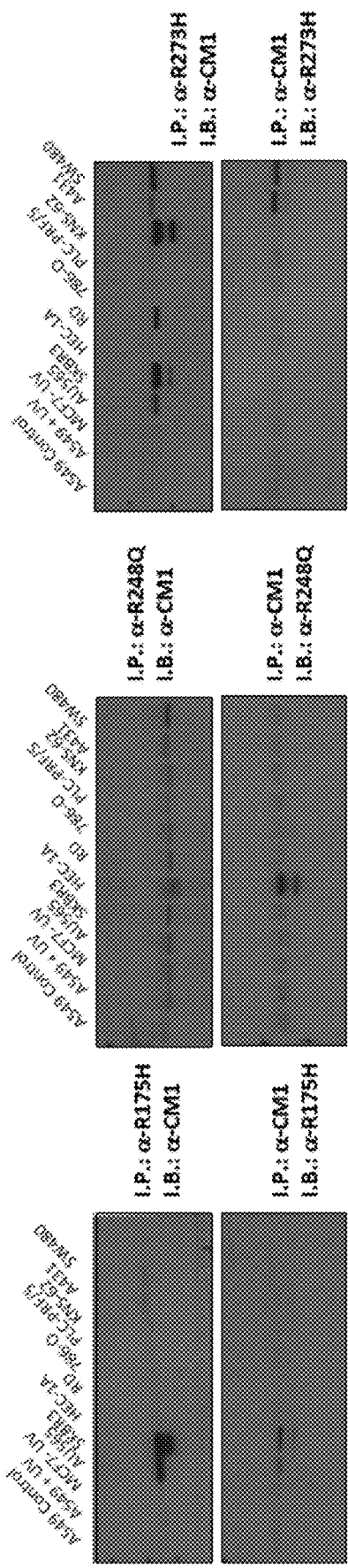
FIG. 15. Photographs showing the results of immunoprecipitation assays using mutant p53-specific antibodies. Protein lysates of the indicated cell lines were used for immunoprecipitation assays using the indicated antibodies. A549 and MCF-7 are wild-type p53 carrying cell lines that were used without or with UV irradiation to induce the endogenous p53 expression. Pull-downs were performed with both the p53-mutant specific mAbs followed by immunoblot with CM1 antibody, and in the reverse order by pull down with CM1 and immunoblotting with the mutant-specific mAbs.

Immunoprecipitation of the endogenous proteins indicated the same trend for the R175H-specific antibody (FIG. 15, left panel). Both the R248Q and the R273H antibodies were also able to specifically detect only their respective mutant proteins when used for immunoblot detection after the primary immunoprecipitation with the pan-p53 CM1 antibody (FIG. 15, middle and right panels). However, when used directly for immunoprecipitation followed by immunodetection with CM1, these two antibodies detected some other p53 mutants as well, likely due to non-specific binding under the conditions tested. Nonetheless, the high level of specificity in direct immunoblotting and upon immunoprecipitation with a pan-p53 antibody highlights the specificity of these antibodies against their respective mutant p53 antigens.

Example 4: Specificity of mAbs Against Specific p53 Hot-Spot Mutants in Immunofluorescence Analyses To test the specificity of the mutant-specific antibodies by immunofluorescence staining, the inventors again utilized the H1299-cells overexpressing the wild-type p53 or the various p53 mutants, or tumor cells lines that express endogenous mutant p53 proteins.

Fixed, transfected cells on 96 well plates were subjected to permeabilization with 0.4% Triton X-100 for 20 minutes. After rinsing with PBS, cells were blocked with 5% BSA in PBSTritonX (PBSTX) for 20 min, followed by incubation in hybridoma supernatant at 4° C. overnight. IgGs were detected using 1:1000 goat Alexaflor 488 Donkey anti-mouse IgG conjugated (Life technologies) in PBSTX with 1% BSA. Then, cells were counterstained with DAPI, and viewed with Incell Analyzer (GE Healthcare).

Figure 16:
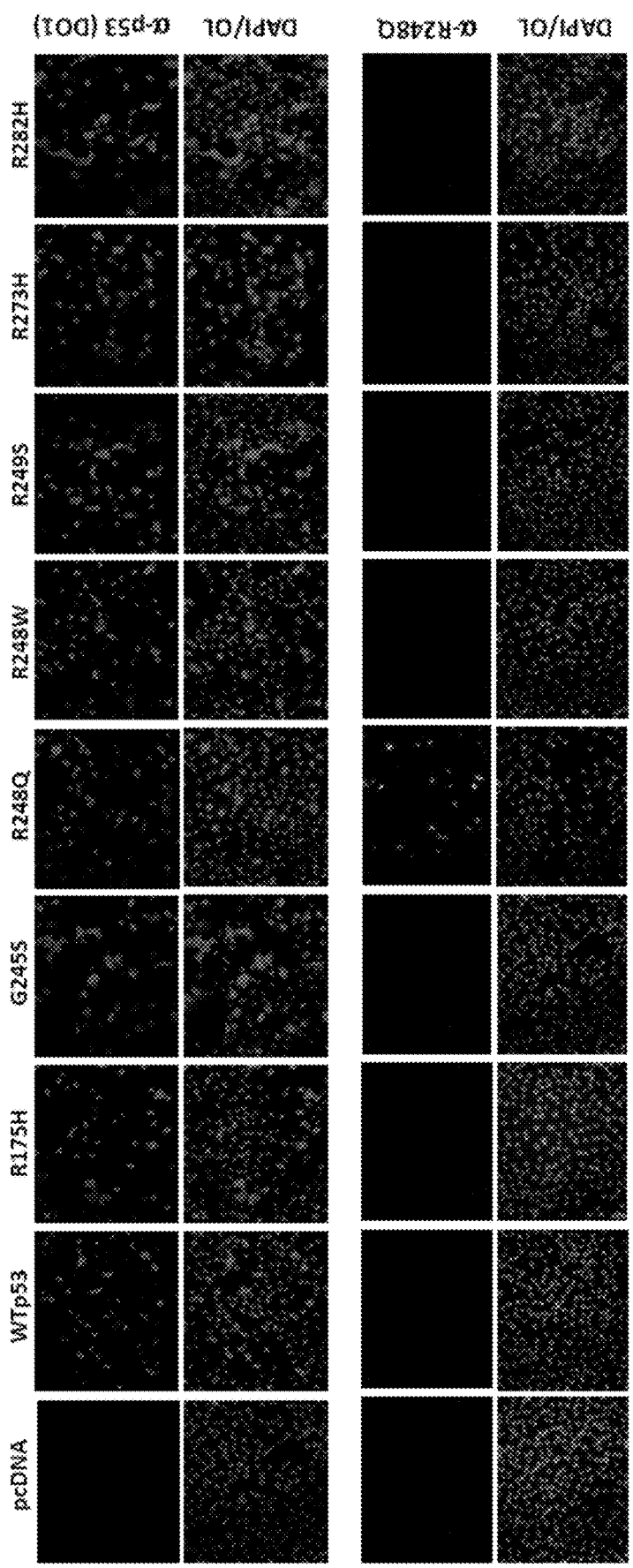
FIG. 16. Photographs showing the results of immunofluorescence analyses. p53-null H1299 cells were transiently transfected with plasmids encoding the indicated p53 mutant or wildtype p53 polypeptide and subjected to immunofluorescence analysis.
Figure 16:
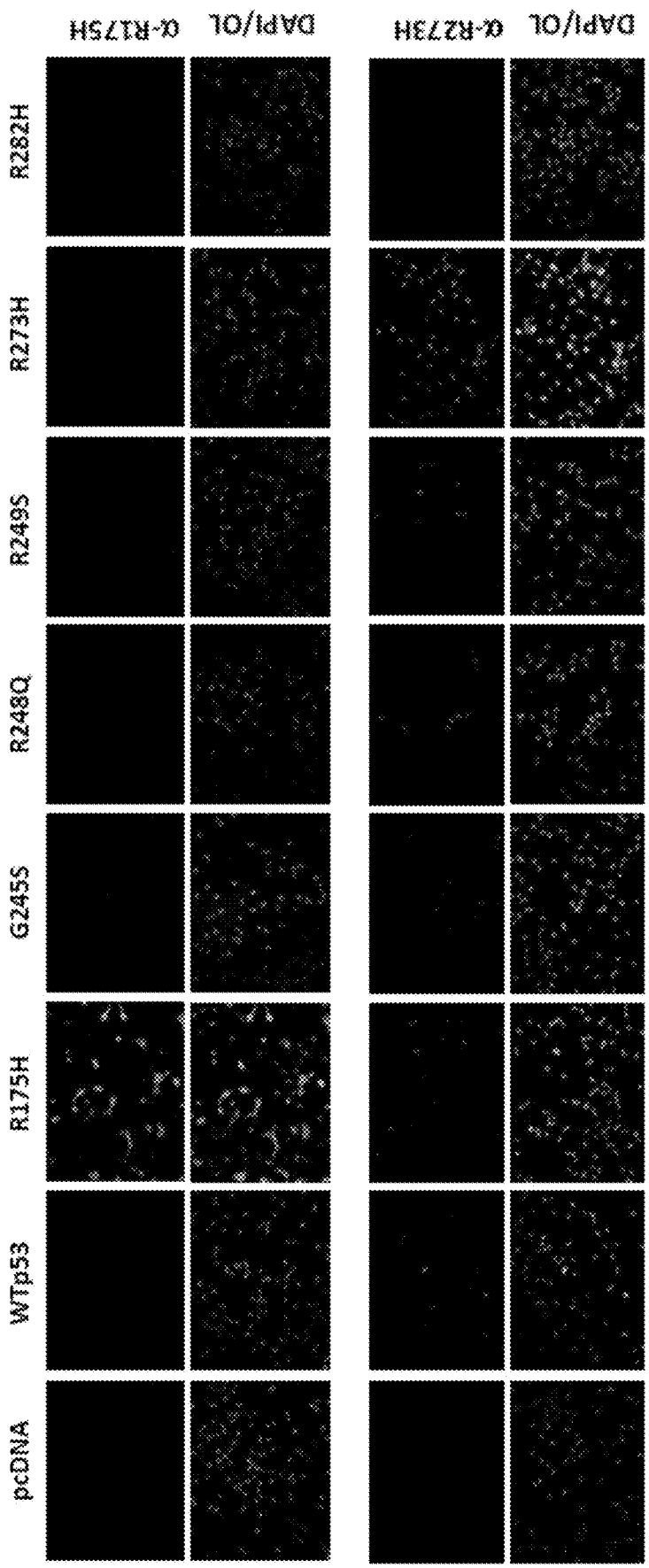
Figure 17A:
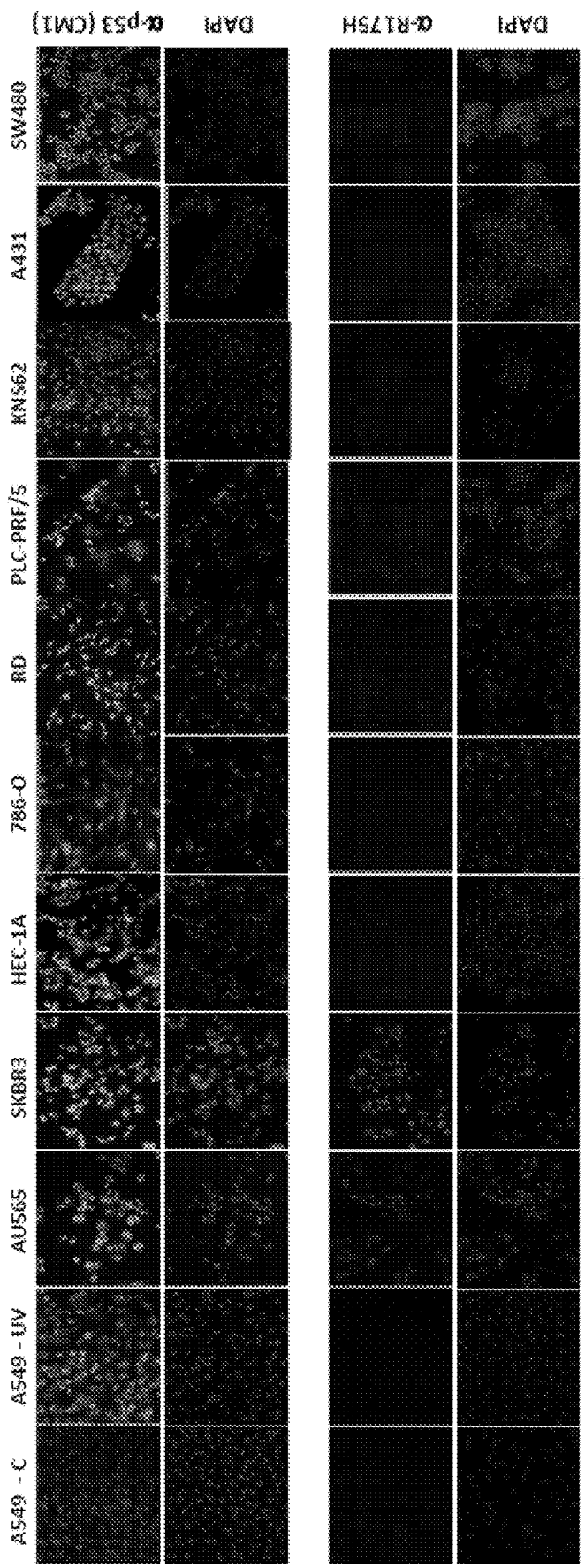
Figure 17A:
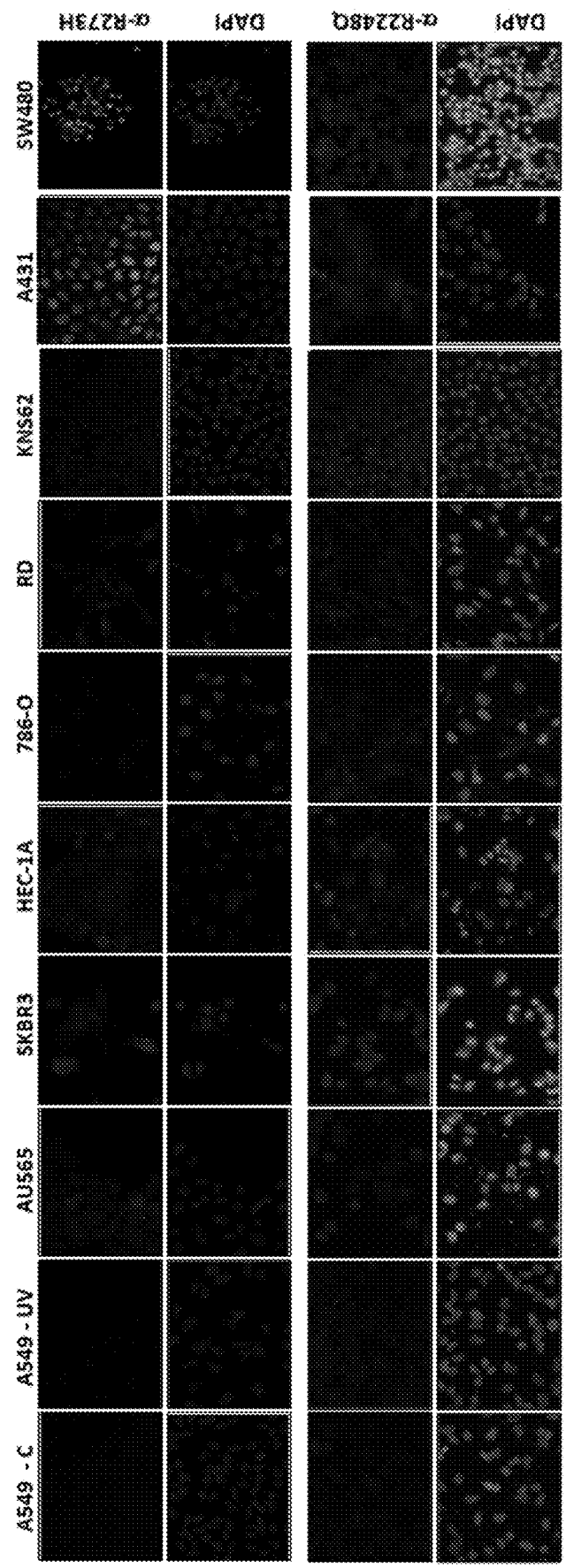

A distinct nuclear staining pattern was observed with the mutation-specific antibodies, which detected only their respective mutant proteins when overexpressed (FIG. 16), or in the endogenous state in tumor cell lines (FIGS. 17A and 17B), though all cells expressed the various p53 forms in abundance, as determined by staining with either the DO1 or the CM1 antibodies.

As observed with analysis by immunoblot and immunoprecipitation, the antibody against the R248Q mutant was extremely specific, and was unable to detect the related R248W mutant protein (FIG. 17B).

Figure 18A:
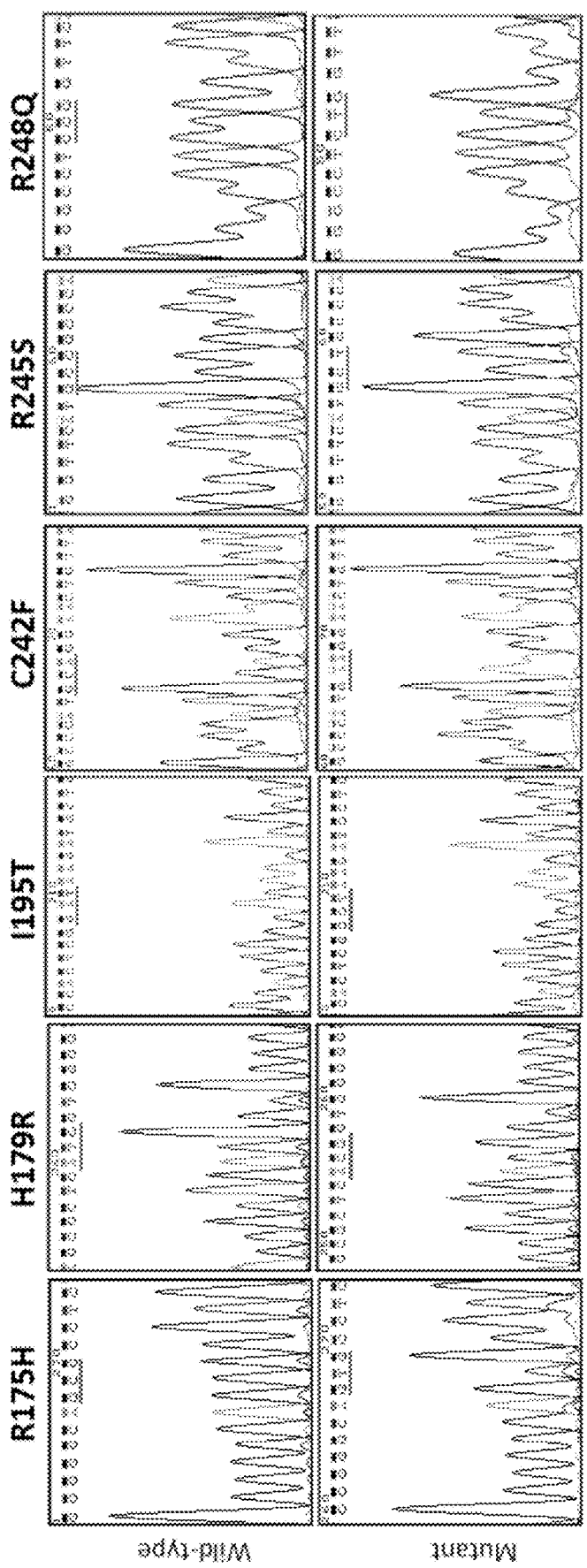
FIGS. 18A and 18B. Photographs relating to immunohistochemical analysis using mutant-specific anti-p53 antibodies. (18A) Sequence analysis of human colon tumour samples to determined mutational status for p53 (SEQ ID NOs: 175-186), and (18B) staining of the paraffin-embedded tumour samples using the indicated anti-p53 antibodies.

Example 5: Analyses of Human Tumor Samples Using mAbs Against the Specific p53 Hot-Spot Mutants by Immunohistochemistry To determine the effectiveness of the p53 mutant-specific antibodies in paraffin-embedded tissues, the inventors analyzed a large number of human tumor samples by immunohistochemical (IHC) analysis. Firstly, a series of tumor samples with known p53 mutations, confirmed by DNA sequencing (FIG. 18A), were examined using the mutant-specific antibodies.

Mouse tumour sections from HT29 xenograft mouse model with p53 R273H genotype and tumour sections generated from p53R172H mutant cell lines were processed into paraffin blocks by the Advanced Molecular Pathology Laboratory (AMPL), Institute of Molecular and Cell Biology. Wax sections of 5 µm were then embedded onto glass slides (Leica Biosystems) and dried for an hour on a 50° C. hot plate. Sections were deparaffinized in xylene (ChemTech Trading) and rehydrated through descending percentages of ethanol (ChemTech Trading) into water. Tissue sections were heated with Target Retrieval Solution, pH9 (Dako) for antigen exposure, then rinsed in PBS. Endogenous peroxidase was blocked with 2% (v/v) hydrogen peroxide (Merck) in PBS for 30 min, rinsed with PBS. Sections were blocked with 10% (v/v) goat serum (Dako) in PBS for 1 h then incubated with biotinylated primary antibodies clones at 4° C. overnight. Sections were washed with water then rinsed in PBS before detection with streptavidin-HRP antibody (BioLegend). Antigen-antibody interaction was then visualized using 3,3-diaminobenzidine as a substrate, and the sections were lightly counterstained with hematoxylin before dehydrating and mounting in Cytoseal 60 synthetic resin (Richard-Allan Scientific™, Fisher Scientific). Slides were imaged under bright field using the AxioImager (Zeiss) light microscope and analyzed with AxioVision Rel 4.8 software (Carl Zeiss AG).

Figure 18B:
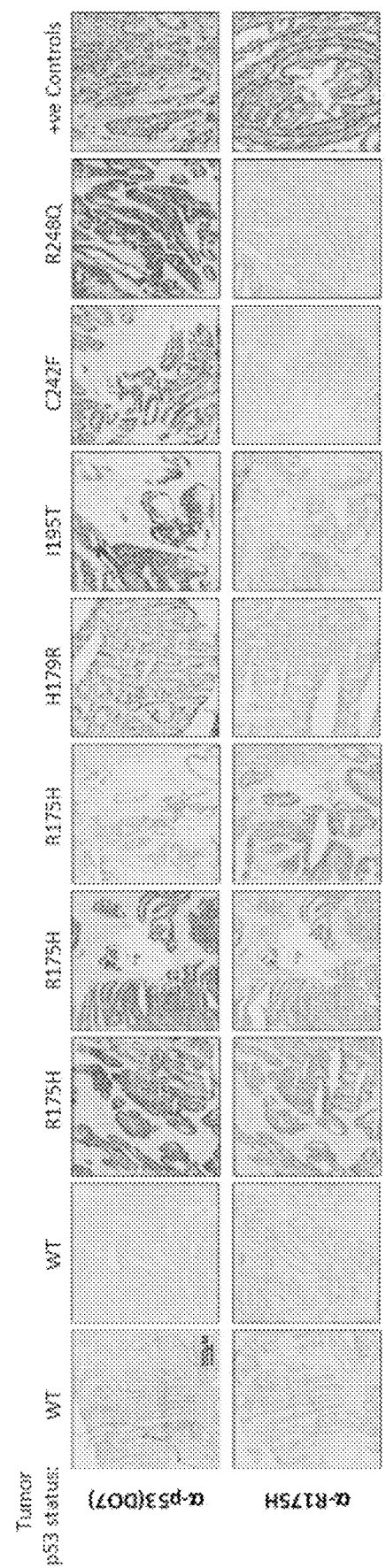

As was the case in the immunofluorescence analyses, the three mutant-specific antibodies stained the samples with the respective mutations in p53, but not the sample with either wild-type p53 or with other mutations (FIG. 18B), demonstrating specificity in the IHC setting.

Figure 19:
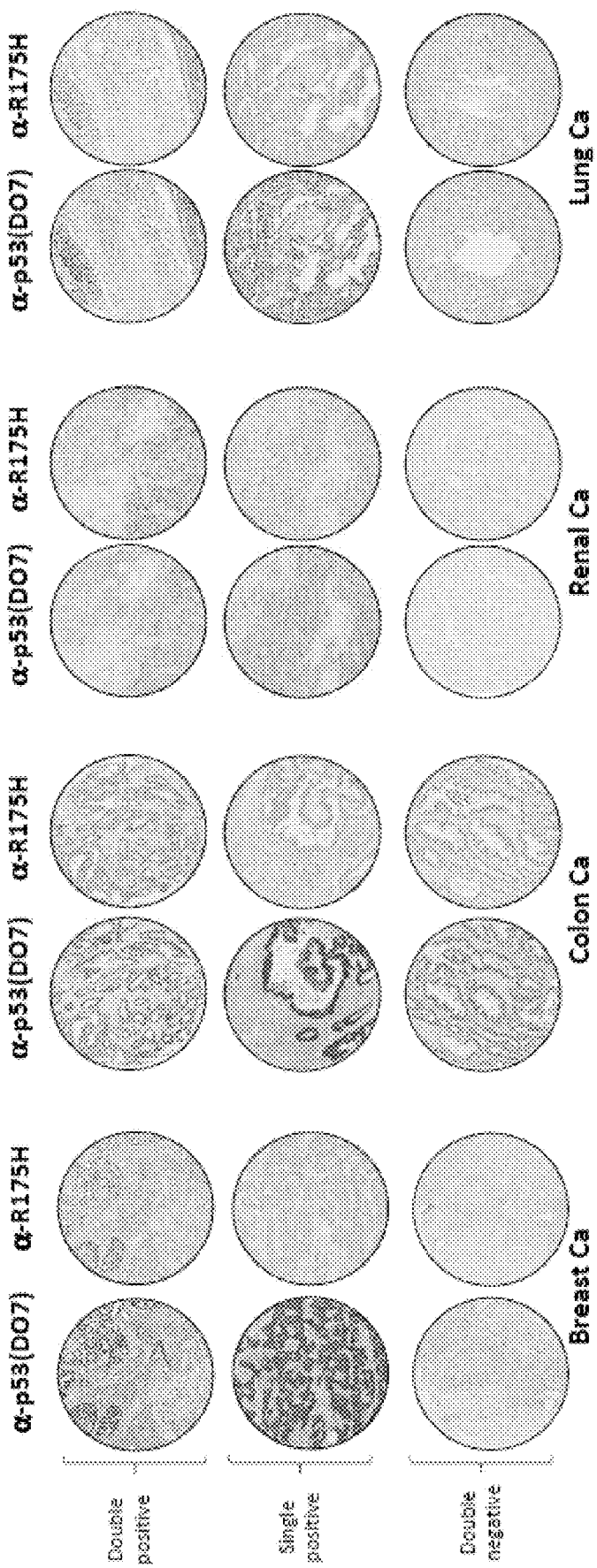
FIG. 19. Photographs showing the results of human tumour microarrays using R175H mutant-specific anti-p53 antibodies. Human tumor microarrays from triple negative breast cancer, colorectal cancers, renal cancers and lung cancers were stained with R175H mutant p53-specific mAb and the pan-p53 mAb DO7. Double positive refers to samples that were stained by both DO7 and the mutation-specific mAb, and single positives were only stained by DO7. There were no samples with only mutation-specific mAb staining without DO7 staining.

The inventors further evaluated several tumor microarrays from colon, breast (triple negative), lung, prostate and renal tumors by staining with these antibodies. Representative results from staining with the pan-p53 antibody suitable for IHC staining (DO7) and the R175H-specific antibodies are shown (FIG. 19). Three groups of samples emerged: one that was stained both by DO7 and the R175H mAb; one that was only positive for DO7; and the last that was negative for both antibodies (FIG. 21). The highest level of DO7 staining was for in the triple negative breast, lung and colon cancer groups, confirming previous data that these cancers have a higher mutation rate for p53 (Olivier et al., 2004 IARC Sci Publ 157:247-270), and are therefore positive for staining by anti-p53 antibodies. Staining by the R175H-mAb mirrored that of DO7 in the first group, suggesting that both the antibodies were recognizing the same cells in this group. A few samples were sequenced to determine the p53 mutational status, and found that all samples that were stained by both antibodies carried a R175H mutation. By contrast, samples that were stained by DO7 only had mutations in other residues of p53 but not on R175, and the samples that were negative for both antibodies had no mutations in p53.

Figure 20A:
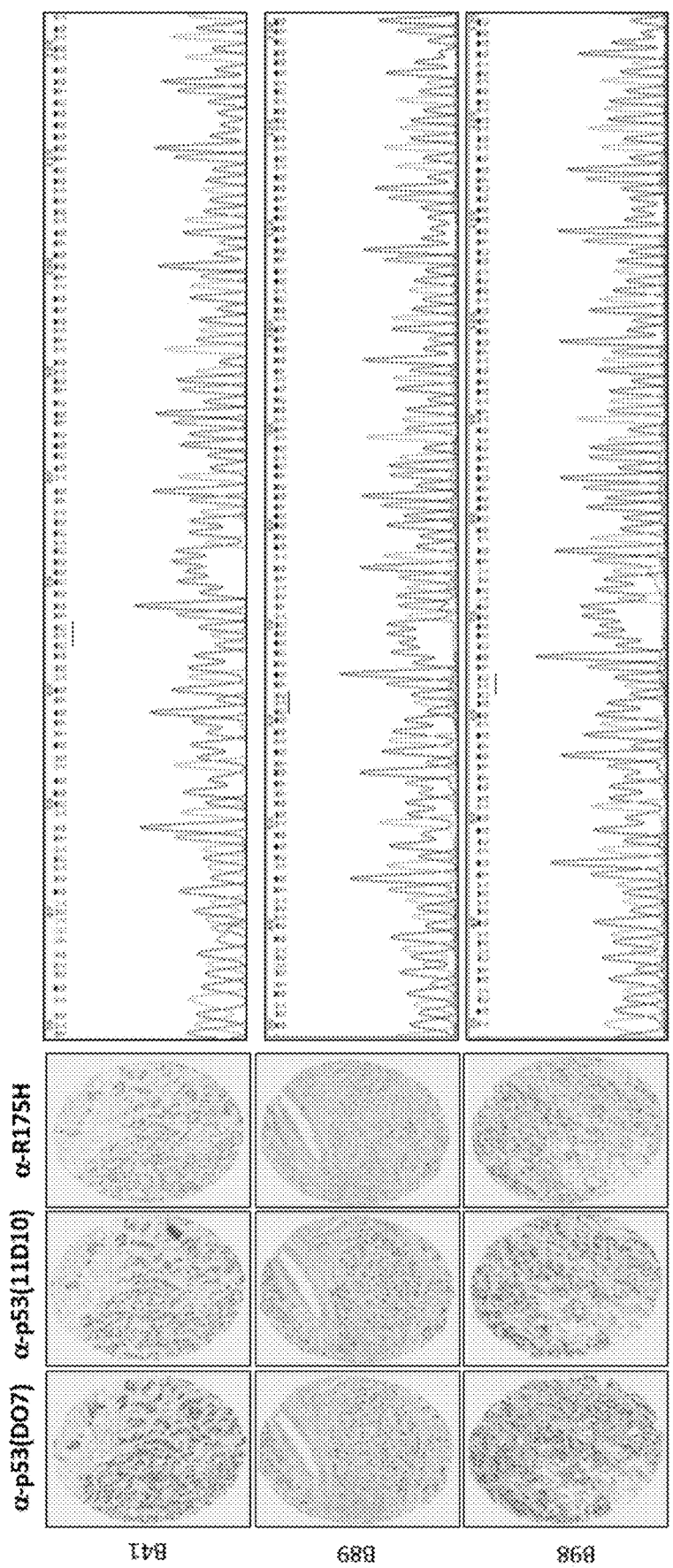
FIGS. 20A and 20B. Chromatograms showing p53 sequence in tumors samples, and staining for anti-p53 antibodies and anti-R175H antibody by immunohistochemistry. Human Triple negative breast cancer samples were stained with anti-p53 (DO7 and 11D1) antibodies and the anti-R175H p53 antibody. (20A) Samples B41, B89 and B98 showing positive staining by the R175H antibody, as well as both anti-p53 antibodies DO7 and 11D1. Sequences show that the samples comprise the R175H mutation (CAG-underlined) (SEQ ID NOs: 187-189). (20B) Sample B27 showing positive staining only by the anti-p53 antibodies DO7 and 11D1 (and not by the anti-R175H antibody), and sample B52, not stained by any of the anti-p53 antibodies. Sequences show that B27 and B57 do not comprise a mutation at position 175 (CGC-underlined) (SEQ ID NOs: 190 and 191).
Figure 20B:
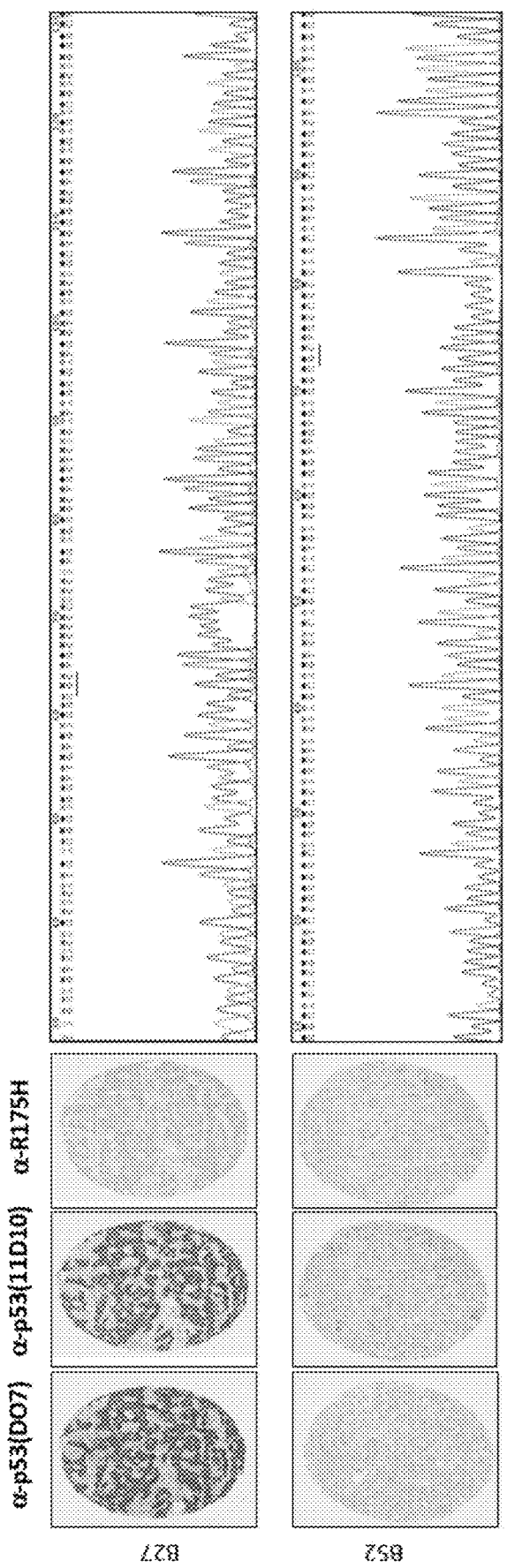

Human triple negative breast cancer samples B41, B89, B98, B27 and B52 were stained with anti-p53 antibodies DO7, 11D1, or the anti-R175H antibody for analysis by immunohistochemistry. Tumor samples B41, B89 and B98 comprising the R175H mutation (CAG—underlined) were positive for staining by all three antibodies (FIG. 20A). Tumor sample B27 not comprising the R175H mutation (CGC—underlined) was only stained by the anti-p53 antibodies DO7 and 11D1 (and not by the anti-R175H antibody), and sample B52 was not stained by any of the anti-p53 antibodies (FIG. 20B).

These data collectively indicate the specificity of these mutant-specific antibodies in paraffin-embedded clinical samples.

Example 6: Comparison of Effectiveness of the Human p53 Mutant-Specific Antibodies with Equivalent Mouse Mutants Finally, the inventors investigated if the antibodies are able to detect the corresponding mouse mutations. The human sequences corresponding to the three mutations studied here are highly homologous in mouse p53 (FIG. 22), and the sequences around the R175 residue are similar to the equivalent mouse R172 residue (Olive et al, 2004 Cell 119, 847-860). Hence, the inventors utilized mouse embryonic fibroblasts (MEFs) from the R172H mice, which contain an equivalent mutation to the R175H in humans (Lang et al., 2004 Cell 119, 861-872), or MEFs with an unrelated mutation R246S, which is equivalent to the human R4249S (Lee et al., 2012 Cancer Cell 22, 751-764).

Figure 23A:
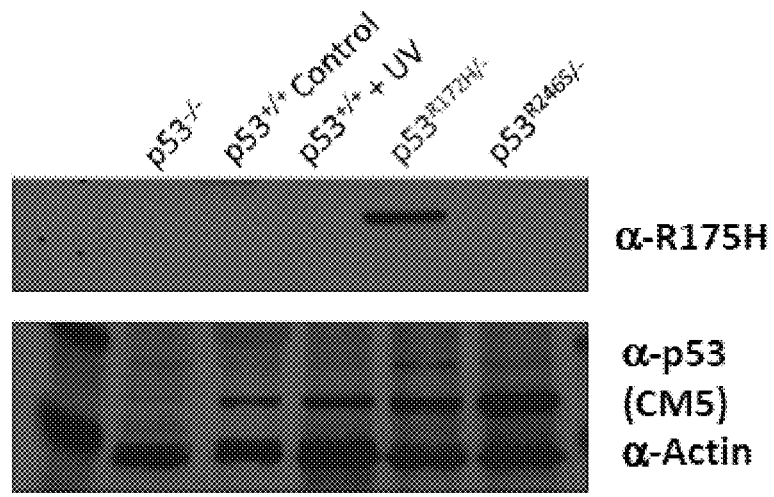
Figure 23B:
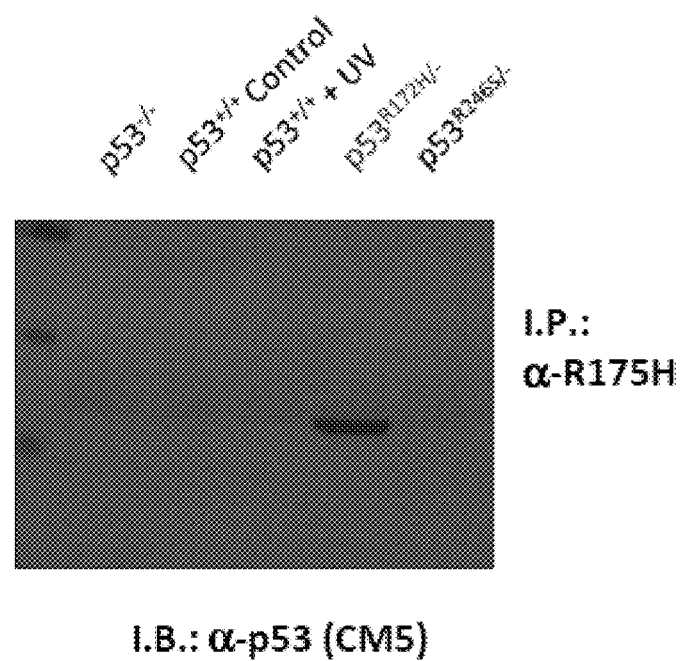
Figure 23C:
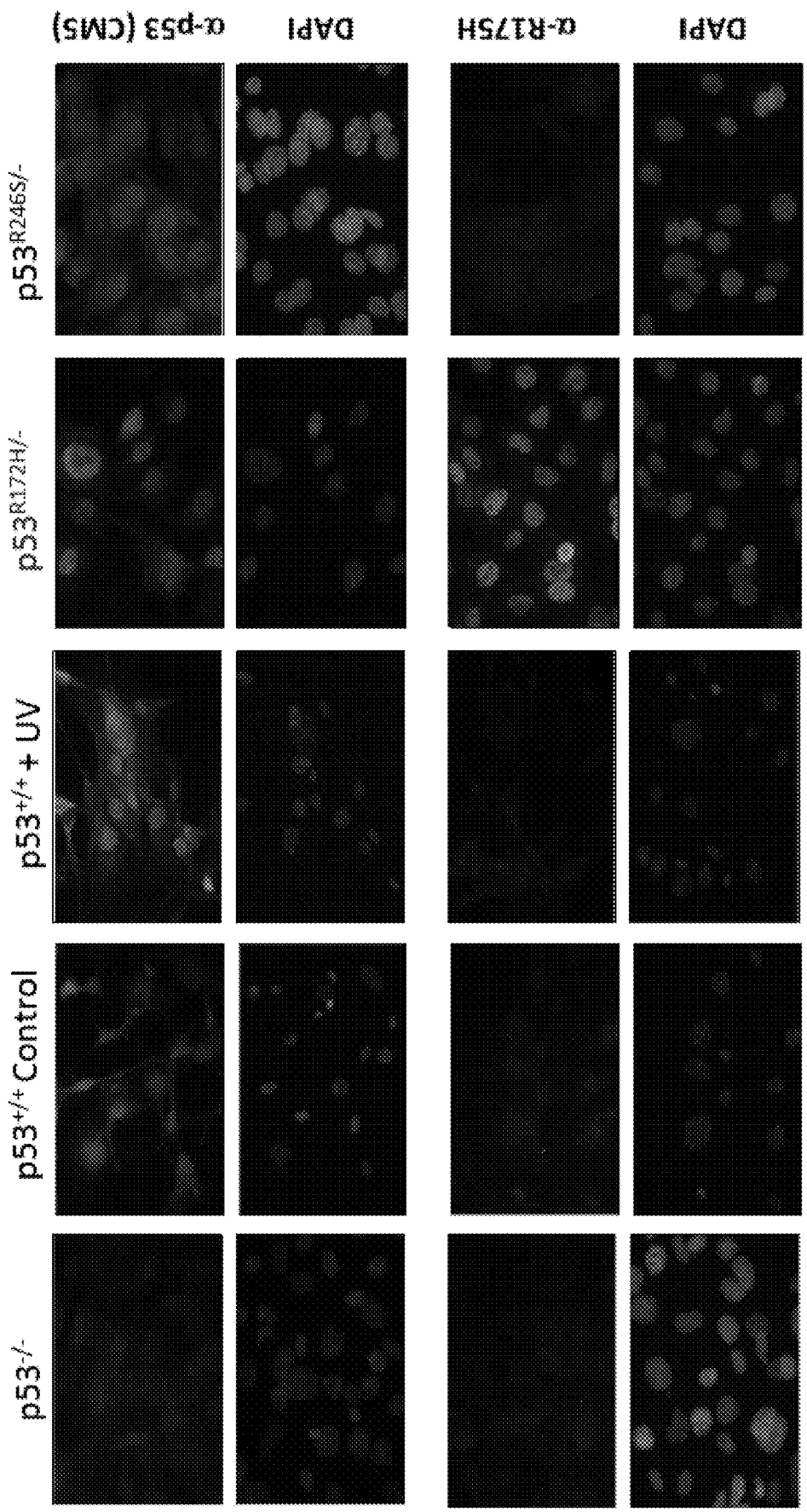
Figure 23D:
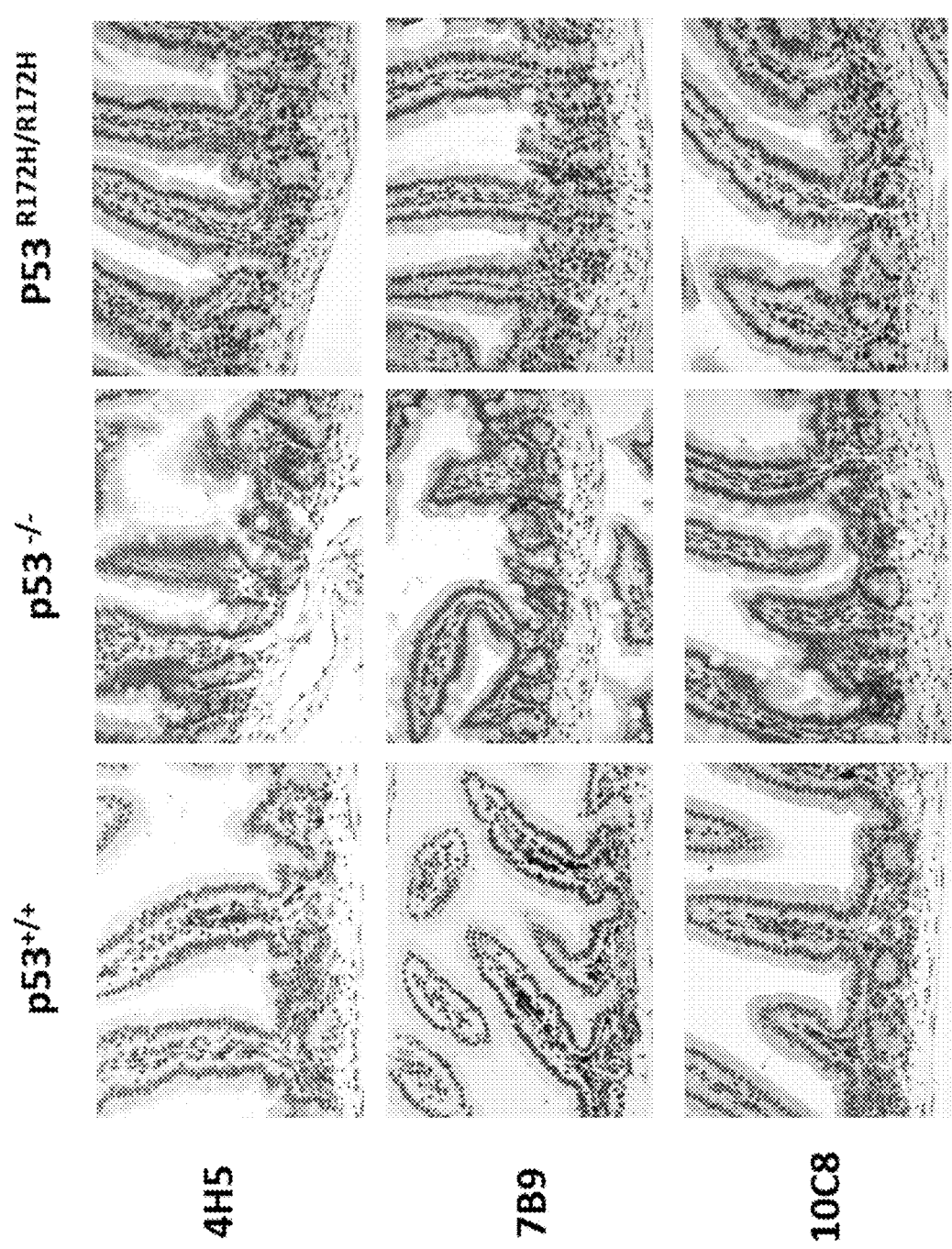

Direct immunoblotting indicated that the anti-R175H antibody was able to detect only the mutant p53 from the R172H MEFs, but not from the R246S or the wild-type MEFs, although these latter cells expressed significant amounts of p53 as determined by the pan-p53 antibody, CM5 (FIG. 23A). Immunoprecipitation with the R175H-specific antibody followed by immunoblotting also demonstrated that the antibody was indeed specific and can detect the mouse R172H mutant protein (FIG. 23B). The inventors also tested the ability of the R175H-specific antibody by immunofluorescence (FIG. 23C) and IHC (FIG. 23D) analyses, which confirmed its specificity, highlighting the utility of these antibodies in different species.

Immunostaining for IHC analyses was performed on formalin fixed paraffin-embedded (FFPE) 5 µm sections. Antigen retrieval was performed using with Dako Tris/EDTA target retrieval solution, pH9. Blocking was performed with DAKO 10% goat serum. Secondary antibody was Dako Envision™+/HRP. Develop with DAKO liquid DAB+. Images were captured with a Zeiss AxioImager upright microscope using 40× objective lens.

Example 7: Monoclonal Anti-Mutant p53 Antibodies 7.1 R175H Mutant p53 Antibody Clones 4H5, 7B9 and 10C8

Anti-R175H p53 mouse monoclonal antibodies were raised by immunising mice with immunogen comprising three copies of the R175H p53 mutation inserted in the active site sequence of TrxA, as described in Example 1 (see FIG. 1A).

Hybridoma clones producing anti-R175H p53 mouse monoclonal antibodies were obtained. The amino acid sequences of the light and heavy chain variable domain sequences were determined and are shown in FIGS. 24 and 25. The DNA sequences encoding the light and heavy chain variable domain sequences for the antibodies are shown in FIG. 27.

The CDRs were predicted using VBASE2 (Retter et al. Nucleic Acids Research (2005) 33 (Database issue): D671-674, incorporated by reference hereinabove).

7.2 R248Q Mutant p53 Antibody Clones 3G11 and 4H2

Anti-R248Q p53 mouse monoclonal antibodies were raised by immunising mice with immunogen comprising three copies of the R248Q p53 mutation inserted in the active site sequence of TrxA, as described in Example 1 (see FIG. 1B).

Hybridoma clones producing anti-R248Q p53 mouse monoclonal antibodies were obtained. The amino acid sequences of the light and heavy chain variable domain sequences were determined and are shown in FIGS. 28 and 29. The DNA sequences encoding the light and heavy chain variable domain sequences for the antibodies are shown in FIG. 31. The CDRs were predicted using VBASE2 as above.

7.3 R273H Mutant p53 Antibody Clone 13E4

Anti-R273H p53 mouse monoclonal antibodies were raised by immunising mice with immunogen comprising three copies of the R273H p53 mutation inserted in the active site sequence of TrxA, as described in Example 1 (see FIG. 1C).

A hybridoma clone producing anti-R273H p53 mouse monoclonal antibodies was obtained. The amino acid sequences of the light and heavy chain variable domain sequences were determined and are shown in FIGS. 32 and 33. The DNA sequences encoding the light and heavy chain variable domain sequences for antibody clone 13E4 are shown in FIG. 34.

The CDRs were predicted using VBASE2 as above.

Example 8: Characterisation of Monoclonal Anti-Mutant p53 Antibodies 8.1 R175H Mutant p53 Antibody Clones 4H5, 7B9 and 10C8

Western blot analysis was performed on cell extracts obtained from R172H mouse thymic lymphoma cell line cells, T47D cells, WiDr cells and DKO cells using cell culture supernatant of hybridoma clones 4H5, 7B9 and 10C8. The results are shown in FIG. 35. Antibodies from each clone were specific for R175H mutant p53.

Immunofluorescence analyses were also performed using R172H mouse thymic lymphoma cell line cells, TKO cells, C6 cells, H1299 cells, T47D cells, and H1299 cells transfected with a construct expressing R175H mutant p53, using cell culture supernatant of hybridoma clones 4H5, 7B9 and 10C8. The results are shown in FIG. 36A to 36C. Antibodies from each clone were specific for mouse R172H mutant p53.

The epitope recognised by the antibodies 4H5, 7B9 and 10C8 is shown in the context of human R175H p53 in FIG. 10.

The antibody clones were further investigated for their ability to recognise R175H p53 by immunohistochemical (IHC) analysis of mouse intestinal tissue sections obtained from p53 knockout mice or irradiated, R172H p53 positive mice, using cell culture supernatant of hybridoma clones 4H5, 7B9 and 10C8. The results are shown in FIG. 37. The antibodies were able to detect R172H mutant p53 in mouse intestinal tissue sections by IHC.

Antibody clone 4H5 was further analysed for ability to visualise and monitor R175H-positive cancer in vivo. Mouse tumour cells derived from P53$^{R172H/R172H}$ mice were transfected with luciferase gene and used to establish a tumour model. Mice were injected IV with 100 μg of XenoLight CF750-labelled anti-R175H mutant p53 antibody clone 4H5, and imaged by IVIS analysis at 6 h, 24, 72 h and 7 days post-injection. The results of the experiment are shown in FIG. 38. The antibody was demonstrated to be suitable for visualisation and monitoring tumour in vivo.

8.2 R248Q Mutant p53 Antibody Clones 3G11 and 4H2

Western blot analysis was performed on cell extracts obtained from TKO cells, and HCC70 cells (which possess the R248Q mutation) using cell culture supernatant of hybridoma clones 3G11 and 4H2. The results are shown in FIG. 39. The antibodies were specific for R248Q mutant p53.

Immunofluorescence analyses were also performed using TKO cells, HCC70 cells and OVCAR3 cells (which possess the R248Q mutation), using cell culture supernatant of hybridoma clones 3G11 and 4H2. The results are shown in FIGS. 40A and 40B. Antibodies from each clone were specific for R248Q mutant p53.

The epitopes recognised by antibody clones 3G11 and 4H2 were analysed by peptide phage display analysis (FIGS. 8B and 7B). The epitopes recognised by the antibodies are shown in the context of human R248Q p53 in FIG. 10.

8.3 R273H Mutant p53 Antibody Clone 13E4

Western blot analysis was performed on cell extracts obtained from T47D cells and MB468 cells (which possess the R273H mutation) using cell culture supernatant of hybridoma clone 13E4. The results are shown in FIG. 41. Antibody from clone 13E4 was specific for R273H mutant p53.

Immunofluorescence analysis was also performed using T47D cells, and WiDr cells expressing R273H mutant p53, using cell culture supernatant of hybridoma clone 13E4. The results are shown in FIG. 42. Antibody from clone 13E4 was specific for R273H mutant p53.

The epitope recognised by 13E4 antibody is shown in the context of human R273H p53 in FIG. 10.

Antibody clone 13E4 was further analysed for ability to visualise and monitor R273H-positive cancer in vivo. Cells of the p53-R273H-mutant HT29 tumour cell line were transfected with luciferase gene and used to establish a tumour model. Mice were injected IV with 100 μg of XenoLight CF750-labelled anti-R273H mutant p53 antibody clone 13E4, and imaged by IVIS analysis at 72 hours post-injection. The results of the experiment are shown in FIG. 43. The antibody was demonstrated to be suitable for visualisation and monitoring tumour in vivo.

Example 9: Chimeric Mouse Fv-Human IgG1 Fc Anti-Mutant p53 Antibodies

Mouse Fv-Human IgG1 Fc chimeric versions of the anti-mutant p53 antibodies were prepared.

Variable regions of the heavy and light chains were cloned from parental 4H5, 7B9, 10C8, 3G11, 4H2 and 13E4 mouse monoclonal antibody clones into pTT5 vectors each containing the human IgG1 constant region.

Mouse-human chimeric heavy- and light-chain plasmids were co-transfected into HEK293-6e cells at 1 g total plasmid per million cells, using 2 μL of 293-fectin transfection reagent per μg of plasmid. Culture supernatant containing secreted chimeric antibodies was harvested and purified using protein G agarose beads, 4 to 6 days post-transfection.

Chimeric antibody was eluted off beads using 0.1 M glycine-HCl (pH 2.7) neutralised with 1 M Tris (pH 9.0) and dialysed into PBS.

The chimeric antibodies were determined to be able to recognise their respective mutant p53 by ELISA (test concentration 1 ng/μL).

Mouse-Fv-Human IgG1 Fc chimeric versions of anti-R175H p53 antibody clones 4H5, 7B9 and 10C8 were also investigated for ability to recognise R175H p53 by IHC analysis of mouse intestinal tissue sections obtained from irradiated, R172H p53 positive mice. The results are shown in FIG. 44. Chimeric versions of the antibodies were able to detect R172H mutant p53 in mouse intestinal tissue sections by IHC.

Example 10: Analysis of the Ability of Anti-p53 Mutant Antibody to Treat Cancer In Vivo The inventors investigated the ability of the monoclonal anti-mutant p53 antibodies to treat cancer in vivo.

Briefly, mice were injected with 5×10$^6$ SKBR3 cells (human breast cancer cells) carrying a luciferase gene. SKBR3 cells carry the R175H mutation in p53 (see e.g. FIG. 13). The luciferase gene allowed monitoring of tumor growth in vivo, by detection of luciferase activity. Four days after mice have been injected with the SKBR-3 cells, mice were treated either with 100 μl of anti-R175H antibody, or 100 μl of IgG antibody control. Injections were repeated every four days (as indicated by the arrows in FIG. 45). Tumor growth was monitored throughout the experiment by measuring luciferase luminescence. The results are shown in FIG. 45, which demonstrates an anti-cancer effect in mice treated with the anti-R175H antibody, as evidenced by reduced levels of luciferase activity as compared to the control treatment group.

Example 11: Analysis of the Ability of the Immunogens to be Used to Generate an Immune Response to Mutant p53 Polypeptides The inventors also investigated the ability of the immunogens described in Example 1 to be used as vaccines, for stimulating an immune response against p53 mutant polypeptides.

Groups of mice were immunised with the immunogens, and the polyclonal antibody response was analysed by ELISA to determine whether the immunogens can be used as vaccines to trigger antibody responses.

Figure 46A:
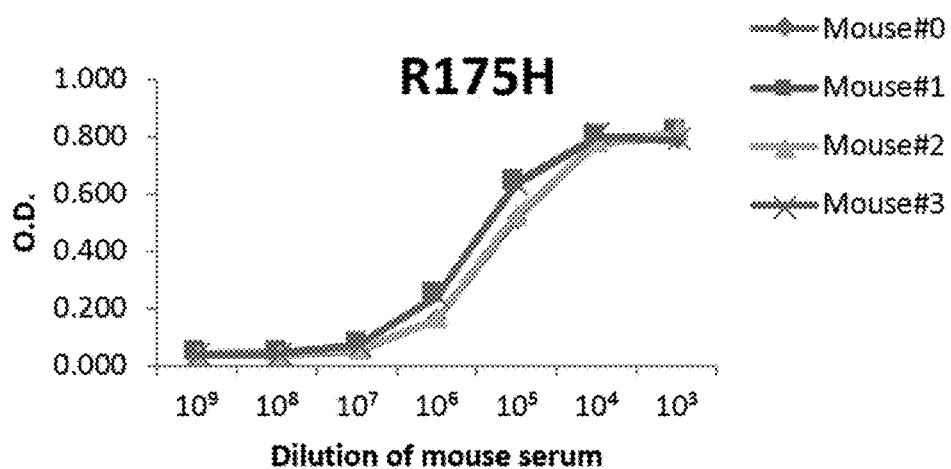
Figure 46B:
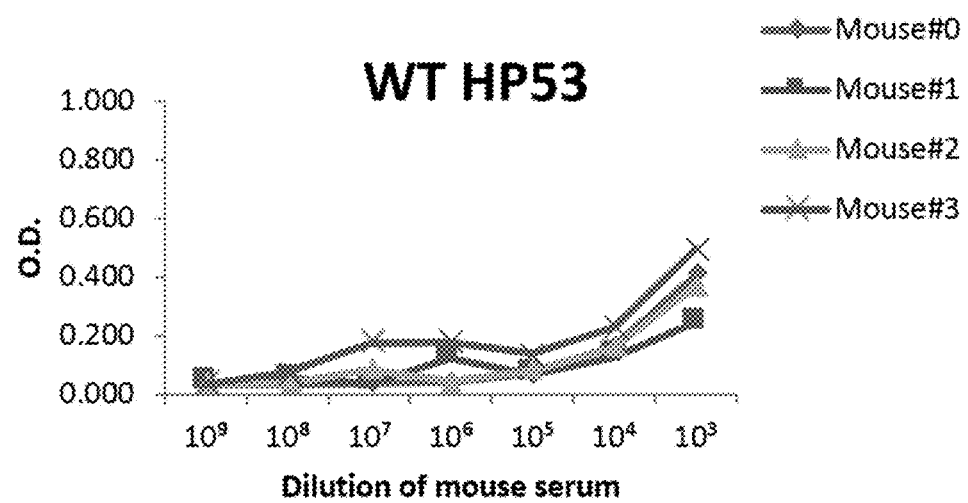
Figure 46C:
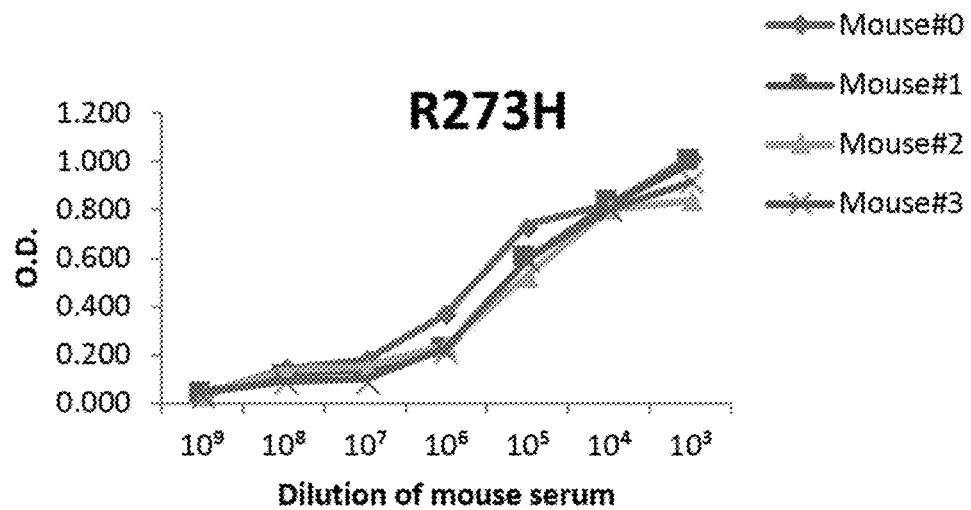
Figure 46D:
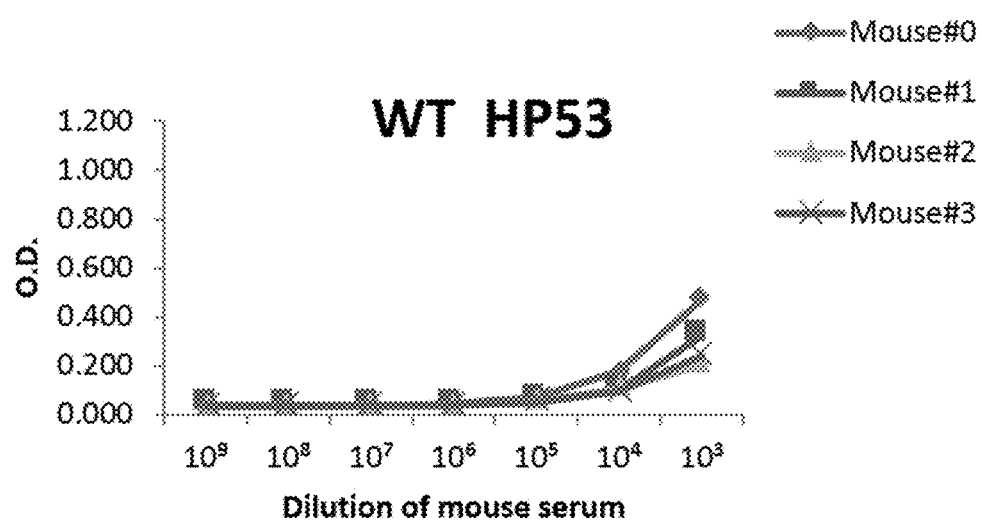
Figure 46E:
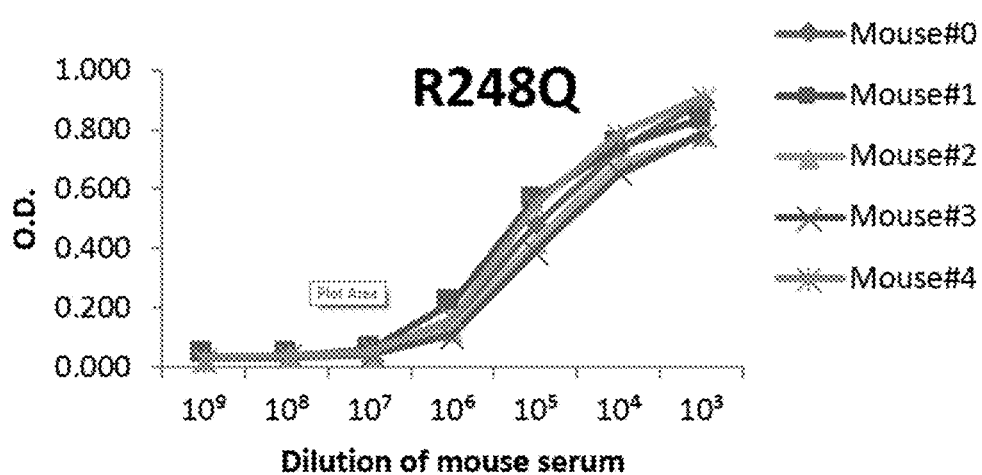
Figure 46F:
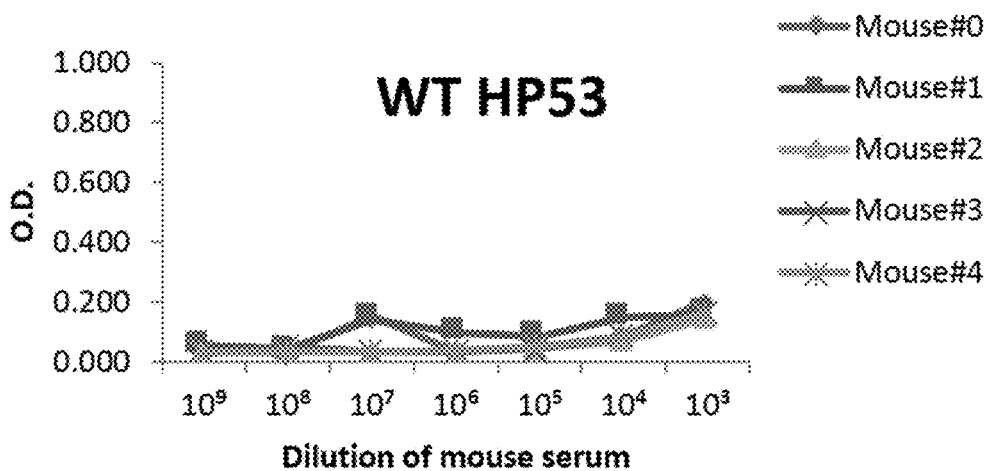

The results are shown in FIGS. 46A-46E. Immunization with the different mutant p53 immunogens is shown to induce the production of antibodies which are highly specific for peptide corresponding to the respective p53 mutant (FIGS. 46A, 46C and 46E), and which display minimal interaction with wildtype human p53 (FIGS. 46B, 46D and 46F). These results demonstrate that the mutant p53 immunogens are capable of triggering an antibody response, and that this immunity is specific to the respective p53 mutant.

The inventors next investigated whether the antibodies generated in response to immunisation with the immunogens were capable of recognising mutant p53 polypeptides. Sera was obtained from mice injected with the R175H, R248Q or R273H immunogens described in Example 1, and analysed for ability to recognise mutant p53 polypeptides by immunofluorescence analysis. The results are shown in FIGS. 47A-47C, which demonstrate that the antibodies generated in mice in response to immunisation with immunogen were capable of recognising the corresponding mutant p53 polypeptide.

Example 12: Conclusion

The inventors have successfully generated p53 mutant-specific antibodies against three commonly-occurring p53 hot-spot mutations in the DBD region—the R175H, R248Q and R273H (Vikhanskaya et al., Nucleic Acids Res (2007) 35:2093-2104). The antibodies are characterised, and their utility in a variety of biochemical and histological assays is demonstrated, as is their usefulness to treat cancer in vivo.

The inventors have for the first time been able to generate antibodies capable of specifically binding to single point mutants of p53, which do not cross-react with wildtype p53, raised using immunogen in which antigen expression is enhanced by the provision of multiple copies of the region containing the mutation, displayed by protrusion from the protein body into solution, using TrxA as a fusion partner. This approach consistently led to the generation of mAb clones against several p53 mutants, with high specificity and selectivity.

The present experimental examples demonstrate generation of antibodies to three of the most common hot-spot mutations found in p53, namely R175H, R248Q and R273H. The mAbs generated against these mutants were specific in their ability to discern between the intended antigens and other mutations or the wildtype p53 protein, in a variety of techniques, ranging from immunoblotting, immunoprecipitation, immunofluorescence and immunohistochemistry. The inventors have moreover demonstrated the ability to inhibit growth of tumor cells comprising the corresponding p53 mutation in a human xenograft cancer mouse model in vivo.

Furthermore, the antibodies were able to detect the corresponding mutations in other species such as mouse, as demonstrated with the R175H mutation, and thus, should be applicable to the other mouse mutants, given the sequence conservation across species (see e.g. FIG. 22), thereby proving to be valuables tools for fundamental research.

The mutant-specific antibodies are useful tools to dissect out the individual and combined roles of both the wild-type and mutant p53 proteins in the same cell, potentially even at the single cell level, and during the clonal evolution of the cancer cell.

The utility of the mutant-specific mAbs for IHC analysis of human tumor samples highlights that these mAbs are very useful tools in pathological analyses in determining p53 status, which could be easily implemented and is significantly cost effective compared to DNA-sequencing technologies.

The TrxA presentation system utilised in the present examples will be useful for generating mAbs against other mutations in p53 which can be of clinical utility, and also for generating mAbs against other mutations found in tumor suppressors and oncogenes. Monoclonal antibodies which are able to discriminate between proteins differing by only a single amino-acid could be clinically useful as diagnostic and therapeutic agents.

Moreover, the inventors have demonstrated the usefulness of the immunogens for vaccination strategy, demonstrating the ability to induce an antibody response capable recognising mutants of p53.

In a therapeutic context, such mutant-specific antibodies are likely to be very safe as they will not have any side-effects in normal cells of patients that do not carry the mutation. It is expected that such antibodies would be superior to the currently available general antibodies against proteins that are either overexpressed or deregulated in disease.

Example 13: Effect of Mutant-Specific Anti-p53 Antibody on Tumour Growth In Vivo The inventors next investigated the effect of administration of a monoclonal p53 mutant-specific antibody on growth of cancer cells in in vivo.

Briefly, SCID mice were injected subcutaneously at their flanks with 5×10$^6$ luciferase labelled SKBR cells (which carry the R175H mutation in p53-see e.g. FIG. 13)). From day 4, mice were injected intravenously every 4 days with 100 µl of monoclonal antibody specific for the R175H mutant p53 (a175) or isotype control antibody (IgG). Tumour growth was monitored by measuring luciferase activity.

The results of the experiment are shown in FIG. 48. A strong anti-cancer effect was observed in mice treated with the monoclonal antibody specific for the R175H mutant p53.

Example 14: Preparation of Mouse-Human Chimeric Anti-p53 Mutant Antibodies

The inventors prepared chimeric mouse-human versions of the anti-R175H antibody clones 4H5, 7B9 and 10C8, the anti-R273H antibody clone 13E4 and the anti-R248Q antibody clones 3G11 and 4H2.

DNA encoding the variable heavy and light chains of the parental mouse monoclonal antibodies were cloned from parental mouse monoclonal antibodies into separate pTT5 vectors each containing the human constant region. Mouse-human chimeric heavy- and light-chain plasmids were co-transfected into HEK293-6e cells at 1 µg total plasmid per 1×10$^6$ cells, using 2 µl of 293-fectin transfection reagent per microgram of plasmid.

4-6 days after transfection, the cell culture supernatant containing the secreted mouse-human chimeric antibodies was harvested, and the antibodies were purified using protein G agarose beads. The chimeric mouse-human antibodies were eluted off beads using 0.1 M glycine-HCl (pH 2.7) neutralised with 1 M Tris (pH 9.0) and dialysed into PBS. The mouse-human chimeric antibodies comprise mice Fv and human Fc.

Mouse-human chimeric anti-p53 mutant R175H antibody clone VL sequences are shown in FIGS. 49 and 51, and the VH sequences are shown in FIGS. 50 and 52.

Mouse-human chimeric anti-p53 mutant R273H antibody clone 13E4 VL sequence is shown in FIGS. 53 and 55, and the VH sequence is shown in FIGS. 54 and 56.

Mouse-human chimeric anti-p53 mutant R248Q antibody clone VL sequences are shown in FIGS. 57 and 59, and the VH sequences are shown in FIGS. 58 and 60.

Example 15: Characterisation of Mouse-Human Chimeric Anti-p53 Mutant Antibodies

Mouse-Human Chimeric Anti-p53 R175H Antibodies

The mouse human chimeric anti-p53 R175H antibodies were analysed by ELISA for binding to R175H mutant p53.

The results are shown in FIG. 61. The chimeric anti-p53 R175H antibodies (MH 4H5, MH 7B9, MH 10C8) antibodies produced positive signals between 0.1 and 1 ng/µl concentrations, bound specifically only to human p53 R175H full length protein and not human p53 R273H full length, human p53 wild-type full length, or mouse p53 wild-type full length protein. Commercial anti-p53 antibody (1C12) was included as a positive control antibody.

Binding was also analysed by western blot, and the results are shown in FIG. 62. Detection of denatured endogenous p53 in human cell lines via western blot (antibodies were used at a concentration of 1 ng/µl) confirmed the specificity of the chimeric anti-p53 R175H antibodies (MH 4H5, MH 7B9, MH 10C8). The antibodies only detected p53 from the SKBR3 cell line which harbours the R175H mutation in p53, and not from the p53-null H1299 cell line, the wildtype 53 cell lines MCF7 and A549, nor the R273H cell lines A431 and SW480.

The antibodies were further analysed for their ability to bind specifically to R175H mutant p53 by immunohistochemical analysis of binding to different cancer cell lines fixed in 4% paraformaldehyde and embedded in paraffin. The mouse human chimeric anti-p175H antibodies were shown only to stain SKBR3 cells. Representative images from the analysis using MH 7B9 are shown in FIG. 63.

Mouse-Human Chimeric Anti-p53 R273H Antibody

The mouse human chimeric anti-p53 R273H antibody 13E4 was analysed by ELISA for binding to R273H mutant p53.

The results are shown in FIG. 64. The chimeric anti-p53 R175H antibody MH 13E4 bound to human p53 R273H full length protein much more than it bound to thioredoxin, human p53 R175H full length and human p53 wild-type full length protein.

Binding was also analysed by western blot, and the results are shown in FIG. 65. Detection of denatured endogenous p53 in human cell lines via western blot (antibodies were used at a concentration of 1 ng/µl) confirmed the specificity of MH 13E4, which only detected p53 from the A431 and SW480 cell lines which harbour the R273H mutation in p53, and not from the p53-null H1299 cell line, the wildtype 53 cell lines MCF7 and A549, nor the R175H cell line SKBR3.

The antibody was further analysed for ability to bind specifically to R273H mutant p53 by immunohistochemical analysis of binding to different cancer cell lines fixed in 4% paraformaldehyde and embedded in paraffin. MH 13E4 was found only to stain cells harbouring the R273H mutation (i.e. A431 cells)—see FIG. 66.

Mouse-Human Chimeric Anti-p53 R248Q Antibodies

The mouse human chimeric anti-p53 R248Q antibodies were analysed by ELISA for binding to R248Q mutant p53. The antibodies were used in the experiments at at final concentration of 1 ng/µl.

The results are shown in FIG. 67. The chimeric anti-p53 R248Q antibodies (MH 3G11 and MH 4H2) antibodies were found to bind to full-length R248Q p53, and not to full-length R175H or R273H p53, or full-length wildtype human or mouse p53. Commercial anti-p53 antibody (1C12) was included as a positive control antibody.

Example 16: Evaluation of Anti-p53 Mutant Antibodies as Diagnostic Antibodies for Tumor Imaging In Vivo The inventors next investigated whether anti-p53 mutant antibodies were useful for tumor imaging in vivo.

Briefly, 100 µg of fluorescently-labeled R273H specific mAb MH 13E4 (or fluorescently labelled IgG control), was injected intravenously into mice bearing HT29 tumors (which harbour the R273H mutation in p53). Mice were imaged using the IVIS Sprectrum in vivo imaging system for trafficking mAbs 72 hours after antibody injection.

The results are shown in FIG. 68. MH 13E4 specifically detected R273H mutant p53-positive HT29 xenograft tumours in nude mice.

In a separate experiment, 100 µg of fluorescently-labeled R175H specific mAb MH 4H5 or MH 7B9, was injected i.v. into mice bearing R175H mutant p53-positive clone32 tumors. Mice were imaged using the IVIS Sprectrum in vivo imaging system for trafficking mAbs at 6 h and 24 h, and on Days 2, 3 and 7 following antibody injection. The clone 32 cells express luciferase, and so the location of the tumor cells could be analysed by detection of luciferase activity.

The results are shown in FIG. 69. MH 4H5 and MH 7B9 antibodies detected R175H mutant p53 and were retained in the tumours for up to 7 days. Specificity of the antibodies for the tumour cells is demonstrated by detection of luciferase at the same position as the antibodies.

In a further experiment, it was investigated whether anti-p53 mutant R175H antibodies could detect spontaneously arising R175H p53 tumours. 100 µg of fluorescently-labeled R175H specific mAb MH 4H5 was injected i.v. into mice having the murine R172H mutation in murine p53. Mutant $p53^{R172H}$ mice are highly susceptible to the spontaneous development of tumours harbouring the R172H mutation in murine p53. Mice were imaged using the IVIS Sprectrum in vivo imaging system for trafficking mAbs on Day2 and Day3 following antibody injections.

The results are shown in FIG. 70. MH 4H5 was able to detect spontaneously occurring mutant murine p53 R172H tumours.

Example 17: Evaluation of Therapeutic Utility of Anti-p53 Mutant Antibodies to Treat Cancer In Vivo The inventors next investigated whether the anti-p53 mutant antibodies were useful as a treatment for cancer in vivo.

Anti-p53 Mutant R175H Antibodies

In a first experiment, the therapeutic effect of administration of the monoclonal antibody 13E4 was analysed in a HT 29-luciferase xenograft tumor model. Briefly, nude Balb/c mice (n=3) were subcutaneously inoculated with $5 \times 10^6$ HT29-luc cells on Day 0, and followed by i.v. injection of 15 mg/kg of control IgG or 13E4 mAb on Days 3, 7, 11, 14, 18 and 21. Mice were analysed at Day 28. Tumour growth was determined by measuring average photon intensity.

A schematic representation of the treatment schedule is shown in FIG. 71A. The results of the experiment are shown in FIG. 71B. Mice treated with 13E4 mAb showed an inhibition of 81.62% tumour size as compared to mice treated with IgG control antibody.

In a second experiment, the therapeutic effect of administration of the monoclonal antibody 13E4 was analysed in a HT 29-luciferase xenograft tumor model. Briefly, nude Balb/c mice (n=3) were subcutaneously inoculated with $5 \times 10^6$ HT29-luc cells on Day 0 on each flank, and followed by i.v. injection of 10 mg/kg of control IgG or 13E4 mAb on Days 4, 7, 11, 14, 18, 21, 25, 28, 32 and 35. Mice were analysed on Days 7, 14, 21, 28 and 35. The tumour volume was measured every week following inoculation by luminescence imaging of luciferase expressing HT29 tumour cells. At the end of the experiments tumours were excised from mice and the mass of the tumours was recorded.

Figure 72A:
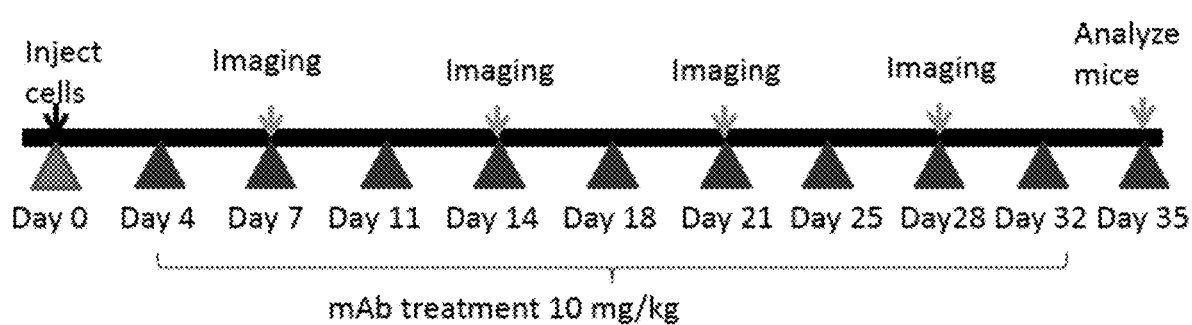
Figure 72B:
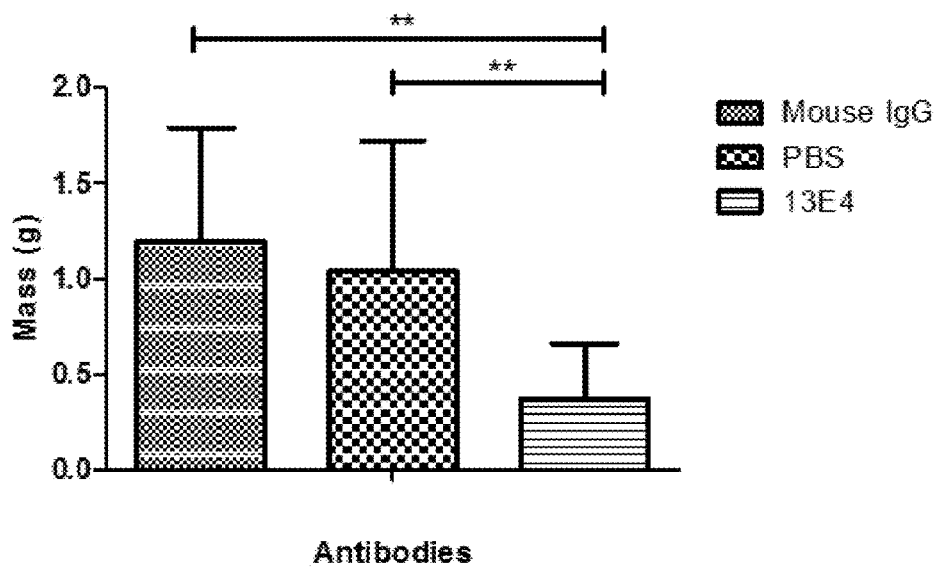
Figure 72C:
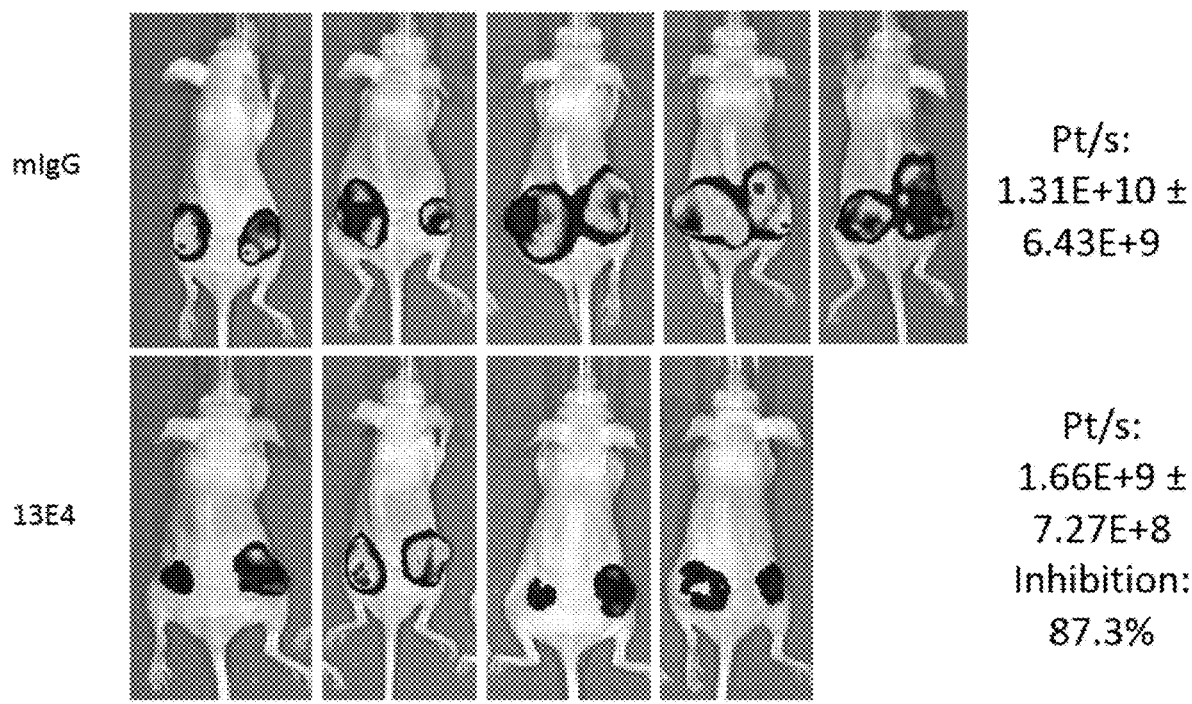
Figure 72D:
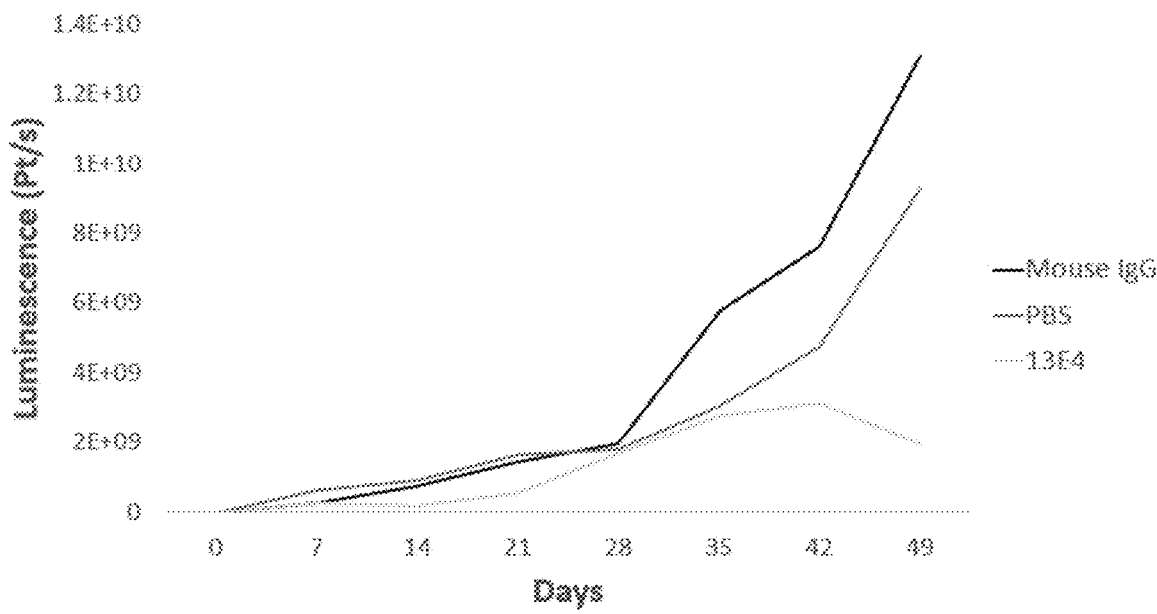

A schematic representation of the treatment schedule is shown in FIG. 72A, and the results of the experiment are shown in FIGS. 72B, 72C and 72D. Mice treated with 13E4 mAb showed an inhibition of 87.3% tumour size as compared to mice treated with IgG control antibody, and the tumor mass was approximately 2.5 time less than the weight of tumours obtained from mice treated with control IgG. FIG. 72D shows inhibition of tumor growth by 13E4 over time.

In a further experiment, the anti-p53 mutant R175H antibody 4H5 was analysed for its ability to inhibit growth of spontaneously-occurring murine p53 mutant R172H-positive cancer. Briefly, a mouse tumor cell line, clone32, was generated from p53R172H mutant mouse. $3 \times 10^6$ clone32 cells were injected into syngeneic B6 mice on Day 0, and 100 µg of 4H5, 7B9 (mAb specific to R175H), 13E4 (specific to R273H) and 11D10 (reactive to both human and mouse p53) were i.v. injected into mice on Days 3, 6, 9, 12, 15, 18, 21 and 24. Mice were sacrifice on Day 25 for analysis and tumor measurement.

A schematic representation of the treatment schedule is shown in FIG. 73A, and the results of the experiment are shown in FIG. 73B. The average of tumor weight in 4H5 (R175H mAb) treated mice was 75% less than the weight of tumors in the control IgG treated group. 7B9 (R175H mAb), 13E4 (R273H mAb), 11D10 (p53 mAb) did not show significant effects on the weight on the syngeneic mouse tumor.

Example 18: Evaluation of Immunogens Used to Raise p53 Mutant Antibodies as Vaccine Candidates The inventors next investigated whether the immunogens used to raise the p53 mutant-specific antibodies of the present invention were capable of vaccinating subjects against the development of p53 mutant cancers.

Wildtype BALB/C or B6 mice and mutant p53R172H mice were injected with TrxR175H protein (see Example 1) on Days 0, 21, 42, 63 and 84. Serum was collected 7 days after each injection and analysed by ELISA, cell staining and western blot. Antigens used for ELISA analysis were thioredoxin protein (Trx), Trx-R175H protein or the full-length R175H mutant p53 protein. On day 87, p53 R175H-positive tumor cells were injected into the mice.

Figure 74A:
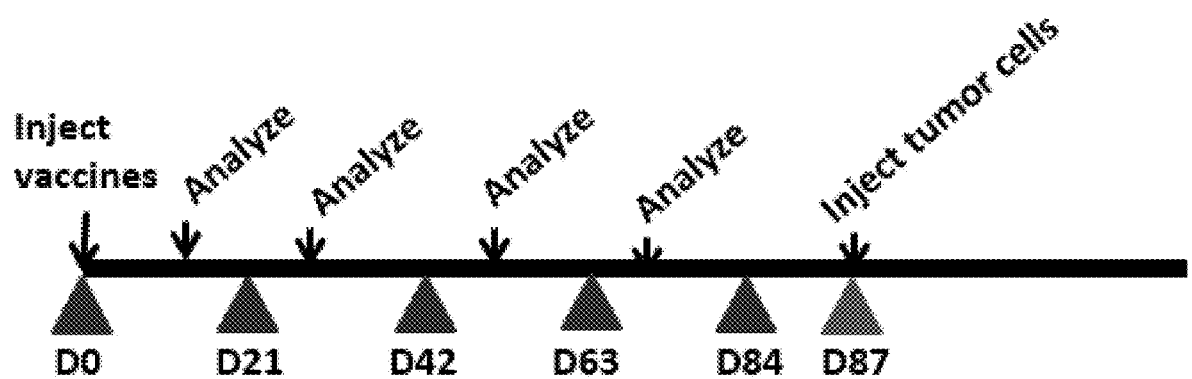
Figure 74B:
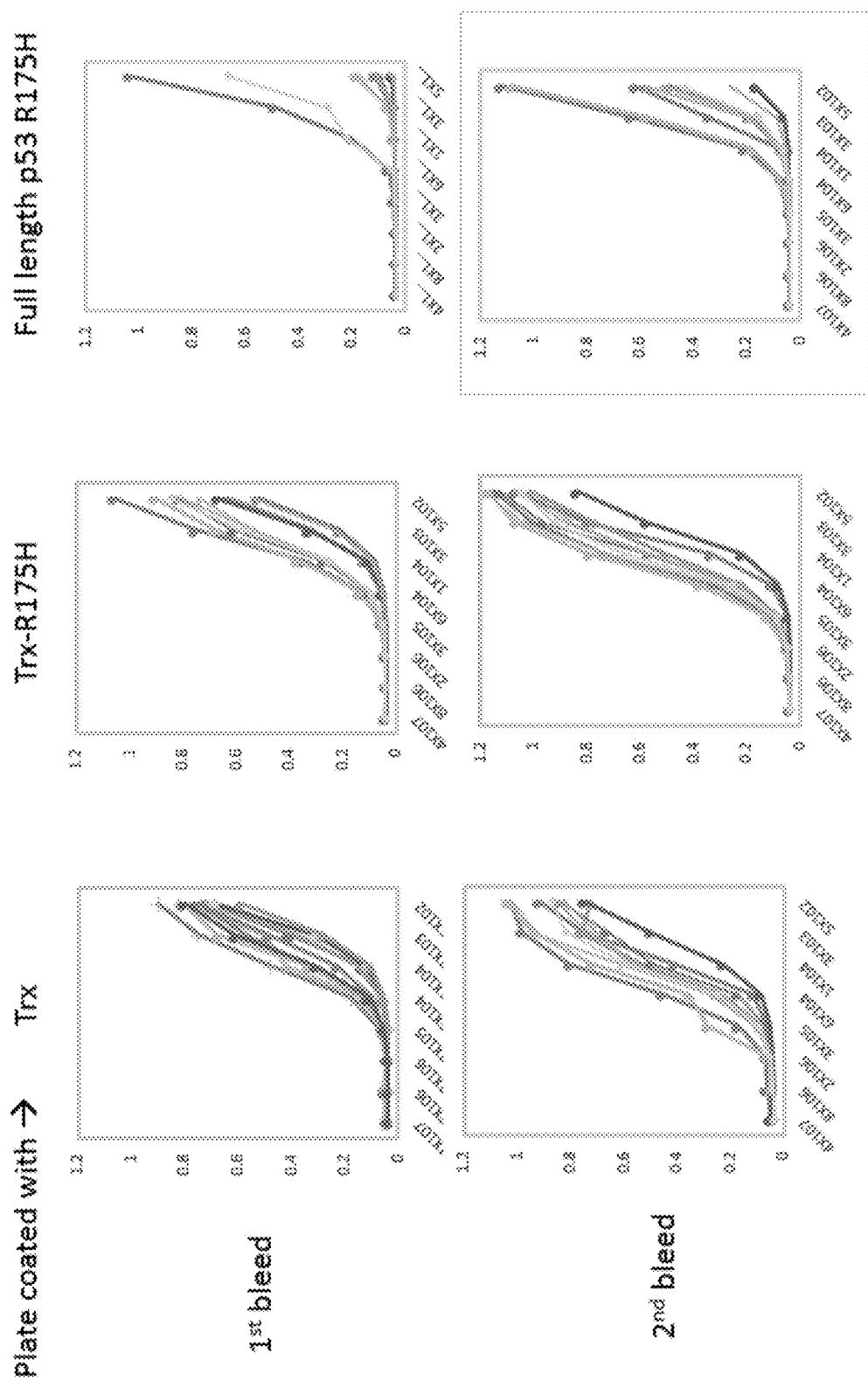

A schematic representation of the experimental procedures is shown in FIG. 74A. The results of the ELISA analysis are shown in FIG. 74B, and show that serum obtained at the indicated time points (after the first and second immunizations) reacted with TrxR175H protein and the full-length R175H mutant p53 protein.

Figure 74D:
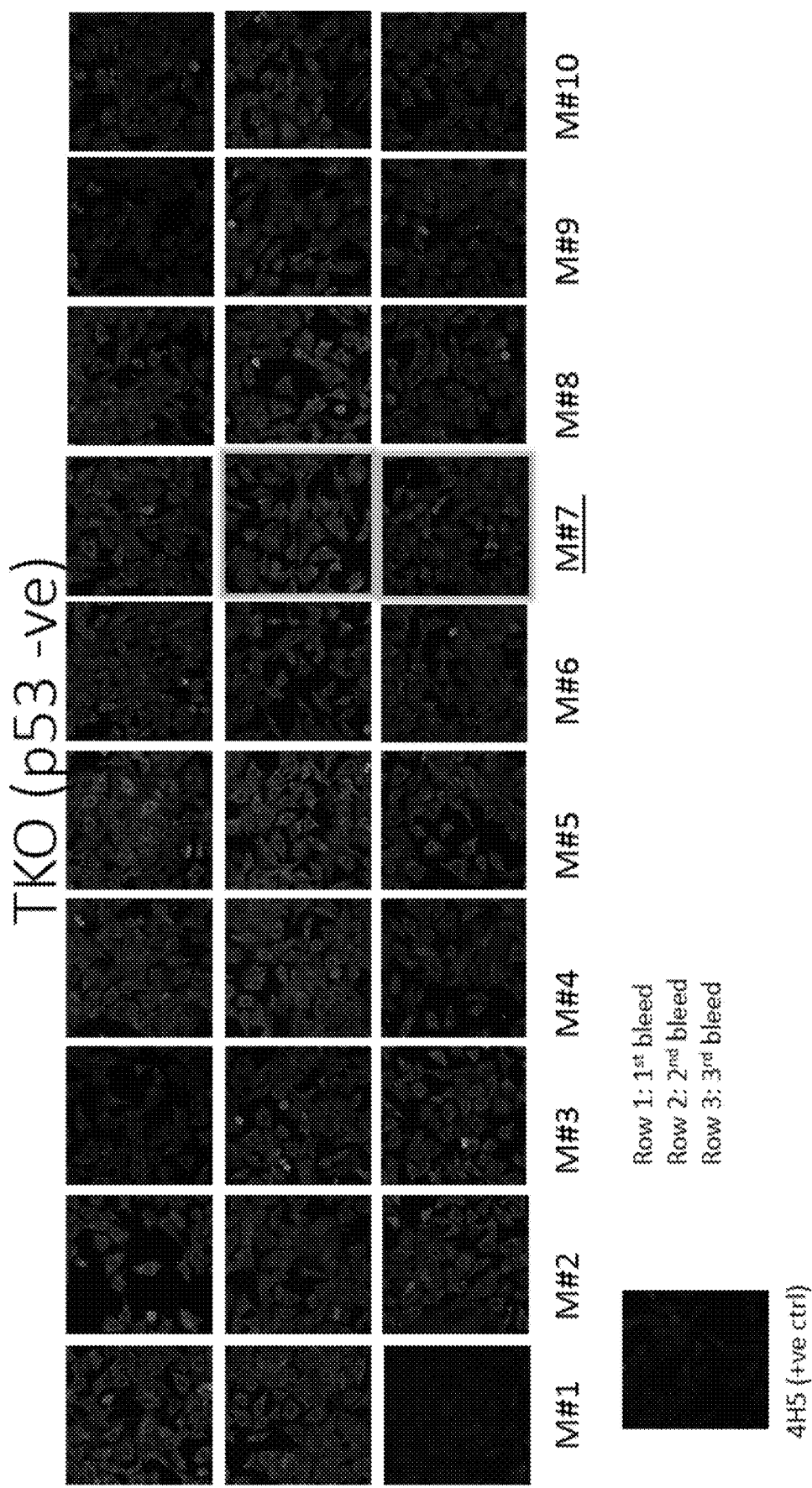

FIGS. 74C and 74D show the results of staining of SKBR3 cells (which harbour the R175H mutation) and TKO cells (p53 null) with serum obtained from the first and second bleeds from 10 different mice (M #1-M #10). Antibody in the serum of TrxR175H immunized mice showed positive staining on p53R175H expressing SKBR3 cells but not the p53 knock out TKO cells.

Figure 74E:
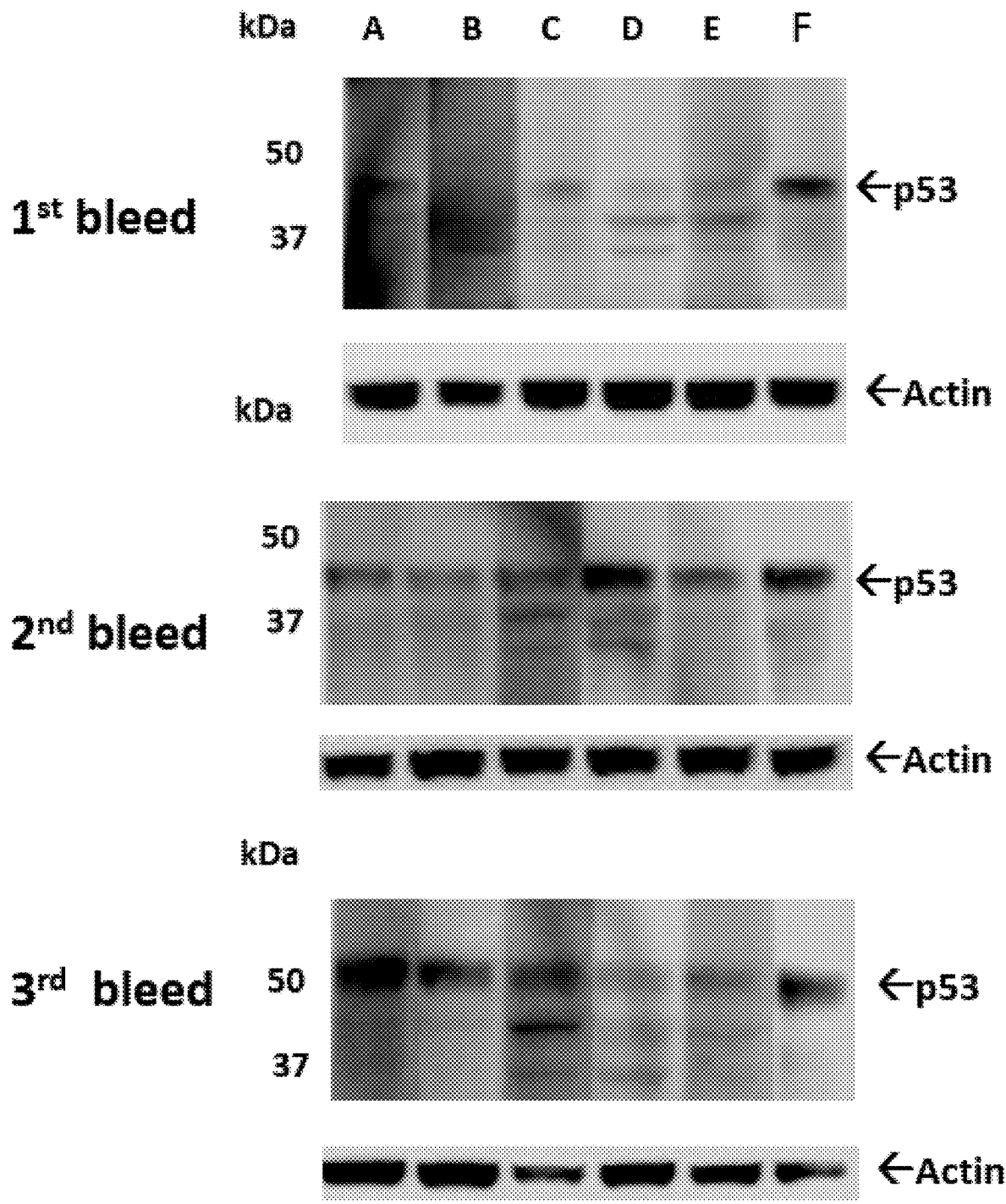

FIG. 74E shows the results of western blot analysis of reactivity of anti-p53R175H antibodies in the serum of mice immunised with TrxR175H against cell lysates from SKBR3 cells. Serum was used at a 1:1000 dilution. Lanes A-E contain serum from five different mice, and lane F is a positive control containing antibody DO1. The results show that after the second injection all of the mice analysed contained antibody specific for full-length R175H mutant p53 protein.

Figure 74F:
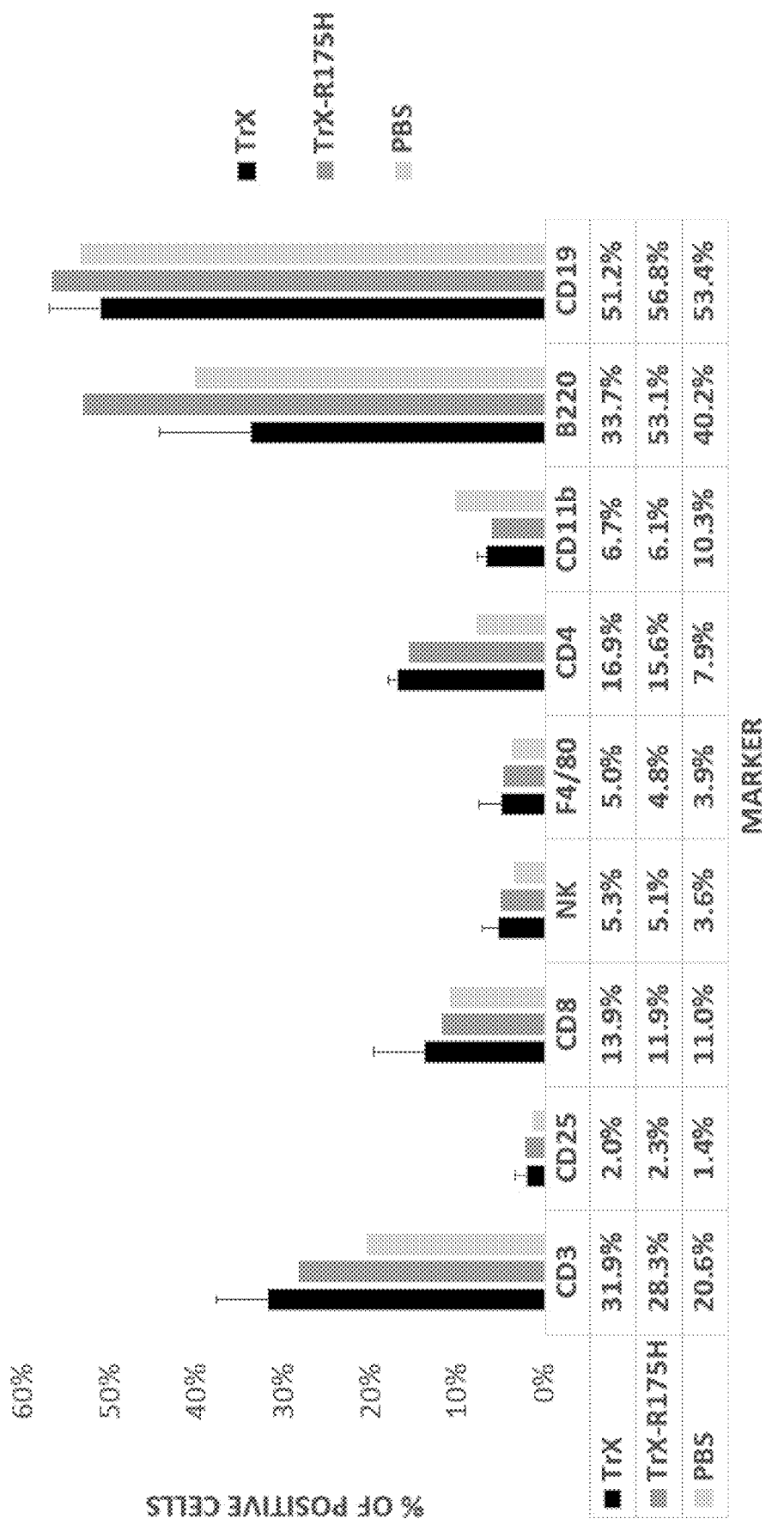

FIG. 74F shows the results of the analysis of the levels of cells of different immune cell subsets following immunisation with Trx, TrxR175H or PBS. 3 days after the 5th injection mice were sacrificed and splenocytes were analysed by flow cytometry. The percentage of T cells was found to be increased by immunisation with TrxR175H or Trx as compared to PBS in $p53^{R172H/R172H}$ mutant mice.

Taken together, the ELISA, cell staining, western blot and flow cytometry data demonstrate that TrxR175H can effectively elicit both T cell and B cell responses to mutant R175H p53.

SEQUENCE LISTING

```
Sequence total quantity: 258
SEQ ID NO: 1              moltype = AA   length = 393
FEATURE                   Location/Qualifiers
source                    1..393
                          mol_type = protein
                          organism = Homo sapiens
SEQUENCE: 1
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT EVVRRCPHHE  180
RCSDSDGLAP PQHLIRVEGN LRVEYLDDRN TFRHSVVVPY EPPEVGSDCT TIHYNYMCNS  240
SCMGGMNRRP ILTIITLEDS SGNLLGRNSF EVRVCACPGR DRRTEEENLR KKGEPHHELP  300
PGSTKRALPN NTSSSPQPKK KPLDGEYFTL QIRGRERFEM FRELNEALEL KDAQAGKEPG  360
GSRAHSSHLK SKKGQSTSRH KKLMFKTEGP DSD                              393

SEQ ID NO: 2              moltype = AA   length = 206
FEATURE                   Location/Qualifiers
source                    1..206
                          mol_type = protein
                          organism = Homo sapiens
SEQUENCE: 2
KTYQGSYGFR LGFLHSGTAK SVTCTYSPAL NKMFCQLAKT CPVQLWVDST PPPGTRVRAM   60
AIYKQSQHMT EVVRRCPHHE RCSDSDGLAP PQHLIRVEGN LRVEYLDDRN TFRHSVVVPY  120
EPPEVGSDCT TIHYNYMCNS SCMGGMNRRP ILTIITLEDS SGNLLGRNSF EVRVCACPGR  180
DRRTEEENLR KKGEPHHELP PGSTKR                                      206

SEQ ID NO: 3              moltype = AA   length = 393
FEATURE                   Location/Qualifiers
REGION                    1..393
                          note = Synthetic construct: mutant p53 polypeptide
source                    1..393
                          mol_type = protein
                          organism = synthetic construct
SEQUENCE: 3
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT EVVRHCPHHE  180
RCSDSDGLAP PQHLIRVEGN LRVEYLDDRN TFRHSVVVPY EPPEVGSDCT TIHYNYMCNS  240
SCMGGMNRRP ILTIITLEDS SGNLLGRNSF EVRVCACPGR DRRTEEENLR KKGEPHHELP  300
PGSTKRALPN NTSSSPQPKK KPLDGEYFTL QIRGRERFEM FRELNEALEL KDAQAGKEPG  360
GSRAHSSHLK SKKGQSTSRH KKLMFKTEGP DSD                              393

SEQ ID NO: 4              moltype = AA   length = 393
FEATURE                   Location/Qualifiers
REGION                    1..393
                          note = Synthetic construct: mutant p53 polypeptide
source                    1..393
                          mol_type = protein
                          organism = synthetic construct
SEQUENCE: 4
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT EVVRRCPHHE  180
RCSDSDGLAP PQHLIRVEGN LRVEYLDDRN TFRHSVVVPY EPPEVGSDCT TIHYNYMCNS  240
SCMGGMNQRP ILTIITLEDS SGNLLGRNSF EVRVCACPGR DRRTEEENLR KKGEPHHELP  300
PGSTKRALPN NTSSSPQPKK KPLDGEYFTL QIRGRERFEM FRELNEALEL KDAQAGKEPG  360
GSRAHSSHLK SKKGQSTSRH KKLMFKTEGP DSD                              393

SEQ ID NO: 5              moltype = AA   length = 393
FEATURE                   Location/Qualifiers
REGION                    1..393
                          note = Synthetic construct: mutant p53 polypeptide
source                    1..393
                          mol_type = protein
                          organism = synthetic construct
SEQUENCE: 5
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT EVVRRCPHHE  180
RCSDSDGLAP PQHLIRVEGN LRVEYLDDRN TFRHSVVVPY EPPEVGSDCT TIHYNYMCNS  240
SCMGGMNRRP ILTIITLEDS SGNLLGRNSF EVHVCACPGR DRRTEEENLR KKGEPHHELP  300
PGSTKRALPN NTSSSPQPKK KPLDGEYFTL QIRGRERFEM FRELNEALEL KDAQAGKEPG  360
GSRAHSSHLK SKKGQSTSRH KKLMFKTEGP DSD                              393

SEQ ID NO: 6              moltype = AA   length = 393
FEATURE                   Location/Qualifiers
REGION                    1..393
                          note = Synthetic construct: mutant p53 polypeptide
```

```
source                  1..393
                        mol_type = protein
                        organism = synthetic construct
SEQUENCE: 6
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRCPHHE   180
RCSDSDGLAP PQHLIRVEGN LRVEYLDDRN TFRHSVVVPY EPPEVGSDCT TIHYNYMCNS   240
SCMGGMNWRP ILTIITLEDS SGNLLGRNSF EVRVCACPGR DRRTEEENLR KKGEPHHELP   300
PGSTKRALPN NTSSSPQPKK KPLDGEYFTL QIRGRERFEM FRELNEALEL KDAQAGKEPG   360
GSRAHSSHLK SKKGQSTSRH KKLMFKTEGP DSD                                393

SEQ ID NO: 7            moltype = AA   length = 393
FEATURE                 Location/Qualifiers
REGION                  1..393
                        note = Synthetic construct: mutant p53 polypeptide
source                  1..393
                        mol_type = protein
                        organism = synthetic construct
SEQUENCE: 7
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRCPHHE   180
RCSDSDGLAP PQHLIRVEGN LRVEYLDDRN TFRHSVVVPY EPPEVGSDCT TIHYNYMCNS   240
SCMGSMNRRP ILTIITLEDS SGNLLGRNSF EVRVCACPGR DRRTEEENLR KKGEPHHELP   300
PGSTKRALPN NTSSSPQPKK KPLDGEYFTL QIRGRERFEM FRELNEALEL KDAQAGKEPG   360
GSRAHSSHLK SKKGQSTSRH KKLMFKTEGP DSD                                393

SEQ ID NO: 8            moltype = AA   length = 393
FEATURE                 Location/Qualifiers
REGION                  1..393
                        note = Synthetic construct: mutant p53 polypeptide
source                  1..393
                        mol_type = protein
                        organism = synthetic construct
SEQUENCE: 8
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRCPHHE   180
RCSDSDGLAP PQHLIRVEGN LRVEYLDDRN TFRHSVVVPY EPPEVGSDCT TIHYNYMCNS   240
SCMGGMNRRP ILTIITLEDS SGNLLGRNSF EVCVCACPGR DRRTEEENLR KKGEPHHELP   300
PGSTKRALPN NTSSSPQPKK KPLDGEYFTL QIRGRERFEM FRELNEALEL KDAQAGKEPG   360
GSRAHSSHLK SKKGQSTSRH KKLMFKTEGP DSD                                393

SEQ ID NO: 9            moltype = AA   length = 393
FEATURE                 Location/Qualifiers
REGION                  1..393
                        note = Synthetic construct: mutant p53 polypeptide
source                  1..393
                        mol_type = protein
                        organism = synthetic construct
SEQUENCE: 9
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRCPHHE   180
RCSDSDGLAP PQHLIRVEGN LRVEYLDDRN TFRHSVVVPY EPPEVGSDCT TIHYNYMCNS   240
SCMGGMNRRP ILTIITLEDS SGNLLGRNSF EVRVCACPGR DWRTEEENLR KKGEPHHELP   300
PGSTKRALPN NTSSSPQPKK KPLDGEYFTL QIRGRERFEM FRELNEALEL KDAQAGKEPG   360
GSRAHSSHLK SKKGQSTSRH KKLMFKTEGP DSD                                393

SEQ ID NO: 10           moltype = AA   length = 393
FEATURE                 Location/Qualifiers
REGION                  1..393
                        note = Synthetic construct: mutant p53 polypeptide
source                  1..393
                        mol_type = protein
                        organism = synthetic construct
SEQUENCE: 10
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRCPHHE   180
RCSDSDGLAP PQHLIRVEGN LRVEYLDDRN TFRHSVVVPY EPPEVGSDCT TIHYNYMCNS   240
SCMGGMNRSP ILTIITLEDS SGNLLGRNSF EVRVCACPGR DRRTEEENLR KKGEPHHELP   300
PGSTKRALPN NTSSSPQPKK KPLDGEYFTL QIRGRERFEM FRELNEALEL KDAQAGKEPG   360
GSRAHSSHLK SKKGQSTSRH KKLMFKTEGP DSD                                393
```

```
SEQ ID NO: 11            moltype = AA  length = 393
FEATURE                  Location/Qualifiers
REGION                   1..393
                         note = Synthetic construct: mutant p53 polypeptide
source                   1..393
                         mol_type = protein
                         organism = synthetic construct
SEQUENCE: 11
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRCPHHE   180
RCSDSDGLAP PQHLIRVEGN LRVEYLDDRN TFRHSVVVPY EPPEVGSDCT TIHYNYMCNS   240
SCMGDMNRRP ILTIITLEDS SGNLLGRNSF EVRVCACPGR DRRTEEENLR KKGEPHHELP   300
PGSTKRALPN NTSSSPQPKK KPLDGEYFTL QIRGRERFEM FRELNEALEL KDAQAGKEPG   360
GSRAHSSHLK SKKGQSTSRH KKLMFKTEGP DSD                                393

SEQ ID NO: 12            moltype = AA  length = 393
FEATURE                  Location/Qualifiers
REGION                   1..393
                         note = Synthetic construct: mutant p53 polypeptide
source                   1..393
                         mol_type = protein
                         organism = synthetic construct
SEQUENCE: 12
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRFPHHE   180
RCSDSDGLAP PQHLIRVEGN LRVEYLDDRN TFRHSVVVPY EPPEVGSDCT TIHYNYMCNS   240
SCMGGMNRRP ILTIITLEDS SGNLLGRNSF EVRVCACPGR DRRTEEENLR KKGEPHHELP   300
PGSTKRALPN NTSSSPQPKK KPLDGEYFTL QIRGRERFEM FRELNEALEL KDAQAGKEPG   360
GSRAHSSHLK SKKGQSTSRH KKLMFKTEGP DSD                                393

SEQ ID NO: 13            moltype = AA  length = 393
FEATURE                  Location/Qualifiers
REGION                   1..393
                         note = Synthetic construct: mutant p53 polypeptide
source                   1..393
                         mol_type = protein
                         organism = synthetic construct
SEQUENCE: 13
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRCPHYE   180
RCSDSDGLAP PQHLIRVEGN LRVEYLDDRN TFRHSVVVPY EPPEVGSDCT TIHYNYMCNS   240
SCMGGMNRRP ILTIITLEDS SGNLLGRNSF EVRVCACPGR DRRTEEENLR KKGEPHHELP   300
PGSTKRALPN NTSSSPQPKK KPLDGEYFTL QIRGRERFEM FRELNEALEL KDAQAGKEPG   360
GSRAHSSHLK SKKGQSTSRH KKLMFKTEGP DSD                                393

SEQ ID NO: 14            moltype = AA  length = 393
FEATURE                  Location/Qualifiers
REGION                   1..393
                         note = Synthetic construct: mutant p53 polypeptide
source                   1..393
                         mol_type = protein
                         organism = synthetic construct
SEQUENCE: 14
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRCPHRE   180
RCSDSDGLAP PQHLIRVEGN LRVEYLDDRN TFRHSVVVPY EPPEVGSDCT TIHYNYMCNS   240
SCMGGMNRRP ILTIITLEDS SGNLLGRNSF EVRVCACPGR DRRTEEENLR KKGEPHHELP   300
PGSTKRALPN NTSSSPQPKK KPLDGEYFTL QIRGRERFEM FRELNEALEL KDAQAGKEPG   360
GSRAHSSHLK SKKGQSTSRH KKLMFKTEGP DSD                                393

SEQ ID NO: 15            moltype = AA  length = 393
FEATURE                  Location/Qualifiers
REGION                   1..393
                         note = Synthetic construct: mutant p53 polypeptide
source                   1..393
                         mol_type = protein
                         organism = synthetic construct
SEQUENCE: 15
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRCPHHE   180
RCSDSDGLAP PQHLIRVEGN LRVEYLDDRN TFRHSVVVPC EPPEVGSDCT TIHYNYMCNS   240
SCMGGMNRRP ILTIITLEDS SGNLLGRNSF EVRVCACPGR DRRTEEENLR KKGEPHHELP   300
```

```
PGSTKRALPN NTSSSPQPKK KPLDGEYFTL QIRGRERFEM FRELNEALEL KDAQAGKEPG   360
GSRAHSSHLK SKKGQSTSRH KKLMFKTEGP DSD                                393

SEQ ID NO: 16           moltype = AA  length = 393
FEATURE                 Location/Qualifiers
REGION                  1..393
                        note = Synthetic construct: mutant p53 polypeptide
source                  1..393
                        mol_type = protein
                        organism = synthetic construct
SEQUENCE: 16
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT EVVRRCPHHE  180
RCSDSDGLAP PQHLIRVEGN LRVEYLDDRN TFRHSVVVPY EPPEVGSDCT TIHYNYMCNS  240
SCMGGMNRRP ILTIITLEDS SGNLLGRNSF EVRVCACPGR DRRTEEENLR KKGEPHHELP  300
PGSTKRALPN NTSSSPQPKK KPLDGEYFTL QIRGREHFEM FRELNEALEL KDAQAGKEPG  360
GSRAHSSHLK SKKGQSTSRH KKLMFKTEGP DSD                               393

SEQ ID NO: 17           moltype = AA  length = 109
FEATURE                 Location/Qualifiers
source                  1..109
                        mol_type = protein
                        organism = Escherichia coli
SEQUENCE: 17
MSDKIIHLTD DSFDTDVLKA DGAILVDFWA EWCGPCKMIA PILDEIADEY QGKLTVAKLN   60
IDQNPGTAPK YGIRGIPTLL LFKNGEVAAT KVGALSKGQL KEFLDANLA              109

SEQ ID NO: 18           moltype = AA  length = 113
FEATURE                 Location/Qualifiers
REGION                  1..113
                        note = Synthetic construct: Light chain variable domain
                         sequence for Anti-R175H clone 4H5
source                  1..113
                        mol_type = protein
                        organism = synthetic construct
SEQUENCE: 18
DIVLTQSTSS LSVSAGERVT LSCKSSQSLL NSGNQKSYLA WYQQKPGQPP KLLIYGASTR   60
ESGVPDRFTG SGSETDFTLT ISSVQPEDLA VYYCQNDHSY PLTFGAGTKL ELK         113

SEQ ID NO: 19           moltype = AA  length = 12
FEATURE                 Location/Qualifiers
REGION                  1..12
                        note = Synthetic: Anti-R175H clone 4H5 LC-CDR1
source                  1..12
                        mol_type = protein
                        organism = synthetic construct
SEQUENCE: 19
QSLLNSGNQK SY                                                       12

SEQ ID NO: 20           moltype =   length =
SEQUENCE: 20
000

SEQ ID NO: 21           moltype = AA  length = 9
FEATURE                 Location/Qualifiers
REGION                  1..9
                        note = Synthetic: Anti-R175H clones 4H5, 7B9, and 10C8
                         LC-CDR3
source                  1..9
                        mol_type = protein
                        organism = synthetic construct
SEQUENCE: 21
QNDHSYPLT                                                            9

SEQ ID NO: 22           moltype = AA  length = 113
FEATURE                 Location/Qualifiers
REGION                  1..113
                        note = Synthetic construct: Light chain variable domain
                         sequence for Anti-R175H clones 7B9 and 10C8
source                  1..113
                        mol_type = protein
                        organism = synthetic construct
SEQUENCE: 22
DIVMTQSPSS LSVSGGEKVT MSCKSSQSLL NSGNQKSNLA WYQQKPGQPP KLLIYGASTR   60
ESGVPDRFAG SGSGTDFTLT ISSVQAEDLA VYYCQNDHSY PLTFGGGTKL ELK         113

SEQ ID NO: 23           moltype = AA  length = 12
FEATURE                 Location/Qualifiers
```

```
REGION                    1..12
                          note = Synthetic: Anti-R175H clones 7B9 and 10C8 LC-CDR1
source                    1..12
                          mol_type = protein
                          organism = synthetic construct
SEQUENCE: 23
QSLLNSGNQK SN                                                                    12

SEQ ID NO: 24             moltype = AA  length = 115
FEATURE                   Location/Qualifiers
REGION                    1..115
                          note = Synthetic construct: Heavy chain variable domain
                           sequence for Anti-R175H clone 4H5
source                    1..115
                          mol_type = protein
                          organism = synthetic construct
SEQUENCE: 24
EVQLQQSGPE LVKPGASVKI SCKTSGFTFT EYTMHWMKQS HGRSLEWIGR IDPNNGVTVY    60
NQKFKVKATL TVDRSSSTAY LELRSLTSED SAVYYCARWG GDYVTGGGTT LTVSS        115

SEQ ID NO: 25             moltype = AA  length = 8
FEATURE                   Location/Qualifiers
REGION                    1..8
                          note = Synthetic: Anti-R175H clone 4H5 HC-CDR1
source                    1..8
                          mol_type = protein
                          organism = synthetic construct
SEQUENCE: 25
GFTFTEYT                                                                          8

SEQ ID NO: 26             moltype = AA  length = 8
FEATURE                   Location/Qualifiers
REGION                    1..8
                          note = Synthetic: Anti-R175H clone 4H5 HC-CDR2
source                    1..8
                          mol_type = protein
                          organism = synthetic construct
SEQUENCE: 26
IDPNNGVT                                                                          8

SEQ ID NO: 27             moltype = AA  length = 8
FEATURE                   Location/Qualifiers
REGION                    1..8
                          note = Synthetic: Anti-R175H clones 4H5, 7B9, & 10C8 HC-CDR3
source                    1..8
                          mol_type = protein
                          organism = synthetic construct
SEQUENCE: 27
ARWGGDYV                                                                          8

SEQ ID NO: 28             moltype = AA  length = 115
FEATURE                   Location/Qualifiers
REGION                    1..115
                          note = Synthetic construct: Heavy chain variable domain
                           sequence for Anti-R175H clones 7B9 and 10C8
source                    1..115
                          mol_type = protein
                          organism = synthetic construct
SEQUENCE: 28
EVQLQQSGPE LVKPGASVKI SCKTSGYTFT EYTMHWMKQS HGKSLEWIGR INPYSGGTVY    60
NQKFKGKATL TVDKSSSTAY MELRSLTSDD SAVYYCARWG GDYVTGGGTT LTVSS        115

SEQ ID NO: 29             moltype = AA  length = 8
FEATURE                   Location/Qualifiers
REGION                    1..8
                          note = Synthetic: Anti-R175H clones 7B9 & 10C8 HC-CDR1
source                    1..8
                          mol_type = protein
                          organism = synthetic construct
SEQUENCE: 29
GYTFTEYT                                                                          8

SEQ ID NO: 30             moltype = AA  length = 8
FEATURE                   Location/Qualifiers
REGION                    1..8
                          note = Synthetic: Anti-R175H clones 7B9 & 10C8 HC-CDR2
source                    1..8
                          mol_type = protein
                          organism = synthetic construct
```

```
SEQUENCE: 30
INPYSGGT                                                                    8

SEQ ID NO: 31           moltype = AA  length = 12
FEATURE                 Location/Qualifiers
REGION                  1..12
                        note = Synthetic: Anti R175H Light chain CDR 1 consensus
VARIANT                 12
                        note = Xaa = Tyr or Asn
source                  1..12
                        mol_type = protein
                        organism = synthetic construct
SEQUENCE: 31
QSLLNSGNQK SX                                                              12

SEQ ID NO: 32           moltype = AA  length = 8
FEATURE                 Location/Qualifiers
REGION                  1..8
                        note = Synthetic: Anti R175H Heavy chain CDR 1 consensus
VARIANT                 2
                        note = Xaa = Phe or Tyr
source                  1..8
                        mol_type = protein
                        organism = synthetic construct
SEQUENCE: 32
GXTFTEYT                                                                    8

SEQ ID NO: 33           moltype = AA  length = 8
FEATURE                 Location/Qualifiers
REGION                  1..8
                        note = Synthetic: Anti R175H Heavy chain CDR 2 consensus
VARIANT                 2
                        note = Xaa = Asp or Asn
VARIANT                 4
                        note = Xaa = Asn or Tyr
VARIANT                 5
                        note = Xaa = Asn or Ser
VARIANT                 7
                        note = Xaa = Val or Gly
source                  1..8
                        mol_type = protein
                        organism = synthetic construct
SEQUENCE: 33
IXPXXGXT                                                                    8

SEQ ID NO: 34           moltype = DNA  length = 339
FEATURE                 Location/Qualifiers
misc_feature            1..339
                        note = Synthetic nucleotide sequence encoding SEQ ID NO: 18
source                  1..339
                        mol_type = other DNA
                        organism = synthetic construct
SEQUENCE: 34
gatattgtgc tcacccaatc tacatcctcc ctgagtgtgt cagctggaga gagggtcact            60
ttgagctgca agtccagtca gagtctgtta aacagtggaa atcaaaagag ttacttggcc          120
tggtaccagc agaaaccagg gcagcctcct aaactgttga tctacggggc atccactagg          180
gaatctgggg tccctgatcg cttcacaggc agtggatctg aaaccgattt cactcttacc          240
atcagcagtg tgcagcctga agacctggca gtttattatt gtcagaatga tcatagttat          300
ccgctcacgt tcggtgctgg gaccaagctg gagctgaaa                                 339

SEQ ID NO: 35           moltype = DNA  length = 339
FEATURE                 Location/Qualifiers
misc_feature            1..339
                        note = Synthetic nucleotide sequence encoding SEQ ID NO: 22
source                  1..339
                        mol_type = other DNA
                        organism = synthetic construct
SEQUENCE: 35
gatattgtga tgacccagtc tccatcctcc ctgagtgtgt caggaggaga gaaggtcact            60
atgagctgca agtccagtca gagtctgtta aacagtggaa atcaaaagag caacttggcc          120
tggtaccagc agaaaccagg gcagcctcct aaattgttga tctatggggc atccactagg          180
gaatctgggg tccctgatcg cttcgcaggc agtggatctg gaaccgattt cactcttacc          240
atcagcagtg tgcagctga agacctggca gtttattact gtcaaaatga tcatagttat           300
ccgctcacgt tcggtggtgg gaccaagctg gagctgaaa                                 339

SEQ ID NO: 36           moltype = DNA  length = 339
FEATURE                 Location/Qualifiers
misc_feature            1..339
                        note = Synthetic nucleotide sequence encoding SEQ ID NO: 22
```

```
source                  1..339
                        mol_type = other DNA
                        organism = synthetic construct
SEQUENCE: 36
gatattgtga tgacccagtc tccatcctcc ctgagtgtgt caggaggaga gaaggtcact    60
atgagctgca agtccagtca gagtctgtta aacagtggaa atcaaaagag caacttggcc   120
tggtaccagc agaaaccagg gcagcctcct aaattgttga tctatggggc atccactagg   180
gaatctgggg tccctgatcg cttcgcaggc agtggatctg gaaccgattt cactcttacc   240
atcagcagtg tgcaggctga agacctggca gtttattact gtcaaaatga tcatagttat   300
ccgctcacgt tcggtggtgg gaccaagctg gagctgaaa                          339

SEQ ID NO: 37           moltype = DNA   length = 345
FEATURE                 Location/Qualifiers
misc_feature            1..345
                        note = Synthetic nucleotide sequence encoding SEQ ID NO: 24
source                  1..345
                        mol_type = other DNA
                        organism = synthetic construct
SEQUENCE: 37
gaggttcagc tgcagcagtc tggacctgaa ctggtgaagc ctggggcttc agtgaagata    60
tcttgcaaga cttccggatt cacattcact gaatacacca tgcactggat gaaacagagc   120
catggaagga gccttgagtg gatcggacgt attgatccta caaatggtgt tactgtttat   180
aaccagaagt tcaaggtcaa ggccacattg actgtggaca ggtcctccag cacagcctat   240
ctggagctcc gcagtctgac gtctgaggac tctgcagtct attactgtgc aagatggggt   300
ggtgactacg tcacgggggg aggcaccact ctcacagtct cctca                   345

SEQ ID NO: 38           moltype = DNA   length = 345
FEATURE                 Location/Qualifiers
misc_feature            1..345
                        note = Synthetic nucleotide sequence encoding SEQ ID NO: 28
source                  1..345
                        mol_type = other DNA
                        organism = synthetic construct
SEQUENCE: 38
gaggtccagc tgcagcagtc tggacctgag ctggtgaagc ctggggcttc agtgaagata    60
tcctgcaaga cttctggcta cactttcact gaatacacca tgcactggat gaagcagagc   120
catggaaaga gccttgagtg gattggacgt attaatcctt atagtggtgg tactgtctac   180
aaccagaagt tcaagggcaa ggccacattg actgtggaca gtcctccag cacagcctat    240
atggagctcc gcagcctgac atctgatgat tctgcagtct attactgtgc aagatggggt   300
ggtgactacg tcacgggggg aggcaccact ctcacagtct cctca                   345

SEQ ID NO: 39           moltype = DNA   length = 345
FEATURE                 Location/Qualifiers
misc_feature            1..345
                        note = Synthetic nucleotide sequence encoding SEQ ID NO: 28
source                  1..345
                        mol_type = other DNA
                        organism = synthetic construct
SEQUENCE: 39
gaggtgcagc ttcagcagtc gggacctgag ctggtgaagc ctggggcttc agtgaagata    60
tcctgcaaga cttctggcta cactttcact gaatacacca tgcactggat gaagcagagc   120
catggaaaga gccttgagtg gattggacgt attaatcctt atagtggtgg tactgtctac   180
aaccagaagt tcaagggcaa ggccacattg actgtggaca gtcctccag cacagcctat    240
atggagctcc gcagcctgac atctgatgat tctgcagtct attactgtgc aagatggggt   300
ggtgactacg tcacgggggg aggcaccact ctcacagtct cctca                   345

SEQ ID NO: 40           moltype = AA   length = 112
FEATURE                 Location/Qualifiers
REGION                  1..112
                        note = Synthetic construct: Light chain variable domain
                         sequence for Anti-R248Q clone 3G11
source                  1..112
                        mol_type = protein
                        organism = synthetic construct
SEQUENCE: 40
DIVLTQTPLT LSVTIGQPAS ISCKSNQSLL YSDGKTYLNW LLQRPGQSPK RLIYLVSKLD    60
SGVPDRFTGS GSGTDFTLKI SRVEAEDLGL YYCWQGTHFP LTFGAGTKLE LK           112

SEQ ID NO: 41           moltype = AA   length = 11
FEATURE                 Location/Qualifiers
REGION                  1..11
                        note = Synthetic: Anti-R248Q clones 3G11 & 4H2 LC-CDR1
source                  1..11
                        mol_type = protein
                        organism = synthetic construct
SEQUENCE: 41
QSLLYSDGKT Y                                                         11

SEQ ID NO: 42           moltype =     length =
```

```
SEQUENCE: 42
000

SEQ ID NO: 43           moltype = AA  length = 9
FEATURE                 Location/Qualifiers
REGION                  1..9
                        note = Synthetic: Anti-R248Q clones 3G11 & 4H2 LC-CDR3
source                  1..9
                        mol_type = protein
                        organism = synthetic construct
SEQUENCE: 43
WQGTHFPLT                                                                9

SEQ ID NO: 44           moltype = AA  length = 112
FEATURE                 Location/Qualifiers
REGION                  1..112
                        note = Synthetic construct: Light chain variable domain
                         sequence for Anti-R248Q clone 4H2
source                  1..112
                        mol_type = protein
                        organism = synthetic construct
SEQUENCE: 44
DIVITQSPLT LSVTIGQPAS ISCKSDQSLL YSDGKTYLNW LLQRPGQSPK RLIYLVSELD    60
SGVPDRFTGS GSGTDFTLKI SRVEAEDLGL YYCWQGTHFP LTFGAGTKLE LK          112

SEQ ID NO: 45           moltype = AA  length = 116
FEATURE                 Location/Qualifiers
REGION                  1..116
                        note = Synthetic construct: Heavy chain variable domain
                         sequence for Anti-R248Q clone 3G11
source                  1..116
                        mol_type = protein
                        organism = synthetic construct
SEQUENCE: 45
DVQLQQSGPE LVKPGASVKM SCKASGYTFT DYYVKWVKQS PGQSLEWIGD IHPKNGGTNY    60
NQKFKGKAAL TVDKSSSTAY MQLNSLTSED SAVYFCAKMG GYDDYWGQGT TLTVSS      116

SEQ ID NO: 46           moltype = AA  length = 8
FEATURE                 Location/Qualifiers
REGION                  1..8
                        note = Synthetic: Anti-R248Q clones 3G11 & 4H2 HC-CDR1
source                  1..8
                        mol_type = protein
                        organism = synthetic construct
SEQUENCE: 46
GYTFTDYY                                                                 8

SEQ ID NO: 47           moltype = AA  length = 8
FEATURE                 Location/Qualifiers
REGION                  1..8
                        note = Synthetic: Anti-R248Q clone 3G11 HC-CDR2
source                  1..8
                        mol_type = protein
                        organism = synthetic construct
SEQUENCE: 47
IHPKNGGT                                                                 8

SEQ ID NO: 48           moltype = AA  length = 9
FEATURE                 Location/Qualifiers
REGION                  1..9
                        note = Synthetic: Anti-R248Q clone 3G11 HC-CDR3
source                  1..9
                        mol_type = protein
                        organism = synthetic construct
SEQUENCE: 48
AKMGGYDDY                                                                9

SEQ ID NO: 49           moltype = AA  length = 116
FEATURE                 Location/Qualifiers
REGION                  1..116
                        note = Synthetic construct: Heavy chain variable domain
                         sequence for Anti-R248Q clone 4H2
source                  1..116
                        mol_type = protein
                        organism = synthetic construct
SEQUENCE: 49
QVQLKQSGPE LVKPGASVKM SCKASGYTFT DYYLKWVRQS HGKSLEWIGD IDPKNGGTNY    60
NQKFKGKATL TVDKSSSTAY MQLNSLTSED SAVYYCAKQG GFDDYWGQGT TLTVSS      116
```

```
SEQ ID NO: 50             moltype = AA   length = 8
FEATURE                   Location/Qualifiers
REGION                    1..8
                          note = Synthetic: Anti-R248Q clone 4H2 HC-CDR2
source                    1..8
                          mol_type = protein
                          organism = synthetic construct
SEQUENCE: 50
IDPKNGGT                                                                  8

SEQ ID NO: 51             moltype = AA   length = 9
FEATURE                   Location/Qualifiers
REGION                    1..9
                          note = Synthetic: Anti-R248Q clone 4H2 HC-CDR3
source                    1..9
                          mol_type = protein
                          organism = synthetic construct
SEQUENCE: 51
AKQGGFDDY                                                                 9

SEQ ID NO: 52             moltype = AA   length = 8
FEATURE                   Location/Qualifiers
REGION                    1..8
                          note = Synthetic: Anti R248Q Heavy chain CDR 2 consensus
VARIANT                   2
                          note = Xaa = His or Asp
source                    1..8
                          mol_type = protein
                          organism = synthetic construct
SEQUENCE: 52
IXPKNGGT                                                                  8

SEQ ID NO: 53             moltype = AA   length = 9
FEATURE                   Location/Qualifiers
REGION                    1..9
                          note = Synthetic: Anti R248Q Heavy chain CDR 3 consensus
VARIANT                   3
                          note = Xaa = Met or Gln
VARIANT                   6
                          note = Xaa = Tyr or Phe
source                    1..9
                          mol_type = protein
                          organism = synthetic construct
SEQUENCE: 53
AKXGGXDDY                                                                 9

SEQ ID NO: 54             moltype = DNA   length = 336
FEATURE                   Location/Qualifiers
misc_feature              1..336
                          note = Synthetic nucleotide sequence encoding SEQ ID NO: 40
source                    1..336
                          mol_type = other DNA
                          organism = synthetic construct
SEQUENCE: 54
gatattgtgc tgacacagac tccactcact ttgtcggtta ccattggaca accagcctcc   60
atctcttgca agtcaaatca gagcctctta tatagtgatg aaagacata tttgaattgg   120
ttattacaga ggccaggcca gtctccaaag cgcctaatct atctggtgtc taaactggac   180
tctgagtcc ctgacaggtt cactggcagt ggatcaggga cagatttcac actgaaaatc   240
agcagagtgg aggctgagga tttgggactt tattattgct ggcaaggtac acatttcct   300
ctcacgttcg gtgctgggac caagctggag ctgaaa                              336

SEQ ID NO: 55             moltype = DNA   length = 336
FEATURE                   Location/Qualifiers
misc_feature              1..336
                          note = Synthetic nucleotide sequence encoding SEQ ID NO: 44
source                    1..336
                          mol_type = other DNA
                          organism = synthetic construct
SEQUENCE: 55
gacattgtga tcacacagtc tccactcact ttgtcggtta ccattggaca accagcctcc   60
atctcttgca agtcagatca gagcctctta tatagtgatg aaagacata tttgaattgg   120
ctattacaga ggccaggcca gtctccaaag cgcctaatct atctggtgtc tgaactggac   180
tctgagtcc ctgacaggtt cactggcagt ggatcaggga cagatttcac actgaaaatc   240
agcagagtgg aggctgagga tttgggactt tattattgct ggcaaggtac acatttcct   300
ctcacgttcg gtgctgggac caagctggag ctgaaa                              336
```

```
SEQ ID NO: 56          moltype = DNA  length = 348
FEATURE                Location/Qualifiers
misc_feature           1..348
                       note = Synthetic nucleotide sequence encoding SEQ ID NO: 45
source                 1..348
                       mol_type = other DNA
                       organism = synthetic construct
SEQUENCE: 56
gatgtgcagc ttcagcagtc aggacctgag ctggtgaagc ctggggcttc agtgaagatg    60
tcctgtaagg cttctggata cacattcact gactactatg tgaagtgggt gaagcagagt   120
cctggacaga gccttgagtg gattggagat attcatccta agaacggtgg tactaactac   180
aaccagaagt tcaagggcaa ggccgcattg actgtggaca atcctccag cacagcctac    240
atgcagctca acagcctgac atctgaggac tctgcagtct atttctgtgc aaaaatggga   300
ggctacgacg actactgggg ccaaggcacc actctcacag tctcctca              348

SEQ ID NO: 57          moltype = DNA  length = 348
FEATURE                Location/Qualifiers
misc_feature           1..348
                       note = Synthetic nucleotide sequence encoding SEQ ID NO: 49
source                 1..348
                       mol_type = other DNA
                       organism = synthetic construct
SEQUENCE: 57
caggtgcagc tgaagcagtc aggacctgag ctggtgaagc ctggggcttc agtgaagatg    60
tcctgtaagg cttctggata cacattcact gactactatg tgaagtgggt gaggcagagt   120
catggaaaga gccttgagtg gattggagat atagatccca agaatggtgg tactaattac   180
aaccagaagt ttaagggcaa ggccacattg actgtggaca atcctccag cacagcctac    240
atgcagctca acagcctgac atctgaggac tctgcagtct attactgtgc aaaacagggg   300
gggttcgacg actactgggg ccaaggcacc actctcacag tctcctca              348

SEQ ID NO: 58          moltype = AA  length = 112
FEATURE                Location/Qualifiers
REGION                 1..112
                       note = Synthetic construct: Light chain variable domain
                        sequence for Anti-R273H clone 13E4
source                 1..112
                       mol_type = protein
                       organism = synthetic construct
SEQUENCE: 58
DIVMTQSPLS LPVNLGDQVS LSCRSSQSIV HNNGDTYLEW YLQKPGQSPK LLIYKVSNRF    60
SGVPDRFSGS GSGTDFTLKI SRVEAEDLGI YYCFQGSHLP LTFGSGTKLE LK           112

SEQ ID NO: 59          moltype = AA  length = 11
FEATURE                Location/Qualifiers
REGION                 1..11
                       note = Synthetic: Anti-R273H clone 13E4 LC-CDR1
source                 1..11
                       mol_type = protein
                       organism = synthetic construct
SEQUENCE: 59
QSIVHNNGDT Y                                                         11

SEQ ID NO: 60          moltype =   length =
SEQUENCE: 60
000

SEQ ID NO: 61          moltype = AA  length = 9
FEATURE                Location/Qualifiers
REGION                 1..9
                       note = Synthetic: Anti-R273H clone 13E4 LC-CDR3
source                 1..9
                       mol_type = protein
                       organism = synthetic construct
SEQUENCE: 61
FQGSHLPLT                                                             9

SEQ ID NO: 62          moltype = AA  length = 120
FEATURE                Location/Qualifiers
REGION                 1..120
                       note = Synthetic construct: Heavy chain variable domain
                        sequence for Anti-R273H clone 13E4
source                 1..120
                       mol_type = protein
                       organism = synthetic construct
SEQUENCE: 62
EVQLLETGGD LVTPGGSLKL SCAASGFSFS DYYMYWVRQT PEKRLEWVAT ISVGGTYTFY    60
SDNVKGRFVI SRDNARKNLH LEMNSLKSED AAMYYCVRDG NDGKFLGYWG QGTFVTVTVS   120
```

```
SEQ ID NO: 63              moltype = AA   length = 8
FEATURE                    Location/Qualifiers
REGION                     1..8
                           note = Synthetic: Anti-R273H clone 13E4 HC-CDR1
source                     1..8
                           mol_type = protein
                           organism = synthetic construct
SEQUENCE: 63
GFSFSDYY                                                                 8

SEQ ID NO: 64              moltype = AA   length = 8
FEATURE                    Location/Qualifiers
REGION                     1..8
                           note = Synthetic: Anti-R273H clone 13E4 HC-CDR2
source                     1..8
                           mol_type = protein
                           organism = synthetic construct
SEQUENCE: 64
ISVGGTYT                                                                 8

SEQ ID NO: 65              moltype = AA   length = 11
FEATURE                    Location/Qualifiers
REGION                     1..11
                           note = Synthetic: Anti-R273H clone 13E4 HC-CDR3
source                     1..11
                           mol_type = protein
                           organism = synthetic construct
SEQUENCE: 65
VRDGNDGKFL G                                                            11

SEQ ID NO: 66              moltype = DNA   length = 336
FEATURE                    Location/Qualifiers
misc_feature               1..336
                           note = Synthetic nucleotide sequence encoding SEQ ID NO: 58
source                     1..336
                           mol_type = other DNA
                           organism = synthetic construct
SEQUENCE: 66
gatattgtga tgacacaatc tccactctcc ctgcctgtca atcttggaga tcaagtctcc         60
ctctcttgca gatctagtca gagcattgta cataataatg gagacaccta tttagaatgg        120
tacctacaga aaccaggcca gtctccaaag ctcctgatct acaaagtttc caaccgattt        180
tctggggtcc cagacaggtt cagtggcagt ggatcaggga cagatttcac actcaagatc        240
agcagagtgg aggctgagga tctgggaatt tattactgct ttcaaggttc acatcttccg        300
ctcacgttcg gttctgggac caagctggag ctgaaa                                  336

SEQ ID NO: 67              moltype = DNA   length = 354
FEATURE                    Location/Qualifiers
misc_feature               1..354
                           note = Synthetic nucleotide sequence encoding SEQ ID NO: 62
source                     1..354
                           mol_type = other DNA
                           organism = synthetic construct
SEQUENCE: 67
gaagtgcagc tgttggagac tggggagac ttagtgacgc tggagggtc cctgaaactc           60
tcctgtgcag cctctggatt cagcttcagt gactattata tgtattgggt tcgccagact        120
ccggaaaaga ggctggagtg ggtcgcaact attagtgttg gtggtacata caccttctat        180
tcagacaatg tgaaggggag attcgtcatc tccagagaca tgccaggaa aaatctgcat         240
ctggaaatga acagtctgaa gtctgaggac gcagccatgt attactgtgt aagagatggc        300
aacgatggaa aatttcttgg gtactggggc cagggggactt cgtcactgt cact              354

SEQ ID NO: 68              moltype = AA   length = 5
FEATURE                    Location/Qualifiers
REGION                     1..5
                           note = Synthetic epitope
source                     1..5
                           mol_type = protein
                           organism = synthetic construct
SEQUENCE: 68
HCPHH                                                                    5

SEQ ID NO: 69              moltype =      length =
SEQUENCE: 69
000

SEQ ID NO: 70              moltype =      length =
SEQUENCE: 70
000

SEQ ID NO: 71              moltype =      length =
```

```
SEQUENCE: 71
000

SEQ ID NO: 72          moltype =    length =
SEQUENCE: 72
000

SEQ ID NO: 73          moltype =    length =
SEQUENCE: 73
000

SEQ ID NO: 74          moltype =    length =
SEQUENCE: 74
000

SEQ ID NO: 75          moltype =    length =
SEQUENCE: 75
000

SEQ ID NO: 76          moltype = AA  length = 9
FEATURE                Location/Qualifiers
REGION                 1..9
                       note = Synthetic sequence
source                 1..9
                       mol_type = protein
                       organism = synthetic construct
SEQUENCE: 76
INPYSGGTV                                                                  9

SEQ ID NO: 77          moltype = AA  length = 18
FEATURE                Location/Qualifiers
REGION                 1..18
                       note = Synthetic sequence
source                 1..18
                       mol_type = protein
                       organism = synthetic construct
SEQUENCE: 77
QHMTEVVRHC PHHERCSD                                                        18

SEQ ID NO: 78          moltype = AA  length = 12
FEATURE                Location/Qualifiers
REGION                 1..12
                       note = Synthetic sequence
source                 1..12
                       mol_type = protein
                       organism = synthetic construct
SEQUENCE: 78
TEVVRHCPHH ER                                                              12

SEQ ID NO: 79          moltype = AA  length = 9
FEATURE                Location/Qualifiers
REGION                 1..9
                       note = Synthetic sequence
source                 1..9
                       mol_type = protein
                       organism = synthetic construct
SEQUENCE: 79
VRHCPHHER                                                                  9

SEQ ID NO: 80          moltype = AA  length = 174
FEATURE                Location/Qualifiers
REGION                 1..174
                       note = Synthetic construct
source                 1..174
                       mol_type = protein
                       organism = synthetic construct
SEQUENCE: 80
MSDKIIHLTD DSFDTDVLKA DGAILVDFWA EWCGPGSGSG QHMTEVVRHC PHHERCSDGS           60
GTEVVRHCPH HERGSGVRHC PHHERGSGSG PCKMIAPILD EIADEYQGKL TVAKLNIDQN           120
PGTAPKYGIR GIPTLLLFKN GEVAATKVGA LSKGQLKEFL DANLAGSGHH HHHH                174

SEQ ID NO: 81          moltype = AA  length = 19
FEATURE                Location/Qualifiers
REGION                 1..19
                       note = Synthetic sequence
source                 1..19
                       mol_type = protein
                       organism = synthetic construct
```

```
SEQUENCE: 81
SCMGGMNQRP ILTIITLED                                                    19

SEQ ID NO: 82           moltype = AA  length = 17
FEATURE                 Location/Qualifiers
REGION                  1..17
                        note = Synthetic sequence
source                  1..17
                        mol_type = protein
                        organism = synthetic construct
SEQUENCE: 82
MGGMNQRPIL TIITLED                                                      17

SEQ ID NO: 83           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 83
NSSCMGGMNQ RPILT                                                        15

SEQ ID NO: 84           moltype = AA  length = 186
FEATURE                 Location/Qualifiers
REGION                  1..186
                        note = Synthetic construct
source                  1..186
                        mol_type = protein
                        organism = synthetic construct
SEQUENCE: 84
MSDKIIHLTD DSFDTDVLKA DGAILVDFWA EWCGPGSGSG SCMGGMNQRP ILTIITLEDG        60
SGMGGMNQRP ILTIITLEDG SGNSSCMGGM NQRPILTGSG SGPCKMIAPI LDEIADEYQG       120
KLTVAKLNID QNPGTAPKYG IRGIPTLLLF KNGEVAATKV GALSKGQLKE FLDANLAGSG       180
HHHHHH                                                                 186

SEQ ID NO: 85           moltype = AA  length = 10
FEATURE                 Location/Qualifiers
REGION                  1..10
                        note = Synthetic sequence
source                  1..10
                        mol_type = protein
                        organism = synthetic construct
SEQUENCE: 85
RNSFEVHVCA                                                              10

SEQ ID NO: 86           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 86
NLLGRNSFEV HVCAC                                                        15

SEQ ID NO: 87           moltype = AA  length = 13
FEATURE                 Location/Qualifiers
REGION                  1..13
                        note = Synthetic sequence
source                  1..13
                        mol_type = protein
                        organism = synthetic construct
SEQUENCE: 87
GRNSFEVHVC ACP                                                          13

SEQ ID NO: 88           moltype = AA  length = 173
FEATURE                 Location/Qualifiers
REGION                  1..173
                        note = Synthetic construct
source                  1..173
                        mol_type = protein
                        organism = synthetic construct
SEQUENCE: 88
MSDKIIHLTD DSFDTDVLKA DGAILVDFWA EWCGPGSGSG RNSFEVHVCA GSGNLLGRNS        60
FEVHVCACGS GGRNSFEVHV CACPGSGSGP CKMIAPILDE IADEYQGKLT VAKLNIDQNP       120
GTAPKYGIRG IPTLLLFKNG EVAATKVGAL SKGQLKEFLD ANLAGSGHHH HHH             173
```

-continued

```
SEQ ID NO: 89           moltype =   length =
SEQUENCE: 89
000

SEQ ID NO: 90           moltype = AA   length = 32
FEATURE                 Location/Qualifiers
REGION                  1..32
                        note = Synthetic antigen sequence
source                  1..32
                        mol_type = protein
                        organism = synthetic construct
SEQUENCE: 90
QHMTEVVRHC PHERCSDGSG TEVVRHCPHH ER                                      32

SEQ ID NO: 91           moltype = AA   length = 4
FEATURE                 Location/Qualifiers
source                  1..4
                        mol_type = protein
                        organism = Escherichia coli
SEQUENCE: 91
CGPC                                                                      4

SEQ ID NO: 92           moltype = AA   length = 4
FEATURE                 Location/Qualifiers
REGION                  1..4
                        note = Linker sequence
source                  1..4
                        mol_type = protein
                        organism = synthetic construct
SEQUENCE: 92
GSGS                                                                      4

SEQ ID NO: 93           moltype = AA   length = 18
FEATURE                 Location/Qualifiers
source                  1..18
                        mol_type = protein
                        organism = Homo sapiens
SEQUENCE: 93
QHMTEVVRRC PHHERCSD                                                      18

SEQ ID NO: 94           moltype = AA   length = 12
FEATURE                 Location/Qualifiers
REGION                  1..12
                        note = Synthetic sequence
source                  1..12
                        mol_type = protein
                        organism = synthetic construct
SEQUENCE: 94
GGVLHLPHHT RN                                                            12

SEQ ID NO: 95           moltype = AA   length = 12
FEATURE                 Location/Qualifiers
REGION                  1..12
                        note = Synthetic sequence
source                  1..12
                        mol_type = protein
                        organism = synthetic construct
SEQUENCE: 95
ADNHEPHPLA CD                                                            12

SEQ ID NO: 96           moltype = AA   length = 12
FEATURE                 Location/Qualifiers
REGION                  1..12
                        note = Synthetic sequence
source                  1..12
                        mol_type = protein
                        organism = synthetic construct
SEQUENCE: 96
TRHQPHHSLP PR                                                            12

SEQ ID NO: 97           moltype = AA   length = 12
FEATURE                 Location/Qualifiers
REGION                  1..12
                        note = Synthetic sequence
source                  1..12
                        mol_type = protein
                        organism = synthetic construct
```

```
SEQUENCE: 97
TPHQPHHSFT PR                                                                      12

SEQ ID NO: 98           moltype = AA  length = 12
FEATURE                 Location/Qualifiers
REGION                  1..12
                        note = Synthetic sequence
source                  1..12
                        mol_type = protein
                        organism = synthetic construct
SEQUENCE: 98
VSTGVHYPHH SA                                                                      12

SEQ ID NO: 99           moltype = AA  length = 12
FEATURE                 Location/Qualifiers
REGION                  1..12
                        note = Synthetic sequence
source                  1..12
                        mol_type = protein
                        organism = synthetic construct
SEQUENCE: 99
VDMHHYPHHY KD                                                                      12

SEQ ID NO: 100          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 100
ILASHRPHHY GY                                                                      12

SEQ ID NO: 101          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 101
LCTPLLHPIH HL                                                                      12

SEQ ID NO: 102          moltype = AA  length = 16
FEATURE                 Location/Qualifiers
source                  1..16
                        mol_type = protein
                        organism = Homo sapiens
SEQUENCE: 102
GMNRRPILTI ITLEDS                                                                  16

SEQ ID NO: 103          moltype = AA  length = 16
FEATURE                 Location/Qualifiers
REGION                  1..16
                        note = Synthetic sequence
source                  1..16
                        mol_type = protein
                        organism = synthetic construct
SEQUENCE: 103
GMNQRPILTI ITLEDS                                                                  16

SEQ ID NO: 104          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 104
ELWQNVRPFL WV                                                                      12

SEQ ID NO: 105          moltype = AA  length = 12
FEATURE                 Location/Qualifiers
REGION                  1..12
                        note = Synthetic sequence
source                  1..12
                        mol_type = protein
                        organism = synthetic construct
```

```
SEQUENCE: 105
SRPADHWPRH NE                                                                         12

SEQ ID NO: 106          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 106
SSRPMAHWPI KV                                                                         12

SEQ ID NO: 107          moltype = AA  length = 11
FEATURE                 Location/Qualifiers
REGION                  1..11
                        note = Synthetic sequence
source                  1..11
                        mol_type = protein
                        organism = synthetic construct
SEQUENCE: 107
VSSRPSSHWP I                                                                          11

SEQ ID NO: 108          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 108
SNTPHWPGRP GI                                                                         12

SEQ ID NO: 109          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 109
INTPRDWAYG GL                                                                         12

SEQ ID NO: 110          moltype = AA  length = 11
FEATURE                 Location/Qualifiers
REGION                  1..11
                        note = Synthetic sequence
source                  1..11
                        mol_type = protein
                        organism = synthetic construct
SEQUENCE: 110
FNQPPRSGRV I                                                                          11

SEQ ID NO: 111          moltype = AA  length = 12
FEATURE                 Location/Qualifiers
source                  1..12
                        mol_type = protein
                        organism = Homo sapiens
SEQUENCE: 111
GRNSFEVRVC AC                                                                         12

SEQ ID NO: 112          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 112
GRNSFEVHVC AC                                                                         12

SEQ ID NO: 113          moltype = AA  length = 12
FEATURE                 Location/Qualifiers
REGION                  1..12
                        note = Synthetic sequence
source                  1..12
                        mol_type = protein
                        organism = synthetic construct
```

```
SEQUENCE: 113
GKTYSYHMQL YT                                                           12

SEQ ID NO: 114          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 114
YHVGGILGRL FM                                                           12

SEQ ID NO: 115          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 115
YNTFPYHLGY TL                                                           12

SEQ ID NO: 116          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 116
DNASSSKVHH GH                                                           12

SEQ ID NO: 117          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 117
TFVHGNTWTI VN                                                           12

SEQ ID NO: 118          moltype = AA  length = 11
FEATURE                 Location/Qualifiers
REGION                  1..11
                        note = Synthetic sequence
source                  1..11
                        mol_type = protein
                        organism = synthetic construct
SEQUENCE: 118
TNTMHAVHHP L                                                            11

SEQ ID NO: 119          moltype = AA  length = 14
FEATURE                 Location/Qualifiers
REGION                  1..14
                        note = Synthetic sequence
source                  1..14
                        mol_type = protein
                        organism = synthetic construct
SEQUENCE: 119
RNSFEVHVCA CPGR                                                         14

SEQ ID NO: 120          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 120
YNQTHHPHHQ EY                                                           12

SEQ ID NO: 121          moltype = AA  length = 12
FEATURE                 Location/Qualifiers
REGION                  1..12
                        note = Synthetic sequence
```

```
                        -continued source                  1..12
                        mol_type = protein
                        organism = synthetic construct
SEQUENCE: 121
GAPEVHHPAH QA                                                             12

SEQ ID NO: 122          moltype = AA   length = 12
FEATURE                 Location/Qualifiers
REGION                  1..12
                        note = Synthetic sequence
source                  1..12
                        mol_type = protein
                        organism = synthetic construct
SEQUENCE: 122
KTLSHAPHHS KE                                                             12

SEQ ID NO: 123          moltype = AA   length = 12
FEATURE                 Location/Qualifiers
REGION                  1..12
                        note = Synthetic sequence
source                  1..12
                        mol_type = protein
                        organism = synthetic construct
SEQUENCE: 123
HSPVHTPHGS GK                                                             12

SEQ ID NO: 124          moltype = AA   length = 12
FEATURE                 Location/Qualifiers
REGION                  1..12
                        note = Synthetic sequence
source                  1..12
                        mol_type = protein
                        organism = synthetic construct
SEQUENCE: 124
TPHQPHHSFT PR                                                             12

SEQ ID NO: 125          moltype = AA   length = 12
FEATURE                 Location/Qualifiers
REGION                  1..12
                        note = Synthetic sequence
source                  1..12
                        mol_type = protein
                        organism = synthetic construct
SEQUENCE: 125
DSHFLHYPHH SN                                                             12

SEQ ID NO: 126          moltype = AA   length = 11
FEATURE                 Location/Qualifiers
REGION                  1..11
                        note = Synthetic sequence
source                  1..11
                        mol_type = protein
                        organism = synthetic construct
SEQUENCE: 126
ESTGHSPHQH N                                                              11

SEQ ID NO: 127          moltype = AA   length = 12
FEATURE                 Location/Qualifiers
REGION                  1..12
                        note = Synthetic sequence
source                  1..12
                        mol_type = protein
                        organism = synthetic construct
SEQUENCE: 127
STPVHTPHHA HY                                                             12

SEQ ID NO: 128          moltype = AA   length = 12
FEATURE                 Location/Qualifiers
REGION                  1..12
                        note = Synthetic sequence
source                  1..12
                        mol_type = protein
                        organism = synthetic construct
SEQUENCE: 128
SGSLQHRPHP RN                                                             12
```

```
SEQ ID NO: 129         moltype = AA  length = 12
FEATURE                Location/Qualifiers
REGION                 1..12
                       note = Synthetic sequence
source                 1..12
                       mol_type = protein
                       organism = synthetic construct
SEQUENCE: 129
VGSPQHWPHH SN                                                              12

SEQ ID NO: 130         moltype = AA  length = 12
FEATURE                Location/Qualifiers
REGION                 1..12
                       note = Synthetic sequence
source                 1..12
                       mol_type = protein
                       organism = synthetic construct
SEQUENCE: 130
VGSPQHWPHH CN                                                              12

SEQ ID NO: 131         moltype = AA  length = 12
FEATURE                Location/Qualifiers
REGION                 1..12
                       note = Synthetic sequence
source                 1..12
                       mol_type = protein
                       organism = synthetic construct
SEQUENCE: 131
VGSPQHWPHH SK                                                              12

SEQ ID NO: 132         moltype = AA  length = 12
FEATURE                Location/Qualifiers
REGION                 1..12
                       note = Synthetic sequence
source                 1..12
                       mol_type = protein
                       organism = synthetic construct
SEQUENCE: 132
LEVNHWGHHY RT                                                              12

SEQ ID NO: 133         moltype = AA  length = 11
FEATURE                Location/Qualifiers
REGION                 1..11
                       note = Synthetic sequence
source                 1..11
                       mol_type = protein
                       organism = synthetic construct
SEQUENCE: 133
GGSGHQSGHR P                                                               11

SEQ ID NO: 134         moltype = AA  length = 12
FEATURE                Location/Qualifiers
REGION                 1..12
                       note = Synthetic sequence
source                 1..12
                       mol_type = protein
                       organism = synthetic construct
SEQUENCE: 134
SLGHKSHHFI AA                                                              12

SEQ ID NO: 135         moltype = AA  length = 12
FEATURE                Location/Qualifiers
REGION                 1..12
                       note = Synthetic sequence
source                 1..12
                       mol_type = protein
                       organism = synthetic construct
SEQUENCE: 135
FDLRDYMHMP HH                                                              12

SEQ ID NO: 136         moltype = AA  length = 12
FEATURE                Location/Qualifiers
REGION                 1..12
                       note = Synthetic sequence
source                 1..12
                       mol_type = protein
                       organism = synthetic construct
```

```
SEQUENCE: 136
SSTHYSWSLM DA                                                           12

SEQ ID NO: 137          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 137
GPSCHYCFTG LP                                                           12

SEQ ID NO: 138          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 138
WSVPPGRHIH YS                                                           12

SEQ ID NO: 139          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 139
FSVPSGHYIR AN                                                           12

SEQ ID NO: 140          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 140
FSVRPFHYAQ DN                                                           12

SEQ ID NO: 141          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 141
FSVPFDRIQE TP                                                           12

SEQ ID NO: 142          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 142
FSVRPYDPQI EN                                                           12

SEQ ID NO: 143          moltype = AA  length = 12
FEATURE                 Location/Qualifiers
REGION                  1..12
                        note = Synthetic sequence
source                  1..12
                        mol_type = protein
                        organism = synthetic construct
SEQUENCE: 143
HSVWYANGSV KT                                                           12

SEQ ID NO: 144          moltype = AA  length = 21
FEATURE                 Location/Qualifiers
REGION                  1..21
                        note = Synthetic sequence
```

```
source                  1..21
                        mol_type = protein
                        organism = synthetic construct
SEQUENCE: 144
SVVVPYEPPE VGSDCTTIHY N                                              21

SEQ ID NO: 145          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 145
MTEVVRHCPH HER                                                       13

SEQ ID NO: 146          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 146
ATEVVRHCPH HER                                                       13

SEQ ID NO: 147          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 147
MAEVVRHCPH HER                                                       13

SEQ ID NO: 148          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 148
MTAVVRHCPH HER                                                       13

SEQ ID NO: 149          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 149
MTEAVRHCPH HER                                                       13

SEQ ID NO: 150          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 150
MTEVARHCPH HER                                                       13

SEQ ID NO: 151          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 151
MTEVVAHCPH HER                                                       13
```

```
SEQ ID NO: 152           moltype = AA   length = 13
FEATURE                  Location/Qualifiers
REGION                   1..13
                         note = Synthetic sequence
source                   1..13
                         mol_type = protein
                         organism = synthetic construct
SEQUENCE: 152
MTEVVRACPH HER                                                          13

SEQ ID NO: 153           moltype = AA   length = 13
FEATURE                  Location/Qualifiers
REGION                   1..13
                         note = Synthetic sequence
source                   1..13
                         mol_type = protein
                         organism = synthetic construct
SEQUENCE: 153
MTEVVRHAPH HER                                                          13

SEQ ID NO: 154           moltype = AA   length = 13
FEATURE                  Location/Qualifiers
REGION                   1..13
                         note = Synthetic sequence
source                   1..13
                         mol_type = protein
                         organism = synthetic construct
SEQUENCE: 154
MTEVVRHCAH HER                                                          13

SEQ ID NO: 155           moltype = AA   length = 13
FEATURE                  Location/Qualifiers
REGION                   1..13
                         note = Synthetic sequence
source                   1..13
                         mol_type = protein
                         organism = synthetic construct
SEQUENCE: 155
MTEVVRHCPA HER                                                          13

SEQ ID NO: 156           moltype = AA   length = 13
FEATURE                  Location/Qualifiers
REGION                   1..13
                         note = Synthetic sequence
source                   1..13
                         mol_type = protein
                         organism = synthetic construct
SEQUENCE: 156
MTEVVRHCPH AER                                                          13

SEQ ID NO: 157           moltype = AA   length = 13
FEATURE                  Location/Qualifiers
REGION                   1..13
                         note = Synthetic sequence
source                   1..13
                         mol_type = protein
                         organism = synthetic construct
SEQUENCE: 157
MTEVVRHCPH HAR                                                          13

SEQ ID NO: 158           moltype = AA   length = 13
FEATURE                  Location/Qualifiers
REGION                   1..13
                         note = Synthetic sequence
source                   1..13
                         mol_type = protein
                         organism = synthetic construct
SEQUENCE: 158
MTEVVRHCPH HEA                                                          13

SEQ ID NO: 159           moltype = AA   length = 4
FEATURE                  Location/Qualifiers
REGION                   1..4
                         note = Synthetic sequence
source                   1..4
                         mol_type = protein
                         organism = synthetic construct
```

```
SEQUENCE: 159
HHER                                                                              4

SEQ ID NO: 160          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 160
RNSFEVHVCA CPG                                                                   13

SEQ ID NO: 161          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 161
ANSFEVHVCA CPG                                                                   13

SEQ ID NO: 162          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 162
RASFEVHVCA CPG                                                                   13

SEQ ID NO: 163          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 163
RNAFEVHVCA CPG                                                                   13

SEQ ID NO: 164          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 164
RNSAEVHVCA CPG                                                                   13

SEQ ID NO: 165          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 165
RNSFAVHVCA CPG                                                                   13

SEQ ID NO: 166          moltype = AA  length = 13
FEATURE                 Location/Qualifiers
REGION                  1..13
                        note = Synthetic sequence
source                  1..13
                        mol_type = protein
                        organism = synthetic construct
SEQUENCE: 166
RNSFEAHVCA CPG                                                                   13

SEQ ID NO: 167          moltype = AA  length = 13
FEATURE                 Location/Qualifiers
REGION                  1..13
                        note = Synthetic sequence
```

```
source                    1..13
                          mol_type = protein
                          organism = synthetic construct
SEQUENCE: 167
RNSFEVAVCA CPG                                                                13

SEQ ID NO: 168            moltype = AA   length = 13
FEATURE                   Location/Qualifiers
REGION                    1..13
                          note = Synthetic sequence
source                    1..13
                          mol_type = protein
                          organism = synthetic construct
SEQUENCE: 168
RNSFEVHACA CPG                                                                13

SEQ ID NO: 169            moltype = AA   length = 13
FEATURE                   Location/Qualifiers
REGION                    1..13
                          note = Synthetic sequence
source                    1..13
                          mol_type = protein
                          organism = synthetic construct
SEQUENCE: 169
RNSFEVHVAA CPG                                                                13

SEQ ID NO: 170            moltype = AA   length = 13
FEATURE                   Location/Qualifiers
REGION                    1..13
                          note = Synthetic sequence
source                    1..13
                          mol_type = protein
                          organism = synthetic construct
SEQUENCE: 170
RNSFEVHVCA APG                                                                13

SEQ ID NO: 171            moltype = AA   length = 13
FEATURE                   Location/Qualifiers
REGION                    1..13
                          note = Synthetic sequence
source                    1..13
                          mol_type = protein
                          organism = synthetic construct
SEQUENCE: 171
RNSFEVHVCA CAG                                                                13

SEQ ID NO: 172            moltype = AA   length = 13
FEATURE                   Location/Qualifiers
REGION                    1..13
                          note = Synthetic sequence
source                    1..13
                          mol_type = protein
                          organism = synthetic construct
SEQUENCE: 172
RNSFEVHVCA CPA                                                                13

SEQ ID NO: 173            moltype = AA   length = 4
FEATURE                   Location/Qualifiers
REGION                    1..4
                          note = Synthetic sequence
source                    1..4
                          mol_type = protein
                          organism = synthetic construct
SEQUENCE: 173
VHVC                                                                          4

SEQ ID NO: 174            moltype = AA   length = 393
FEATURE                   Location/Qualifiers
REGION                    1..393
                          note = Synthetic construct
source                    1..393
                          mol_type = protein
                          organism = synthetic construct
SEQUENCE: 174
MEEPQSDPSV EPPLSQETFS DLWKLLPENN VLSPLPSQAM DDLMLSPDDI EQWFTEDPGP             60
DEAPRMPEAA PPVAPAPAAP TPAAPAPAPS WPLSSSVPSQ KTYQGSYGFR LGFLHSGTAK            120
SVTCTYSPAL NKMFCQLAKT CPVQLWVDST PPPGTRVRAM AIYKQSQHMT EVVRHCPHHE            180
RCSDSDGLAP PQHLIRVEGN LRVEYLDDRN TFRHSVVVPY EPPEVGSDCT TIHYNYMCNS            240
SCMGGMNQRP ILTIITLEDS SGNLLGRNSF EVHVCACPGR DRRTEEENLR KKGEPHHELP            300
```

```
PGSTKRALPN NTSSSPQPKK KPLDGEYFTL QIRGRERFEM FRELNEALEL KDAQAGKEPG    360
GSRAHSSHLK SKKGQSTSRH KKLMFKTEGP DSD                                393

SEQ ID NO: 175          moltype = DNA   length = 14
FEATURE                 Location/Qualifiers
source                  1..14
                        mol_type = other DNA
                        organism = Homo sapiens
SEQUENCE: 175
gggggcagcg cctc                                                     14

SEQ ID NO: 176          moltype = DNA   length = 14
FEATURE                 Location/Qualifiers
source                  1..14
                        mol_type = other DNA
                        organism = Homo sapiens
SEQUENCE: 176
gggggcagtg cctc                                                     14

SEQ ID NO: 177          moltype = DNA   length = 16
FEATURE                 Location/Qualifiers
source                  1..16
                        mol_type = other DNA
                        organism = Homo sapiens
SEQUENCE: 177
agcgctcatg gtgggg                                                   16

SEQ ID NO: 178          moltype = DNA   length = 16
FEATURE                 Location/Qualifiers
source                  1..16
                        mol_type = other DNA
                        organism = Homo sapiens
SEQUENCE: 178
gcgctcacgg tggggg                                                   16

SEQ ID NO: 179          moltype = DNA   length = 19
FEATURE                 Location/Qualifiers
source                  1..19
                        mol_type = other DNA
                        organism = Homo sapiens
SEQUENCE: 179
ccactcggat aagatgctg                                                19

SEQ ID NO: 180          moltype = DNA   length = 19
FEATURE                 Location/Qualifiers
source                  1..19
                        mol_type = other DNA
                        organism = Homo sapiens
SEQUENCE: 180
ccactcgggt aagatgctg                                                19

SEQ ID NO: 181          moltype = DNA   length = 19
FEATURE                 Location/Qualifiers
source                  1..19
                        mol_type = other DNA
                        organism = Homo sapiens
SEQUENCE: 181
gcccatgcag gaactgtta                                                19

SEQ ID NO: 182          moltype = DNA   length = 19
FEATURE                 Location/Qualifiers
source                  1..19
                        mol_type = other DNA
                        organism = Homo sapiens
SEQUENCE: 182
gcccatgaag gaactgtta                                                19

SEQ ID NO: 183          moltype = DNA   length = 16
FEATURE                 Location/Qualifiers
source                  1..16
                        mol_type = other DNA
                        organism = Homo sapiens
SEQUENCE: 183
cggttcatgc cgccca                                                   16
```

```
SEQ ID NO: 184          moltype = DNA  length = 16
FEATURE                 Location/Qualifiers
source                  1..16
                        mol_type = other DNA
                        organism = Homo sapiens
SEQUENCE: 184
cggttcatgc tgccca                                                           16

SEQ ID NO: 185          moltype = DNA  length = 13
FEATURE                 Location/Qualifiers
source                  1..13
                        mol_type = other DNA
                        organism = Homo sapiens
SEQUENCE: 185
gggcctccgg ttc                                                              13

SEQ ID NO: 186          moltype = DNA  length = 13
FEATURE                 Location/Qualifiers
source                  1..13
                        mol_type = other DNA
                        organism = Homo sapiens
SEQUENCE: 186
gggcctctgg ttc                                                              13

SEQ ID NO: 187          moltype = DNA  length = 95
FEATURE                 Location/Qualifiers
source                  1..95
                        mol_type = other DNA
                        organism = Homo sapiens
SEQUENCE: 187
tacagcagtc acagcacatg acggaggttg tgaggcactg cccccaccat gagcgctgct           60
cagatagcga tggtgagcag ctggggctgg agaga                                      95

SEQ ID NO: 188          moltype = DNA  length = 102
FEATURE                 Location/Qualifiers
source                  1..102
                        mol_type = other DNA
                        organism = Homo sapiens
SEQUENCE: 188
gcagtcacag cacatgacgg aggttgtgag gcactgcccc catcatgagc gctgctcaga           60
tagcgatggt gagcagctgg ggctggagag acgacagggc tg                             102

SEQ ID NO: 189          moltype = DNA  length = 101
FEATURE                 Location/Qualifiers
source                  1..101
                        mol_type = other DNA
                        organism = Homo sapiens
SEQUENCE: 189
agcagtcaca gcacatgacg gaggttgtga ggcactgccc ccaccatgag cgctgctcag           60
atagcgatgg tgagcagctg gggctggaga gacgacaggg c                              101

SEQ ID NO: 190          moltype = DNA  length = 103
FEATURE                 Location/Qualifiers
source                  1..103
                        mol_type = other DNA
                        organism = Homo sapiens
SEQUENCE: 190
cagcagtcac agcacatgac ggaggttgtg aggcgctgcc cccaccatga gcgctgctca           60
gatagcgatg gtgagcagct ggggctggag agacgacagg gct                            103

SEQ ID NO: 191          moltype = DNA  length = 97
FEATURE                 Location/Qualifiers
source                  1..97
                        mol_type = other DNA
                        organism = Homo sapiens
SEQUENCE: 191
ggcacccgcg tccgcgccat ggccatctac aagcagtcac agcacatgac ggaggttgtg           60
aggcgctgcc cccaccatga gcgctgctca gatagcc                                    97

SEQ ID NO: 192          moltype = AA  length = 58
FEATURE                 Location/Qualifiers
source                  1..58
                        mol_type = protein
                        organism = Homo sapiens
SEQUENCE: 192
MTEVVRRCPH HERCSDSDGL APPQHLIRVE GNLRVEYLDD RNTFRHSVVV PYEPPEVG             58

SEQ ID NO: 193          moltype = AA  length = 58
```

```
FEATURE                 Location/Qualifiers
source                  1..58
                        mol_type = protein
                        organism = Macaca mulatta
SEQUENCE: 193
MTEVVRRCPH HERCSDSDGL APPQHLIRVE GNLRVEYSDD RNTFRHSVVV PYEPPEVG      58

SEQ ID NO: 194          moltype = AA  length = 58
FEATURE                 Location/Qualifiers
source                  1..58
                        mol_type = protein
                        organism = Tupaia belangeri
SEQUENCE: 194
VTEVVRRCPH HERCSDSDGL APPQHLIRVE GNLHAEYSDD RNTFRHSVVV PYEPPEVG      58

SEQ ID NO: 195          moltype = AA  length = 58
FEATURE                 Location/Qualifiers
source                  1..58
                        mol_type = protein
                        organism = Oryctolagus cuniculus
SEQUENCE: 195
MTEVVRRCPH HERCSDSDGL APPQHLIRVE GNLRAEYLDD RNTFRHSVVV PYEPPEVG      58

SEQ ID NO: 196          moltype = AA  length = 59
FEATURE                 Location/Qualifiers
source                  1..59
                        mol_type = protein
                        organism = Delphinapterus leucas
SEQUENCE: 196
MTEVVRRCPH HERCSDYSDG LAPPQHLIRV EGNLRAEYLD DRNTFRHSVV VPYEPPEVG     59

SEQ ID NO: 197          moltype = AA  length = 59
FEATURE                 Location/Qualifiers
source                  1..59
                        mol_type = protein
                        organism = Sus scrofa
SEQUENCE: 197
MTEVVRRCPH HERSSDYSDG LAPPQHLIRV EGNLRAEYLD DRNTFRHSVV VPYEPPEVG     59

SEQ ID NO: 198          moltype = AA  length = 59
FEATURE                 Location/Qualifiers
source                  1..59
                        mol_type = protein
                        organism = Canis familiaris
SEQUENCE: 198
VTEVVRRCPH HERCSDSSDG LAPPQHLIRV EGNLRAKYLD DRNTFRHSVV VPYEPPEVG     59

SEQ ID NO: 199          moltype = AA  length = 59
FEATURE                 Location/Qualifiers
source                  1..59
                        mol_type = protein
                        organism = Felis catus
SEQUENCE: 199
MTEVVRRCPH HERCPDSSDG LAPPQHLIRV EGNLHAKYLD DRNTFRHSVV VPYEPPEVG     59

SEQ ID NO: 200          moltype = AA  length = 58
FEATURE                 Location/Qualifiers
source                  1..58
                        mol_type = protein
                        organism = Cavia porcellus
SEQUENCE: 200
MTEVVRRCPH HERCSDSDGL APPQHLIRVE GNLHAEYVDD RTTFRHSVVV PYEPPEVG      58

SEQ ID NO: 201          moltype = AA  length = 59
FEATURE                 Location/Qualifiers
source                  1..59
                        mol_type = protein
                        organism = Ovis aries
SEQUENCE: 201
MTEVVRRCPH HERSSDYSDG LAPPQHLIRV EGNLRAEYFD DRNTFRHSVV VPYESPEIE     59

SEQ ID NO: 202          moltype = AA  length = 58
FEATURE                 Location/Qualifiers
source                  1..58
                        mol_type = protein
                        organism = Mesocricetus auratus
SEQUENCE: 202
MTEVVRRCPH HERSSEGDGL APPQHLIRVE GNMHAEYLDD KQTFRHSVVV PYEPPEVG      58
```

```
SEQ ID NO: 203          moltype = AA   length = 58
FEATURE                 Location/Qualifiers
source                  1..58
                        mol_type = protein
                        organism = Cricetulus griseus
SEQUENCE: 203
MTEVVRRCPH HERSSEGDSL APPQHLIRVE GNLHAEYLDD KQTFRHSVVV PYEPPEVG      58

SEQ ID NO: 204          moltype = AA   length = 59
FEATURE                 Location/Qualifiers
source                  1..59
                        mol_type = protein
                        organism = Bos taurus
SEQUENCE: 204
MTEVVRRCPH HERSSDYSDG LAPPQHLIRV EGNLRAEYLD DRNTFRHSVV VPYESPEID     59

SEQ ID NO: 205          moltype = AA   length = 58
FEATURE                 Location/Qualifiers
source                  1..58
                        mol_type = protein
                        organism = Rattus norvegicus
SEQUENCE: 205
MTEVVRRCPH HERCSDGDGL APPQHLIRVE GNPYAEYLDD RQTFRHSVVV PYEPPEVG      58

SEQ ID NO: 206          moltype = AA   length = 58
FEATURE                 Location/Qualifiers
source                  1..58
                        mol_type = protein
                        organism = Mus musculus
SEQUENCE: 206
MTEVVRRCPH HERCSDGDGL APPQHLIRVE GNLYPEYLED RQTFRHSVVV PYEPPEAG      58

SEQ ID NO: 207          moltype = AA   length = 59
FEATURE                 Location/Qualifiers
source                  1..59
                        mol_type = protein
                        organism = Equus caballus
SEQUENCE: 207
MTEVVRRCPH HERCSDSSDG LAPPQHLIRV EGNLRAEYLD DRNTFRHSVV VPYEPPEVG     59

SEQ ID NO: 208          moltype = AA   length = 59
FEATURE                 Location/Qualifiers
source                  1..59
                        mol_type = protein
                        organism = Equus asinus
SEQUENCE: 208
MTEVVRRCPH HERCSDSSDG LAPPQHLIRV EGNLRAEYLD DRNTLRHSVV VPYEPPEVG     59

SEQ ID NO: 209          moltype = AA   length = 59
FEATURE                 Location/Qualifiers
source                  1..59
                        mol_type = protein
                        organism = Gallus gallus
SEQUENCE: 209
VAEVVRRCPH HERCGGGTDG LAPAQHLIRV EGNPQARYHD DETTKRHSVV VPYEPPEVG     59

SEQ ID NO: 210          moltype = AA   length = 59
FEATURE                 Location/Qualifiers
source                  1..59
                        mol_type = protein
                        organism = Xenopus laevis
SEQUENCE: 210
VAEVKRCPH HERSVEPGED AAPPSHLMRV EGNLQAYYME DVNSGRHSVC VPYEGPQVG      59

SEQ ID NO: 211          moltype = AA   length = 59
FEATURE                 Location/Qualifiers
source                  1..59
                        mol_type = protein
                        organism = Oncorhynchus mykiss
SEQUENCE: 211
VADVVRRCPH HQSTSENNEG PAPRGHLVRV EGNQRSEYME DGNTLRHSVL VPYEPPQVG     59

SEQ ID NO: 212          moltype = AA   length = 58
FEATURE                 Location/Qualifiers
source                  1..58
                        mol_type = protein
                        organism = Danio rerio
SEQUENCE: 212
VAEVVRRCPH HERTPDGDNL APAGHLIRVE GNQRANYRED NITLRHSVFV PYEAPQLG      58
```

```
SEQ ID NO: 213          moltype = AA   length = 59
FEATURE                 Location/Qualifiers
source                  1..59
                        mol_type = protein
                        organism = Ictalurus punctatus
SEQUENCE: 213
VAEVVRRCPH HERSNDSSDG PAPPGHLLRV EGNSRAVYQE DGNTQAHSVV VPYEPPQVG        59

SEQ ID NO: 214          moltype = AA   length = 55
FEATURE                 Location/Qualifiers
source                  1..55
                        mol_type = protein
                        organism = Xiphophorus maculatus
SEQUENCE: 214
VGEVVKRCPH HQSEDLSDNK SHLIRVEGSQ LAQYFEDPNT RRHSVTVPYE RPQLG            55

SEQ ID NO: 215          moltype = AA   length = 60
FEATURE                 Location/Qualifiers
source                  1..60
                        mol_type = protein
                        organism = Homo sapiens
SEQUENCE: 215
SDCTTIHYNY MCNSSCMGGM NRRPILTIIT LEDSSGNLLG RNSFEVRVCA CPGRDRRTEE       60

SEQ ID NO: 216          moltype = AA   length = 60
FEATURE                 Location/Qualifiers
source                  1..60
                        mol_type = protein
                        organism = Tupaia belangeri
SEQUENCE: 216
SDCTTIHYNY MCNSSCMGGM NRRPILTIIT LEDSSGKLLG RNSFEVRICA CPGRDRRTEE       60

SEQ ID NO: 217          moltype = AA   length = 60
FEATURE                 Location/Qualifiers
source                  1..60
                        mol_type = protein
                        organism = Callithrix sp.
SEQUENCE: 217
SECTTIHYNY MCNSSCMGGM NRRPILTIIT LEGSSGNLLG RNSFEVRVCA CPGRDRRTEE       60

SEQ ID NO: 218          moltype = AA   length = 60
FEATURE                 Location/Qualifiers
source                  1..60
                        mol_type = protein
                        organism = Oryctolagus cuniculus
SEQUENCE: 218
SDCTTIHYNY MCNSSCMGGM NRRPILTIIT LEDSSGNLLG RNSFEVRVCA CPGRDRRTEE       60

SEQ ID NO: 219          moltype = AA   length = 60
FEATURE                 Location/Qualifiers
source                  1..60
                        mol_type = protein
                        organism = Delphinapterus leucas
SEQUENCE: 219
SDCTTIHYNF MCNSSCMGGM NRRPILTIIT LEDSNGNLLG RNSFEVRVCA CPGRDRRTEE       60

SEQ ID NO: 220          moltype = AA   length = 60
FEATURE                 Location/Qualifiers
source                  1..60
                        mol_type = protein
                        organism = Sus scrofa
SEQUENCE: 220
SDCTTIHYNF MCNSSCMGGM NRRPILTIIT LEDASGNLLG RNSFEVRVCA CPGRDRRTEE       60

SEQ ID NO: 221          moltype = AA   length = 60
FEATURE                 Location/Qualifiers
source                  1..60
                        mol_type = protein
                        organism = Canis familiaris
SEQUENCE: 221
SDYTTIHYNY MCNSSCMGGM NRRPILTIIT LEDSSGNVLG RNSFEVRVCA CPGRDRRTEE       60

SEQ ID NO: 222          moltype = AA   length = 60
FEATURE                 Location/Qualifiers
source                  1..60
                        mol_type = protein
                        organism = Felis catus
```

-continued

```
SEQUENCE: 222
SDCTTIHYNF MCNSSCMGGM NRRPIITIIT LEDSNGKLLG RNSFEVRVCA CPGRDRRTEE    60

SEQ ID NO: 223          moltype = AA  length = 60
FEATURE                 Location/Qualifiers
source                  1..60
                        mol_type = protein
                        organism = Cavia porcellus
SEQUENCE: 223
SDCTTIHYNY MCNSSCMGGM NRRPILTIIT LEDSSGKLLG RDSFEVRVCA CPGRDRRTEE    60

SEQ ID NO: 224          moltype = AA  length = 60
FEATURE                 Location/Qualifiers
source                  1..60
                        mol_type = protein
                        organism = Ovis aries
SEQUENCE: 224
SECTTIHYNF MCNSSCMGGM NRRPILTIIT LEDSRGNLLG RSSFEVRVCA CPGRDRRTEE    60

SEQ ID NO: 225          moltype = AA  length = 60
FEATURE                 Location/Qualifiers
source                  1..60
                        mol_type = protein
                        organism = Mesocricetus auratus
SEQUENCE: 225
SDCTTIHYNY MCNSSCMGGM NRRPILTIIT LEDPSGNLLG RNSFEVRICA CPGRDRRTEE    60

SEQ ID NO: 226          moltype = AA  length = 60
FEATURE                 Location/Qualifiers
source                  1..60
                        mol_type = protein
                        organism = Bos taurus
SEQUENCE: 226
SECTTIHYNF MCNSSCMGGM NRRPILTIIT LEDSCGNLLG RNSFEVRVCA CPGRDRRTEE    60

SEQ ID NO: 227          moltype = AA  length = 60
FEATURE                 Location/Qualifiers
source                  1..60
                        mol_type = protein
                        organism = Rattus norvegicus
SEQUENCE: 227
SDYTTIHYKY MCNSSCMGGM NRRPILTIIT LEDSSGNLLG RDSFEVRVCA CPGRDRRTEE    60

SEQ ID NO: 228          moltype = AA  length = 60
FEATURE                 Location/Qualifiers
source                  1..60
                        mol_type = protein
                        organism = Mus musculus
SEQUENCE: 228
SEYTTIHYKY MCNSSCMGGM NRRPILTIIT LEDSSGNLLG RDSFEVRVCA CPGRDRRTEE    60

SEQ ID NO: 229          moltype = AA  length = 60
FEATURE                 Location/Qualifiers
source                  1..60
                        mol_type = protein
                        organism = Equus caballus
SEQUENCE: 229
SDCTTIHYNF MCNSSCMGGM NRRPILTIIT LEDSSGNLLG RNSFEVRVCA CPGRDRRTEE    60

SEQ ID NO: 230          moltype = AA  length = 60
FEATURE                 Location/Qualifiers
source                  1..60
                        mol_type = protein
                        organism = Gallus gallus
SEQUENCE: 230
SDCTTVLYNF MCNSSCMGGM NRRPILTILT LEGPGGQLLG RRCFEVRVCA CPGRDRKIEE    60

SEQ ID NO: 231          moltype = AA  length = 60
FEATURE                 Location/Qualifiers
source                  1..60
                        mol_type = protein
                        organism = Xenopus laevis
SEQUENCE: 231
TECTTVLYNY MCNSSCMGGM NRRPILTIIT LETPQGLLLG RRCFEVRVCA CPGRDRRTEE    60

SEQ ID NO: 232          moltype = AA  length = 60
FEATURE                 Location/Qualifiers
```

```
source                  1..60
                        mol_type = protein
                        organism = Oncorhynchus mykiss
SEQUENCE: 232
SECTTVLYNF MCNSSCMGGM NRRPILTIIT LETQEGQLLG RRSFEVRVCA CPGRDRKTEE    60

SEQ ID NO: 233          moltype = AA  length = 60
FEATURE                 Location/Qualifiers
source                  1..60
                        mol_type = protein
                        organism = Danio rerio
SEQUENCE: 233
AEWTTVLLNY MCNSSCMGGM NRRPILTIIT LETQEGQLLG RRSFEVRVCA CPGRDRKTEE    60

SEQ ID NO: 234          moltype = AA  length = 60
FEATURE                 Location/Qualifiers
source                  1..60
                        mol_type = protein
                        organism = Ictalurus punctatus
SEQUENCE: 234
SQSTTVLYNY MCNSSCMGGM NRRPILTIIT LETQDGHLLG RRTFEVRVCA CPGRDRKTEE    60

SEQ ID NO: 235          moltype = AA  length = 60
FEATURE                 Location/Qualifiers
source                  1..60
                        mol_type = protein
                        organism = Xiphophorus maculatus
SEQUENCE: 235
SEMTILLSF MCNSSCMGGM NRRPILTILT LETTEGEVLG RRCFEVRVCA CPGRDRKTEE     60

SEQ ID NO: 236          moltype = AA  length = 4
FEATURE                 Location/Qualifiers
REGION                  1..4
                        note = Linker sequence
source                  1..4
                        mol_type = protein
                        organism = synthetic construct
SEQUENCE: 236
SGSG                                                                  4

SEQ ID NO: 237          moltype = AA  length = 113
FEATURE                 Location/Qualifiers
REGION                  1..113
                        note = Mouse-human chimeric anti-R175H clone 4H5
source                  1..113
                        mol_type = protein
                        organism = synthetic construct
SEQUENCE: 237
DIVLTQSTSS LSVSAGERVT LSCKSSQSLL NSGNQKSYLA WYQQKPGQPP KLLIYGASTR    60
ESGVPDRFTG SGSETDFTLT ISSVQPEDLA VYYCQNDHSY PLTFGAGTKL ELK          113

SEQ ID NO: 238          moltype = AA  length = 113
FEATURE                 Location/Qualifiers
REGION                  1..113
                        note = Mouse-human chimeric anti-R175H clone 7B9
source                  1..113
                        mol_type = protein
                        organism = synthetic construct
SEQUENCE: 238
DIVMTQSPSS LSVSGGEKVT MSCKSSQSLL NSGNQKSNLA WYQQKPGQPP KLLIYGASTR    60
ESGVPDRFAG SGSGTDFTLT ISSVQAEDLA VYYCQNDHSY PLTFGGGTKL ELK          113

SEQ ID NO: 239          moltype = AA  length = 115
FEATURE                 Location/Qualifiers
REGION                  1..115
                        note = Mouse-human chimeric anti-R175H clone 4H5
source                  1..115
                        mol_type = protein
                        organism = synthetic construct
SEQUENCE: 239
EVQLQQSGPE LVKPGASVKI SCKTSGFTFT EYTMHWMKQS HGRSLEWIGR IDPNNGVTVY    60
NQKFKVKATL TVDRSSSTAY LELRSLTSED SAVYYCARWG GDYVTGGGTT LTVSS        115

SEQ ID NO: 240          moltype = AA  length = 115
FEATURE                 Location/Qualifiers
REGION                  1..115
                        note = Mouse-human chimeric anti-R175H clone 7B9
```

```
source                   1..115
                         mol_type = protein
                         organism = synthetic construct
SEQUENCE: 240
EVQLQQSGPE LVKPGASVKI SCKTSGYTFT EYTMHWMKQS HGKSLEWIGR INPYSGGTVY    60
NQKFKGKATL TVDKSSSTAY MELRSLTSDD SAVYYCARWG GDYVTGGGTT LTVSS        115

SEQ ID NO: 241           moltype = AA   length = 115
FEATURE                  Location/Qualifiers
REGION                   1..115
                         note = Mouse-human chimeric anti-R175H clone 10C8
source                   1..115
                         mol_type = protein
                         organism = synthetic construct
SEQUENCE: 241
EVQLQQSGPE LVKPGASVKI SCKTSGYTFT EYTMHWMKQS HGKSLEWIGR INPYSGGTVY    60
NQKFKGKATL TVDKSSSTAY MELRSLTSDD SAVYYCARWG GDYVTGGGTT LTVSS        115

SEQ ID NO: 242           moltype = DNA   length = 339
FEATURE                  Location/Qualifiers
misc_feature             1..339
                         note = Mouse-human chimeric anti-R175H clone 4H5 Light
                           Chain variable domain
source                   1..339
                         mol_type = other DNA
                         organism = synthetic construct
SEQUENCE: 242
gatattgtgc tcacccaatc tacatcctcc ctgagtgtgt cagctggaga gagggtcact    60
ttgagctgca agtccagtca gagtctgtta aacagtggaa atcaaaagag ttacttggcc   120
tggtaccagc agaaaccagg gcagcctcct aaactgttga tctacgggca atccactagg   180
gaatctgggg tccctgatcg cttcacaggc agtggatctg aaaccgattt cactcttacc   240
atcagcagtg tgcagcctga agacctggca gtttattatt gtcagaatga tcatagttat   300
ccgctcacgt tcggtgctgg gaccaagctg gagctgaaa                          339

SEQ ID NO: 243           moltype = DNA   length = 339
FEATURE                  Location/Qualifiers
misc_feature             1..339
                         note = Mouse-human chimeric anti-R175H clone 7B9 Llight
                           Chain variable domain
source                   1..339
                         mol_type = other DNA
                         organism = synthetic construct
SEQUENCE: 243
gatattgtga tgacccagtc tccatcctcc ctgagtgtgt caggaggaga gaaggtcact    60
atgagctgca agtccagtca gagtctgtta aacagtggaa atcaaaagag caacttggcc   120
tggtaccagc agaaaccagg gcagcctcct aaattgttga tctatggggc atccactagg   180
gaatctgggg tccctgatcg cttcgcaggc agtggatctg gaaccgattt cactcttacc   240
atcagcagtg tgcaggctga agacctggca gtttattact gtcaaaatga tcatagttat   300
ccgctcacgt tcggtggtgg gaccaagctg gagctgaaa                          339

SEQ ID NO: 244           moltype = DNA   length = 345
FEATURE                  Location/Qualifiers
misc_feature             1..345
                         note = Mouse-human chimeric anti-R175H clone 4H5 Heavy
                           Chain variable domain
source                   1..345
                         mol_type = other DNA
                         organism = synthetic construct
SEQUENCE: 244
gaggttcagc tgcagcagtc tggacctgaa ctggtgaagc ctggggcttc agtgaagata    60
tcttgcaaga cttccggatt cacattcact gaatacacca tgcactggat gaaacagagc   120
catggaagga gccttgagtg gatcggacgt attgatccta caatggtgt tactgtttat   180
aaccagaagt tcaaggtcaa ggccacattg actgtggaca ggtcctccag cacagcctat   240
ctggagctcc gcagtctgac gtctgaggac tctgcagtct attactgtgc aagatggggt   300
ggtgactacg tcacgggggg aggcaccact ctcacagtct cctca                   345

SEQ ID NO: 245           moltype = DNA   length = 345
FEATURE                  Location/Qualifiers
misc_feature             1..345
                         note = Mouse-human chimeric anti-R175H clone 7B9 Heavy
                           Chain variable domain
source                   1..345
                         mol_type = other DNA
                         organism = synthetic construct
SEQUENCE: 245
gaggtccagc tgcagcagtc tggacctgag ctggtgaagc ctggggcttc agtgaagata    60
tcctgcaaga cttctggcta cactttcact gaatacacca tgcactggat gaagcagagc   120
catggaaaga gccttgagtg gattggacgt attaatcctt atagtggtgg tactgtctac   180
aaccagaagt tcaagggcaa ggccacattg actgtggaca gtcctccag cacagcctat    240
```

```
atggagctcc gcagcctgac atctgatgat tctgcagtct attactgtgc aagatggggt    300
ggtgactacg tcacgggggg aggcaccact ctcacagtct cctca                    345

SEQ ID NO: 246          moltype = DNA   length = 345
FEATURE                 Location/Qualifiers
misc_feature            1..345
                        note = Mouse-human chimeric anti-R175H clone 10C8 Heavy
                          Chain variable domain
source                  1..345
                        mol_type = other DNA
                        organism = synthetic construct
SEQUENCE: 246
gaggtgcagc ttcagcagtc gggacctgag ctggtgaagc ctggggcttc agtgaagata    60
tcctgcaaga cttctggcta cactttcact gaatacacca tgcactggat gaagcagagc   120
catggaaaga gccttgagtg gattggacgt attaatcctt atagtggtgg tactgtctac   180
aaccagaagt tcaagggcaa ggccacattg actgtggaca gtcctccagc acagcctat    240
atggagctcc gcagcctgac atctgatgat tctgcagtct attactgtgc aagatggggt    300
ggtgactacg tcacgggggg aggcaccact ctcacagtct cctca                    345

SEQ ID NO: 247          moltype = AA   length = 112
FEATURE                 Location/Qualifiers
REGION                  1..112
                        note = Mouse-human chimeric anti-R273H clone 13E4
source                  1..112
                        mol_type = protein
                        organism = synthetic construct
SEQUENCE: 247
DIVMTQSPLS LPVNLGDQVS LSCRSSQSIV HNNGDTYLEW YLQKPGQSPK LLIYKVSNRF     60
SGVPDRFSGS GSGTDFTLKI SRVEAEDLGI YYCFQGSHLP LTFGSGTKLE LK            112

SEQ ID NO: 248          moltype = AA   length = 120
FEATURE                 Location/Qualifiers
REGION                  1..120
                        note = Mouse-human chimeric anti-R273H clone 13E4
source                  1..120
                        mol_type = protein
                        organism = synthetic construct
SEQUENCE: 248
EVQLLETGGD LVTPGGSLKL SCAASGFSFS DYYMYWVRQT PEKRLEWVAT ISVGGTYTFY     60
SDNVKGRFVI SRDNARKNLH LEMNSLKSED AAMYYCVRDG NDGKFLGYWG QGTFVTVTVS    120

SEQ ID NO: 249          moltype = DNA   length = 336
FEATURE                 Location/Qualifiers
misc_feature            1..336
                        note = Mouse-human chimeric anti-R273H clone 13E4 light
                          chain variable domain
source                  1..336
                        mol_type = other DNA
                        organism = synthetic construct
SEQUENCE: 249
gatattgtga tgacacaatc tccactctcc ctgcctgtca atcttggaga tcaagtctcc     60
ctctcttgca gatctagtca gagcattgta cataataatg gagacaccta tttagaatgg    120
tacctacaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggaatt tattactgct ttcaaggttc acatcttccg    300
ctcacgttcg gttctgggac caagctggag ctgaaa                              336

SEQ ID NO: 250          moltype = DNA   length = 360
FEATURE                 Location/Qualifiers
misc_feature            1..360
                        note = Mouse-human chimeric anti-R273H clone 13E4 heavy
                          chain variable domain
source                  1..360
                        mol_type = other DNA
                        organism = synthetic construct
SEQUENCE: 250
gaagtgcagc tgttggagac tgggggagac ttagtgacgc tggaggtc cctgaaactc      60
tcctgtgcag cctctggatt cagcttcagt gactattata tgtattgggt tcgccagact   120
ccggaaaaga ggctgagtg gtcgcaact attagtgttg gtggtacata caccttctat     180
tcagacaatg tgaaggggag attcgtcatc tccagagaca tgccaggaa aaatctgcat    240
ctggaaatga acagtctgaa gtctgaggac gcagccatgt attactgtgt aagagatggc   300
aacgatggaa aatttcttgg gtactgggc caggggactt cgtcactgt cactgtctct    360

SEQ ID NO: 251          moltype = AA   length = 112
FEATURE                 Location/Qualifiers
REGION                  1..112
                        note = Mouse-human chimeric anti-R248Q clone 3G11
```

| | | |
|---|---|---|
| source | 1..112<br>mol_type = protein<br>organism = synthetic construct | |
| SEQUENCE: 251 | | |
| DIVLTQTPLT LSVTIGQPAS ISCKSNQSLL YSDGKTYLNW LLQRPGQSPK RLIYLVSKLD | | 60 |
| SGVPDRFTGS GSGTDFTLKI SRVEAEDLGL YYCWQGTHFP LTFGAGTKLE LK | | 112 |
| | | |
| SEQ ID NO: 252<br>FEATURE<br>REGION | moltype = AA length = 112<br>Location/Qualifiers<br>1..112<br>note = Mouse-human chimeric anti-R248Q clone 4H2 | |
| source | 1..112<br>mol_type = protein<br>organism = synthetic construct | |
| SEQUENCE: 252 | | |
| DIVITQSPLT LSVTIGQPAS ISCKSDQSLL YSDGKTYLNW LLQRPGQSPK RLIYLVSELD | | 60 |
| SGVPDRFTGS GSGTDFTLKI SRVEAEDLGL YYCWQGTHFP LTFGAGTKLE LK | | 112 |
| | | |
| SEQ ID NO: 253<br>FEATURE<br>REGION | moltype = AA length = 116<br>Location/Qualifiers<br>1..116<br>note = Mouse-human chimeric anti-R248Q clone 3G11 | |
| source | 1..116<br>mol_type = protein<br>organism = synthetic construct | |
| SEQUENCE: 253 | | |
| DVQLQQSGPE LVKPGASVKM SCKASGYTFT DYYVKWVKQS PGQSLEWIGD IHPKNGGTNY | | 60 |
| NQKFKGKAAL TVDKSSSTAY MQLNSLTSED SAVYFCAKMG GYDDYWGQGT TLTVSS | | 116 |
| | | |
| SEQ ID NO: 254<br>FEATURE<br>REGION | moltype = AA length = 116<br>Location/Qualifiers<br>1..116<br>note = Mouse-human chimeric anti-R248Q clone 4H2 | |
| source | 1..116<br>mol_type = protein<br>organism = synthetic construct | |
| SEQUENCE: 254 | | |
| QVQLKQSGPE LVKPGASVKM SCKASGYTFT DYYLKWVRQS HGKSLEWIGD IDPKNGGTNY | | 60 |
| NQKFKGKATL TVDKSSSTAY MQLNSLTSED SAVYYCAKQG GFDDYWGQGT TLTVSS | | 116 |
| | | |
| SEQ ID NO: 255<br>FEATURE<br>misc_feature | moltype = DNA length = 336<br>Location/Qualifiers<br>1..336<br>note = Mouse-human chimeric anti-R248Q clone 3G11 light<br>chain variable domain | |
| source | 1..336<br>mol_type = other DNA<br>organism = synthetic construct | |
| SEQUENCE: 255 | | |
| gatattgtgc tgacacagac tccactcact ttgtcggtta ccattggaca accagcctcc | | 60 |
| atctcttgca agtcaaatca gagcctctta tatagtgatg gaaagacata tttgaattgg | | 120 |
| ttattacaga ggccaggcca gtctccaaag cgcctaatct atctggtgtc taaactggac | | 180 |
| tctggagtcc ctgacaggtt cactggcagt ggatcaggga cagatttcac actgaaaatc | | 240 |
| agcagagtgg aggctgagga tttgggactt tattattgct ggcaaggtac acatttcct | | 300 |
| ctcacgttcg gtgctgggac caagctggag ctgaaa | | 336 |
| | | |
| SEQ ID NO: 256<br>FEATURE<br>misc_feature | moltype = DNA length = 336<br>Location/Qualifiers<br>1..336<br>note = Mouse-human chimeric anti-R248Q clone 4H2 light<br>chain variable domain | |
| source | 1..336<br>mol_type = other DNA<br>organism = synthetic construct | |
| SEQUENCE: 256 | | |
| gacattgtga tcacacagtc tccactcact ttgtcggtta ccattggaca accagcctcc | | 60 |
| atctcttgca agtcagatca gagcctctta tatagtgatg gaaagacata tttgaattgg | | 120 |
| ctattacaga ggccaggcca gtctccaaag cgcctaatct atctggtgtc tgaactggac | | 180 |
| tctggagtcc ctgacaggtt cactggcagt ggatcaggga cagatttcac actgaaaatc | | 240 |
| agcagagtgg aggctgagga tttgggactt tattattgct ggcaaggtac acatttcct | | 300 |
| ctcacgttcg gtgctgggac caagctggag ctgaaa | | 336 |
| | | |
| SEQ ID NO: 257<br>FEATURE<br>misc_feature | moltype = DNA length = 348<br>Location/Qualifiers<br>1..348<br>note = Mouse-human chimeric anti-R248Q clone 3G11 heavy | |

```
                    chain variable domain
source              1..348
                    mol_type = other DNA
                    organism = synthetic construct
SEQUENCE: 257
gatgtgcagc ttcagcagtc aggacctgag ctggtgaagc ctggggcttc agtgaagatg    60
tcctgtaagg cttctggata cacattcact gactactatg tgaagtgggt gaagcagagt   120
cctggacaga gccttgagtg gattggagat attcatccta agaacggtgg tactaactac   180
aaccagaagt tcaagggcaa ggccgcattg actgtggaca aatcctccag cacagcctac   240
atgcagctca acagcctgac atctgaggac tctgcagtct atttctgtgc aaaaatggga   300
ggctacgacg actactgggg ccaaggcacc actctcacag tctcctca               348

SEQ ID NO: 258      moltype = DNA  length = 348
FEATURE             Location/Qualifiers
misc_feature        1..348
                    note = Mouse-human chimeric anti-R248Q clone 4H2 heavy
                     chain variable domain
source              1..348
                    mol_type = other DNA
                    organism = synthetic construct
SEQUENCE: 258
caggtgcagc tgaagcagtc aggacctgag ctggtgaagc ctggggcttc agtgaagatg    60
tcctgtaagg cttctggata cacattcact gactactatc tgaagtgggt gaggcagagt   120
catggaaaga gccttgagtg gattggagat atagatccca agaatggtgg tactaattac   180
aaccagaagt ttaagggcaa ggccacattg actgtggaca aatcctccag cacagcctac   240
atgcagctca acagcctgac atctgaggac tctgcagtct attactgtgc aaaacagggg   300
gggttcgacg actactgggg ccaaggcacc actctcacag tctcctca               348
```

The invention claimed is:

1. An antibody, or antigen binding fragment, which is capable of binding to R175H p53 polypeptide, optionally isolated, having the amino acid sequences i) to vi):

i) LC-CDR1:
QSLLNSGNQKSX$_1$;  (SEQ ID NO: 31)

ii) LC-CDR2:
GAS;

iii) LC-CDR3:
QNDHSYPLT;  (SEQ ID NO: 21)

iv) HC-CDR1:
GX$_2$TFTEYT;  (SEQ ID NO: 32)

v) HC-CDR2:
IX$_3$PX$_4$X$_5$GX$_6$T; and  (SEQ ID NO: 33)

vi) HC-CDR3:
ARWGGDYV;  (SEQ ID NO: 27)

wherein X$_1$=Y or N; X$_2$=F or Y; X$_3$=D or N; X$_4$=N or Y; X$_5$=N or S; and X$_6$=V or G.

2. The antibody, or antigen binding fragment, according to claim 1, wherein HC-CDR2 is one of IDPNNGVT (SEQ ID NO:26) or INPYSGGT (SEQ ID NO: 30).

3. The antibody, or antigen binding fragment, according to claim 1, having at least one light chain variable region incorporating the following CDRs:

LC-CDR1:
QSLLNSGNQKSX$_1$;  (SEQ ID NO: 31)

LC-CDR2:
GAS; and

LC-CDR3:
QNDHSYPLT.  (SEQ ID NO: 21)

4. The antibody, or antigen binding fragment, according to claim 1, having at least one light chain variable region incorporating the following CDRs:

LC-CDR1:
QSLLNSGNQKSY;  (SEQ ID NO: 19)

LC-CDR2:
GAS; and

LC-CDR3:
QNDHSYPLT.  (SEQ ID NO: 21)

5. The antibody, or antigen binding fragment, according to claim 1, having at least one heavy chain variable region incorporating the following CDRs:

HC-CDR1:
GFTFTEYT;  (SEQ ID NO: 25)

HC-CDR2:
IDPNNGVT; and  (SEQ ID NO: 26)

HC-CDR3:
ARWGGDYV.  (SEQ ID NO: 27)

6. The antibody, or antigen binding fragment, according to claim 1, having at least one heavy chain variable region incorporating the following CDRs:

HC-CDR1:
GYTFTEYT;  (SEQ ID NO: 29)

-continued

```
HC-CDR2:
                              (SEQ ID NO: 30)
   INPYSGGT; and

HC-CDR3:
                              (SEQ ID NO: 27)
   ARWGGDYV.
```

7. An antibody, or antigen binding fragment according to claim 1, comprising a light chain and a heavy chain variable region sequence, wherein:
   the light chain sequence has at least 85% sequence identity to the light chain sequence of SEQ ID NO:18 or 22, or SEQ ID NO:237 or 94, and;
   the heavy chain sequence has at least 85% sequence identity to the heavy chain sequence of SEQ ID NO:24 or 28, or SEQ ID NO:239, 240 or 241.

8. An antibody, or antigen binding fragment, optionally isolated, which is capable of binding to R175H p53 polypeptide, which is a bispecific antibody or a bispecific antigen binding fragment comprising (i) an antigen binding fragment according to claim 1, and (ii) an antigen binding fragment capable of binding to a polypeptide other than R175H p53 polypeptide.

9. An antibody, or antigen binding fragment according to claim 1, conjugated to a drug moiety or a detectable moiety.

10. A chimeric antigen receptor (CAR) comprising the antibody, or antigen binding fragment, according to claim 1, optionally comprised in a cell.

11. An isolated nucleic acid encoding the antibody, or antigen binding fragment, of claim 1, optionally comprised in a vector, further optionally comprised in a host cell.

* * * * *